(12) United States Patent
Kerovuo et al.

(10) Patent No.: US 7,592,434 B2
(45) Date of Patent: Sep. 22, 2009

(54) PECTATE LYASES, NUCLEIC ENCODING THEM AND METHODS FOR MAKING AND USING THEM

(75) Inventors: Janne Kerovuo, San Diego, CA (US); Arne Solbak, San Diego, CA (US); Kevin Gray, San Diego, CA (US); Ryan McCann, San Diego, CA (US); Shalaka Purohit, San Diego, CA (US); Joel Gerendash, San Diego, CA (US); Giselle Janssen, San Carlos, CA (US); Samun Dahod, Bristol, WI (US)

(73) Assignee: Verenium Corporation, San Diego, CA (US)

( * ) Notice: Subject to any disclaimer, the term of this patent is extended or adjusted under 35 U.S.C. 154(b) by 0 days.

(21) Appl. No.: 10/501,442

(22) PCT Filed: Apr. 2, 2004

(86) PCT No.: PCT/US2004/010229

§ 371 (c)(1),
(2), (4) Date: Oct. 29, 2005

(87) PCT Pub. No.: WO2004/090099

PCT Pub. Date: Oct. 21, 2004

(65) Prior Publication Data

US 2006/0210971 A1 Sep. 21, 2006

Related U.S. Application Data

(60) Provisional application No. 60/460,842, filed on Apr. 4, 2003, provisional application No. 60/484,798, filed on Jul. 3, 2003.

(51) Int. Cl.
*C07H 21/04* (2006.01)
*C12N 9/88* (2006.01)
*C12N 1/20* (2006.01)
*C12N 15/63* (2006.01)
*C12P 21/00* (2006.01)

(52) U.S. Cl. .................. 536/23.1; 435/232; 435/252.3; 435/320.1; 435/71.1

(58) Field of Classification Search ........................ None
See application file for complete search history.

(56) References Cited

U.S. PATENT DOCUMENTS

| 4,788,066 | A  | 11/1988 | Witt |
| 5,582,681 | A  | 12/1996 | Back et al. |
| 5,605,793 | A  | 2/1997  | Stemmer |
| 5,709,796 | A  | 1/1998  | Fuqua et al. |
| 5,830,696 | A  | 11/1998 | Short |
| 5,912,407 | A  | 6/1999  | Miller et al. |
| 5,939,250 | A  | 8/1999  | Short |
| 5,980,581 | A  | 11/1999 | Patterson et al. |
| 6,017,751 | A  | 1/2000  | von der Osten et al. |
| 6,021,536 | A  | 2/2000  | Wasinger et al. |
| 6,024,766 | A  | 2/2000  | Wasinger |
| 6,066,233 | A  | 5/2000  | Olsen et al. |
| 6,077,316 | A  | 6/2000  | Lund et al. |
| 6,162,260 | A  | 12/2000 | Liu et al. |
| 6,187,580 | B1 | 2/2001  | Andersen et al. |
| 6,197,070 | B1 | 3/2001  | Horner et al. |
| 6,221,406 | B1 | 4/2001  | Meschonat et al. |
| 6,241,849 | B1 | 6/2001  | Franks |
| 6,258,590 | B1 | 7/2001  | Lange et al. |
| 6,261,828 | B1 | 7/2001  | Lund |
| 6,264,925 | B1 | 7/2001  | Fuglsang et al. |
| 6,309,871 | B1 | 10/2001 | Outtrup et al. |
| 6,329,333 | B1 | 12/2001 | Merz et al. |
| 6,333,301 | B1 | 12/2001 | Kamiya et al. |
| 6,365,561 | B1 | 4/2002  | Vinson et al. |
| 6,368,843 | B1 | 4/2002  | Andersen et al. |
| 6,399,351 | B1 | 6/2002  | Bjornvad et al. |
| 6,399,561 | B1 | 6/2002  | Schneider et al. |
| 6,410,064 | B1 | 6/2002  | Akazawa |
| 6,429,000 | B1 | 8/2002  | Andersen et al. |
| 6,551,358 | B2 | 4/2003  | Miller et al. |
| 2002/0115194 | A1 | 8/2002 | Lange et al. |
| 2002/0142438 | A1 | 10/2002 | Andersen et al. |
| 2003/0040454 | A1 | 2/2003 | Cuperus et al. |
| 2004/0034888 | A1 | 2/2004 | Liu et al. |

FOREIGN PATENT DOCUMENTS

| EP | 0552728 A1 | 7/1993 |
| WO | WO 95/14807 A1 | 6/1995 |
| WO | WO 97/01629 A1 | 1/1997 |
| WO | WO 98/24965 A1 | 6/1998 |
| WO | WO 00/26464 A2 | 5/2000 |
| WO | WO 01/79440 A2 | 10/2001 |
| WO | WO 02/081815 A2 | 10/2002 |
| WO | WO 02/092741 A2 | 11/2002 |
| WO | WO 03/002705 A1 | 1/2003 |
| WO | WO 03/002810 A1 | 1/2003 |

OTHER PUBLICATIONS

EST database Accession No. G128381 van der Hoeven et al Jan. 31, 2001. Alignment with sid 1.*

(Continued)

*Primary Examiner*—Sheridan Swope
(74) *Attorney, Agent, or Firm*—Jennifer Risser

(57) ABSTRACT

The invention is directed to polypeptides having pectate lyase (pectinase) activity, polynucleotides encoding the polypeptides, and methods for making and using these polynucleotides and polypeptides. The polypeptides of the invention can be used as pectate lyases to catalyze the beta-elimination or hydrolysis of pectin and/or polygalacturonic acid, such as 1,4-linked alpha-D-galacturonic acid. The invention provides methods of treating fibers, fabrics or any pectate- or polygalacturonic acid-comprising material using one or more pectate lyases of the invention.

19 Claims, 10 Drawing Sheets

OTHER PUBLICATIONS

NiceZyme view of Enzyme: EC 4.2.2.2. Downloaded Feb. 15, 2008.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Carthew et al, Gene silencing by double-stranded RNA. Curr Opin Cell Biol. Apr. 2001;13(2):244-8. Review.*
USPTO in house alignment of SEQ ID No. 78 with GenBank Accession No. AAG29353 from Brown et al, Biochem J. Apr. 1, 2001;355(Pt 1):155-65.*
USPTO in house alignment of SEQ ID No. 132 with GenBank Accession No. AAG29353, residues 327-649, from Brown et al, Biochem J. Apr. 1, 2001;355(Pt 1):155-65.*
Takao, et. Al., "Molecular cloning, DNA sequence and expression of the gene encoding for thremostable pectate lyase of thermophilic Bacillus sp. TS 47", Bioscience Biotechnology and Biochemistry, 2001, 65(2):322-329.
Kluskens, et. al., "Molecular and biochemical characterization of the thermoactive family 1 pectate lyase from the hyperthermophilic bacterium Thermotoga maritima.", *Biochem J.*, 2003, 370(2):615-659.
EMBL Database AE012106, May 28, 2002.
Uniprot Database Q8A515, Jun. 1, 2003.
Al-Hooti, Chemical composition and quality of date syrup as affected by pectinase/cellulase enzyme treatment, *Food Chemistry*, 2002, 79:215-220.
Bartling, "Synergism between *Erwinia* pectate lyase isoenzymes that depolymerize both pectate and pectin", *Microbiology*, 1995, 141:873-881.
Essa, et. al., "Effect of macerate enzymes on the yield, quality, volatile compounds and rheological property of prickly pear juice", *Nahrung/Food*, 2002, 46(4):245-250.
Essa, "Effect of pectinase enzyme treatment on the rheological, physical and chemical properties of plum, banana and guava juices", *Polish Journal of Food and Nutrition Sciences*, 2002, 11(3):13-19.
Hoondal, et. al., "Microbial alkaline pectinases and their industrial applications: a review", *Applied Microbiology and Biotechnology*, 2002, 59:409-418.
Hurlbert, et. al., "Differences in the solution structures of the parallel β-helical pectate lyases as determined by limited proteolysis", *Biochimica et Biophysica Acta*, 2002, 1599(1-2):9-20.
Angayarkanni, et. al., "Improvement of Tea Leaves Fermentation with *Aspergillus* ssp. Pectinase", *Journal of Bioscience and Bioengineering*, 2002, 94(4):299-303.
Malathi, et. al., In Vitro Evaluation of Nonstarch Polysaccharide Digestibility of Feed Ingredients by Enzymes, *Poultry Science*, 2001, 80(3):302-305.
Nasuno, et. al., "Polygalacturonase of *Erwinia carotovra*", *J. Biol. Chem.*, 1966, 241:5298-5306.
Revilla, et al., "Addition of pectolytic enzymes: an enological practice which improves the chromaticity and stability of red wines", *International Journal of Food Science & Technology*, 2003, 38(1):29-36.
Tamaru, et. al., "Pectate lyase A, an enzymatic subunit of the *Clostridium cellolovorans* cellulosome", *PNAS*, 2001, 98(7):4125-4129.
Nelson, et. al., "Pectate lyase", NCBI Database AAD35518, Jun. 1, 1999.
Brown, et. al., Pectate lyase 10A, from *Pseudomonas cellulosa* is a modular enzyme containing a family 2a carbohydrate-binding module, *Biochem J.*, 2001, 355:155-165.
EMBL Database AF279264, Nov. 5, 2000.
Uniprot Database Q9F7L3_9GAMM, Mar. 1, 2001.
EMBL Database AB062880, Apr. 23, 2002.
Uniprot Database Q8RR73_9BACI, Jun. 1, 2002.

* cited by examiner

FIGURE 5A

| SEQ ID NO: in provisional | Relative Substrate Specificity | Relative Substrate Specificity Value | Characterization Activity Temp | Characterization Activity pH | Enzyme | Characterization Description | Characterization Substrate |
|---|---|---|---|---|---|---|---|
| 101, 102 | | | | | Pectinase | | |
| 1, 2 | | | room temp | 9 | Pectate lyase | pga assay | Polygalacturonic acid |
| 103, 104 | | | | | Pectate lyase | | |
| 105, 106 | Cotton | 4.8 | 40 | 9 | Pectate lyase | Application Bioscouring | Cotton |
| 107, 108 | Cotton | 1.5 | 40 | 9 | Pectate lyase | Application Bioscouring | Cotton |
| 107, 108 | | | room temp | | Pectate lyase | pga assay | Polygalacturonic acid |
| 109, 110 | | | | | Pectate lyase | | |
| 11, 12 | | | | | Pectinase | | |
| 111, 112 | | | | | Pectate lyase | | |
| 113, 114 | | | | | Pectate lyase | | |
| 115, 116 | | | room temp | 9 | Pectate lyase | pga assay | Polygalacturonic acid |
| 117, 118 | Cotton | 3 | 40 | 9 | Pectate lyase | Application Bioscouring | Cotton |
| 119, 120 | | | room temp | 9 | Pectate lyase | Application bioscouring | |
| 121, 122 | Cotton | 7.8 | 50 | 9 | Pectate lyase | Application Bioscouring | |
| 121, 122 | Cotton | 10.3 | 40 | 9 | Pectate lyase | Application Bioscouring | |
| 123, 124 | Cotton | 3.6 | 40 | 9 | Pectate lyase | Application Bioscouring | |
| 125, 126 | Cotton | 2.5 | 40 | 9 | Pectate lyase | Application Bioscouring | |
| 127, 128 | | | room temp | 9 | Pectate lyase | pga assay | Polygalacturonic acid |
| 127, 128 | | | room temp | 11 | Pectate lyase | pga assay | Polygalacturonic acid |
| 129, 130 | Cotton | 1.8 | 40 | 9 | Pectate lyase | Application Bioscouring | Cotton |
| 13, 14 | | | room temp | 9 | Pectate lyase | pga assay | Polygalacturonic acid |
| 15, 16 | | | | | Pectate lyase | | |
| 17, 18 | | | | 9 | Pectate lyase | pga assay | Polygalacturonic acid |
| 19, 20 | | | | | Pectate lyase | | |
| 21, 22 | | | room temp | 10 | Pectate lyase | pga assay | Polygalacturonic acid |
| 23, 24 | | | room temp | 9 | Pectate lyase | pga assay | Polygalacturonic acid |
| 25, 26 | | | | | Pectate lyase | | |
| 25, 26 | | | | | Pectate lyase | | |
| 27, 28 | | | | | Pectinase | | |
| 29, 30 | | | | | Pectinase | | |
| 3, 4 | | | | | | | |

FIGURE 5B

| | | | | | | | |
|---|---|---|---|---|---|---|---|
| 31, 32 | Cotton | 4.3 | 40 | 9 | Pectate lyase | Application Bioscouring | Cotton |
| 31, 32 | | | room temp | 8 | Pectate lyase | pga assay | Polygalacturonic acid |
| 33, 34 | | 1.6 | room temp | 9 | Pectate lyase | pga assay | Polygalacturonic acid |
| 35, 36 | Cotton | | 40 | 9 | Pectate lyase | Application Bioscouring | Cotton |
| 35, 36 | | 11.2 | room temp | 9 | Pectate lyase | pga assay | Polygalacturonic acid |
| 37, 38 | Cotton | | 50 | 9 | Pectate lyase | Application Bioscouring | Cotton |
| 39, 40 | | 2 | room temp | 9 | Pectate lyase | pga assay | Polygalacturonic acid |
| 41, 42 | Cotton | | 40 | 9 | Pectate lyase | Application Bioscouring | Cotton |
| 43, 44 | | | | | Pectate lyase | | |
| 45, 46 | | | room temp | 9 | Pectate lyase | pga assay | Polygalacturonic acid |
| 47, 48 | | | room temp | 10 | Pectate lyase | pga assay | Polygalacturonic acid |
| 49, 50 | | | | | Pectate lyase | | |
| 5, 6 | | | | | Pectate lyase | | |
| 51, 52 | Cotton | 13.4 | 40 | 9 | Pectate lyase | Application Bioscouring | Cotton |
| 53, 54 | | | | | Pectate lyase | | |
| 55, 56 | | | room temp | 9 | Pectate lyase | pga assay | Polygalacturonic acid |
| 55, 56 | | | room temp | 9 | Pectate lyase | pga assay | Polygalacturonic acid |
| 57, 58 | Cotton | 12.5 | 40 | 9 | Pectate lyase | pga assay | Polygalacturonic acid |
| 59, 60 | | | room temp | 10 | Pectate lyase | pga assay | Polygalacturonic acid |
| 61, 62 | Cotton | 9.8 | 40 | 9 | Pectate lyase | Application Bioscouring | Cotton |
| 61, 62 | | | room temp | 9 | Pectate lyase | pga assay | Polygalacturonic acid |
| 63, 64 | | | room temp | 9 | Pectate lyase | pga assay | Polygalacturonic acid |
| 65, 66 | | | room temp | 9 | Pectate lyase | pga assay | Polygalacturonic acid |
| 67, 68 | Cotton | 0.8 | 40 | 10 | Pectate lyase | Application Bioscouring | Cotton |
| 69, 70 | | | room temp | 9 | Pectate lyase | pga assay | Polygalacturonic acid |
| 7, 8 | | | | | Pectinase | | |
| 71, 72 | Cotton | 16.2 | 40 | 9 | Pectate lyase | Application Bioscouring | Cotton |
| 73, 74 | | | room temp | 9 | Pectate lyase | pga assay | Polygalacturonic acid |
| 73, 74 | | | | | Pectinase | | |
| 75, 76 | Cotton | 1.6 | 40 | 9 | Pectate lyase | Application Bioscouring | Cotton |
| 77, 78 | | | 40 | 9 | Pectate lyase | pga assay | Polygalacturonic acid |
| 79, 80 | Cotton | | 40 | 9 | Pectate lyase | Application Bioscouring | Cotton |
| 81, 82 | Cotton | 3.2 | room temp | 9 | Pectate lyase | pga assay | Polygalacturonic acid |
| 81, 82 | | | | | Pectate lyase | | |
| 83, 84 | Cotton | | 40 | 9 | Pectate lyase | Application Bioscouring | Cotton |

FIGURE 5C

| | | | | | | | |
|---|---|---|---|---|---|---|---|
| 85, 86 | Cotton | 0.1 | 40 | 9 | Pectate lyase | Application Bioscouring | Cotton |
| 85, 86 | Cotton | 9.4 | room temp | 9 | Pectate lyase | pga assay | Polygalacturonic acid |
| 87, 88 | | | 40 | 9 | Pectate lyase | Application Bioscouring | Cotton |
| 89, 90 | | | | 10 | Pectinase | | |
| 9, 10 | | | room temp | | Pectate lyase | pga assay | Polygalacturonic acid |
| 91, 92 | | | | | Pectate lyase | | |
| 93, 94 | | | | | Pectate lyase | | |
| 95, 96 | Cotton | 5.4 | 40 | 9 | Pectate lyase | Application Bioscouring | Cotton |
| 95, 96 | | | room temp | 9 | Pectate lyase | pga assay | Polygalacturonic acid |
| 97, 98 | | | | | Pectate lyase | | |
| 99, 100 | Cotton | 16 | 50 | 9 | Pectate lyase | Application Bioscouring | Cotton |
| 99, 100 | Cotton | 12.2 | 40 | 9 | Pectate lyase | Application Bioscouring | Cotton |

FIGURE 6

Pectate lyase GSSM™ upmutants

| Upmutant | A118H | A182V | T190L | A197G | S208K | T219M | T223E | S255R | S263K | N275Y | Y309W | S312V |
|---|---|---|---|---|---|---|---|---|---|---|---|---|
| A | x |   |   |   | x | x |   |   |   |   |   | x |
| B | x |   | x | x | x | x |   |   |   | x | x | x |
| C | x | x |   |   | x |   |   | x | x | x | x |   |
| D | x | x | x |   | x |   | x |   | x | x | x |   |
| E | x |   |   |   | x |   |   |   |   | x | x |   |
| F | x | x |   |   | x |   |   |   |   | x | x | x |
| G | x |   | x | x | x |   | x | x | x | x | x | x |
| H | x | x | x | x | x |   | x |   | x | x | x | x |
| I | x |   |   | x | x |   | x |   |   |   | x |   |
| J | x |   | x | x | x | x |   | x | x | x | x | x |
| K | x | x | x | x | x |   | x |   | x | x | x | x |
| L | x | x | x | x | x |   | x | x | x | x | x |   |
| M | x |   |   | x | x |   |   |   | x |   | x |   |
| N | x |   |   | x | x | x |   |   | x | x | x | x |
| O | x |   |   | x | x |   |   | x |   | x | x | x |
| P | x | x |   |   | x |   |   |   | x |   | x |   |
| Q | x |   | x | x | x |   |   |   |   | x | x | x |
| R | x |   | x | x | x | x | x |   | x | x | x |   |
| S | x |   | x | x | x | x |   |   | x | x | x |   |

FIGURE 7

| Upmutant | Melting temperature (°C) | Specific Activity (SA) at 30°C | SA at 40°C | SA at 50°C | SA at 60°C | SA at 70°C |
|---|---|---|---|---|---|---|
| AA | 60.6 | 370.3 | 582.1 | 848.2 | ND | ND |
| BB | 58.3 | 366.8 | 542.4 | 648.6 | ND | ND |
| CC | 57 | 331.1 | 439.7 | 713.6 | ND | ND |
| DD | 58 | 468.6 | 595.8 | 714.6 | ND | ND |
| EE | 60 | 102.2 | 202.5 | 378.1 | ND | ND |
| FF | 58.5 | 585.5 | 744.5 | 955.8 | ND | ND |
| GG | 57.2 | 323.8 | 590.4 | 909.3 | ND | ND |
| HH | 58.7 | 267.6 | 425.5 | 706.3 | ND | ND |
| II | 57.8 | 357.1 | 527.3 | 875.1 | ND | ND |
| JJ | 57.5 | 372.2 | 537.6 | 834.9 | ND | ND |
| KK | 58.9 | 444.1 | 678.9 | 859.4 | ND | ND |
| LL | 58.4 | 375.2 | 557.6 | 1007.1 | ND | ND |
| A | 71 | ND | ND | 311.1 | 483.3 | 777.7 |
| B | 70.4 | ND | ND | 317.0 | 432.4 | 628.0 |
| C | 72.5 | ND | ND | 377.6 | 468.6 | 849.1 |
| D | 73.25 | ND | ND | 323.8 | 352.2 | 926.4 |
| E | 71 | ND | ND | 340.4 | 557.6 | 641.7 |
| F | 71.75 | ND | ND | 389.3 | 550.8 | 438.3 |
| G | 73 | ND | ND | 297.4 | 545.9 | 790.4 |
| H | 72.25 | ND | ND | 356.1 | 480.3 | 980.2 |
| I | 70.4 | ND | ND | 363.9 | 701.4 | 666.2 |
| J | 72.8 | ND | ND | 241.6 | 622.2 | 694.6 |
| K | 71.5 | ND | ND | 298.4 | 701.4 | 700.4 |
| L | 73 | ND | ND | 245.5 | 947.0 | 1003.7 |
| M | 73 | ND | ND | 304.2 | 547.8 | 309.1 |
| N | 73 | ND | ND | 685.8 | 1010.5 | 1284.5 |
| O | 71.3 | ND | ND | 268.0 | 517.5 | 330.7 |
| P | 72 | ND | ND | 398.2 | 542.9 | 689.7 |
| Q | 70.8 | ND | ND | 354.1 | 382.5 | 526.3 |
| R | 71.9 | ND | ND | 361.0 | 408.9 | 722.0 |
| S | 70.9 | ND | ND | 753.3 | 1186.6 | 579.1 |

US 7,592,434 B2

PECTATE LYASES, NUCLEIC ENCODING THEM AND METHODS FOR MAKING AND USING THEM

RELATED APPLICATIONS

This application is a national phase application claiming the benefit of priority under 35 U.S.C. §371 to Patent Convention Treaty (PCT) International Application Serial No. PCT/US2004/010229, filed Apr. 2, 2004 (published as WO 2004/090099, on Oct. 21, 2004), which claims the benefit of priority under 35 U.S.C. §119(e) of U.S. Provisional Application Nos. 60/460,842, filed Apr. 4, 2003; and 60/484,798, filed Jul. 3, 2003. Each of the aforementioned applications is explicitly incorporated herein by reference in its entirety and for all purposes.

TECHNICAL FIELD

This invention relates to molecular and cellular biology, biochemistry and biotechnology. In particular, the invention is directed to polypeptides having a pectate lyase activity, e.g., a pectinase, polynucleotides encoding the polypeptides, and methods for making and using these polynucleotides and polypeptides. The polypeptides of the invention can be used as pectate lyases to catalyze the beta-elimination or hydrolysis of pectin and/or polygalacturonic acid, such as 1,4-linked alpha-D-galacturonic acid. They can be used in variety of industrial applications, e.g., to treat plant cell walls, such as those in cotton or other natural fibers. In another exemplary industrial application, the polypeptides of the invention can be used in textile scouring.

BACKGROUND

Cotton fiber consists of a primary and a secondary cell wall. The secondary cell wall is practically pure cellulose, whereas the primary cell wall is a complex lattice of pectin, protein, waxes, pigments, hemicellulose and cellulose. In textile scouring of cellulosic material (e.g. knitted or woven cotton fabric) alkaline conditions (up to 10% NaOH) and high temperatures (up to 100° C.) are needed for effective removal of primary cell wall components. This harsh chemical treatment results in raw material losses and in substantial environmental burden. There are several different enzymes that have the ability to degrade pectin; these are the pectinases, pectin methylesterases, pectin lyases and pectate lyases.

"Size" is the name given to the substance or mixture of substances that is applied to the warp thread before weaving. The size forms a coating around the surface of the thread before weaving. This coating provides the lubrication and prevents the breakage of warp thread during the weaving operation. Some common chemicals used to prepare sizes are Polyacrylic Acid (PA), Polyvinyl Alcohol (PVA), Starch, and Modified Starch. Cellulosic fibers including cotton, rayon and blend of these with synthetic fibers such as polyester, is usually sized with starch-based sizes. Desizing process removes the size before dyeing, printing and/or finishing. Starch sizes can be removed by hot acid wash, which will hydrolyze starch. However, acid hydrolysis results in loss of raw material since cellulose is also prone to acid hydrolysis. Starch sizes can also be removed by using hydrogen peroxide to degrade starch by oxidation. Desizing can also be an enzymatic process. Amylases have been used for many years in textile industry for removal of starch sizes. Conditions (e.g., pH and temperature) for enzymatic desizing are dictated by the operating conditions of the enzyme. Most amylases used in the application are relatively thermostable, however, they are neutral or acidic optimum enzymes.

"Scouring" is a process in which desized cotton fabric is processed to solubilize and extract undesired non-cellulosic material naturally found in cotton and also to remove applied impurities such as machinery lubricants. Scouring uses highly alkaline chemicals to remove the non-cellulosic material, which has a serious environmental impact. Additionally, the chemicals partially degrade the cellulose in the cotton fiber which causes a loss of fiber strength and raw materials and as such is a non-optimal process. The final step in the cotton fabric pretreatment process is bleaching in which the natural pigments and matter present in the fiber are bleached. A thermostable alkaline pectinolytic enzyme that could target specifically the non-cellulosic material could reduce or eliminate the use of harsh chemicals lessening the burden on the environment while maintaining the integrity and strength of the cotton fiber.

SUMMARY

The invention provides isolated or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:131, SEQ ID NO:133, over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues, encodes at least one polypeptide having a pectate lyase activity, and the sequence identities are determined by analysis with a sequence comparison algorithm or by a visual inspection.

Exemplary nucleic acids of the invention also include isolated or recombinant nucleic acids encoding a polypeptide having a sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and subsequences thereof and variants thereof. In one aspect, the polypeptide has a pectate lyase activity.

In one aspect, the invention also provides pectate lyase-encoding nucleic acids with a common novelty in that they are derived from mixed cultures. The invention provides pectate lyase-encoding nucleic acids isolated from mixed cultures comprising a nucleic acid sequence of the invention, e.g., having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:131, SEQ ID NO:133, over a region of at least about 50, 75, 100, 150, 200, 250, 300, 350, 400, 450, 500, 550, 600, 650, 700, 750, 800, 850, 900, 950, 1000, 1050, 1100, 1150, or more.

In one aspect, the invention also provides pectate lyase-encoding nucleic acids with a common novelty in that they are derived from environmental sources, e.g., mixed environmental sources. In one aspect, the invention provides pectate lyase-encoding nucleic acids isolated from environmental sources, e.g., mixed environmental sources, comprising a nucleic acid of the invention, e.g., a sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention over a region of at least about 50, 75, 100, 150, 200, 250, 300, 350, 400, 450, 500, 550, 600, 650, 700, 750, 800, 850, 900, 950, 1000, 1050, 1100, 1150, 1200 or more, residues, wherein the nucleic acid encodes at least one binding or hybridization. The probe can comprise an oligonucleotide comprising at least about 10 to 50, about 20 to 60, about 30 to 70, about 40 to 80, or about 60 to 100 consecutive bases of a sequence comprising a sequence of the invention, or fragments or subsequences thereof.

The invention provides a nucleic acid probe for identifying a nucleic acid encoding a polypeptide having a pectate lyase activity, wherein the probe comprises a nucleic acid comprising a sequence at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid of the invention, wherein the sequence identities are determined by analysis with a sequence comparison algorithm or by visual inspection.

The probe can comprise an oligonucleotide comprising at least about 10 to 50, about 20 to 60, about 30 to 70, about 40 to 80, or about 60 to 100 consecutive bases of a nucleic acid sequence of the invention, or a subsequence thereof.

The invention provides an amplification primer sequence pair for amplifying a nucleic acid encoding a polypeptide having a pectate lyase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence.

The invention provides methods of amplifying a nucleic acid encoding a polypeptide having a pectate lyase activity comprising amplification of a template nucleic acid with an amplification primer sequence pair capable of amplifying a nucleic acid sequence of the invention, or fragments or subsequences thereof.

The invention provides expression cassettes comprising a nucleic acid of the invention or a subsequence thereof. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector.

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cell comprising a nucleic acid of the invention or an expression cassette (e.g., a vector) of the invention, or a cloning vehicle of the invention. In one aspect, the transformed cell can be a bacterial cell, a mammalian cell, a fungal cell, a yeast cell, an insect cell or a plant cell. In one aspect, the plant cell can be a potato, wheat, rice, corn, tobacco or barley cell.

The invention provides transgenic non-human animals comprising a nucleic acid of the invention or an expression cassette (e.g., a vector) of the invention. In one aspect, the animal is a mouse.

The invention provides transgenic plants comprising a nucleic acid of the invention or an expression cassette (e.g., a vector) of the invention. The transgenic plant can be a corn plant, a potato plant, a tomato plant, a wheat plant, an oilseed plant, a rapeseed plant, a soybean plant, a rice plant, a barley plant or a tobacco plant.

The invention provides transgenic seeds comprising a nucleic acid of the invention or an expression cassette (e.g., a vector) of the invention. The transgenic seed can be a corn seed, a wheat kernel, an oilseed, a rapeseed, a soybean seed, a palm kernel, a sunflower seed, a sesame seed, a peanut or a tobacco plant seed.

The invention provides an antisense oligonucleotide comprising a nucleic acid sequence complementary to or capable of hybridizing under stringent conditions to a nucleic acid of the invention. The invention provides methods of inhibiting the translation of a pectate lyase message in a cell comprising administering to the cell or expressing in the cell an antisense oligonucleotide comprising a nucleic acid sequence complementary to or capable of hybridizing under stringent conditions to a nucleic acid of the invention.

The invention provides an isolated or recombinant polypeptide comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide or peptide of the invention over a region of at least about 20, 30, 40, 50, 60, 70, 75, 100, 125, 150, 175, 200, 225, 250, 300, 350 or more residues, or over the full length of the polypeptide, and the sequence identities are determined by analysis with a sequence comparison algorithm or by a visual inspection. Exemplary polypeptide or peptide sequences of the invention include SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, and subsequences thereof and variants thereof. Exemplary polypeptides also include fragments of at least about 10, 15, 20, 25, 30, 35, 40, 45, 50, 75, 100, 150, 200, 250, 300, 350, 400, 450, 500, 550, 600 or more residues in length, or over the full length of an enzyme. A peptide of the invention can be, e.g., an immunogenic fragment, a motif (e.g., a binding site), a signal sequence, a prepro sequence or an active site. Exemplary polypeptide or peptide sequences of the invention include sequence encoded by a nucleic acid of the invention. Exemplary polypeptide or peptide sequences of the invention include polypeptides or peptides specifically bound by an antibody of the polypeptide having a pectate lyase activity, and the sequence identities are determined by analysis with a sequence comparison algorithm or by a visual inspection.

In one aspect, the sequence comparison algorithm is a BLAST version 2.2.2 algorithm where a filtering setting is set to blastall -p blastp -d "nr pataa" -F F, and all other options are set to default.

Another aspect of the invention is an isolated or recombinant nucleic acid including at least 10 consecutive bases of a nucleic acid sequence of the invention, sequences substantially identical thereto, and the sequences complementary thereto.

In one aspect, pectate lyase activity comprises catalysis of beta-elimination (trans-elimination) or hydrolysis of pectin or polygalacturonic acid (pectate). The pectate lyase activity can comprise the breakup or dissolution of plant cell walls. The pectate lyase activity can comprise beta-elimination (trans-elimination) or hydrolysis of 1,4-linked alpha-D-galacturonic acid. The pectate lyase activity can comprise catalysis of beta-elimination (trans-elimination) or hydrolysis of methyl-esterified galacturonic acid. The pectate lyase activity can be exo-acting or endo-acting. In one aspect, the pectate lyase activity is endo-acting and acts at random sites within a polymer chain to give a mixture of oligomers. In one aspect, the pectate lyase activity is exo-acting and acts from one end of a polymer chain and produces monomers or dimers. The pectate lyase activity can catalyze the random cleavage of alpha-1,4-glycosidic linkages in pectic acid (polygalacturonic acid) by trans-elimination or hydrolysis. The pectate lyase activity can comprise activity the same or similar to pectate lyase (EC 4.2.2.2), poly(1,4-alpha-D-galacturonide) lyase, polygalacturonate lyase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) or exo-poly-alpha-galacturonosidase (EC 3.2.1.82). The pectate lyase activity can comprise beta-elimination (trans-elimination) or hydrolysis of galactan to galactose or galactooligomers. The pectate lyase activity can comprise beta-elimination (trans-elimination) or hydrolysis of a plant fiber. The plant fiber can comprise cotton fiber, hemp fiber or flax fiber.

In one aspect, the isolated or recombinant nucleic acid encodes a polypeptide having a pectate lyase activity that is thermostable. The polypeptide can retain a pectate lyase activity under conditions comprising a temperature range of between about 37° C. to about 95° C.; between about 55° C. to about 85° C., between about 70° C. to about 95° C., or, between about 90° C. to about 95° C.

In another aspect, the isolated or recombinant nucleic acid encodes a polypeptide having a pectate lyase activity that is thermotolerant. The polypeptide can retain a pectate lyase activity after exposure to a temperature in the range from greater than 37° C. to about 95° C. or anywhere in the range from greater than 55° C. to about 85° C. In one aspect, the polypeptide retains a pectate lyase activity after exposure to a temperature in the range from greater than 90° C. to about 95° C. at pH 4.5.

The invention provides isolated or recombinant nucleic acids comprising a sequence that hybridizes under stringent conditions to a nucleic acid comprising a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:131, SEQ ID NO:133, or fragments or subsequences thereof. In one aspect, the nucleic acid encodes a polypeptide having a pectate lyase activity. The nucleic acid can be at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200 or more residues in length or the full length of the gene or transcript. In one aspect, the stringent conditions include a wash step comprising a wash in 0.2×SSC at a temperature of about 65° C. for about 15 minutes.

The invention provides a nucleic acid probe for identifying a nucleic acid encoding a polypeptide having a pectate lyase activity, wherein the probe comprises at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more, consecutive bases of a sequence comprising a sequence of the invention, or fragments or subsequences thereof, wherein the probe identifies the nucleic acid by invention. In one aspect, the isolated or recombinant polypeptide of the invention (with or without a signal sequence) has pectate lyase activity.

Another aspect of the invention is an isolated or recombinant polypeptide or peptide including at least 10 consecutive bases of a polypeptide or peptide sequence of the invention, sequences substantially identical thereto, and the sequences complementary thereto.

In one aspect, pectate lyase activity comprises catalysis of beta-elimination (trans-elimination) or hydrolysis of pectin or polygalacturonic acid (pectate). The pectate lyase activity can comprise the breakup or dissolution of plant cell walls. The pectate lyase activity can comprise beta-elimination (trans-elimination) or hydrolysis of 1,4-linked alpha-D-galacturonic acid. The pectate lyase activity can comprise catalysis of beta-elimination (trans-elimination) or hydrolysis of methyl-esterified galacturonic acid. The pectate lyase activity can be exo-acting or endo-acting. In one aspect, the pectate lyase activity is endo-acting and acts at random sites within a polymer chain to give a mixture of oligomers. In one aspect, the pectate lyase activity is exo-acting and acts from one end of a polymer chain and produces monomers or dimers. The pectate lyase activity can catalyze the random cleavage of alpha-1,4-glycosidic linkages in pectic acid (polygalacturonic acid) by trans-elimination or hydrolysis. The pectate lyase activity can comprise activity the same or similar to pectate lyase (EC 4.2.2.2), poly(1,4-alpha-D-galacturonide) lyase, polygalacturonate lyase (EC 4.2.2.2), pectin lyase (EC 4.2.2.10), polygalacturonase (EC 3.2.1.15), exopolygalacturonase (EC 3.2.1.67), exo-polygalacturonate lyase (EC 4.2.2.9) or exo-poly-alpha-galacturonosidase (EC 3.2.1.82). The pectate lyase activity can comprise beta-elimination (trans-elimination) or hydrolysis of galactan to galactose or galactooligomers. The pectate lyase activity can comprise beta-elimination (trans-elimination) or hydrolysis of a plant fiber. The plant fiber can comprise cotton fiber, hemp fiber or flax fiber.

In one aspect, the pectate lyase activity is thermostable. The polypeptide can retain a pectate lyase activity under conditions comprising a temperature range of between about 37° C. to about 95° C., between about 55° C. to about 85° C., between about 70° C. to about 95° C., or between about 90° C. to about 95° C. In another aspect, the pectate lyase activity can be thermotolerant. The polypeptide can retain a pectate lyase activity after exposure to a temperature in the range from greater than 37° C. to about 95° C., or in the range from greater than 55° C. to about 85° C. In one aspect, the polypeptide can retain a pectate lyase activity after exposure to a temperature in the range from greater than 90° C. to about 95° C. at pH 4.5.

In one aspect, the isolated or recombinant polypeptide can comprise the polypeptide of the invention that lacks a signal sequence. In one aspect, the isolated or recombinant polypeptide can comprise the polypeptide of the invention comprising a heterologous signal sequence, such as a heterologous pectate lyase or non-pectate lyase signal sequence.

In one aspect, the invention provides chimeric proteins comprising a first domain comprising a signal sequence of the invention (e.g., as set forth in Table 2, below) and at least a second domain. The protein can be a fusion protein. The second domain can comprise an enzyme. The enzyme can be a pectate lyase.

In one aspect, the pectate lyase activity comprises a specific activity at about 37° C. in the range from about 100 to about 1000 units per milligram of protein. In another aspect, the pectate lyase activity comprises a specific activity from about 500 to about 750 units per milligram of protein. Alternatively, the pectate lyase activity comprises a specific activity at 37° C. in the range from about 500 to about 1200 units per milligram of protein. In one aspect, the pectate lyase activity comprises a specific activity at 37° C. in the range from about 750 to about 1000 units per milligram of protein. In another aspect, the thermotolerance comprises retention of at least half of the specific activity of the pectate lyase at 37° C. after being heated to the elevated temperature. Alternatively, the thermotolerance can comprise retention of specific activity at 37° C. in the range from about 500 to about 1200 units per milligram of protein after being heated to the elevated temperature.

The invention provides the isolated or recombinant polypeptide of the invention, wherein the polypeptide comprises at least one glycosylation site. In one aspect, glycosylation can be an N-linked glycosylation. In one aspect, the polypeptide can be glycosylated after being expressed in a *P. pastoris* or a *S. pombe*.

In one aspect, the polypeptide can retain a pectate lyase activity under conditions comprising about pH 6.5, pH 6, pH 5.5, pH 5, pH 4.5 or pH 4. In another aspect, the polypeptide can retain a pectate lyase activity under conditions comprising about pH 7, pH 7.5 pH 8.0, pH 8.5, pH 9, pH 9.5, pH 10, pH 10.5 or pH 11.

In one aspect, the isolated or recombinant polypeptide can comprise the polypeptide of the invention that lacks a signal sequence and/or a prepro domain. In one aspect, the isolated or recombinant polypeptide can comprise the polypeptide of the invention comprising a heterologous signal sequence and/or prepro domain, such as a heterologous pectate lyase signal sequence.

In one aspect, the invention provides a signal sequence comprising a peptide comprising/consisting of a sequence as set forth in residues 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44 of a polypeptide of the invention. In one aspect, the invention provides chimeric proteins comprising a first domain comprising a signal sequence of the invention and at least a second domain. The protein can be a fusion protein. The second domain can comprise an enzyme. The enzyme can be a pectate lyase, e.g., an enzyme of the invention.

The invention provides chimeric polypeptides comprising at least a first domain comprising signal peptide (SP), a prepro domain, a catalytic domain (CD), or an active site of a pectate lyase of the invention and at least a second domain comprising a heterologous polypeptide or peptide, wherein the heterologous polypeptide or peptide is not naturally associated with the signal peptide (SP), prepro domain or catalytic domain (CD). In one aspect, the heterologous polypeptide or peptide is not a pectate lyase. The heterologous polypeptide or peptide can be amino terminal to, carboxy terminal to or on both ends of the signal peptide (SP), prepro domain or catalytic domain (CD).

The invention provides protein preparations comprising a polypeptide of the invention, wherein the protein preparation comprises a liquid, a solid or a gel.

The invention provides heterodimers comprising a polypeptide of the invention and a second domain. In one aspect, the second domain can be a polypeptide and the heterodimer can be a fusion protein. In one aspect, the second domain can be an epitope or a tag. In one aspect, the invention provides homodimers comprising a polypeptide of the invention.

The invention provides immobilized polypeptides having a pectate lyase activity, wherein the polypeptide comprises a polypeptide of the invention, a polypeptide encoded by a nucleic acid of the invention, or a polypeptide comprising a polypeptide of the invention and a second domain. In one aspect, the polypeptide can be immobilized on a cell, a metal, a resin, a polymer, a ceramic, a glass, a microelectrode, a graphitic particle, a bead, a gel, a plate, an array or a capillary tube.

The invention provides arrays comprising an immobilized nucleic acid of the invention. The invention provides arrays comprising an antibody of the invention.

The invention provides isolated or recombinant antibodies that specifically bind to a polypeptide of the invention or to a polypeptide encoded by a nucleic acid of the invention. The antibody can be a monoclonal or a polyclonal antibody. The invention provides hybridomas comprising an antibody of the invention, e.g., an antibody that specifically binds to a polypeptide of the invention or to a polypeptide encoded by a nucleic acid of the invention.

The invention provides food supplements for an animal comprising a polypeptide of the invention, e.g., a polypeptide encoded by the nucleic acid of the invention. In one aspect, the polypeptide in the food supplement can be glycosylated. The invention provides edible enzyme delivery matrices comprising a polypeptide of the invention, e.g., a polypeptide encoded by the nucleic acid of the invention. In one aspect, the delivery matrix comprises a pellet. In one aspect, the polypeptide can be glycosylated. In one aspect, the pectate lyase activity is thermotolerant. In another aspect, the pectate lyase activity is thermostable.

The invention provides method of isolating or identifying a polypeptide having a pectate lyase activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having a pectate lyase activity.

The invention provides methods of making an anti-pectate lyase antibody comprising administering to a non-human animal a nucleic acid of the invention or a polypeptide of the invention or subsequences thereof in an amount sufficient to generate a humoral immune response, thereby making an anti-pectate lyase antibody. The invention provides methods of making an anti-pectate lyase immune comprising administering to a non-human animal a nucleic acid of the invention or a polypeptide of the invention or subsequences thereof in an amount sufficient to generate an immune response.

The invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

The invention provides methods for identifying a polypeptide having a pectate lyase activity comprising the following steps: (a) providing a polypeptide of the invention; or a polypeptide encoded by a nucleic acid of the invention; (b) providing a pectate lyase substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having a pectate lyase activity.

The invention provides methods for identifying a pectate lyase substrate comprising the following steps: (a) providing a polypeptide of the invention; or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as a pectate lyase substrate.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

The invention provides methods for identifying a modulator of a pectate lyase activity comprising the following steps:

(a) providing a polypeptide of the invention or a polypeptide encoded by a nucleic acid of the invention; (b) providing a test compound; (c) contacting the polypeptide of step (a) with the test compound of step (b) and measuring an activity of the pectate lyase, wherein a change in the pectate lyase activity measured in the presence of the test compound compared to the activity in the absence of the test compound provides a determination that the test compound modulates the pectate lyase activity. In one aspect, the pectate lyase activity can be measured by providing a pectate lyase substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of pectate lyase activity. An increase in the amount of the substrate or a decrease in the amount of the reaction product with the test compound as compared to the amount of substrate or reaction product without the test compound identifies the test compound as an inhibitor of pectate lyase activity.

The invention provides computer systems comprising a processor and a data storage device wherein said data storage device has stored thereon a polypeptide sequence or a nucleic acid sequence of the invention (e.g., a polypeptide encoded by a nucleic acid of the invention). In one aspect, the computer system can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. The invention provides computer readable media having stored thereon a polypeptide sequence or a nucleic acid sequence of the invention. The invention provides methods for identifying a feature in a sequence comprising the steps of: (a) reading the sequence using a computer program which identifies one or more features in a sequence, wherein the sequence comprises a polypeptide sequence or a nucleic acid sequence of the invention; and (b) identifying one or more features in the sequence with the computer program. The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence of the invention; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

The invention provides methods for isolating or recovering a nucleic acid encoding a polypeptide having a pectate lyase activity from an environmental sample comprising the steps of: (a) providing an amplification primer sequence pair for amplifying a nucleic acid encoding a polypeptide having a pectate lyase activity, wherein the primer pair is capable of amplifying a nucleic acid of the invention; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide having a pectate lyase activity from an environmental sample. One or each member of the amplification primer sequence pair can comprise an oligonucleotide comprising at least about 10 to 50 consecutive bases of a sequence of the invention.

The invention provides methods for isolating or recovering a nucleic acid encoding a polypeptide having a pectate lyase activity from an environmental sample comprising the steps of: (a) providing a polynucleotide probe comprising a nucleic acid of the invention or a subsequence thereof; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide having a pectate lyase activity from an environmental sample. The environmental sample can comprise a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide having a pectate lyase activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant pectate lyase polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis (GSSM™), synthetic ligation reassembly (SLR) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until a pectate lyase having an altered or different activity or an altered or different stability from that of a polypeptide encoded by the template nucleic acid is produced. In one aspect, the variant pectate lyase polypeptide is thermotolerant, and retains some activity after being exposed to an elevated temperature. In another aspect, the variant pectate lyase polypeptide has increased glycosylation as compared to the pectate lyase encoded by a template nucleic acid. Alternatively, the variant pectate lyase polypeptide has a pectate lyase activity under a high temperature, wherein the pectate lyase encoded by the template nucleic acid is not active under the high temperature. In one aspect, the method can be iteratively repeated until a pectate lyase coding sequence having an altered codon usage from that of the template nucleic acid is produced. In another aspect, the method can be iteratively repeated until a pectate lyase gene having higher or lower level of message expression or stability from that of the template nucleic acid is produced.

The invention provides methods for modifying codons in a nucleic acid encoding a polypeptide having a pectate lyase activity to increase its expression in a host cell, the method comprising the following steps: (a) providing a nucleic acid of the invention encoding a polypeptide having a pectate lyase activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a polypeptide having a pectate lyase activity; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid encoding a pectate lyase.

The invention provides methods for modifying codons in a nucleic acid encoding a polypeptide having a pectate lyase activity to increase its expression in a host cell, the method comprising the following steps: (a) providing a nucleic acid of the invention encoding a pectate lyase polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having a pectate lyase activity to decrease its expression in a host cell, the method comprising the following steps: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified pectate lyase active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a nucleic acid of the invention, and the nucleic acid encodes a pectate lyase active site or a pectate lyase substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified pectate lyase active sites or substrate binding sites. In one aspect, the method comprises mutagenizing the first nucleic acid of step (a) by a method comprising an optimized directed evolution system, gene site-saturation mutagenesis (GSSM™), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis (GSSM™), synthetic ligation reassembly (SLR) and a combination thereof. In another aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the following steps: (a) providing a plurality of biosynthetic enzymes capable of synthesizing or modifying a small molecule, wherein one of the enzymes comprises a pectate lyase enzyme encoded by a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions. The invention provides methods for modifying a small molecule comprising the following steps: (a) providing a pectate lyase enzyme, wherein the enzyme comprises a polypeptide of the invention, or, a polypeptide encoded by a nucleic acid of the invention, or a subsequence thereof; (b) providing a small molecule; and (c) reacting the enzyme of step (a) with the small molecule of step (b) under conditions that facilitate an enzymatic reaction catalyzed by the pectate lyase enzyme, thereby modifying a small molecule by a pectate lyase enzymatic reaction. In one aspect, the method can comprise a plurality of small molecule substrates for the enzyme of step (a), thereby generating a library of modified small molecules produced by at least one enzymatic reaction catalyzed by the pectate lyase enzyme. In one aspect, the method can comprise a plurality of additional enzymes under conditions that facilitate a plurality of biocatalytic reactions by the enzymes to form a library of modified small molecules produced by the plurality of enzymatic reactions. In another aspect, the method can further comprise the step of testing the library to determine if a particular modified small molecule that exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of a pectate lyase enzyme comprising the steps of: (a) providing a pectate lyase enzyme, wherein the enzyme comprises a polypeptide of the invention, or a polypeptide encoded by a nucleic acid of the invention, or a subsequence thereof; and (b) deleting a plurality of amino acid residues from the sequence of step (a) and testing the remaining subsequence for a pectate lyase activity, thereby determining a functional fragment of a pectate lyase enzyme. In one aspect, the pectate lyase activity is measured by providing a pectate lyase substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In another aspect, the method can comprise culturing the selected cell, thereby generating a new cell strain comprising a newly engineered phenotype.

The invention provides methods of increasing thermotolerance or thermostability of a pectate lyase polypeptide, the method comprising glycosylating a pectate lyase polypeptide, wherein the polypeptide comprises at least thirty contiguous amino acids of a polypeptide of the invention; or a polypeptide encoded by a nucleic acid sequence of the invention, thereby increasing the thermotolerance or thermostability of the pectate lyase polypeptide. In one aspect, the pectate lyase specific activity can be thermostable or thermotolerant at a temperature in the range from greater than about 37° C. to about 95° C.

The invention provides methods for overexpressing a recombinant pectate lyase polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

The invention provides methods of making a transgenic plant comprising the following steps: (a) introducing a heterologous nucleic acid sequence into the cell, wherein the heterologous nucleic acid sequence comprises a nucleic acid sequence of the invention, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In one aspect, the plant cell can be a potato, corn, rice, wheat, tobacco, or barley cell.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid of the invention; (b) growing the plant under conditions wherein the heterologous nucleic acids sequence is expressed in the plant cell.

The invention provides isolated or recombinant signal sequence comprising or consisting of signal peptides (SP) as set forth in Table 2. The invention provides isolated or recombinant signal sequences consisting of a sequence as set forth in residues 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, and/or 1 to 44, of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128 or SEQ ID NO:130, SEQ ID NO:132, SEQ ID NO:134.

The invention provides isolated or recombinant peptides consisting of a pectin methyl esterase domain (PED) or a catalytic domain (CD) as set forth in Table 2.

The invention provides chimeric polypeptides comprising at least a first domain comprising signal peptide (SP), a pectin methyl esterase domain (PED) or a catalytic domain (CD) as set forth in Table 2 and at least a second domain comprising a heterologous polypeptide or peptide, wherein the heterologous polypeptide or peptide is not naturally associated with the signal peptide (SP), pectin methyl esterase domain (PED) or catalytic domain (CD). In one aspect, the heterologous polypeptide or peptide is not a pectate lyase. The heterologous polypeptide or peptide can be amino terminal to, carboxy terminal to or on both ends of the signal peptide (SP), pectin methyl esterase domain (PED) or catalytic domain (CD).

The invention provides isolated or recombinant nucleic acids encoding a chimeric polypeptide, wherein the chimeric polypeptide comprises at least a first domain comprising signal peptide (SP), a pectin methyl esterase domain (PED) or a catalytic domain (CD) as set forth in Table 2 and at least a second domain comprising a heterologous polypeptide or peptide, wherein the heterologous polypeptide or peptide is not naturally associated with the signal peptide (SP), pectin methyl esterase domain (PED) or catalytic domain (CD).

The invention provides method of increasing thermotolerance or thermostability of a pectate lyase, the method comprising glycosylating a pectate lyase, wherein the polypeptide comprises at least thirty contiguous amino acids of a polypeptide of the invention, thereby increasing the thermotolerance or thermostability of the pectate lyase.

The invention provides methods for overexpressing a recombinant pectate lyase in a cell comprising expressing a vector comprising a nucleic acid of the invention, wherein overexpression is effected by use of a high activity promoter, a dicistronic vector or by gene amplification of the vector.

The invention provides methods of making a transgenic plant comprising the following steps: (a) introducing a heterologous nucleic acid sequence into the cell, wherein the heterologous nucleic sequence comprises a nucleic acid of the invention, thereby producing a transformed plant cell; (b) producing a transgenic plant from the transformed cell. In one aspect, step (a) further comprises introducing the heterologous nucleic acid sequence by electroporation or microinjection of plant cell protoplasts. Step (a) can comprise introducing the heterologous nucleic acid sequence directly to plant tissue by DNA particle bombardment or by using an *Agrobacterium tumefaciens* host.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a sequence of the invention; (b) growing the plant under conditions wherein the heterologous nucleic acids sequence is expressed in the plant cell.

The invention provides methods for hydrolyzing, breaking up or disrupting a pectin- or pectate (polygalacturonic acid)-comprising composition comprising the following steps: (a) providing a polypeptide of the invention having a pectate lyase activity, or a polypeptide encoded by a nucleic acid of the invention; (b) providing a composition comprising a pectin or a pectate; and (c) contacting the polypeptide of step (a) with the composition of step (b) under conditions wherein the polypeptide hydrolyzes, breaks up or disrupts the pectin- or pectate-comprising composition. In one aspect, the composition comprises a plant cell wall or a bacterial cell wall. The plant can be a cotton plant, a hemp plant or a flax plant.

The invention provides methods for liquefying or removing a pectin or pectate (polygalacturonic acid) from a composition comprising the following steps: (a) providing a polypeptide of the invention having a pectate lyase activity, or a polypeptide encoded by a nucleic acid of the invention; (b) providing a composition comprising a pectin or pectate (polygalacturonic acid); and (c) contacting the polypeptide of step (a) with the composition of step (b) under conditions wherein the polypeptide removes or liquefies the pectin or pectate (polygalacturonic acid).

The invention provides detergent compositions comprising a polypeptide of the invention, or a polypeptide encoded by a nucleic acid of the invention, wherein the polypeptide has a pectate lyase activity. In one aspect, the pectate lyase is a nonsurface-active pectate lyase or a surface-active pectate lyase. The pectate lyase can be formulated in a non-aqueous liquid composition, a cast solid, a granular form, a particulate form, a compressed tablet, a gel form, a paste or a slurry form.

The invention provides methods for washing an object comprising the following steps: (a) providing a composition comprising a polypeptide of the invention having a pectate lyase activity; (b) providing an object; and (c) contacting the polypeptide of step (a) and the object of step (b) under conditions wherein the composition can wash the object.

The invention provides textiles or fabrics comprising a polypeptide of the invention, or a polypeptide encoded by a nucleic acid of the invention. The invention provides methods for fiber, thread, textile or fabric scouring comprising the following steps: (a) providing a polypeptide of the invention having a pectate lyase activity, or a polypeptide encoded by a nucleic acid of the invention; (b) providing a fiber, a thread, a textile or a fabric; and (c) contacting the polypeptide of step (a) and the textile or fabric of step (b) under conditions wherein the pectate lyase can scour the fiber, thread, textile or fabric. In one aspect, the pectate lyase is an alkaline active and thermostable pectate lyase. The desizing and scouring treatments can be combined in a single bath. The method can further comprise addition of an alkaline and thermostable amylase in the contacting of step (c). The desizing or scouring treatments can comprise conditions of between about pH 8.5 to pH 10.0 and temperatures of at about 40° C. The method can further comprise addition of a bleaching step. The desizing, scouring and bleaching treatments can be done simultaneously or sequentially in a single-bath container. The bleaching treatment can comprise hydrogen peroxide or at least one peroxy compound that can generate hydrogen peroxide when dissolved in water, or combinations thereof, and at least one bleach activator. The fiber, thread, textile or fabric can comprise a cellulosic material. The cellulosic material can comprise a crude fiber, a yarn, a woven or knit textile, a cotton, a linen, a flax, a ramie, a rayon, a hemp, a jute or a blend of natural or synthetic fibers.

The invention provides feeds or foods comprising a polypeptide of the invention, or a polypeptide encoded by a nucleic acid of the invention. The invention provides methods improving the extraction of oil from an oil-rich plant material comprising the following steps: (a) providing a polypeptide of the invention having a pectate lyase activity, or a polypeptide encoded by a nucleic acid of the invention; (b) providing an oil-rich plant material; and (c) contacting the polypeptide of step (a) and the oil-rich plant material. In one aspect, the oil-rich plant material comprises an oil-rich seed. The oil can be a soybean oil, an olive oil, a rapeseed (canola) oil or a sunflower oil.

The invention provides methods for preparing a fruit or vegetable juice, syrup, puree or extract comprising the following steps: (a) providing a polypeptide of the invention having a pectate lyase activity, or a polypeptide encoded by a nucleic acid of the invention; (b) providing a composition or a liquid comprising a fruit or vegetable material; and (c) contacting the polypeptide of step (a) and the composition, thereby preparing the fruit or vegetable juice, syrup, puree or extract.

The invention provides papers or paper products or paper pulps comprising a pectate lyase of the invention, or a polypeptide encoded by a nucleic acid of the invention. The invention provides methods for treating a paper or a paper or wood pulp comprising the following steps: (a) providing a polypeptide of the invention having a pectate lyase activity, or a polypeptide encoded by a nucleic acid of the invention; (b) providing a composition comprising a paper or a paper or wood pulp; and (c) contacting the polypeptide of step (a) and the composition of step (b) under conditions wherein the pectate lyase can treat the paper or paper or wood pulp.

The invention provides pharmaceutical compositions comprising a polypeptide of the invention, or a polypeptide encoded by a nucleic acid of the invention. The pharmaceutical composition can act as a digestive aid.

The invention provides oral care products comprising a polypeptide of the invention, or a polypeptide encoded by a nucleic acid of the invention. The oral care product can comprise a toothpaste, a dental cream, a gel or a tooth powder, an odontic, a mouth wash, a pre- or post brushing rinse formulation, a chewing gum, a lozenge or a candy.

The invention provides isolated or recombinant nucleic acids having a sequence comprising a sequence modification of SEQ ID NO:131, wherein the modification of SEQ ID NO:131 comprises one or more of the following changes: the nucleotides at residues 352 to 354 are CAT or CAC, the nucleotides at residues 544 to 546 are GTG, GTT, GTC, or GTA, the nucleotides at residues 568 to 570 are TTG, TTA, CTT, CTC, CTA, or CTG, the nucleotides at residues 589 to 591 are GGT, GGC, GGA, or GGG, the nucleotides at residues 622 to 624 are AAG or AAA, the nucleotides at residues 655 to 657 are ATG, the nucleotides at residues 667 to 669 are GAG or GAA, the nucleotides at residues 763 to 765 are CGG, CGT, CGC, CGA, AGA, AGG, the nucleotides at residues 787 to 789 are AAG or AAA, the nucleotides at residues 823 to 825 are TAT or TAC, the nucleotides at residues 925 to 927 are TGG, or the nucleotides at residues 934 to 936 are GTT, GTG, GTC, or GTA. In one aspect, the nucleic acid encodes a polypeptide having a pectate lyase activity, which can be thermotolerant or thermostable.

The invention provides isolated or recombinant nucleic acids having a sequence comprising a sequence modification of a nucleic acid of the invention (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129), wherein the sequence modification comprises one or more of the following changes: the nucleotides at the equivalent of residues 352 to 354 of SEQ ID NO:131 are changed to CAT or CAC, the nucleotides at the equivalent of residues 544 to 546 of SEQ ID NO:131 are changed to GTG, GTT, GTC, or GTA, the nucleotides at the equivalent of residues 568 to 570 of SEQ ID NO:131 are changed to TTG, TTA, CTT, CTC, CTA, or CTG, the nucleotides at the equivalent of residues 589 to 591 of SEQ ID NO:131 are changed to GGT, GGC, GGA, or GGG, the nucleotides at the equivalent of residues 622 to 624 of SEQ ID NO:131 are changed to AAG or AAA, the nucleotides at the equivalent of residues 655 to 657 of SEQ ID NO:131 are changed to ATG, the nucleotides at the equivalent of residues 667 to 669 of SEQ ID NO:131 are GAG or GAA, the nucleotides at the equivalent of residues 763 to 765 of SEQ ID NO:131 are changed to CGG, CGT, CGC, CGA, AGA, AGG, the nucleotides at the equivalent of residues 787 to 789 of SEQ ID NO:131 are changed to AAG or AAA, the nucleotides at the equivalent of residues 823 to 825 of SEQ ID NO:131 are changed to TAT or TAC, the nucleotides at the equivalent of residues 925 to 927 of SEQ ID NO:131 are changed to TGG, or the nucleotides at the equivalent of residues 934 to 936 of SEQ ID NO:131 are changed to GTT, GTG, GTC, or GTA. In one aspect, the nucleic acid encodes a polypeptide having a pectate lyase activity, which can be thermotolerant or thermostable.

The invention provides isolated or recombinant polypeptides having a sequence comprising a sequence modification of SEQ ID NO:132, wherein the modification of SEQ ID NO:132 comprises one or more of the following mutations: the alanine at amino acid position 118 is histidine, the alanine at amino acid position 182 is valine, the threonine at amino acid position 190 is leucine, the alanine at amino acid position 197 is glycine, the serine at amino acid position 208 is lysine, the threonine at amino acid position 219 is methionine, the threonine at amino acid position 223 is glutamic acid, the serine at amino acid position 255 is arginine, the serine at amino acid position 263 is lysine, the asparagine at amino acid position 275 is tyrosine, the tyrosine at amino acid position 309 is tryptophan, or, the serine at amino acid position 312 is valine. In one aspect, the polypeptide has a pectate lyase activity, which can be thermotolerant or thermostable.

The invention provides isolated or recombinant polypeptides having a sequence comprising a sequence modification of a polypeptide of the invention (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130), wherein the sequence modification comprises one or more of the following changes: the amino acid at the equivalent of the alanine at residue 118 of SEQ ID NO:132 is changed to a histidine, the amino acid at the equivalent of the alanine at residue 182 of SEQ ID NO:132 is changed to a valine, the amino acid at the equivalent of the threonine at residue 190 of SEQ ID NO:132 is changed to a leucine, the amino acid at the equivalent of the alanine at residue 197 of SEQ ID NO:132 is changed to a glycine, the amino acid at the equivalent of the serine at residue 208 of SEQ ID NO:132 is changed to a lysine, the amino acid at the equivalent of the threonine at residue 219 of SEQ ID NO:132 is changed to a methionine, the amino acid at the equivalent of the threonine at residue 223 of SEQ ID NO:132 is changed to a glutamic acid, the amino acid at the equivalent of the serine at residue 255 of SEQ ID NO:132 is changed to a arginine, the amino acid at the equivalent of the serine at residue 263 of SEQ ID NO:132 is changed to a lysine, the amino acid at the equivalent of the asparagine at residue 275 of SEQ ID NO:132 is changed to a tyrosine, the amino acid at the equivalent of the tyrosine at residue 309 of SEQ ID NO:132 is changed to a tryptophan, or, the amino acid at the equivalent of the serine at residue 312 of SEQ ID NO:132 is changed to a valine. In one aspect, the polypeptide has a pectate lyase activity, which can be thermotolerant or thermostable.

The invention provides methods for generating a modified pectate-lyase encoding nucleic acid comprising making one or more sequence modifications to a pectate-lyase encoding nucleic acid, wherein the changes in the pectate-lyase encoding nucleic acid are equivalent to one or more of the following: changing nucleotides at the equivalent of residues 352 to 354 of SEQ ID NO:131 to CAT or CAC, changing nucleotides at the equivalent of residues 544 to 546 of SEQ ID NO:131 to GTG, GTT, GTC, or GTA, changing nucleotides at the equivalent of residues 568 to 570 of SEQ ID NO:131 to TTG, TTA, CTT, CTC, CTA, or CTG, changing nucleotides at the equivalent of residues 589 to 591 of SEQ ID NO:131 to GGT, GGC, GGA, or GGG, changing nucleotides at the equivalent of residues 622 to 624 of SEQ ID NO:131 to AAG or AAA, changing nucleotides at the equivalent of residues 655 to 657 of SEQ ID NO:131 to ATG, changing nucleotides at the equivalent of residues 667 to 669 of SEQ ID NO:131 to GAG or GAA, the nucleotides at the equivalent of residues 763 to 765 of SEQ ID NO:131 to CGG, CGT, CGC, CGA, AGA, AGG, changing nucleotides at the equivalent of residues 787 to 789 of SEQ ID NO:131 to AAG or AAA, changing nucleotides at the equivalent of residues 823 to 825 of SEQ ID NO:131 to TAT or TAC, changing nucleotides at the equivalent of residues 925 to 927 of SEQ ID NO:131 to TGG, or changing nucleotides at the equivalent of residues 934 to 936 of SEQ ID NO:131 to GTT, GTG, GTC, or GTA. In one aspect, the modified pectate lyase activity has a thermotolerant or thermostable activity. In one aspect, the pectate-lyase encoding nucleic acid comprises a nucleic acid having a sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131 or SEQ ID NO:133.

The invention provides methods for generating a modified pectate lyase comprising making one or more sequence modifications to a pectate lyase, wherein the changes in the pectate lyase are equivalent to one or more of the following changes: the amino acid at the equivalent of the alanine at residue 118 of SEQ ID NO:132 is changed to a histidine, the amino acid at the equivalent of the alanine at residue 182 of SEQ ID NO:132 is changed to a valine, the amino acid at the equivalent of the threonine at residue 190 of SEQ ID NO:132 is changed to a leucine, the amino acid at the equivalent of the alanine at residue 197 of SEQ ID NO:132 is changed to a glycine, the amino acid at the equivalent of the serine at residue 208 of SEQ ID NO:132 is changed to a lysine, the amino acid at the equivalent of the threonine at residue 219 of SEQ ID NO:132 is changed to a methionine, the amino acid at the equivalent of the threonine at residue 223 of SEQ ID NO:132 is changed to a glutamic acid, the amino acid at the equivalent of the serine at residue 255 of SEQ ID NO:132 is changed to a arginine, the amino acid at the equivalent of the serine at residue 263 of SEQ ID NO:132 is changed to a lysine, the amino acid at the equivalent of the asparagine at residue 275 of SEQ ID NO:132 is changed to a tyrosine, the amino acid at the equivalent of the tyrosine at residue 309 of SEQ ID NO:132 is changed to a tryptophan, or, the amino acid at the equivalent of the serine at residue 312 of SEQ ID NO:132 is changed to a valine. In one aspect, the pectate lyase comprises a sequence of the invention (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128 or SEQ ID NO:130). In one aspect, the modified pectate lyase activity has a thermotolerant or thermostable activity.

The invention provides formulations comprising at least one enzyme of the invention comprising dosages in the range of between about 1 gram per ton and 100 or more grams per ton (per ton treated material, e.g., per ton fabric, cloth or the like), between about 10 grams per ton and 90 grams per ton, between about 20 grams per ton and 80 gram per ton, between about 30 grams per ton and 70 grams per ton, between about 40 grams per ton and 50 grams per ton. For example, exemplary formulations comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc. to 100, 200, 300, 400, 500, etc. or more grams per ton.

Alternatively, the invention provides formulations comprising at least one enzyme of the invention comprising dosages in the range of between about 1 µg per gram and 100 or more µg per gram (per gram treated material, e.g., per gram fabric, cloth or the like), between about 10 µg per gram and 90 µg per gram, between about 20 µg per gram and 80 µg per gram, between about 30 µg per gram and 70 µg per gram, between about 40 µg per gram and 50 µg per gram. For example, exemplary formulations comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, etc. to 100, 200, 300, 400, 500, etc. or more µg per gram (e.g., per gram fabric, cloth or the like).

Alternatively, the invention provides formulations comprising at least one enzyme of the invention comprising dosages in the range of between about 0.5 mg per pound and 50 or more mg per pound (per pound treated material, e.g., per pound fabric, cloth or the like), between about 1 mg per pound and 45 mg per pound, between about 5 mg per pound and 40 mg per pound, between about 10 mg per pound and 35 mg per pound, between about 15 mg per pound and 30 mg per pound.

For example, exemplary formulations comprise about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. to 50 or more mg per pound (e.g., per pound fabric, cloth or the like).

The invention provides formulations comprising at least one enzyme of the invention comprising dosages comprising an enzyme strength of between about 100 to 40,000 units/ml, 200 to 30,000 units/ml, 500 to 30,000 units/ml, 1000 to 20,000 units/ml, 1000 to 25,000 units/ml, 1000 to 15,000 units/ml, 1000 to 10000 units/ml, 1000 to 5000 units/ml, between about 2000 to 20000 units/ml, between about 2000 to 15000 units/ml, between about 2000 to 10000 units/ml, or between about 2000 to 4000 units/ml, or, between about 200 to 25,000 units/ml, 200 to 20,000 units/ml, 200 to 15000 units/ml, 200 to 10,000 units/ml, between about 400 to 8000 units/ml, between about 600 to 6000 units/ml, between about 800 to 4000 units/ml, or between about 1000 to 2000 units/ml., or, wherein the dosage comprises an enzyme strength of about 1000 u/ml. or, wherein the dosage comprises an enzyme strength of about 3000 units/ml.

In one aspect, the formulation comprises a lyophilized enzyme (e.g., an enzyme of the invention), or, the formulation is a water-based formulation comprising an enzyme of the invention. In one aspect, the formulation comprises a lyophilized enzyme resuspended in water. In one aspect, a formulation of the invention further comprises a glycerol, sucrose, sodium chloride, dextrin, propylene glycol, sorbitol, sodium sulphate or TRIS, or an equivalent. In one aspect, a formulation of the invention further comprises a buffer, e.g., a buffer comprising pH 7, 35% glycerol, 0.1% sodium benzoate, 0.1% potassium sorbate; pH 7, 35% glycerol, 300 ppm proxel; pH 7, 10% sodium chloride, 25% glycerol, 0.1% sodium benzoate, 0.1% potassium sorbate; pH 7, 10% sodium chloride, 25% glycerol, 300 ppm proxel; pH 5.5, 35% glycerol, 0.1% sodium benzoate, 0.1% potassium sorbate; pH 5.5, 35% glycerol, 300 ppm proxel; pH 5.5, 10% sodium chloride, 25% glycerol, 0.1% sodium benzoate, 0.1% potassium sorbate; or, 20 mM acetate buffer, pH 5.5, 35% glycerol; 20 mM MOPS, pH 7 or 25 mM MOPS, 50 mM NaCl, pH 7.5; pH 5.0, 40 mM TRIS; pH 7.0, 40 mM TRIS; pH 8.0, 40 mM TRIS; pH 7.5, 50% glycerol; pH 7.5, 20% NaCl; pH 7.5, 30% propylene glycol; pH 7.5, 100 mM sodium sulfate; pH 5.5, 35% glycerol; or, any combination thereof, or, equivalents thereof.

The invention provides bioscouring processes comprising the following steps: (a) providing a pectate lyase of the invention; (b) providing a pectin- or polygalacturonic acid-comprising material; (c) contacting the pectate lyase of (a) with the material of (b) under alkaline conditions, e.g., a pH great than 7.5, or, conditions comprising between about pH 8 and pH 9 or greater, e.g., pH 8.5, in bicarbonate buffer or equivalent. In one aspect, the method also comprises a non-ionic wetting agent, e.g., at about 1 g/L. In one aspect, the pectate lyase ratio is in an enzyme bath between about 10:1 to 50:1 L pectate lyase:kg of material. In one aspect, the pectate lyase dose is between about 0.1 and 0.2 ml of a concentrated extract per kg of material, or equivalent. Alternatively, the pectate lyase dose is between about 0.1 ml to 1 ml of a concentrated extract per kg of material, or equivalent. In one aspect, the temperature range is between about 50° C. to 70° C. In one aspect, the treatment time is about 20 min. In one aspect of the bioscouring processes of the invention, the material comprises a fabric or a cloth. In one aspect, the pectate lyase dose is about 0.137 ml of a concentrated extract per kg of material, or equivalent. In one aspect, the contacting step further comprises use of a chelant, wherein the chelant is excluded from the enzyme bath and is added after about 20 minutes of enzyme treatment and retained for about 10 minutes before discharging bath.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

The patent or application file contains at least one drawing executed in color. Copies of this patent or patent application publication with color drawing(s) will be provided by the Office upon request and payment of the necessary fee.

FIG. 5 is a chart summary of the relative substrate specificity, relative substrate specificity value, characterization activity temperature, characterization activity pH, enzyme activity, characterization description and characterization substrate of exemplary pectate lyases of the invention.

FIG. 6 is a summary of pectate lyase polypeptides of the invention, characterized as "upmutants," as discussed in detail, below.

FIG. 7 is a table summarizing exemplary melting temperatures and specific activities (SA) of exemplary enzymes of the invention at various temperatures.

Like reference symbols in the various drawings indicate like elements.

DETAILED DESCRIPTION

Figure 1:
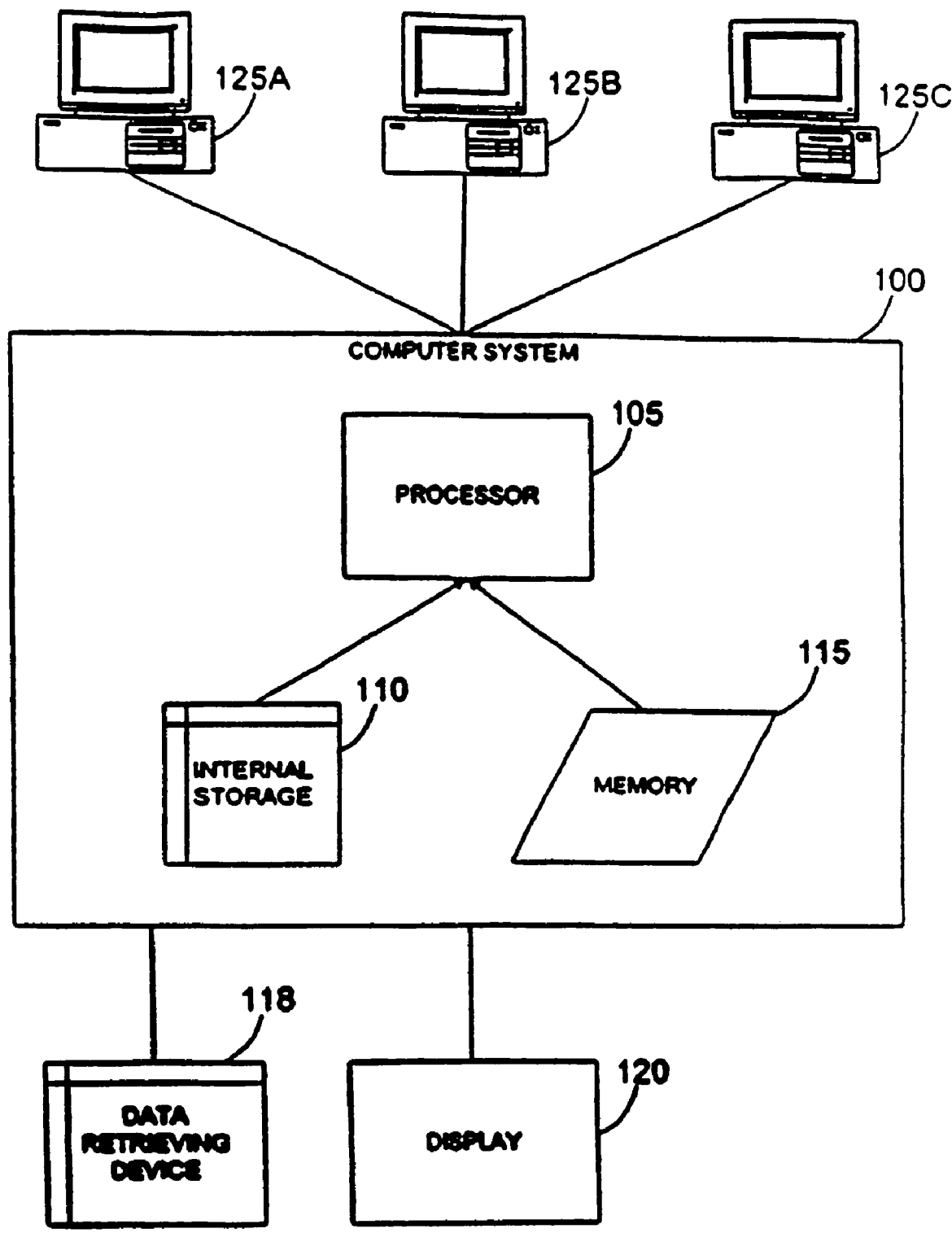
FIG. 1 is a block diagram of a computer system.

The invention provides polypeptides having a pectate lyase activity, polynucleotides encoding the polypeptides, and methods for making and using these polynucleotides and polypeptides. In one aspect, the pectate lyases of the invention are used to catalyze the beta-elimination (trans-elimination) and/or hydrolysis of pectin and/or polygalacturonic acid (pectate) or other plant wall constituents, e.g., homogalacturonan or rhamnogalacturonan, including 1,4-linked alpha-D-galacturonic acid. The pectate lyases of the invention can also be used for the hydrolysis of plant cell walls, e.g., in treating natural fibers comprising pectin, for example, cotton fibers.

Use of the pectate lyases of the invention to hydrolyze primary cell wall pectin can eliminate the need for caustics and high temperatures in cotton fiber scouring. Use of the pectate lyases of the invention also can significantly reduce the amount of water used to rinse treated fibers, e.g., knitted or woven cotton fabric, after chemical scouring. Use of the pectate lyases of the invention also can reduce raw material losses in chemical scouring. In one aspect, a pectate lyase of the invention, e.g., an alkaline and/or thermostable pectate lyase, is used for bioscouring. Thus, the invention provides processes in which desized cotton fabrics are processed to solubilize and extract undesired non-cellulosic material in fabrics and other cellulosic materials using an enzyme of the invention. The processes of the invention can be used to solubilize and/or extract materials naturally found in cotton and/or to remove applied impurities, such as machinery lubricants.

FIGS. 5 and 7 are chart summaries of, inter alia, the relative substrate specificity, relative substrate specificity value, characterization activity temperature, characterization activity pH, enzyme activity, characterization description and characterization substrate of exemplary pectate lyases of the invention.

The pectate lyase preparations of the invention (including those for treating or processing feeds or foods, treating fibers and textiles, waste treatments, plant treatments, and the like) can further comprise one or more enzymes, for example, proteases, cellulases (endo-beta-1,4-glucanases), beta-glucanases (endo-beta-1,3(4)-glucanases), lipases, cutinases, peroxidases, laccases, amylases, pectate lyases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectin methylesterases, cellobiohydrolases, transglutaminases; or mixtures thereof.

Definitions

The term "pectate lyase" includes all polypeptides having a pectate lyase, or pectinase, activity, including the beta-elimination (trans-elimination) and/or hydrolysis of pectin and/or polygalacturonic acid (pectate) or other plant wall constituents, e.g., homogalacturonan or rhamnogalacturonan, including 1,4-linked alpha-D-galacturonic acid. In one aspect, pectate lyase activity includes catalysis of the cleavage of glycosidic linkages of pectic substances, e.g., catalyzing the beta-elimination (trans-elimination) and/or hydrolysis of plant cell walls (e.g., the breakup or dissolution of cell walls comprising pectin, e.g., plant cell walls). In one aspect, pectate lyase activity includes catalyzing the beta-elimination (trans-elimination) and/or hydrolysis of methyl-esterified galacturonic acid, including partially or completely methyl-esterified polygalacturonic acid. In one aspect, the pectate lyase activity is mainly endo-acting, e.g., cutting the polymer (e.g., polygalacturonic acid) at random sites within a chain to give a mixture of oligomers, or the pectate lyase activity may be exo-acting, attacking from one end of the polymer and producing monomers or dimers, or, a combination thereof. In one aspect, the pectate lyase activity comprises catalyzing the random cleavage of alpha-1,4-glycosidic linkages in pectic acid (polygalacturonic acid) by trans-elimination. In one aspect, pectate lyase activity includes polypeptides having activity the same or similar to pectate lyase (EC 4.2.2.2), poly(1,4-alpha-D-galacturonide) lyase, polygalacturonate lyase (EC 4.2.2.2), pectin lyase (EC 4.2.2.10), polygalacturonase (EC 3.2.1.15), exo-polygalacturonase (EC 3.2.1.67), exo-polygalacturonate lyase (EC 4.2.2.9) and/or exo-poly-alpha-galacturonosidase (EC 3.2.1.82).

A polypeptide can be routinely assayed for pectate lyase activity (e.g., tested to see if the protein is within the scope of the invention) by any method, e.g., a PGA assay for pectate lyases. In this test pectate lyase activity is measured at desired temperature and pH using 0.2% polygalacturonic acid (Sigma, P3850) in 25 mM Tris HCl –25 mM Glycine NaOH buffer. One unit of enzyme activity is defined as the amount of protein that produced 1 μmol of unsaturated oligogalacturonides per minute equivalent to 1 μmol of unsaturated digalacturonide, using molecular extinction coefficient value of 4600 $M^{-1}cm^{-1}$ at 235 nm for dimer. Protein can be determined for homogenous purified protein by measuring absorbance at 280 nm, using extinction coefficient value specific for each protein based on sequence.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

As used herein, the terms "computer," "computer program" and "processor" are used in their broadest general contexts and incorporate all such devices, as described in detail, below. A "coding sequence of" or a "sequence encodes" a particular polypeptide or protein, is a nucleic acid sequence which is transcribed and translated into a polypeptide or protein when placed under the control of appropriate regulatory sequences.

The term "expression cassette" as used herein refers to a nucleotide sequence which is capable of affecting expression of a structural gene (i.e., a protein coding sequence, such as a pectate lyase of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. Thus, expression cassettes also include plasmids, expression vectors, recombinant viruses, any form of recombinant "naked DNA" vector, and the like.

"Operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

A "vector" comprises a nucleic acid that can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

As used herein, the term "promoter" includes all sequences capable of driving transcription of a coding sequence in a cell, e.g., a plant cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

"Tissue-specific" promoters are transcriptional control elements that are only active in particular cells or tissues or organs, e.g., in plants or animals. Tissue-specific regulation may be achieved by certain intrinsic factors that ensure that genes encoding proteins specific to a given tissue are expressed. Such factors are known to exist in mammals and plants so as to allow for specific tissues to develop.

The term "plant" includes whole plants, plant parts (e.g., leaves, stems, flowers, roots, etc.), plant protoplasts, seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. As used herein, the term "transgenic plant" includes plants or plant cells into which a heterologous nucleic acid sequence has been inserted, e.g., the nucleic acids and various recombinant constructs (e.g., expression cassettes) of the invention.

"Plasmids" can be commercially available, publicly available on an unrestricted basis, or can be constructed from available plasmids in accord with published procedures. Equivalent plasmids to those described herein are known in the art and will be apparent to the ordinarily skilled artisan.

The term "gene" includes a nucleic acid sequence comprising a segment of DNA involved in producing a transcription product (e.g., a message), which in turn is translated to produce a polypeptide chain, or regulates gene transcription, reproduction or stability. Genes can include regions preceding and following the coding region, such as leader and trailer, promoters and enhancers, as well as, where applicable, intervening sequences (introns) between individual coding segments (exons).

The phrases "nucleic acid" or "nucleic acid sequence" includes oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

"Amino acid" or "amino acid sequence" include an oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

The term "isolated" includes a material removed from its original environment, e.g., the natural environment if it is naturally occurring. For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

As used herein, the term "recombinant" can include nucleic acids adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 10%, 15%, 20%, 30%, 40%, 50%, 60%, 70%, 80%, 90%, 95%, 98% or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

A promoter sequence can be "operably linked to" a coding sequence when RNA polymerase which initiates transcription at the promoter will transcribe the coding sequence into mRNA, as discussed further, below.

"Oligonucleotide" includes either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

The phrase "substantially identical" in the context of two nucleic acids or polypeptides, can refer to two or more sequences that have, e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133 (nucleic acids) SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134 (polypeptides), over a region of at least about 10, 20, 30, 40, 50, 100, 150, 200, 250, 300, 350, 400, 450, 500, 550, 600, 650, 700, 750, 800, 850, 900, 950, 1000 or more residues, or a region ranging from between about 50 residues to the full length of the nucleic acid or polypeptide. Nucleic acid sequences of the invention can be substantially identical over the entire length of a polypeptide coding region.

A "substantially identical" amino acid sequence also can include a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a pectate lyase, resulting in modification of the structure of the polypeptide, without significantly altering its biological activity. For example, amino- or carboxyl-terminal amino acids that are not required for pectate lyase activity can be removed.

"Hybridization" includes the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

"Variant" includes polynucleotides or polypeptides of the invention modified at one or more base pairs, codons, introns, exons, or amino acid residues (respectively) yet still retain the biological activity of a pectate lyase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM™ and any combination thereof. Techniques for producing variant pectate lyase having activity at a pH or temperature, for example, that is different from a wild-type pectate lyase, are included herein.

The term "saturation mutagenesis" or "GSSM™" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

Generating and Manipulating Nucleic Acids

The invention provides isolated and recombinant nucleic acids, e.g., polynucleotides having a sequence identity to an exemplary nucleic acid of the invention, e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:110, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131 or SEQ ID NO:133; nucleic acids encoding polypeptides of the invention, e.g., sequences as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132 or SEQ ID NO:134.

The nucleic acids of the invention can also comprise expression cassettes, such as expression vectors, where in one aspect they encode a polypeptide of the invention. The invention also includes methods for discovering new pectate lyase sequences using the nucleic acids of the invention. The invention also includes methods for inhibiting the expression of pectate lyase genes, transcripts and polypeptides using the nucleic acids of the invention. Also provided are methods for modifying the nucleic acids of the invention by, e.g., synthetic ligation reassembly, optimized directed evolution system and/or gene site saturation mutagenesis (GSSM™).

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, iRNA (i.e., RNAi), antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the E. coli lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Tissue-Specific Plant Promoters

The invention provides expression cassettes that can be expressed in a tissue-specific manner, e.g., that can express a pectate lyase of the invention in a tissue-specific manner. The invention also provides plants or seeds that express a pectate lyase of the invention in a tissue-specific manner. The tissue-specificity can be seed specific, stem specific, leaf specific, root specific, fruit specific and the like.

In one aspect, a constitutive promoter such as the CaMV 35S promoter can be used for expression in specific parts of the plant or seed or throughout the plant. For example, for overexpression, a plant promoter fragment can be employed which will direct expression of a nucleic acid in some or all tissues of a plant, e.g., a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of Agrobacterium tumefaciens, and other transcription initiation regions from various plant genes known to those of skill. Such genes include, e.g., ACT11 from Arabidopsis (Huang (1996) Plant Mol. Biol. 33:125-139); Cat3 from Arabidopsis (GenBank No. U43147, Zhong (1996) Mol. Gen. Genet. 251:196-203); the gene encoding stearoyl-acyl carrier protein desaturase from Brassica napus (Genbank No. X74782, Solocombe (1994) Plant Physiol. 104:1167-1176); GPc1 from maize (GenBank No. X15596; Martinez (1989) J. Mol. Biol 208:551-565); the Gpc2 from maize (GenBank No. U45855, Manjunath (1997) Plant Mol. Biol. 33:97-112); plant promoters described in U.S. Pat. Nos. 4,962,028; 5,633,440.

The invention uses tissue-specific or constitutive promoters derived from viruses which can include, e.g., the tobamovirus subgenomic promoter (Kumagai (1995) Proc. Natl. Acad. Sci. USA 92:1679-1683; the rice tungro bacilliform virus (RTBV), which replicates only in phloem cells in infected rice plants, with its promoter which drives strong phloem-specific reporter gene expression; the cassaya vein mosaic virus (CVMV) promoter, with highest activity in vascular elements, in leaf mesophyll cells, and in root tips (Verdaguer (1996) Plant Mol. Biol. 31:1129-1139).

Alternatively, the plant promoter may direct expression of pectate lyase-expressing nucleic acid in a specific tissue, organ or cell type (i.e. tissue-specific promoters) or may be otherwise under more precise environmental or developmental control or under the control of an inducible promoter. Examples of environmental conditions that may affect transcription include anaerobic conditions, elevated temperature, the presence of light, or sprayed with chemicals/hormones. For example, the invention incorporates the drought-inducible promoter of maize (Busk (1997) supra); the cold, drought, and high salt inducible promoter from potato (Kirch (1997) Plant Mol. Biol. 33:897 909).

Tissue-specific promoters can promote transcription only within a certain time frame of developmental stage within that tissue. See, e.g., Blazquez (1998) Plant Cell 10:791-800, characterizing the Arabidopsis LEAFY gene promoter. See also Cardon (1997) Plant J 12:367-77, describing the transcription factor SPL3, which recognizes a conserved sequence motif in the promoter region of the A. thaliana floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids of the invention are operably linked to a promoter active primarily only in cotton fiber cells. In one aspect, the nucleic acids of the invention are operably linked to a promoter active primarily during the stages of cotton fiber cell elongation, e.g., as described by Rinehart (1996) supra. The nucleic acids can be operably linked to the Fbl2A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids of the invention. Examples of root-specific promoters include the promoter from the alcohol dehydrogenase gene (DeLisle (1990) Int. Rev. Cytol. 123:39-60). Other promoters that can be used to express the nucleic acids of the invention include, e.g., ovule-specific, embryo-specific, endosperm-specific, integument-specific, seed coat-specific promoters, or some combination thereof; a leaf-specific promoter (see, e.g., Busk (1997) Plant J. 11:1285 1295, describing a leaf-specific promoter in maize); the ORF 13 promoter from *Agrobacterium rhizogenes* (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves and, to a lesser extent, of flowers can be used (see, e.g., Blume (1997) Plant J. 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically- (e.g., hormone- or pesticide-) induced promoters, i.e., promoter responsive to a chemical which can be applied to the transgenic plant in the field, expression of a polypeptide of the invention can be induced at a particular stage of development of the plant. Thus, the invention also provides for transgenic plants containing an inducible gene encoding for polypeptides of the invention whose host range is limited to target plant species, such as corn, rice, barley, wheat, potato or other crops, inducible at any stage of development of the crop.

One of skill will recognize that a tissue-specific plant promoter may drive expression of operably linked sequences in tissues other than the target tissue. Thus, a tissue-specific promoter is one that drives expression preferentially in the target tissue or cell type, but may also lead to some expression in other tissues as well.

The nucleic acids of the invention can also be operably linked to plant promoters which are inducible upon exposure to chemicals reagents. These reagents include, e.g., herbicides, synthetic auxins, or antibiotics which can be applied, e.g., sprayed, onto transgenic plants. Inducible expression of the pectate lyase-producing nucleic acids of the invention will allow the grower to select plants with the optimal pectate lyase expression and/or activity. The development of plant parts can thus controlled. In this way the invention provides the means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences of the invention are also under the control of a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324).

If proper polypeptide expression is desired, a polyadenylation region at the 3'-end of the coding region should be included. The polyadenylation region can be derived from the natural gene, from a variety of other plant genes, or from genes in the *Agrobacterial* T-DNA.

Expression Vectors and Cloning Vehicles

The invention provides expression vectors and cloning vehicles comprising nucleic acids of the invention, e.g., sequences encoding the pectate lyases of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The expression vector can comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells can also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The nucleic acids of the invention can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal mini-chromosome containing supercoiled DNA, see, e.g., Covey (1990) Proc. Natl. Acad. Sci. USA 87:1633-1637. Alternatively, coding sequences, i.e., all or sub-fragments of sequences of the invention can be inserted into a plant host cell genome becoming an integral part of the host chromosomal DNA. Sense or antisense transcripts can be expressed in this manner. A vector comprising the sequences (e.g., promoters or coding regions) from nucleic acids of the invention can comprise a marker gene that confers a selectable phenotype on a plant cell or a seed. For example, the marker may encode biocide resistance, particularly antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, e.g., vectors from *Agrobacterium* spp., potato virus X (see, e.g., Angell (1997) EMBO J. 16:3675-3684), tobacco mosaic virus (see, e.g., Casper (1996) Gene 173:69-73), tomato bushy stunt virus (see, e.g., Hillman (1989) Virology 169:42-50), tobacco etch virus (see, e.g., Dolja (1997) Virology 234: 243-252), bean golden mosaic virus (see, e.g., Morinaga (1993) Microbiol Immunol. 37:471-476), cauliflower mosaic virus (see, e.g., Cecchini (1997) Mol. Plant Microbe Interact. 10: 1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

In one aspect, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

Host Cells and Transformed Cells

The invention also provides a transformed cell comprising a nucleic acid sequence of the invention, e.g., a sequence encoding a pectate lyase of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Bacillus cereus, Salmonella typhimurium* and various species within the genera *Bacillus, Streptomyces*, and *Staphylococcus*. Exemplary insect cells include *Drosophila S2* and *Spodoptera Sf9*. Exemplary yeast cells include *Pichia pastoris, Saccharomyces cerevisiae* or *Schizosaccharomyces pombe*. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann. Rev. Genet. 22:421-477, U.S. Pat. No. 5,750,870.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include CaPO$_4$ precipitation, liposome fusion, lipofection (e.g., LIPOFECTN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Amplification of Nucleic Acids

In practicing the invention, nucleic acids of the invention and nucleic acids encoding the pectate lyases of the invention, or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences. In one aspect, the invention provides a nucleic acid amplified by a primer pair of the invention, e.g., a primer pair as set forth by about the first (the 5') 15, 16, 17, 18, 19, 20, 21, 22, 23, 24, or 25 residues of a nucleic acid of the invention, and about the first (the 5') 15, 16, 17, 18, 19, 20, 21, 22, 23, 24, or 25 residues of the complementary strand (e.g., of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133).

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, and nucleic acids encoding SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134) over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention. The extent of sequence identity (homology) may be determined using any computer program and associated parameters, including those described herein, such as BLAST 2.2.2. or FASTA version 3.0t78, with the default parameters.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W. H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence, e.g., a sequence of the invention, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, contiguous residues ranging anywhere from 20 to the full length of an exemplary polypeptide or nucleic acid sequence of the invention are compared to a reference sequence of the same number of contiguous positions after the two sequences are optimally aligned. If the reference sequence has the requisite sequence identity to an exemplary polypeptide or nucleic acid sequence of the invention, e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to a sequence of the invention, that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l.

Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Databases containing genomic information annotated with some functional information are maintained by different organization, and are accessible via the internet.

BLAST, BLAST 2.0 and BLAST 2.2.2 algorithms are also used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blastp. There are about 38 setting options in the BLAST 2.2.2 program. In this exemplary aspect of the invention, all default values are used except for the default filtering setting (i.e., all parameters set to default except filtering which is set to OFF); in its place a "-F F" setting is used, which disables filtering. Use of default filtering often results in Karlin-Altschul violations due to short length of sequence.

The default values used in this exemplary aspect of the invention include:

"Filter for low complexity: ON
Word Size: 3
Matrix: Blosum62
Gap Costs: Existence:11
Extension:1"

Other default settings can be: filter for low complexity OFF, word size of 3 for protein, BLOSUM62 matrix, gap existence penalty of −11 and a gap extension penalty of −1. An exemplary NCBI BLAST 2.2.2 program setting has the "-W" option default to 0. This means that, if not set, the word size defaults to 3 for proteins and 11 for nucleotides.

Computer Systems and Computer Program Products

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects of the invention include systems (e.g., internet based systems), particularly computer systems, which store and manipulate the sequences and sequence information described herein. One example of a computer system 100 is illustrated in block diagram form in FIG. 1. As used herein, "a computer system" refers to the hardware components, software components, and data storage components used to analyze a nucleotide or polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (preferably implemented as RAM) and one or more internal data storage devices 110, such as a hard drive and/or other computer readable media having data recorded thereon. The computer system 100 can further include one or more data retrieving device 118 for reading the data stored on the internal data storage devices 110. The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device. The computer system 100 includes a display 120 which is used to display output to a computer user. It should also be noted that the computer system 100 can be linked to other computer systems 125a-c in a network or wide area network to provide centralized access to the computer system 100. Software for accessing and processing the nucleotide or amino acid sequences of the invention can reside in main memory 115 during execution. In some aspects, the computer system 100 may further comprise a sequence comparison algorithm for comparing a nucleic acid sequence of the invention. The algorithm and sequence(s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of the invention stored on a computer readable medium to reference sequences stored on a computer readable medium to identify homologies or structural motifs.

Figure 2:
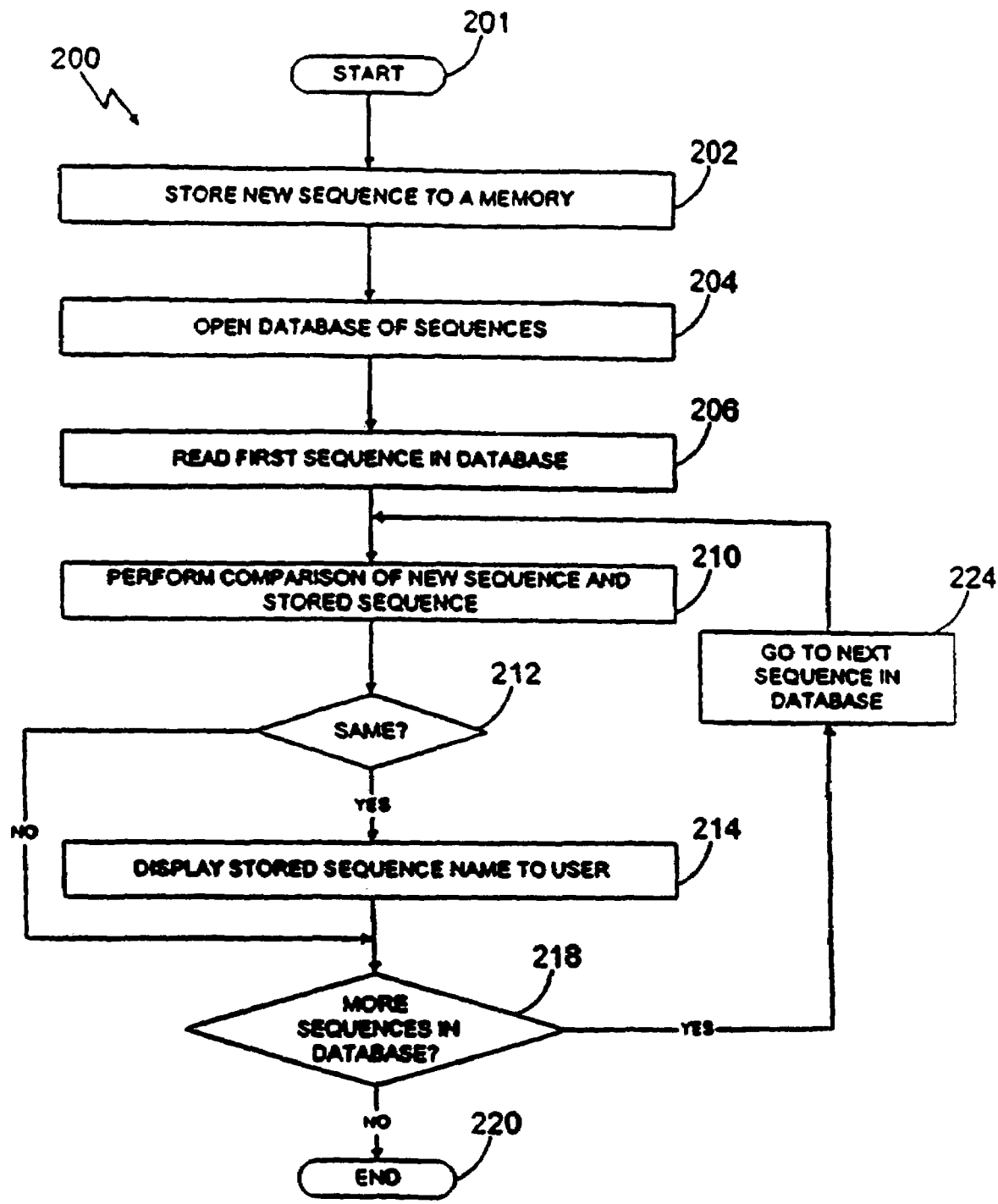
FIG. 2 is a flow diagram illustrating one aspect of a process for comparing a new nucleotide or protein sequence with a database of sequences in order to determine the homology levels between the new sequence and the sequences in the database.
Figure 3:
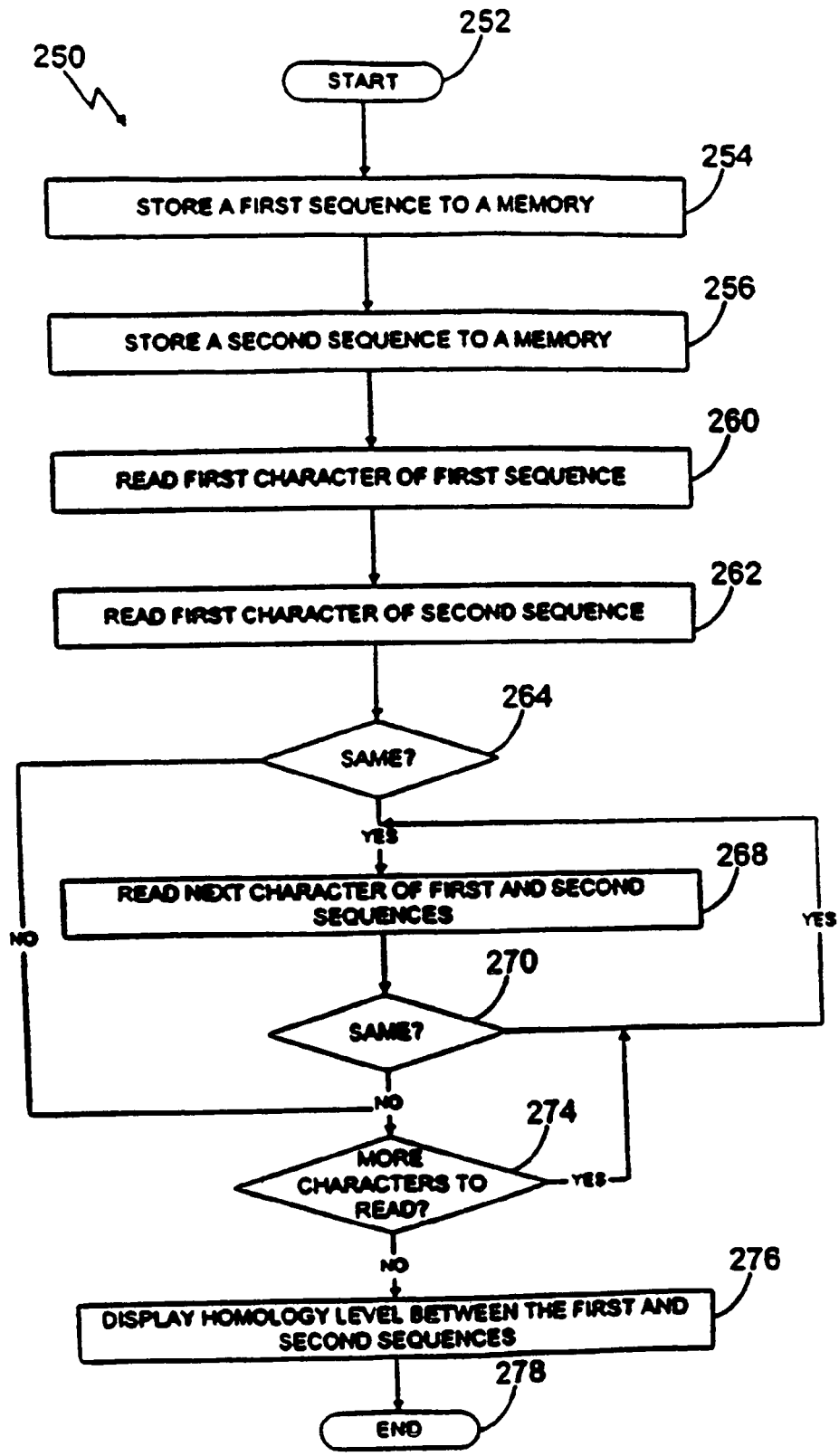
FIG. 3 is a flow diagram illustrating one aspect of a process in a computer for determining whether two sequences are homologous.

The parameters used with the above algorithms may be adapted depending on the sequence length and degree of homology studied. In some aspects, the parameters may be the default parameters used by the algorithms in the absence of instructions from the user. FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device. The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system. Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database. It should be noted that if a determination had been made at the decision state 212 that the sequences were not homologous, then the process 200 would move immediately to the decision state 218 in order to determine if any other sequences were available in the database for comparison. Accordingly, one aspect of the invention is a computer system comprising a processor, a data storage device having stored thereon a nucleic acid sequence of the invention and a sequence comparer for conducting the comparison. The sequence comparer may indicate a homology level between the sequences compared or identify structural motifs, or it may identify structural motifs in sequences which are compared to these nucleic acid codes and polypeptide codes. FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with an every character in a second sequence, the homology level would be 100%.

Alternatively, the computer program can compare a reference sequence to a sequence of the invention to determine whether the sequences differ at one or more positions. The program can record the length and identity of inserted, deleted or substituted nucleotides or amino acid residues with respect to the sequence of either the reference or the invention. The computer program may be a program which determines whether a reference sequence contains a single nucleotide polymorphism (SNP) with respect to a sequence of the invention, or, whether a sequence of the invention comprises a SNP of a known sequence. Thus, in some aspects, the computer program is a program which identifies SNPs. The method may be implemented by the computer systems described above and the method illustrated in FIG. 3. The method can be performed by reading a sequence of the invention and the reference sequences through the use of the computer program and identifying differences with the computer program.

Figure 4:
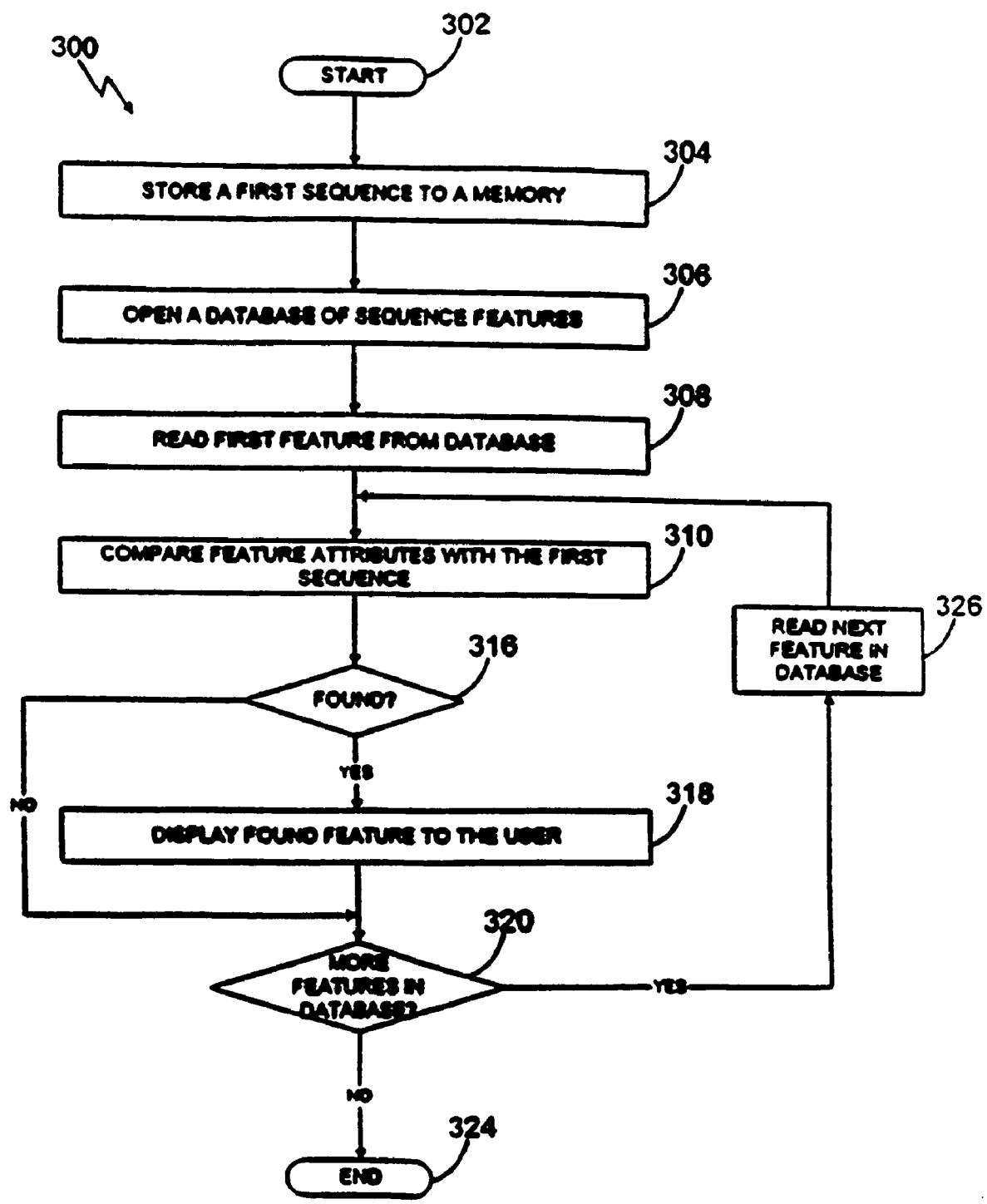
FIG. 4 is a flow diagram illustrating one aspect of an identifier process 300 for detecting the presence of a feature in a sequence.

In other aspects the computer based system comprises an identifier for identifying features within a nucleic acid or polypeptide of the invention. An "identifier" refers to one or more programs which identifies certain features within a nucleic acid sequence. For example, an identifier may comprise a program which identifies an open reading frame (ORF) in a nucleic acid sequence. FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, the invention provides a computer program that identifies open reading frames (ORFs).

A polypeptide or nucleic acid sequence of the invention can be stored and manipulated in a variety of data processor programs in a variety of formats. For example, a sequence can be stored as text in a word processing file, such as Microsoft-WORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence of the invention. The programs and databases used to practice the invention include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al.

Comp. App. Biosci. 6:237-245, 1990), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Hybridization of Nucleic Acids

The invention provides isolated or recombinant nucleic acids that hybridize under stringent conditions to an exemplary sequence of the invention (e.g., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133), or a nucleic acid that encodes a polypeptide of the invention (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134). The stringent conditions can be highly stringent conditions, medium stringent conditions and/or low stringent conditions, including the high and reduced stringency conditions described herein. In one aspect, it is the stringency of the wash conditions that set forth the conditions which determine whether a nucleic acid is within the scope of the invention, as discussed below.

In alternative embodiments, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, e.g., hybridization probes, labeling probes, PCR oligonucleotide probes, IRNA, antisense or sequences encoding antibody binding peptides (epitopes), motifs, active sites and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C.

Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art. Hybridization conditions are discussed further, below.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na$^+$ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

These methods may be used to isolate nucleic acids of the invention.

Oligonucleotides Probes and Methods for Using Them

The invention also provides nucleic acid probes that can be used, e.g., for identifying nucleic acids encoding a polypeptide with a pectate lyase activity or fragments thereof or for identifying pectate lyase genes. In one aspect, the probe comprises at least 10 consecutive bases of a nucleic acid of the invention. Alternatively, a probe of the invention can be at least about 5, 6, 7, 8, 9, 10, 15, 20, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention, see discussion below, including, e.g., capillary arrays. The probes of the invention can also be used to isolate other nucleic acids or polypeptides.

The probes of the invention can be used to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids. In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency can vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization can be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM NaH$_2$PO4, pH 7.0, 5.0 mM Na$_2$EDTA, 0.5% SDS, 10× Denhardt's, and 0.5 mg/ml polyriboadenylic acid. Approximately 2×10$^7$ cpm (specific activity 4-9×10$^8$ cpm/ug) of $^{32}$P end-labeled oligonucleotide probe can then added to the solution. After 12-16 hours of incubation, the membrane is washed for 30 minutes at room temperature (RT) in 1×SET (150 mM NaCl, 20 mM Tris hydrochloride, pH 7.8, 1 mM Na$_2$EDTA) containing 0.5% SDS, followed by a 30 minute wash in fresh 1×SET at Tm−10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)−(600/N) where N is the length of the probe. If the hybridization is carried out in a solution containing formamide, the melting temperature may be calculated using the equation: Tm=81.5+16.6(log [Na+])+0.41 (fraction G+C)−(0.63% formamide)−(600/N) where N is the length of the probe. Prehybridization may be carried out in 6×SSC, 5× Denhardt's reagent, 0.5% SDS, 100 μg denatured fragmented salmon sperm DNA or 6×SSC, 5× Denhardt's reagent, 0.5% SDS, 100 μg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15 M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 99%, 98%, 97%, at least 95%, at least 90%, at least 85%, at least 80%, at least 75%, at least 70%, at least 65%, at least 60%, at least 55%, or at least 50% homology to a nucleic acid sequence of the invention comprising at least about 10, 15, 20, 25, 30, 35, 40, 50, 75, 100, 150, 200, 250, 300, 350, 400, 500, 550, 600, 650, 700, 750, 800, 850, 900, 950, 1000, or more consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acid of the invention.

Additionally, the probes and methods of the invention can be used to isolate nucleic acids which encode polypeptides having at least about 99%, at least 95%, at least 90%, at least 85%, at least 80%, at least 75%, at least 70%, at least 65%, at least 60%, at least 55%, or at least 50% sequence identity (homology) to a polypeptide of the invention comprising at least 5, 10, 15, 20, 25, 30, 35, 40, 50, 75, 100, or 150 consecutive amino acids, as determined using a sequence alignment algorithm (e.g., such as the FASTA version 3.0t78 algorithm with the default parameters, or a BLAST 2.2.2 program with exemplary settings as set forth herein).

Inhibiting Expression of Pectate Lyase The invention provides nucleic acids complementary to (e.g., antisense sequences to) the nucleic acid sequences of the invention. Antisense sequences are capable of inhibiting the transport, splicing or transcription of pectate lyase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind pectate lyase gene or message, in either case preventing or inhibiting the production or function of pectate lyase. The association can be through sequence specific hybridization. Another useful class of inhibitors includes oligonucleotides which cause inactivation or cleavage of pectate lyase message. The oligonucleotide can have enzyme activity which causes such cleavage, such as ribozymes. The oligonucleotide can be chemically modified or conjugated to an enzyme or composition capable of cleaving the complementary nucleic acid. A pool of many different such oligonucleotides can be screened for those with the desired activity. Thus, the invention provides various compositions for the inhibition of pectate lyase expression on a nucleic acid and/or protein level, e.g., antisense, iRNA and ribozymes comprising pectate lyase sequences of the invention and the anti-pectate lyase antibodies of the invention.

Inhibition of pectate lyase expression can have a variety of industrial applications. For example, inhibition of pectate lyase expression can slow or prevent "soft-rot" spoilage. "Soft-rot" spoilage occurs when pectin, a major structural polysaccharide in the plant cell wall, is enzymatically degraded. This can lead to the deterioration, or rot, of fruits and vegetables. In one aspect, use of compositions of the invention that inhibit the expression and/or activity of pectate lyases, e.g., antibodies, antisense oligonucleotides, ribozymes and RNAi, are used to slow or prevent "soft-rot" spoilage. Thus, in one aspect, the invention provides methods and compositions comprising application onto a plant or plant product (e.g., a fruit, seed, root, leaf, etc.) antibodies, antisense oligonucleotides, ribozymes and RNAi of the invention to slow or prevent "soft-rot" spoilage. These compositions also can be expressed by the plant (e.g., a transgenic plant) or another organism (e.g., a bacterium or other microorganism transformed with a pectate lyase gene of the invention).

Inhibition of pectate lyase expression also can prevent or slow the normal growth of the powdery mildew pathogen *Erysiphe cichoracearum*. This powdery mildew resistance represents a form of disease resistance based on the loss of a gene required during a compatible interaction rather than the activation of known host defense pathways. See, e.g., Vogel (2002) Plant Cell 14:2095-2106. Thus, in one aspect, the invention provides methods and compositions comprising application onto a plant or plant product (e.g., a fruit, seed, root, leaf, etc.) antibodies, antisense oligonucleotides, ribozymes and RNAi of the invention to slow or prevent growth of the powdery mildew pathogen.

Antisense Oligonucleotides

The invention provides antisense oligonucleotides capable of binding pectate lyase message which can inhibit proteolytic activity by targeting mRNA. Strategies for designing antisense oligonucleotides are well described in the scientific and patent literature, and the skilled artisan can design such pectate lyase oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphorodithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense pectate lyase sequences of the invention (see, e.g., Gold (1995) J. of Biol. Chem. 270:13581-13584).

Inhibitory Riboymes

The invention provides ribozymes capable of binding pectate lyase message. These ribozymes can inhibit pectate lyase activity by, e.g., targeting mRNA. Strategies for designing ribozymes and selecting the pectate lyase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The ribozyme of the invention, e.g., an enzymatic ribozyme RNA molecule, can be formed in a hammerhead motif, a hairpin motif, as a hepatitis delta virus motif, a group I intron motif and/or an RNaseP-like RNA in association with an RNA guide sequence. Examples of hammerhead motifs are described by, e.g., Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting. Those skilled in the art will recognize that a ribozyme of the invention, e.g., an enzymatic RNA molecule of this invention, can have a specific substrate binding site complementary to one or more of the target gene RNA regions. A ribozyme of the invention can have a nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising a pectate lyase sequence of the invention. The RNAi molecule comprises a double-stranded RNA (dsRNA) molecule. The RNAi can inhibit expression of a pectate lyase gene. In one aspect, the RNAi is about 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an organ or an animal. Methods for making and using RNAi molecules for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding a pectate lyase, the variant nucleic acids generated by these methods (e.g., SEQ ID NO:133) and polypeptides encoded by them (e.g., SEQ ID NO:134, as discussed below). These methods can be repeated or used in various combinations to generate pectate lyases having an altered or different activity or an altered or different stability from that of a pectate lyase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene in vitro, in vivo or ex vivo, followed by its reinsertion into the cell.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photo-activated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor, thereby mutating the sequence. Intercalating agents such as proflavine, acriflavine, quinacrine and the like can be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis (GSSM™), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Gates et al. (1996) "Affinity selective isolation of ligands from peptide libraries through display on a lac repressor 'headpiece dimer'" Journal of Molecular Biology 255: 373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154,367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100: 468-500; and Zoller & Smith (1987) Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional protocols that can be used to practice the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shotgun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Protocols that can be used to practice the invention are described, e.g., in U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Protocols that can be used to practice the invention (providing details regarding various diversity generating methods) are described, e.g., in U.S. patent application Ser. No. (U.S. Ser. No.) 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STR-ANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410.

Non-stochastic, or "directed evolution," methods include, e.g., saturation mutagenesis (GSSM™), synthetic ligation reassembly (SLR), or a combination thereof are used to modify the nucleic acids of the invention to generate pectate lyases with new or altered properties (e.g., activity under highly acidic or alkaline conditions, high temperatures, and the like). Polypeptides encoded by the modified nucleic acids can be screened for an activity before testing for proteolytic or other activity. Any testing modality or protocol can be used, e.g., using a capillary array platform. See, e.g., U.S. Pat. Nos. 6,361,974; 6,280,926; 5,939,250.

Saturation Mutagenesis, or, GSSM™

In one aspect, codon primers containing a degenerate N,N,G/T sequence are used to introduce point mutations into a polynucleotide, e.g., a pectate lyase or an antibody of the invention, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position X 100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., pectate lyases) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., *E. coli* host, using, e.g., an expression vector) and subjected to expression screening. When an individual progeny polypeptide is identified by screening to display a favorable change in property (when compared to the parental polypeptide, such as increased proteolytic activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. This invention provides for the use of any mutagenizing process (es), including saturation mutagenesis, in an iterative manner.

Synthetic Ligation Reassembly (SLR)

The invention provides a non-stochastic gene modification system termed "synthetic ligation reassembly," or simply "SLR," a "directed evolution process," to generate polypeptides, e.g., pectate lyases or antibodies of the invention, with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. patent application Ser. No. (U.S. Ser. No.) 09/332,835 entitled "Synthetic Ligation Reassembly in Directed Evolution" and filed on Jun. 14, 1999 ("U.S. Ser. No. 09/332,835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over 10100 different chimeras. SLR can be used to generate libraries comprised of over 101000 different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s) can be functional in a host cells for gene splicing much in the way that naturally-occurring introns serve functionally in gene splicing.

Optimized Directed Evolution System

The invention provides a non-stochastic gene modification system termed "optimized directed evolution system" to generate polypeptides, e.g., pectate lyases or antibodies of the invention, with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Additional information can also be found, e.g., in U.S. Ser. No. 09/332,835; U.S. Pat. No. 6,361,974.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Ser. No. 09/332,835.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLAB™ (The Mathworks, Natick, Mass.) a programming language and development environment for technical computing.

Iterative Processes

In practicing the invention, these processes can be iteratively repeated. For example, a nucleic acid (or, the nucleic acid) responsible for an altered or new pectate lyase phenotype is identified, re-isolated, again modified, re-tested for activity. This process can be iteratively repeated until a desired phenotype is engineered. For example, an entire biochemical anabolic or catabolic pathway can be engineered into a cell, including, e.g., epoxide hydrolysis activity.

Similarly, if it is determined that a particular oligonucleotide has no affect at all on the desired trait (e.g., a new pectate lyase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is use in methods of the invention that provide variants of polypeptides of the invention, e.g., antibodies, pectate lyases, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one aspect, the invention provides a method for producing a hybrid polynucleotide from at least a first polynucleotide (e.g., a pectate lyase of the invention) and a second polynucleotide (e.g., an enzyme, such as a pectate lyase of the invention or any other pectate lyase, or, a tag or an epitope). The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

The invention also provides additional methods for making sequence variants of the nucleic acid (e.g., pectate lyase) sequences of the invention. The invention also provides additional methods for isolating pectate lyases using the nucleic acids and polypeptides of the invention. In one aspect, the invention provides for variants of a pectate lyase coding sequence (e.g., a gene, cDNA or message) of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM MgCl2, 0.5 mM MnCl2, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91: 10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/:1 in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an E. coli strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811-7815.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11: 1548-1552. Random and site-directed mutagenesis are described, e.g., in Arnold (1993) Current Opinion in Biotechnology 4:450-455.

In some aspects, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965,408; 5,939,250 (see also discussion, above).

The invention also provides variants of polypeptides of the invention (e.g., pectate lyases) comprising sequences in which one or more of the amino acid residues (e.g., of an exemplary polypeptide of the invention) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides of the invention include those with conservative substitutions of sequences of the invention, e.g., the exemplary polypeptides of the invention, including but not limited to the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. Other variants are those in which one or more of the amino acid residues of the polypeptides of the invention includes a substituent group.

Other variants within the scope of the invention are those in which the polypeptide is associated with another compound, such as a compound to increase the half-life of the polypeptide, for example, polyethylene glycol.

Additional variants within the scope of the invention are those in which additional amino acids are fused to the polypeptide, such as a leader sequence, a secretory sequence, a proprotein sequence or a sequence which facilitates purification, enrichment, or stabilization of the polypeptide.

In some aspects, the variants, fragments, derivatives and analogs of the polypeptides of the invention retain the same biological function or activity as the exemplary polypeptides, e.g., pectate lyase activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

The invention provides methods for modifying pectate lyase-encoding nucleic acids to modify codon usage. In one aspect, the invention provides methods for modifying codons in a nucleic acid encoding a pectate lyase to increase or decrease its expression in a host cell. The invention also provides nucleic acids encoding a pectate lyase modified to increase its expression in a host cell, pectate lyase so modified, and methods of making the modified pectate lyases. The method comprises identifying a "non-preferred" or a "less preferred" codon in pectate lyase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli*; gram positive bacteria, such as any *Streptomyces, Lactobacillus gasseri, Lactococcus lactis, Lactococcus cremoris*, any *Bacillus*, e.g., *Bacillus subtilis, Bacillus cereus*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding a pectate lyase isolated from a bacterial cell are modified such that the nucleic acid is optimally expressed in a bacterial cell different from the bacteria from which the pectate lyase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Synthetic Gene Reassembly

In one aspect, the present invention provides a non-stochastic method termed synthetic gene reassembly (e.g., GeneReassembly™, see, e.g., U.S. Pat. No. 6,537,776) for, e.g., modifying pectate lyases of the invention or building new pectate lyases within the scope of the invention. GeneReassembly™ differs from stochastic shuffling in that the nucleic acid building blocks are not shuffled or concatenated or chimerized randomly, but rather are assembled non-stochastically.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends and assembling these nucleic acid building blocks, such that a designed overall assembly order is achieved.

In one aspect, synthetic gene reassembly comprises a method of: 1) preparing a progeny generation of molecule(s) (including a molecule comprising a polynucleotide sequence, e.g., a molecule comprising a polypeptide coding sequence), that is mutagenized to achieve at least one point mutation, addition, deletion, and/or chimerization, from one or more ancestral or parental generation template(s); 2) screening the progeny generation molecule(s), e.g., using a high throughput method, for at least one property of interest (such as an improvement in an enzyme activity); 3) optionally obtaining and/or cataloguing structural and/or and functional information regarding the parental and/or progeny generation molecules; and 4) optionally repeating any of steps 1) to 3). In one aspect, there is generated (e.g., from a parent polynucleotide template), in what is termed "codon site-saturation mutagenesis," a progeny generation of polynucleotides, each having at least one set of up to three contiguous point mutations (i.e. different bases comprising a new codon), such that every codon (or every family of degenerate codons encoding the same amino acid) is represented at each codon position. Corresponding to, and encoded by, this progeny generation of polynucleotides, there is also generated a set of progeny polypeptides, each having at least one single amino acid point mutation. In a one aspect, there is generated, in what is termed "amino acid site-saturation mutagenesis", one such mutant polypeptide for each of the 19 naturally encoded polypeptide-forming alpha-amino acid substitutions at each and every amino acid position along the polypeptide. This yields, for each and every amino acid position along the parental polypeptide, a total of 20 distinct progeny polypeptides including the original amino acid, or potentially more than 21 distinct progeny polypeptides if additional amino acids are used either instead of or in addition to the 20 naturally encoded amino acids Thus, in another aspect, this approach is also serviceable for generating mutants containing, in addition to and/or in combination with the 20 naturally encoded polypeptide-forming alpha-amino acids, other rare and/or not naturally-encoded amino acids and amino acid derivatives. In yet another aspect, this approach is also serviceable for generating mutants by the use of, in addition to and/or in combination with natural or unaltered codon recognition systems of suitable hosts, altered, mutagenized, and/or designer codon recognition systems (such as in a host cell with one or more altered tRNA molecules.

In yet another aspect, this invention relates to recombination and more specifically to a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

In yet another aspect, this invention is serviceable for analyzing and cataloguing, with respect to any molecular property (e.g. an enzymatic activity) or combination of properties allowed by current technology, the effects of any mutational change achieved (including particularly saturation mutagenesis). Thus, a comprehensive method is provided for determining the effect of changing each amino acid in a parental polypeptide into each of at least 19 possible substitutions. This allows each amino acid in a parental polypeptide to be characterized and catalogued according to its spectrum of potential effects on a measurable property of the polypeptide.

In one aspect, an intron may be introduced into a chimeric progeny molecule by way of a nucleic acid building block. Introns often have consensus sequences at both termini in order to render them operational. In addition to enabling gene splicing, introns may serve an additional purpose by providing sites of homology to other nucleic acids to enable homologous recombination. For this purpose, and potentially others, it may be sometimes desirable to generate a large nucleic acid building block for introducing an intron. If the size is overly large easily generating by direct chemical synthesis of two single stranded oligos, such a specialized nucleic acid building block may also be generated by direct chemical synthesis of more than two single stranded oligos or by using a polymerase-based amplification reaction The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one aspect of the invention, the annealed building pieces are treated with an enzyme, such as a ligase (e.g., T4 DNA ligase) to achieve covalent bonding of the building pieces.

Coupling can occur in a manner that does not make use of every nucleotide in a participating overhang. The coupling is particularly lively to survive (e.g. in a transformed host) if the coupling reinforced by treatment with a ligase enzyme to form what may be referred to as a "gap ligation" or a "gapped ligation". This type of coupling can contribute to generation of unwanted background product(s), but it can also be used advantageously increase the diversity of the progeny library generated by the designed ligation reassembly. Certain overhangs are able to undergo self-coupling to form a palindromic coupling. A coupling is strengthened substantially if it is reinforced by treatment with a ligase enzyme. Lack of 5' phosphates on these overhangs can be used advantageously to prevent this type of palindromic self-ligation. Accordingly, this invention provides that nucleic acid building blocks can be chemically made (or ordered) that lack a 5' phosphate group. Alternatively, they can be removed, e.g. by treatment with a phosphatase enzyme, such as a calf intestinal alkaline phosphatase (CIAP), in order to prevent palindromic self-ligations in ligation reassembly processes.

Transgenic Non-human Animals

The invention provides transgenic non-human animals comprising a nucleic acid, a polypeptide (e.g., a pectate lyase), an expression cassette or vector or a transfected or transformed cell of the invention. The invention also provides methods of making and using these transgenic non-human animals.

The transgenic non-human animals can be, e.g., goats, rabbits, sheep, pigs, cows, rats and mice, comprising the nucleic acids of the invention. These animals can be used, e.g., as in vivo models to study pectate lyase activity, or, as models to screen for agents that change the pectate lyase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express an endogenous gene, which is replaced with a gene expressing a pectate lyase of the invention, or, a fusion protein comprising a pectate lyase of the invention.

Transgenic Plants and Seeds

The invention provides transgenic plants and seeds comprising a nucleic acid, a polypeptide (e.g., a pectate lyase), an expression cassette or vector or a transfected or transformed cell of the invention. The invention also provides plant products, e.g., oils, seeds, leaves, extracts and the like, comprising a nucleic acid and/or a polypeptide (e.g., a pectate lyase) of the invention. The transgenic plant can be dicotyledonous (a dicot) or monocotyledonous (a monocot). The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's pectate lyase production is regulated by endogenous transcriptional or translational control elements. The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids of the invention can be used to confer desired traits on essentially any plant, e.g., on starch-producing plants, such as potato, wheat, rice, barley, and the like. Nucleic acids of the invention can be used to manipulate metabolic pathways of a plant in order to optimize or alter host's expression of pectate lyase. The can change pectate lyase activity in a plant. Alternatively, a pectate lyase of the invention can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence of the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327: 70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) *Science* 233:496-498; Fraley (1983) *Proc. Natl. Acad. Sci. USA* 80:4803 (1983); *Gene Transfer to Plants*, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl. Acad. Sci USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., a pectate lyase) of the invention. The desired effects can be passed to future plant generations by standard propagation means.

The nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, *Poa*), forage grass such as *festuca, lolium*, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale,*

*Senecio, Sinapis, Solanum, Sorghum, Theobromus, Trigonelia, Triticum, Vicia, Vitis, Vigna*, and *Zea*.

In alternative embodiments, the nucleic acids of the invention are expressed in plants which contain fiber cells, including, e.g., cotton, silk cotton tree (Kapok, Ceiba pentandra), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum*.

The invention also provides for transgenic plants to be used for producing large amounts of the polypeptides (e.g., a pectate lyase or antibody) of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

In one aspect, the invention provides isolated or recombinant polypeptides having a sequence identity (e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity) to an exemplary sequence of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134. In one aspect, the polypeptide has a pectate lyase (e.g., pectinase) activity.

The identity can be over the full length of the polypeptide, or, the identity can be over a region of at least about 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700 or more residues. Polypeptides of the invention can also be shorter than the full length of exemplary polypeptides. In alternative aspects, the invention provides polypeptides (peptides, fragments) ranging in size between about 5 and the full length of a polypeptide, e.g., an enzyme, such as a pectate lyase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary pectate lyase of the invention. Peptides of the invention can be useful as, e.g., labeling probes, antigens, toleragens, motifs, pectate lyase active sites, carbohydrate binding domains, and the like. Polypeptides of the invention also include antibodies capable of binding to an enzyme of the invention.

The polypeptides of the invention include pectate lyases in an active or inactive form. For example, the polypeptides of the invention include proproteins before "maturation" or processing of prepro sequences, e.g., by a proprotein-processing enzyme, such as a proprotein convertase to generate an "active" mature protein. The polypeptides of the invention include pectate lyases inactive for other reasons, e.g., before "activation" by a post-translational processing event, e.g., an endo- or exo-peptidase or proteinase action, a phosphorylation event, an amidation, a glycosylation or a sulfation, a dimerization event, and the like. Methods for identifying "prepro" domain sequences and signal sequences are well known in the art, see, e.g., Van de Ven (1993) Crit. Rev. Oncog. 4(2): 115-136. For example, to identify a prepro sequence, the protein is purified from the extracellular space and the N-terminal protein sequence is determined and compared to the unprocessed form.

The polypeptides of the invention include all active forms, including active subsequences, e.g., catalytic domains or active sites, of an enzyme of the invention. In one aspect, the invention provides catalytic domains or active sites as set forth below. In one aspect, the invention provides a peptide or polypeptide comprising or consisting of an active site domain as predicted through use of a database such as Pfam (which is a large collection of multiple sequence alignments and hidden Markov models covering many common protein families, The Pfam protein families database, A. Bateman, E. Birney, L. Cerruti, R. Durbin, L. Etwiller, S. R. Eddy, S. Griffiths-Jones, K. L. Howe, M. Marshall, and E. L. L. Sonnhammer, Nucleic Acids Research, 30(1):276-280, 2002) or equivalent.

The invention includes polypeptides with or without a signal sequence and/or a prepro sequence. The invention includes polypeptides with heterologous signal sequences and/or prepro sequences. The prepro sequence (including a sequence of the invention used as a heterologous prepro domain) can be located on the amino terminal or the carboxy terminal end of the protein. The invention also includes isolated or recombinant signal sequences, prepro sequences and catalytic domains (e.g., "active sites") comprising sequences of the invention.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K, Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a pectate lyase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; and, D- or L-alkylamines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl)carbodiimide or 1-ethyl-3(4-azonia-4,4-dimetholpentyl)carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzene-sulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

The invention includes pectate lyases of the invention with and without signal. The polypeptide comprising a signal sequence of the invention can be a pectate lyase of the invention or another pectate lyase or another enzyme or other polypeptide.

The invention includes immobilized pectate lyases, anti-pectate lyase antibodies and fragments thereof. The invention provides methods for inhibiting pectate lyase activity, e.g., using dominant negative mutants or anti-pectate lyase antibodies of the invention. The invention includes heterocomplexes, e.g., fusion proteins, heterodimers, etc., comprising the pectate lyases of the invention.

Polypeptides of the invention can have a pectate lyase activity under various conditions, e.g., extremes in pH and/or temperature, oxidizing agents, and the like. The invention provides methods leading to alternative pectate lyase preparations with different catalytic efficiencies and stabilities, e.g., towards temperature, oxidizing agents and changing wash conditions. In one aspect, pectate lyase variants can be produced using techniques of site-directed mutagenesis and/or random mutagenesis. In one aspect, directed evolution can be used to produce a great variety of pectate lyase variants with alternative specificities and stability.

The proteins of the invention are also useful as research reagents to identify pectate lyase modulators, e.g., activators or inhibitors of pectate lyase activity. Briefly, test samples (compounds, broths, extracts, and the like) are added to pectate lyase assays to determine their ability to inhibit substrate cleavage. Inhibitors identified in this way can be used in industry and research to reduce or prevent undesired proteolysis. As with pectate lyases, inhibitors can be combined to increase the spectrum of activity.

The invention also provides methods of discovering new pectate lyases using the nucleic acids, polypeptides and antibodies of the invention. In one aspect, lambda phage libraries are screened for expression-based discovery of pectate lyases. In one aspect, the invention uses lambda phage libraries in screening to allow detection of toxic clones; improved access to substrate; reduced need for engineering a host, by-passing the potential for any bias resulting from mass excision of the library; and, faster growth at low clone densities. Screening of lambda phage libraries can be in liquid phase or in solid phase. In one aspect, the invention provides screening in liquid phase. This gives a greater flexibility in assay conditions; additional substrate flexibility; higher sensitivity for weak clones; and ease of automation over solid phase screening.

The invention provides screening methods using the proteins and nucleic acids of the invention and robotic automation to enable the execution of many thousands of biocatalytic reactions and screening assays in a short period of time, e.g., per day, as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

The present invention includes pectate lyase enzymes which are non-naturally occurring carbonyl hydrolase variants (e.g., pectate lyase variants) having a different proteolytic activity, stability, substrate specificity, pH profile and/or performance characteristic as compared to the precursor carbonyl hydrolase from which the amino acid sequence of the variant is derived. Specifically, such pectate lyase variants have an amino acid sequence not found in nature, which is derived by substitution of a plurality of amino acid residues of a precursor pectate lyase with different amino acids. The precursor pectate lyase may be a naturally-occurring pectate lyase or a recombinant pectate lyase. The useful pectate lyase variants encompass the substitution of any of the naturally occurring L-amino acids at the designated amino acid residue positions.

Gene Site Saturation Mutagenesis (GSSM™) Variants

The invention provides pectate lyase variants and the nucleic acids that encode them. In one aspect, the invention provides SEQ ID NO:134, encoded by SEQ ID NO:133, respectively. SEQ ID NO:133 is a nucleic acid variant generated by gene site saturation mutagenesis (GSSM™) of SEQ ID NO:131 (which encodes SEQ ID NO:132). SEQ ID NO:131 and SEQ ID NO:132 are truncated variations of the nucleic acid as set forth in SEQ ID NO:77, encoding SEQ ID NO:78, respectively. The following Table 1 summarizes the amino acid changes resulting from the GSSM™-generated variations in their respective encoding nucleic acids (the full length SEQ ID NO:78 encoded by SEQ ID NO:77, and the truncated "parent" SEQ ID NO:132 encoded by SEQ ID NO:131:

TABLE 1

| Mutation - including amino acid position in SEQ ID NOS: 131, 132 | Nucleotide position in truncated wild-type gene (SEQ ID NOS: 131, 132) | Nucleotide position in full length wild-type gene (SEQ ID NOS: 77, 78) | Amino acid position in full length wild-type gene (SEQ ID NOS: 77, 78) |
|---|---|---|---|
| A118H | 352-354 | 1423-1425 | 475 |
| A182V | 544-546 | 1615-1617 | 539 |
| T190L | 568-570 | 1639-1641 | 547 |
| A197G | 589-591 | 1660-1662 | 554 |
| S208K | 622-624 | 1693-1695 | 565 |
| T219M | 655-657 | 1726-1728 | 576 |
| T223E | 667-669 | 1738-1740 | 580 |
| S255R | 763-765 | 1834-1836 | 612 |
| S263K | 787-789 | 1858-1860 | 620 |
| N275Y | 823-825 | 1894-1896 | 632 |
| Y309W | 925-927 | 1996-1998 | 666 |
| S312V | 934-936 | 2005-2007 | 669 |

FIG. 6 is a table summarizing exemplary sequence changes in pectate lyase polypeptides of the invention, characterized as "upmutants." The upmutants identified as A-S are combinatorial upmutants (each have several GSSM™-generated changes). The upmutants identified as AA-LL are single upmutants (one GSSM™-generated change each).

FIG. 7 is a table summarizing exemplary melting temperatures and specific activities (SA) of exemplary enzymes of the invention at various temperatures. Specific activity (U/mg pure enzyme) was measured at different temperatures at pH 9.5 in 25 mM Glycine NaOH 25 mM Tris HCl buffer. One unit of enzymatic activity was defined as the amount of enzyme that produced 1 µmol of unsaturated oligogalacturonides equivalent to 1 µmol of unsaturated digalacturonide per minute. Protein concentrations of the pure enzyme preparations were measured at A280 using a molar extinction coefficient of 73800 M−1cm−1 (1 A280 eq. to 0.50 mg/mL). Melting temperatures were determined with a differential scanning calorimeter.

In these Figures, mutant "N" has a sequence as set forth in SEQ ID NO:134, encoded by SEQ ID NO:133.

Pectate Lyase Signal Sequences, Pectin Methyl Esterase Domains and Catalytic Domains, Carbohydrate Binding Modules and Prepro Domains The invention provides signal sequences (e.g., signal peptides (SPs)), prepro domains and catalytic domains (CDs). The SPs, prepro domains and/or CDs of the invention can be isolated or recombinant peptides or can be part of a fusion protein, e.g., as a heterologous domain in a chimeric protein. The invention provides nucleic acids encoding these catalytic domains (CDs), prepro domains and signal sequences (SPs, e.g., a peptide having a sequence comprising/consisting of amino terminal residues of a polypeptide of the invention).

The invention provides pectate lyase signal sequences (e.g., signal peptides (SPs)) and nucleic acids encoding these signal sequences, e.g., a peptide having a sequence comprising/consisting of amino terminal residues of a polypeptide of the invention, e.g., signal peptides (SPs) as set forth in Table 2, below. In one aspect, the invention provides a signal sequence comprising a peptide comprising/consisting of a sequence as set forth in residues 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44 of a polypeptide of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134.

The invention also provides pectate lyase pectin methyl esterase domains (PEDs) and catalytic domains (CDs) as set forth in Table 2, below.

The pectate lyase signal sequences (SPs), CDs, and/or prepro sequences of the invention can be isolated peptides, or, sequences joined to another hydrolase or a non-pectate lyase polypeptide, e.g., as a fusion (chimeric) protein. In one aspect, the invention provides polypeptides comprising pectate lyase signal sequences of the invention. In one aspect, polypeptides comprising pectate lyase signal sequences SPs, CDs, and/or prepro of the invention comprise sequences heterologous to pectate lyases of the invention (e.g., a fusion protein comprising an SP, CD, and/or prepro of the invention and sequences from another pectate lyase or a non-pectate lyase protein). In one aspect, the invention provides pectate lyases of the invention with heterologous SPs, CDs, and/or prepro sequences, e.g., sequences with a yeast signal sequence. An pectate lyase of the invention can comprise a heterologous SP and/or prepro in a vector, e.g., a pPIC series vector (Invitrogen, Carlsbad, Calif.).

Table 2 summarizes signal sequences (i.e., signal peptides in their isolated form), catalytic domains, carbohydrate binding modules and pectin methyl esterase domains of the invention. For example, Table 2 describes: in row 1, a signal peptide (SP) of the invention at resides 1 to 28 of SEQ ID NO:102 (encoded by SEQ ID NO:101) and a catalytic domain (CD) of the invention at residues 78-459 of SEQ ID NO:102; in row 2, a signal peptide (SP) of the invention at resides 1 to 21 of SEQ ID NO:2 (encoded by SEQ ID NO:1), a pectin methyl esterase domain (PED) at residues 28-308, and a catalytic domain (CD) of the invention at residues; 309-638; at row 3, etc.

TABLE 2

| SEQ ID NO: | Modules (SP = signal peptide, CD = catalytic domain, CBM = carbohydrate binding module, PED = pectin methyl esterase domain) |
|---|---|
| 101, 102 | SP; 1-28, CD; 78-459 |
| 1, 2 | SP; 1-21, PED; 28-308, CD; 309-638 |
| 103, 104 | SP; 1-26, CD; 27-366 |
| 105, 106 | SP; 1-43, CD; 44-400 |
| 107, 108 | SP; 1-31, CD; 32-357 |
| 109, 110 | SP; 1-21, PED; 28-308, CD309-637 |
| 11, 12 | CD; 1-388 |
| 111, 112 | SP; 1-27, CD; 82-461 |
| 113, 114 | SP; 1-18, CD; 19-388 |
| 115, 116 | CD; 1-331 |
| 117, 118 | SP; 1-24, CD; 25-574 |
| 119, 120 | CBM; 1-61, CBM; 134-257, CD; 258-615 |
| 121, 122 | SP; 1-29, CD; 30-348 |
| 123, 124 | SP; 1-21, CD; 22-390 |
| 125, 126 | CD; 24-325 |
| 127, 128 | SP; 1-24, CD; 125-482 |
| 129, 130 | CD; 38-326 |
| 13, 14 | SP; 1-22, CD; 23-354 |
| 15, 16 | SP; 1-33, CD; 34-359 |
| 17, 18 | CD; 1-348 |
| 19, 20 | CD; 1-373 |
| 21, 22 | SP; 1-23, CD; 24-422 |
| 23, 24 | SP; 1-18, CD; 19-393 |
| 25, 26 | SP; 1-15, CD; 16-397 |
| 27, 28 | SP; 1-21, PED; 28-308, CD; 309-638 |
| 29, 30 | SP; 1-27, CD; 77-459 |
| 3, 4 | SP; 1-28, CD; 81-476 |
| 31, 32 | CD; 1-348 |
| 33, 34 | SP; 1-18, CD; 19-346 |
| 35, 36 | CD; 1-356 |
| 37, 38 | SP; 1-35, CD; 36-387 |
| 39, 40 | SP; 1-32, CD; 33-358 |
| 41, 42 | SP; 1-21, CD; 22-359 |
| 43, 44 | CBM; 4-89, CBM; 152-275, CD; 277-633 |
| 45, 46 | SP; 1-20, CD; 21-328 |
| 47, 48 | SP; 1-21, CD; 22-358 |
| 49, 50 | SP; 1-16, CD; 17-340 |
| 5, 6 | CD; 1-358 |
| 51, 52 | CD; 1-376 |
| 53, 54 | SP; 1-31, CBM; 32-124, CBM; 180-303, CD; 304-658 |
| 55, 56 | CD; 1-374 |
| 57, 58 | CD; 1-389 |
| 59, 60 | SP; 1-24, CD; 25-359 |
| 61, 62 | CD; 90-407 |
| 63, 64 | SP; 1-16, CD; 17-340 |
| 65, 66 | SP; 1-28, CD; 29-436 |
| 67, 68 | SP; 1-32, CBM; 33-126, CBM; 184-307, CD; 308-664 |
| 69, 70 | SP; 1-22, CD; 23-344 |
| 7, 8 | CD; 1-374 |
| 71, 72 | SP; 1-20, CD; 21-345 |
| 73, 74 | SP; 1-22, CD; 23-406 |
| 75, 76 | SP; 1-34, CD; 110-555 |
| 77, 78 | SP; 1-33, CBM; 34-126, CBM; 199-322, CD; 323-680 |
| 79, 80 | SP; 1-28, CD; 81-458 |
| 81, 82 | SP; 1-30, CD; 31-354 |
| 83, 84 | PED; 268-556, CD; 782-1164 |
| 85, 86 | CD; 1-383 |
| 87, 88 | SP; 1-32, CD; 33-375 |
| 89, 90 | SP; 1-31, CD; 32-459 |
| 9, 10 | SP; 1-29, CD; 30-371 |
| 91, 92 | CD; 1-374 |
| 93, 94 | CD; 1-353 |
| 95, 96 | SP; 1-31, CD; 32-357 |
| 97, 98 | PED; 45-333, CD; 336-698 |
| 99, 100 | SP; 1-35, CD; 36-593 |

In one aspect, SPs, CDs, and/or prepro sequences of the invention are identified following identification of novel pectate lyase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. The signal sequences can vary in length from 13 to 45 or more amino acid residues. Various methods of recognition of signal sequences are known to those of skill in the art. For example, in one aspect, novel pectate lyase signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

In some aspects pectate lyases of the invention do not have SPs and/or prepro sequences, and/or catalytic domains (CDs). In one aspect, the invention provides polypeptides (e.g., pectate lyases) lacking all or part of an SP, a CD and/or a prepro domain. In one aspect, the invention provides a nucleic acid sequence encoding a signal sequence (SP), a CD, and/or prepro from one pectate lyase operably linked to a nucleic acid sequence of a different pectate lyase or, optionally, a signal sequence (SPs) and/or prepro domain from a non-pectate lyase protein may be desired.

The invention also provides isolated or recombinant polypeptides comprising signal sequences (SPs), prepro domains, pectin methyl esterase domains (PEDs) and catalytic domains (CDs) of the invention and heterologous sequences. The heterologous sequences are sequences not naturally associated (e.g., to a pectate lyase) with an SP, prepro domain, PED, and/or CD. The sequence to which the SP, prepro domains, PED and/or CD are not naturally associated can be on the SP's, prepro domain's, PED's, and/or CD's amino terminal end, carboxy terminal end, and/or on both ends of the SP, prepro domain, PED and/or CD. In one aspect, the invention provides an isolated or recombinant polypeptide comprising (or consisting of) a polypeptide comprising a signal sequence (SP), prepro domain, pectin methyl esterase domain (PED) and/or catalytic domain (CD) of the invention with the proviso that it is not associated with any sequence to which it is naturally associated (e.g., a pectate lyase sequence). Similarly in one aspect, the invention provides isolated or recombinant nucleic acids encoding these polypeptides. Thus, in one aspect, the isolated or recombinant nucleic acid of the invention comprises coding sequence for a signal sequence (SP), prepro domain, pectin methyl esterase domain (PED) and/or catalytic domain (CD) of the invention and a heterologous sequence (i.e., a sequence not naturally associated with the a signal sequence (SP), prepro domain, pectin methyl esterase domain (PED) and/or catalytic domain (CD) of the invention). The heterologous sequence can be on the 3' terminal end, 5' terminal end, and/or on both ends of the SP, prepro domain, PED and/or CD coding sequence.

Glycosylation

The peptides and polypeptides of the invention (e.g., pectate lyases, antibodies) can also be glycosylated, for example, in one aspect, comprising at least one glycosylation site, e.g., an N-linked or O-linked glycosylation. In one aspect, the polypeptide can be glycosylated after being expressed in a *P. pastoris* or a *S. pombe*. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence.

Hybrid (Chimeric) Pectate Lyases and Peptide Libraries

In one aspect, the invention provides hybrid pectate lyases and fusion proteins, including peptide libraries, comprising sequences of the invention. The peptide libraries of the invention can be used to isolate peptide modulators (e.g., activators or inhibitors) of targets, such as pectate lyase substrates, receptors, enzymes. The peptide libraries of the invention can be used to identify formal binding partners of targets, such as ligands, e.g., cytokines, hormones and the like. In one aspect, the invention provides chimeric proteins comprising a signal sequence (SP), pectin methyl esterase domain (PED) and/or catalytic domain (CD) of the invention and a heterologous sequence (see above).

In one aspect, the fusion proteins of the invention (e.g., the peptide moiety) are conformationally stabilized (relative to linear peptides) to allow a higher binding affinity for targets. The invention provides fusions of pectate lyases of the invention and other peptides, including known and random peptides. They can be fused in such a manner that the structure of the pectate lyases is not significantly perturbed and the peptide is metabolically or structurally conformationally stabilized. This allows the creation of a peptide library that is easily monitored both for its presence within cells and its quantity.

Amino acid sequence variants of the invention can be characterized by a predetermined nature of the variation, a feature that sets them apart from a naturally occurring form, e.g., an allelic or interspecies variation of a pectate lyase sequence. In one aspect, the variants of the invention exhibit the same qualitative biological activity as the naturally occurring analogue. Alternatively, the variants can be selected for having modified characteristics. In one aspect, while the site or region for introducing an ammo acid sequence variation is predetermined, the mutation per se need not be predetermined. For example, in order to optimize the performance of a mutation at a given site, random mutagenesis may be conducted at the target codon or region and the expressed pectate lyase variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using assays of proteolytic activities. In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides pectate lyases where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example a alpha-helical or a beta-sheet structure; a charge or a hydrophobic site of the molecule, which can be at an active site; or a side chain. The invention provides substitutions in polypeptide of the invention where (a) a hydrophilic residues, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e. pectate lyase activity) although variants can be selected to modify the characteristics of the pectate lyases as needed.

In one aspect, pectate lyases of the invention comprise epitopes or purification tags, signal sequences or other fusion sequences, etc. In one aspect, the pectate lyases of the invention can be fused to a random peptide to form a fusion polypeptide. By "fused" or "operably linked" herein is meant that the random peptide and the pectate lyase are linked together, in such a manner as to minimize the disruption to the stability of the pectate lyase structure, e.g., it retains pectate lyase activity. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides an interaction library large enough so that at least one of its members will have a structure that gives it affinity for some molecule, protein, or other factor.

Screening Methodologies and "On-line" Monitoring Devices

In practicing the methods of the invention, a variety of apparatus and methodologies can be used to in conjunction with the polypeptides and nucleic acids of the invention, e.g., to screen polypeptides for pectate lyase activity, to screen compounds as potential modulators, e.g., activators or inhibitors, of a pectate lyase activity, for antibodies that bind to a polypeptide of the invention, for nucleic acids that hybridize to a nucleic acid of the invention, to screen for cells expressing a polypeptide of the invention and the like.

Capillary Arrays

Capillary arrays, such as the GIGAMATRIX™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube.

The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

Arrays, or "Biochips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a pectate lyase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-based Screening Methods

The invention provides isolated or recombinant antibodies that specifically bind to a pectate lyase of the invention. These antibodies can be used to isolate, identify or quantify the pectate lyases of the invention or related polypeptides. These antibodies can be used to isolate other polypeptides within the scope the invention or other related pectate lyases. The antibodies can be designed to bind to an active site of a pectate lyase. Thus, the invention provides methods of inhibiting pectate lyases using the antibodies of the invention.

The invention provides fragments of the enzymes of the invention, including immunogenic fragments of a polypeptide of the invention, e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134. The immunogenic peptides of the invention (e.g., the immunogenic fragments of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134) can further comprise adjuvants, carriers and the like.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

Polypeptides or peptides can be used to generate antibodies which bind specifically to the polypeptides, e.g., the pectate lyases, of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides (e.g., pectate lyases) from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, transgenic seeds or plants or plant parts, polypeptides (e.g., pectate lyases) and/or antibodies of the invention. The kits also can contain instructional material teaching the methodologies and industrial uses of the invention, as described herein.

Measuring Metabolic Parameters

The methods of the invention provide whole cell evolution, or whole cell engineering, of a cell to develop a new cell strain having a new phenotype, e.g., a new or modified pectate lyase activity, by modifying the genetic composition of the cell. The genetic composition can be modified by addition to the cell of a nucleic acid of the invention. To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using the pectate lyases of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

identity of all pathway substrates, products and intermediary metabolites identity of all the chemical reactions interconverting the pathway metabolites, the stoichiometry of the pathway reactions, identity of all the enzymes catalyzing the reactions, the enzyme reaction kinetics, the regulatory interactions between pathway components, e.g. allosteric interactions, enzyme-enzyme interactions etc, intracellular compartmentalization of enzymes or any other supramolecular organization of the enzymes, and, the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript (e.g., a pectate lyase message) or generating new (e.g., pectate lyase) transcripts in a cell. This increased or decreased expression can be traced by testing for the presence of a pectate lyase of the invention or by pectate lyase activity assays. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide (e.g., a pectate lyase) or generating new polypeptides in a cell. This increased or decreased expression can be traced by determining the amount of pectate lyase present or by pectate lyase activity assays. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

Industrial Applications

Detergent Compositions

The invention provides detergent compositions comprising one or more polypeptides (e.g., pectate lyases) of the invention, and methods of making and using these compositions. The invention incorporates all methods of making and using detergent compositions, see, e.g., U.S. Pat. Nos. 6,413,928; 6,399,561; 6,365,561; 6,380,147. The detergent compositions can be a one and two part aqueous composition, a non-aqueous liquid composition, a cast solid, a granular form, a particulate form, a compressed tablet, a gel and/or a paste and a slurry form. The pectate lyases of the invention can also be used as a detergent additive product in a solid or a liquid form. Such additive products are intended to supplement or boost the performance of conventional detergent compositions and can be added at any stage of the cleaning process.

The invention also provides methods capable of removing gross food soils, films of food residue and other minor food compositions using these detergent compositions. Pectate lyases of the invention can facilitate the removal of starchy stains by means of catalytic hydrolysis or trans-elimination of pectins, including the disruption of plant and bacterial cell walls. Pectate lyases of the invention can be used in dishwashing detergents in textile laundering detergents.

The actual active enzyme content depends upon the method of manufacture of a detergent composition and is not critical, assuming the detergent solution has the desired enzymatic activity. In one aspect, the amount of pectate lyase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the pectate lyases of the present invention are active in the pH ranges of from about 4 to about 12 and in the temperature range of from about 20° C. to about 95° C. The detergents of the invention can comprise cationic, semi-polar nonionic or zwitterionic surfactants; or, mixtures thereof.

Pectate lyases of the invention can be formulated into powdered and liquid detergents having pH between 4.0 and 12.0 at levels of about 0.01 to about 5% (preferably 0.1% to 0.5%) by weight. These detergent compositions can also include other enzymes such as proteases, cellulases, lipases or endoglycosidases, endo-beta.-1,4-glucanases, beta-glucanases, endo-beta-1,3(4)-glucanases, cutinases, peroxidases, laccases, amylases, glucoamylases, pectinases, reductases, oxidases, phenoloxidases, ligninases, pullulanases, arabinanases, hemicellulases, mannanases, xyloglucanases, xylanases, pectin acetyl esterases, rhamnogalacturonan acetyl esterases, polygalacturonases, rhamnogalacturonases, galactanases, pectin lyases, pectin methylesterases, cellobiohydrolases and/or transglutaminases. These detergent compositions can also include builders and stabilizers.

The addition of pectate lyases of the invention to conventional cleaning compositions does not create any special use limitation. In other words, any temperature and pH suitable for the detergent is also suitable for the compositions of the invention as long as the enzyme is active at or tolerant of the pH and/or temperature of the intended use. In addition, the pectate lyases of the invention can be used in a cleaning composition without detergents, again either alone or in combination with builders and stabilizers.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions.

In one aspect, the invention provides a method for washing an object comprising contacting the object with a polypeptide of the invention under conditions sufficient for washing. A pectate lyase of the invention may be included as a detergent additive. The detergent composition of the invention may, for example, be formulated as a hand or machine laundry detergent composition comprising a polypeptide of the invention. A laundry additive suitable for pre-treatment of stained fabrics can comprise a polypeptide of the invention. A fabric softener composition can comprise a pectate lyase of the invention. Alternatively, a pectate lyase of the invention can be formulated as a detergent composition for use in general household hard surface cleaning operations. In alternative aspects, detergent additives and detergent compositions of the invention may comprise one or more other enzymes such as a protease, a lipase, a cutinase, another pectate lyase, a carbohydrase, a cellulase, a pectinase, a mannanase, an arabinase, a galactanase, a xylanase, an oxidase, e.g., a lactase, and/or a peroxidase (see also, above). The properties of the enzyme(s) of the invention are chosen to be compatible with the selected detergent (i.e. pH-optimum, compatibility with other enzymatic and non-enzymatic ingredients, etc.) and the enzyme(s) is present in effective amounts. In one aspect, pectate lyase enzymes of the invention are used to remove malodorous materials from fabrics. Various detergent compositions and methods for making them that can be used in practicing the invention are described in, e.g., U.S. Pat. Nos. 6,333,301; 6,329,333; 6,326,341; 6,297,038; 6,309,871; 6,204,232; 6,197,070; 5,856,164.

When formulated as compositions suitable for use in a laundry machine washing method, the pectate lyases of the invention can comprise both a surfactant and a builder compound. They can additionally comprise one or more detergent components, e.g., organic polymeric compounds, bleaching agents, additional enzymes, suds suppressors, dispersants, lime-soap dispersants, soil suspension and anti-redeposition agents and corrosion inhibitors. Laundry compositions of the invention can also contain softening agents, as additional detergent components. Such compositions containing carbohydrase can provide fabric cleaning, stain removal, whiteness maintenance, softening, color appearance, dye transfer inhibition and sanitization when formulated as laundry detergent compositions.

The density of the laundry detergent compositions of the invention can range from about 200 to 1500 g/liter, or, about 400 to 1200 g/liter, or, about 500 to 950 g/liter, or, 600 to 800 g/liter, of composition; this can be measured at about 20° C.

The "compact" form of laundry detergent compositions of the invention is best reflected by density and, in terms of composition, by the amount of inorganic filler salt. Inorganic filler salts are conventional ingredients of detergent compositions in powder form. In conventional detergent compositions, the filler salts are present in substantial amounts, typically 17% to 35% by weight of the total composition. In one aspect of the compact compositions, the filler salt is present in amounts not exceeding 15% of the total composition, or, not exceeding 10%, or, not exceeding 5% by weight of the composition. The inorganic filler salts can be selected from the alkali and alkaline-earth-metal salts of sulphates and chlorides, e.g., sodium sulphate.

Liquid detergent compositions of the invention can also be in a "concentrated form." In one aspect, the liquid detergent compositions can contain a lower amount of water, compared to conventional liquid detergents. In alternative aspects, the water content of the concentrated liquid detergent is less than 40%, or, less than 30%, or, less than 20% by weight of the detergent composition. Detergent compounds of the invention can comprise formulations as described in WO 97/01629.

Treating Fibers and Textiles

The invention provides methods of treating fibers, fabrics or any pectate- or polygalacturonic acid-comprising material using one or more pectate lyases of the invention. The pectate lyases can be used in any fiber- or fabric-treating method, which are well known in the art, see, e.g., U.S. Pat. Nos. 6,261,828; 6,077,316; 6,024,766; 6,021,536; 6,017,751; 5,980,581; US Patent Publication No. 20020142438 A1. For example, pectate lyases of the invention can be used in fiber and/or fabric scouring. In one aspect, the feel and appearance of a fabric is improved by a method of the invention comprising contacting the fabric with a pectate lyase of the invention in a solution. In one aspect, the fabric is treated with the solution under pressure. For example, pectate lyases of the invention can be used in the removal of stains.

In one aspect, pectate lyases of the invention are applied during or after the weaving of textiles, or during the desizing stage, or during one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. After the textiles have been woven, a fabric can proceed to a desizing stage. This can be followed by one or more additional fabric processing steps. Desizing is the act of removing "size" from textiles. After weaving, the size coating must be removed before further processing the fabric in order to ensure a homogeneous and wash-proof result.

The enzymes of the invention can be used to scour fabrics or any pectate- or polygalacturonic acid-comprising material, including cotton-containing fabrics, as detergent additives, e.g., in aqueous compositions. For the manufacture of clothes, the fabric can be cut and sewn into clothes or garments. These can be finished before or after the treatment. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The invention provides methods of finishing denim garments, enzymatic desizing and providing softness to fabrics by using any combination of enzymes, such amylases, endoglucanases, and a pectate lyase of the invention.

In one aspect, an alkaline and thermostable amylase and pectate lyase are combined in a single bath desizing and bioscouring. Among advantages of combining desizing and scouring in one step are cost reduction and lower environmental impact due to savings in energy and water usage and lower waste production. Application conditions for desizing and bioscouring can be between about pH 8.5 to pH 10.0 and temperatures at about 40° C. and up. Low enzyme dosages (e.g., about 5 g per a ton of cotton) and short reaction times (e.g., about 15 minutes) can be used to obtain efficient desizing and scouring with out added calcium.

The pectate lyases of the invention can be used in combination with other carbohydrate degrading enzymes, e.g., cellulase, arabinanase, xyloglucanase, pectinase, xylanase, and the like, for the preparation of fibers or for cleaning of fibers. Proteases can also be used in combination. These can be used in combination with detergents. In one aspect, pectate lyases of the invention can be used in treatments to prevent the graying of a textile.

The pectate lyases of the invention can be used to treat any cellulosic material, including fibers (e.g., fibers from cotton, hemp, flax or linen), sewn and unsewn fabrics, e.g., knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, hemp, flax/linen, jute, cellulose acetate fibers, lyocell).

The textile treating processes of the invention (for example, scouring using pectate lyases of the invention) can be used in conjunction with other textile treatments, e.g., desizing and bleaching. Scouring is the removal of non-cellulosic material from the cotton fiber, e.g., the cuticle (mainly consisting of waxes) and primary cell wall (mainly consisting of pectin, protein and xyloglucan). A proper wax removal is necessary for obtaining a high wettability. This is needed for dyeing. Removal of the primary cell walls by the processes of the invention improves wax removal and ensures a more even dyeing. Treating textiles with the processes of the invention can improve whiteness in the bleaching process. The main chemical used in scouring is sodium, hydroxide in high concentrations and at high temperatures. Bleaching comprises oxidizing the textile. Bleaching typically involves use of hydrogen peroxide as the oxidizing agent in order to obtain either a fully bleached (white) fabric or to ensure a clean shade of the dye.

The invention provides a single-bath process for desizing, scouring and bleaching of cellulosic materials. In one aspect, desizing, scouring and bleaching are carried in a single-bath by contacting the cellulosic materials simultaneously or sequentially in a container (a "single-bath") with an enzyme system and a bleaching system comprising hydrogen peroxide or at least one peroxy compound which can generate hydrogen peroxide when dissolved in water, or combinations thereof, and at least one bleach activator. Cellulosic materials including crude fibers, yarn, or woven or knit textiles, made of cotton, linen, flax, ramie, rayon, hemp, jute, or blends of these fibers with each other or with other natural or synthetic fibers, can be treated by the processes of the invention.

The invention also provides alkaline pectinases (pectate lyases active under alkaline conditions). These have wide-ranging applications in textile processing, degumming of plant fibers (e.g., plant bast fibers), treatment of pectic wastewaters, paper making, and coffee and tea fermentations. See, e.g., Hoondal (2002) Applied Microbiology and Biotechnology 59:409-418.

Treating Foods and Food Processing

The pectate lyases of the invention have numerous applications in food processing industry. For example, in one aspect, the pectate lyases of the invention are used to improve the extraction of oil from oil-rich plant material, e.g., oil-rich seeds, for example, soybean oil from soybeans, olive oil from olives, rapeseed oil from rapeseed and/or sunflower oil from sunflower seeds.

The pectate lyases of the invention can be used for separation of components of plant cell materials. For example, pectate lyases of the invention can be used in the separation of pectin-rich material (e.g., cell walls), sugar or starch-rich plant material into components, e.g., sucrose from sugar beet or starch or sugars from potato, pulp or hull fractions. In one aspect, pectate lyases of the invention can be used to separate protein-rich or oil-rich crops into valuable protein and oil and hull fractions. The separation process may be performed by use of methods known in the art.

The pectate lyases of the invention can be used in the preparation of fruit or vegetable juices, syrups, extracts and the like to increase yield. The pectate lyases of the invention can be used in the enzymatic treatment (e.g., hydrolysis of pectins and/or polygalacturonic acid, such as 1,4-linked alpha-D-galacturonic acid) of various plant cell wall-derived materials or waste materials, e.g. from wine or juice production, or agricultural residues such as vegetable hulls, bean hulls, sugar beet pulp, olive pulp, potato pulp, and the like. The pectate lyases of the invention can be used to modify the consistency and appearance of processed fruit or vegetables. For example, the pectate lyases of the invention can be used in the production of clear juices, e.g., from apples, pears or berries; to cloud stable juices, e.g., from apples, pears, berries, citrus or tomatoes; and to treat purees, e.g., from carrots and tomatoes, and to treat date syrup (see, e.g., Sidhu (2002) Food Chemistry 79:215-220). In these processes, the pectate lyases of the invention can be used with other enzymes (e.g., cellulases, amylases, etc.) or other compositions. For example, in one aspect, pectinase and cellulase enzymes are used to improve juice yield, stability and quality from a fruit, e.g., prickly pear fruit. A pectinase of the invention can improve the yield, stability and color (color-assayed as release of anthocyanins or carotenoids) and clarity of a juice. In one aspect, a combination of pectinase and cellulase is used; pectinase at 0.50% v/w can produce a high yield, a sediment-free clear juice and high-quality juice. See, e.g., Essa, Hesham A., et. al., 2002, Nahrung, 46(4):245-250.

In one aspect, an enzyme or enzyme preparation of the invention is used for de-pectinization and viscosity reduction in vegetable and/or fruit juice, e.g., in apple or pear juices or other apple or pear food preparations (e.g., sauces). In one aspect, the fruit or vegetable juice is treated with an enzyme preparation of the invention in an amount effective for degrading pectin-containing material contained in the fruit or vegetable juice.

In one aspect, the enzyme or enzyme preparation is used in the treatment of mash from fruits and vegetables in order to improve the extractability or degradability of the mash. The enzyme preparation can be used in the treatment of mash from apples and pears for juice production, and in the mash treatment of grapes for wine production.

The pectate lyases of the invention can be used to treat plant material to facilitate processing of plant material, including foods, facilitate purification or extraction of plant components such as galactans, pectins and/or polygalacturonic acids. The pectate lyases of the invention can be used to purify pectins from citrus, improve feed value, decrease the water binding capacity, improve the degradability in waste water plants and/or improve the conversion of plant material to ensilage, and the like.

Animal Feeds and Food or Feed Additives

The invention provides methods for treating animal feeds and foods and food or feed additives using pectate lyases of the invention, animals including mammals (e.g., humans), birds, fish and the like. The invention provides animal feeds, foods, and additives comprising pectate lyases of the invention. In one aspect, treating animal feeds, foods and additives using pectate lyases of the invention can help in the availability of nutrients, e.g., starch, in the animal feed or additive. This can result in release of readily digestible and easily absorbed nutrients and sugars.

Pectate lyases of the present invention, in the modification of animal feed or a food, can process the food or feed either in vitro (by modifying components of the feed or food) or in vivo. Pectate lyases can be added to animal feed or food compositions containing high amounts of arabinogalactans or galactans, e.g. feed or food containing plant material from soy bean, rape seed, lupin and the like. When added to the feed or food the pectate lyase significantly improves the in vivo break-down of plant cell wall material, whereby a better utilization of the plant nutrients by the animal (e.g., human) is achieved. In one aspect, the growth rate and/or feed conversion ratio (i.e. the weight of ingested feed relative to weight gain) of the animal is improved. For example the indigestible galactan is degraded by a pectate lyase of the invention, e.g. in combination with beta-galactosidase, to galactose or galactooligomers. These enzyme digestion products are more digestible by the animal. Thus, they can contribute to the available energy of the feed. Also, by the degradation of galactan the pectate lyase of the invention can improve the digestibility and uptake of non-carbohydrate feed constituents such as protein, fat and minerals.

In another aspect, pectate lyase of the invention can be supplied by expressing the enzymes directly in transgenic feed crops (as, e.g., transgenic plants, seeds and the like), such as corn, soy bean, rape seed, lupin and the like. As discussed above, the invention provides transgenic plants, plant parts and plant cells comprising a nucleic acid sequence encoding a polypeptide of the invention. In one aspect, the nucleic acid is expressed such that the pectate lyase of the invention is produced in recoverable quantities. The pectate lyase e can be recovered from any plant or plant part. Alternatively, the plant or plant part containing the recombinant polypeptide can be used as such for improving the quality of a food or feed, e.g., improving nutritional value, palatability, and rheological properties, or to destroy an antinutritive factor.

Paper or Pulp Treatment

The pectate lyases of the invention can be in paper or pulp treatment or paper deinking. For example, in one aspect, the invention provides a paper treatment process using pectate lyases of the invention. In one aspect, the pectate lyases can be used to modify pectin and/or polygalacturonic acid, such as 1,4-linked alpha-D-galacturonic acid. In another aspect, paper components of recycled photocopied paper during chemical and enzymatic deinking processes. In one aspect, pectate lyases of the invention can be used in combination with cellulases. The paper can be treated by the following three processes: 1) disintegration in the presence of pectate lyases of the invention, 2) disintegration with a deinking chemical and pectate lyases of the invention, and/or 3) disintegration after soaking with pectate lyases of the invention. The recycled paper treated with pectate lyases can have a higher brightness due to removal of toner particles as compared to the paper treated with just cellulase. While the invention is not limited by any particular mechanism, the effect of pectate lyases of the invention may be due to its behavior as surface-active agents in pulp suspension.

The invention provides methods of treating paper and paper pulp using one or more pectate lyases of the invention. The pectate lyases of the invention can be used in any paper- or pulp-treating method, which are well known in the art, see, e.g., U.S. Pat. Nos. 6,241,849; 6,066,233; 5,582,681. For example, in one aspect, the invention provides a method for deinking and decolorizing a printed paper containing a dye, comprising pulping a printed paper to obtain a pulp slurry, and dislodging an ink from the pulp slurry in the presence of pectate lyases of the invention (other enzymes can also be added). In another aspect, the invention provides a method for enhancing the freeness of pulp, e.g., pulp made from secondary fiber, by adding an enzymatic mixture comprising pectate lyases of the invention (can also include other enzymes, e.g., cellulase, amylase or glucoamylase enzymes) to the pulp and treating under conditions to cause a reaction to produce an enzymatically treated pulp. The freeness of the enzymatically treated pulp is increased from the initial freeness of the secondary fiber pulp without a loss in brightness.

Repulping: Treatment of Lignocellulosic Materials

The invention also provides a method for the treatment of lignocellulosic fibers, wherein the fibers are treated with pectate lyases of the invention, in an amount which is efficient for improving the fiber properties. The pectate lyases of the invention may also be used in the production of lignocellulosic materials such as pulp, paper and cardboard, from starch-reinforced waste paper and cardboard, especially where repulping occurs at pH above 7 and where pectate lyases can facilitate the disintegration of the waste material through degradation of cell walls. The pectate lyases of the invention can be useful in a process for producing a papermaking pulp from starch-coated printed paper. The process may be performed as described in, e.g., WO 95/14807.

An exemplary process comprises disintegrating the paper to produce a pulp, treating with a pectin-degrading enzyme of the invention before, during or after the disintegrating, and separating ink particles from the pulp after disintegrating and enzyme treatment. See also U.S. Pat. No. 6,309,871 and other US patents cited herein. Thus, the invention includes a method for enzymatic deinking of recycled paper pulp, wherein pectate lyases are applied in an amount which is efficient for effective de-inking of the fiber surface.

Waste Treatment

The pectate lyases of the invention can be used in a variety of other industrial applications, e.g., in waste treatment. For example, in one aspect, the invention provides a solid waste digestion process using pectate lyases of the invention. The methods can comprise reducing the mass and volume of substantially untreated solid waste. Solid waste can be treated with an enzymatic digestive process in the presence of an enzymatic solution (including pectate lyases of the invention) at a controlled temperature. This results in a reaction without appreciable bacterial fermentation from added microorganisms. The solid waste is converted into a liquefied waste and any residual solid waste. The resulting liquefied waste can be separated from said any residual solidified waste. See e.g., U.S. Pat. No. 5,709,796.

Oral Care Products

The invention provides oral care product comprising pectate lyases of the invention. Exemplary oral care products include toothpastes, dental creams, gels or tooth powders, odontics, mouth washes, pre- or post brushing rinse formulations, chewing gums, lozenges, or candy. See, e.g., U.S. Pat. No. 6,264,925.

Brewing and Fermenting

The invention provides methods of brewing (e.g., fermenting) beer comprising pectate lyases of the invention. In one exemplary process, starch-containing raw materials are disintegrated and processed to form a malt. A pectate lyase of the invention is used at any point in the fermentation process. For example, pectate lyases of the invention can be used in the processing of barley malt. The major raw material of beer brewing is barley malt. This can be a three stage process. First, the barley grain can be steeped to increase water content, e.g., to around about 40%. Second, the grain can be germinated by incubation at 15 to 25° C. for 3 to 6 days when enzyme synthesis is stimulated under the control of gibberellins. In one aspect, pectate lyases of the invention are added at this (or any other) stage of the process. The action of pectate lyases results in an increase in fermentable reducing sugars. This can be expressed as the diastatic power, DP, which can rise from around 80 to 190 in 5 days at 12° C. Pectate lyases of the invention can be used in any beer or alcoholic beverage producing process, as described, e.g., in U.S. Pat. Nos. 5,762,991; 5,536,650; 5,405,624; 5,021,246; 4,788,066.

Other Industrial Applications

The invention also includes a method of increasing the flow of production fluids from a subterranean formation by removing a viscous, pectin-containing, damaging fluid formed during production operations and found within the subterranean formation which surrounds a completed well bore comprising allowing production fluids to flow from the well bore; reducing the flow of production fluids from the formation below expected flow rates; formulating an enzyme treatment by blending together an aqueous fluid and a polypeptide of the invention; pumping the enzyme treatment to a desired location within the well bore; allowing the enzyme treatment to degrade the viscous, pectin-containing, damaging fluid, whereby the fluid can be removed from the subterranean formation to the well surface; and wherein the enzyme treatment is effective to attack the pectin in cell walls.

The invention will be further described with reference to the following examples; however, it is to be understood that the invention is not limited to such examples.

EXAMPLES

Example 1

Pectate Lyase Activity Assays

The following example describes exemplary pectate lyase activity assays to determine the catalytic activity of a pectate lyase. These exemplary assays can be used to determine if a polypeptide is within the scope of the invention.

APSU Unit Viscosity Assay

APSU units: The APSU unit assay is a viscosity measurement using the substrate polygalacturonic acid with no added calcium.

The substrate 5% polygalacturonic acid sodium salt (Sigma P-1879) is solubilized in 0.1 M glycine buffer pH 10. The 4 ml substrate is preincubated for 5 min at 40° C. The enzyme is added (in a volume of 250 µl) and mixed for 10 sec on a mixer at maximum speed, it is then incubated for 20 min at 40° C. For a standard curve double determination of a dilution of enzyme concentration in the range of 5 APSU/ml to above 100 APSU/ml with minimum of 4 concentrations between 10 and 60 APSU per ml. The viscosity can be measured using a MIVI 600™ (Sofraser, Villemandeur, France). The viscosity can be measured as mV after 10 sec. The GRAFPAD PRISM™ Prism program, using a non linear fit with a one phase exponential decay with a plateau, can be used for calculations. The plateau plus span is the mV obtained without enzyme. See, e.g., U.S. Pat. No. 6,368,843.

Beta-elimination Assay

An exemplary lyase assay (at 235 nm) for the determination of the beta-elimination activity measures increases in absorbance at 235 nm. The substrate 0.1% polygalacturonic acid sodium salt (Sigma P-1879) is solubilized in 0.1 M Glycine buffer pH 10. For calculation of the catalytic rate an increase of 5.2 absorbency at 235 units per min corresponds to formation of 1 µmol of unsaturated product (see, e.g., Nasuna (1966) J. Biol. Chem. 241:5298-5306; Bartling (1995) Microbiology 141:873-881). Steady state condition is measured using a 0.5 ml cuvette with a 1 cm light path on a HP diode array spectrophotometer in a temperature controlled cuvette holder with continuous measurement of the absorbency at 235 nm. For steady state a linear increase for at least 200 sec can be used for calculation of the rate. It is used for converting pmol per min product. See, e.g., U.S. Pat. No. 6,368,843.

Agar Assay

Pectate lyase activity can be measured by an agar assay. A test solution is applied to 4 mm holes punched out in agar plates (e.g., LB agar), containing 0.7% w/v sodium polygalacturonate (Sigma P 1879). The plates are then incubated for 6 h at a particular temperature (e.g., 75° C.). The plates are then soaked in either (i) 1M $CaCl_2$ for 0.5 h or (ii) 1% mixed alkyl trimethylammonium Br (MTAB, Sigma M-7635) for 1 h. Both of these procedures cause the precipitation of polygalacturonate within the agar. Pectate lyase activity can be detected by the appearance of clear zones within a background of precipitated polygalacturonate. Sensitivity of the assay is calibrated using dilution of a standard preparation of pectate lyase.

Endpoint Analysis—Trans-elimination at 235 nm for Pectate Lyases (High Calcium Method: 1 mM Calcium in the Final Incubation Mixture). In this method, the substrate and enzyme is incubated for 20 min at 37° C. followed by measurement at 235 nm of the formation of double bounds. Finally, the rate of the degradation is calculated based on the molar extinction coefficient in terms of Trans Units.

Procedure: Mixing of 0.5 ml enzyme dilution with 0.5 ml substrate solution. Substrate: Polygalacturonic acid from Sigma P-1879 lot 77H3784. Buffer 2×0.1M Glycine pH 10+, 2.0 mmol $CaCl_2$, Stop reagent: 0.02 M $H_3PO_4$, Temperature of incubation 37° C., Reaction time 20 min. Extinction coefficient of the trans-elimination 0.0052 µmol $cm^{-1}$. Enzyme diluted in ion-free water to 0.5 to 5 APSU per ml. Main value in duplicate 0.5 ml. The 2% w/v substrate in 2×.buffer is mixed with 0.5 ml diluted enzyme. Both pre-incubated 5 min on water bath at 37° C. Incubate for 20 min. Stop using 5 ml stop reagent and mix. Blank mix enzyme and stop reagent first and then ad substrate all in the same volume.

| | |
|---|---|
| Enzyme | 0.5 ml |
| Substrate | 0.5 ml |
| Stop | 5 ml |
| Total volume | 6 ml |

Measure the absorbency at 235 nm in a 1 cm cuvette. Calculate the formation of trans-elimination per min using the extinction coefficient of 0.0052 µmol $cm^{-1}$. See, e.g., U.S. Pat. No. 6,368,843.

Example 2

Cotton Bio-Scouring Application Assay

The following example describes an exemplary Cotton Scouring Application Assay using the pectate lyase enzymes of the invention. Use of the pectate lyases of the invention to hydrolyze primary cell wall pectin ("bioscouring") can eliminate the need for caustics and high temperatures in cotton fiber scouring.

Materials/Preparation:
Requires 50 mM Sodium-Bicarbonate buffer at optimum pH
1:10 dilution of Calloway 1663 surfactant
50 mM Phosphate buffer pH 6
   Mix 43.3 mL of 1.0 M Na—P monobasic, 6.6 mL of 1.0 M Na—P dibasic, adjust volume to 1 L with D.I. water. Adjust pH to 6
Ruthenium Red (R-2751 SIGMA)
   Add 0.5 g of Ruthenium Red to the 1 L Phosphate Buffer producing a final concentration of 0.05%.
NaOAc (5 g/L pH 5)
Cotton fabric 400R (Testfabrics Inc.) which is desized prior scouring Scouring Procedure:
1. Place 1.0 g of desized cotton fabric (into each Labomat beaker).
2. Each experiment should use a blank, untreated cotton (no enzyme added).
3. Add 50 mL of 50 mM Sodium-Bicarbonate buffer at pH 8.5-9 to each beaker and 2.5 mL of 1:10 dilution of Calloway Surfactant 1663.
4. Tighten the lids using an Allen wrench and install the beakers into the Labomat. making sure that the beakers are distributed evenly on the rotary rack. Connect beaker 1 with the temperature detecting cable to the connector in the middle of the rack.
5. Ramp up the heat to the desired temperature and hold for 10 minutes.
6. Add 50-200 uL of enzyme (e.g., a pectate lyase of the invention) at a concentration previously diluted to 0.1 ug/uL through septum in the beaker using a syringe. Total enzyme concentration used to scour 1 gram cotton fabric can be between 5-20 ug.
7. Run the reaction in the Labomat at temperature for 15 minutes.
8. Rinse the cotton fabric twice by pouring the cotton fabric into the hand and squeezing the cotton dry, place the cotton back into the beaker and filling the beaker with D.I. water and repeating this step again, finish with squeezing the excess water out of the cotton.
9. Soak the cotton fabric in NaOAc (5 g/L pH 5) for 2 minutes.
10. Repeat the 2× rinse cycle in step 8.
11. Place the cotton fabric on weigh-boats and allow the fabric to dry overnight in the laminar flow biohoods.

Dyeing Procedure:
1. Place the treated cotton fabric in the Labomat beakers.
2. Add 100 mL of 0.05% Ruthenium Red, Na—P buffer pH 6 to each beaker.
3. Tighten the lids using an Allen wrench and install the beakers into the Labomat making sure that the beakers are distributed evenly on the rotary rack. Connect beaker 1 with the temperature detecting cable to the connector in the middle of the rack.
4. Ramp up the heat to 50° C. and hold for 30 minutes.
5. Rinse the fabric twice by pouring the cotton into the hand and squeezing the cotton dry, place the fabric back into the beaker and filling the beaker with D.I. water and repeating this step again, finish with squeezing the excess water out of the fabric.
6. Place the dyed fabric into the beaker and add 100 mL of D.I. water.
7. Tighten the lids using Allen wrench and install the beakers into the Labomat making sure that the beakers are distributed evenly on the rotary rack.
8. Ramp up the heat to 100° C. and hold for 10 minutes; cool the beakers down to 60° C.
9. Repeat the 2× rinse cycle in step 5.
10. Place the dyed fabric on weigh-boats and allow the fabric to dry overnight in the laminar flow biohoods.

Enzyme Scouring Quantification.
1. Calibrate the GretagMacbeth Color Eye 7000A by selecting the Color Eye Icon on the desk top of the computer.
2. Place the black lens over the orifice and hit enter when the program request the calibration of the negative thresh hold.
3. Place the white filter over the orifice and hit enter when the program request the calibration of the white balance.
4. Place the dry dyed fabric over the orifice and push F4 to read the fabric whiteness.
5. Record the L* number, turn the fabric over to read the other side and record the L* number. Compute the average L* number for each sample.
6. Graph the delta L for each cotton scoured sample by subtracting the samples L* number with the untreated fabric L*.

Example 3

A Single-bath Process for Desizing and Scouring

The following example describes an exemplary single-bath process for desizing and scouring. The invention provides methods and compositions for desizing, scouring and bleaching of cellulosic materials by contacting the cellulosic materials simultaneously or sequentially in a single-bath process with an enzyme system comprising a pectate lyase of the invention. The single-bath process can further comprise a bleaching system comprising hydrogen peroxide or at least one peroxy compound which generates hydrogen peroxide when dissolved in water, or combinations thereof, and at least one bleach activator.

Cellulosic materials including crude fibers, yarn, or woven or knit textiles, made of cotton, linen, flax, ramie, rayon, hemp, jute, or blends of these fibers with each other or with other natural or synthetic fibers, can be treated by this single-bath process of the invention. In one aspect, a fabric weighing is loaded into a container, which is subsequently filled with a buffer solution (e.g., 20 mM Na phosphate buffer, pH 9.2) comprising a pectate lyase of the invention (e.g., 3000 APSU/kg-fiber of pectate lyase), wetting agent (e.g., 0.5 g/L), $H_2O_2$ (e.g., 1.7 g/L) and stabilizer (e.g., 0.75 g/L). The fabric can be treated, e.g., at 55° C. for about 15 min, after which temperature was raised at 5° C./min to 70° C. for 1 h. The fabric is then washed thoroughly with water to remove the residual chemicals and dried at room temperature overnight.

Example 4

Assay for Detecting Thermotolerant Enzymes

The following example describes an exemplary assay for detecting thermotolerant enzymes that can be used to determine if an enzyme is within the scope of the invention. This example describes an absorbance based screening ("discovery) assay for detecting thermotolerant enzymes, which, in one aspect, can be characterized as "up-mutants" from a "parental" pectate lyase gene. This exemplary protocol can be used for variants, or mutants, generated by either the GSSM™ or combinatorial methods.

Materials and Preparations
  a. Polygalacturonic Acid (PGA), and 2% [Sigma P-3889]
  b. UV (friendly) 96 Well Flat Bottom Plates [Thomson Instrument 931801 B]
  c. COSTAR 96 Well Plates
  d. Adhesive PCR Foil Seals [Marsh AB-0626]
  e. B-PER [PIERCE 78248]
  f. LBamp100 or LBcarb100
  g. TRIS pH 8.0 (250 mM, 10×)
  h. Glycine (250 mM, 10×)
  i. 0.2% Polygalacturonic Acid Substrate for enzyme activity detection: 100 mL of each of the following: 10× Tris, 10× Glycine, and 2% PGA, plus 700 mL of holy water.
  j. Plates: aliquot 200 µL of medium, LBamp100 or LBcarb100, into the wells of both the COSTAR and the UV friendly 96 well flat bottom plates Colony Picking and Plate Replication GSSM™ or combinatorial mutant clones colonies were picked with an Autogen (Framingham, Mass.) colony picker and the cells were inoculated into LBamp 100 medium. A total of 168 GSSM™ clones were screened per residue site or 13,000 clones from the combinatorial library 2328 were screened. The mutated clones were picked into rows A, B, C, E, F, G, and H of the 96 well plate. Wild Type (wt) clone (SEQ ID NO:132, encoded by SEQ ID NO:131) were picked into row D as a control. After completing the colony picking, the plates were incubated overnight (approximately 18 hrs) at 37° C., shaking at 150 RPM. These plates will be referred to as the master plates from now on.

Copies of each master plate were made into UV friendly plates (now called "assay plates") using the automated plate replicator. Once replication was complete, the assay plates were placed in a humidified 30° C. incubator overnight.

Primary Assay

Figure 8:
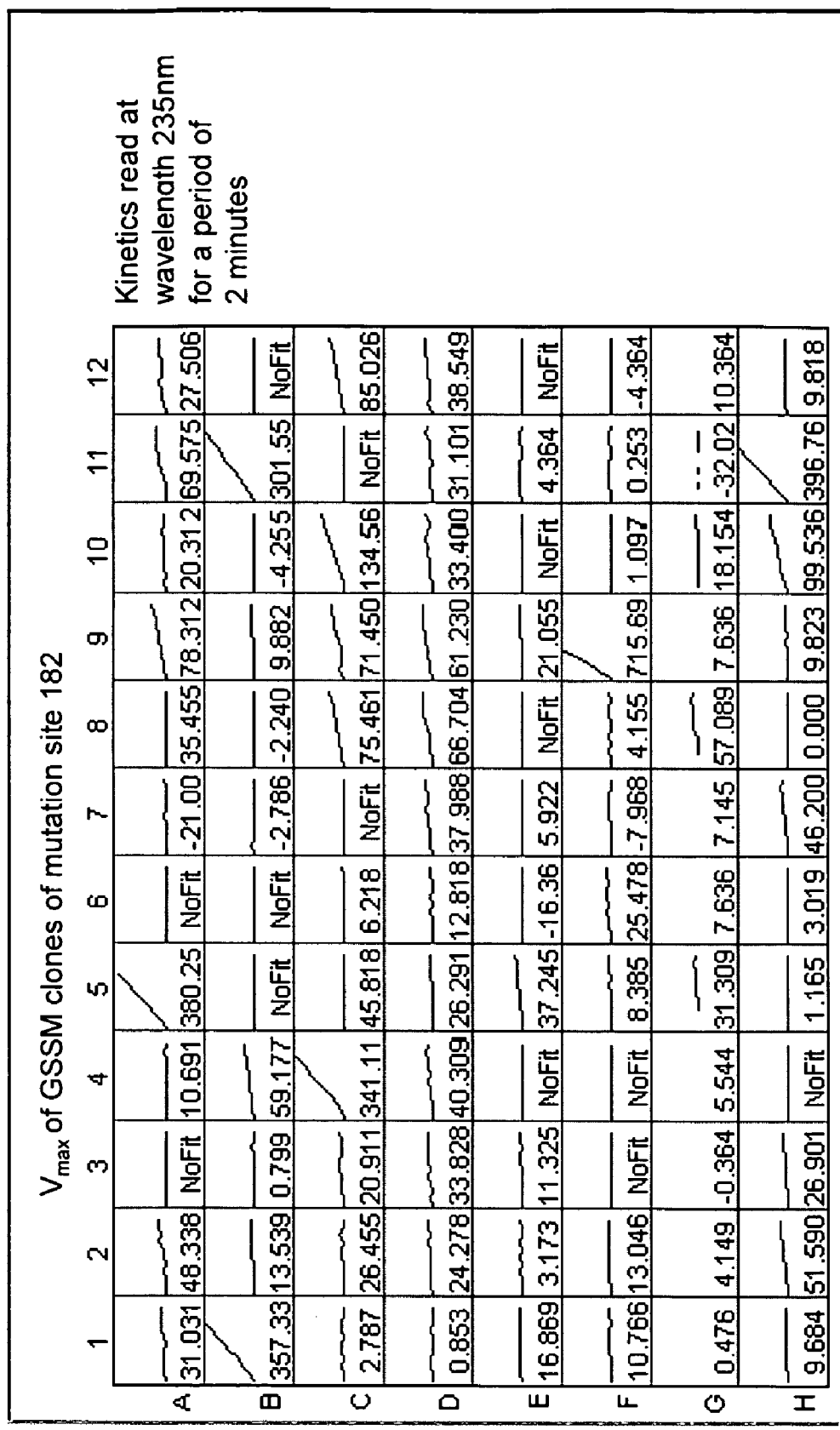
FIG. 8 summarizes data from activity assays of exemplary thermotolerant enzymes of the invention, as described in Example 4, below.

Cell densities in each well of all plates were determined at $OD_{600}$ using a SPECTRAMAX™ (Molecular Devices Corporation, Sunnyvale Calif.) system. All assay plates were then sealed with PCR Foil Seals and then spun at 2200 rpm in an Eppendorf centrifuge for 10 minutes. Using the Power-Washer system, the supernatant was then aspirated out of the assay plates leaving only the cells behind. 20 µL of B-PER™ (Pierce Biotechnology, Rockford, Ill.) was then added to each well and the assay plates were resealed. The plates were then placed on a plate shaker for 10 minutes in order to ensure proper cell lyses. The plates were then placed in an incubator preheated to 50° C. for 50 minutes for the GSSM™ assay or 70° C. for 25 minutes for the combinatorial up-mutant assay. The assay plates were then removed from the incubator after the proper heat challenge time and quickly cooled to room temperature. The SPECTRAMAX™ was used to read kinetics at wavelength 235 nm over a 2 minute period. Any putative hit that performed better that wild type was broken out for a secondary assay. FIG. 8 illustrates a residue with multiple positive hits. In FIG. 8, Row D contains the residual activity of the wild type (wt), SEQ ID NO:132, and rows A, B, C, E, F, G, H are the GSSM™ clones of mutation site 182.

Secondary Assay

All wells that showed an improved enzymatic rate compared to the wild type performance were identified and the clones from the respective master plate were broken out. Using aseptic techniques, a sterile toothpick was used in the well of a putative hit from the master plate. Cells adhering to the toothpick were transferred to a new plate selecting a new well with 200 µL LBamp100. Also, in the same manner, row D was filled with WT for each break out plate. The secondary master plates were placed in the 30° C. humidified incubator overnight. The secondary master plates were then pin tooled into UV friendly 96 well plates. The secondary assay plates were then placed in a 30° C. humidified incubator overnight. Cell densities in each well of all plates were determined at $OD_{600}$ using the SpectraMax systems. All assay plates were then sealed with PCR Foil Seals and then spun at 2200 rpm in an Eppendorf Centrifuge for 10 minutes. The remaining steps of the secondary assay were the same as indicated for the primary assay. Any confirmed hits that performed better that wild type were broken out and tested again in the tertiary assay.

Tertiary Assay

5 µL of culture from wells that confirmed improved thermotolerance activity from the wild type clone were aliquotted onto a small LBcarb100 petri dish to make streak plates. 5 µL of one of the control "wild type" (wt) (SEQ ID NO:132, encoded by SEQ ID NO:131) wells was also used to make a streak plate. The streak plates were incubated at 37° C. overnight. A small section of an individual colony was scraped and the cells were inoculated 5 mL of LBcarb100. The culture was allowed to grow overnight at 37° C. at 200 RPM. The confirmed hit was then diluted to $OD_{600}$=0.2. 200 µL of a confirmed clone was aliquotted into a well, filling an entire row on the 96 well UV friendly plate. The same was done for a wt control. All plates were then sealed and spun at 2000 rpm in the Eppendorf Centrifuge for 10 minutes. The remaining steps of the tertiary assay were the same as indicated for the primary assay. At the end, all putative hits that performed better that wild type were sent for sequencing. Glycerol stocks were also prepared.

Example 5

Processes and Formulations for Enzymes of the Invention

The following example describes exemplary processes (e.g., a bioscouring process) and formulations of the invention. Compositions and processes of the invention were tested using the exemplary pectate lyase having a sequence as set forth in SEQ ID NO:134, encoded by, e.g., SEQ ID NO:133 ("SEQ ID NO:134").

Definition of Unit:

Pectate lyase activity (of SEQ ID NO: 134) was routinely measured using 0.2% (w/v) polygalacturonic acid (Sigma, P3850) in 25 mM Tris HCl-25 mM Glycine NaOH buffer. One unit of enzyme activity was defined as the amount of protein that produced 1 μmol of unsaturated oligogalacturonides per minute equivalent to 1 μmol of unsaturated digalacturonide, using molecular extinction coefficient value of 4600 $M^{-1}cm^{-1}$ at 235 nm for dimer.

SpectraMax instrumentation in 96-well UV plates was used.

Formulation Strength:

The enzymes of the invention can be formulated in any dosage to suit a particular need; assays for determining the optimal dosage for any particular formulation are known in the art, and several are described herein. In alternative aspects, formulations of the invention can have a low strength of between about 2000 to 4000 u/ml (where u=unit). This is comparable to the other products on the market. In one aspect, the formulation minimum is about 1000 u/ml, and, in another aspect, the formulation maximum is about 10,000 u/ml, e.g., the formulation can comprise an enzyme of the invention in an amount of between about 1000 u/ml and 10,000 u/ml.

Solubility studies with lyophilized product (SEQ ID NO:134) resuspended in water indicated that the solubility of the enzyme can be as high as 25000 u/ml at 4° C. Therefore, in one aspect, the invention provides formulations having a level as high as about 25000 u/ml, or more. In one aspect the invention provides formulations comprising an enzyme of the invention in an amount of between about 100 u/ml and 25000 u/ml, 30000 u/ml, 35000 u/ml or 40000 u/ml, or more.

Formulation Design:

The invention provides formulations comprising at least one enzyme of the invention, and, in alternative aspects, further comprising any additive(s). Formulations of the invention can be based on known additives in other, e.g., analogous, enzyme formulations. For example, formulations of the invention can comprise the additives and/or conditions set forth in Tables 3, 4, 5 and 6, below, or any variation thereof. For example, formulations of the invention can comprise glycerol, sucrose, sodium chloride, dextrin, propylene glycol, sorbitol, sodium sulphate or TRIS, or an equivalent.

In one aspect, a formulation of the invention can be a water based formulation, or, an oil-based formulation.

Two phases of formulation stability studies were conducted; these studies used the exemplary enzyme SEQ ID NO:134:

Accelerated Stability Study at 37° C.
Note: these are buffer based formulations.
Screen various additives
Test different pH values
Formulations at approximately 2000 u/ml.
SEQ ID NO:134 was the exemplary enzyme tested

TABLE 3

(SN = sample number)

| SN | pH | Glycerol | Sucrose | Sodium chloride | Dextrin | Propylene glycol | sorbitol | Sodium sulphate | Effective TRIS Conc. |
|---|---|---|---|---|---|---|---|---|---|
| 1 | 5 | | | | | | | | 40 mM |
| 2 | 6 | | | | | | | | 40 mM |
| 3 | 7 | | | | | | | | 40 mM |
| 4 | 8 | | | | | | | | 40 mM |
| 5 | 7.5 | 35% | | | | | | | 20 mM |
| 6 | 7.5 | 50% | | | | | | | 20 mM |
| 7 | 7.5 | | 35% | | | | | | 20 mM |
| 8 | 7.5 | | | 20% | | | | | 20 mM |
| 9 | 7.5 | | | | 10% | | | | 20 mM |
| 10 | 7.5 | | | | | 30% | | | 20 mM |
| 11 | 7.5 | | | | | | | 100 mM | 20 mM |
| 12 | 7.5 | | | | | | 35% | | 20 mM |
| 13 | 5.5 | 35% | | | | | | | 40 mM |
| 14 | 5.5 | 50% | | | | | | | 40 mM |

Best performing formulations (using SEQ ID NO:134 as an exemplary enzyme of the invention) based on physical appearance and retention of greater than 80% activity:

TABLE 4

| Formulation | Additive |
|---|---|
| 1 | pH 5.0, 40 mM TRIS |
| 3 | pH 7.0, 40 mM TRIS |
| 4 | pH 8.0, 40 mM TRIS |
| 6 | pH 7.5, 50% glycerol |
| 8 | pH 7.5, 20% NaCl |
| 10 | pH 7.5, 30% propylene glycol |
| 11 | pH 7.5, 100 mM sodium sulfate |
| 13 | pH 5.5, 35% glycerol |

In alternative aspects, the formulations of the invention can be at approximately 10,000 u/ml, or in an amount of between about 100 u/ml, 200 u/ml, 300 u/ml, 400 u/ml or 500 u/ml and 10,000 u/ml, 15,000 u/ml, 20,000 u/ml, 25000 u/ml, 30000 u/ml, 35000 u/ml or 40000 u/ml, or more. In alternative aspects, the formulations of the invention can be at approximately 500 to 30,000 units/ml, 1000 to 25,000 units/ml, or, between about 1000 to 20,000 units/ml, 1000 to 15,000 units/ml, 1000 to 10000 units/ml, 1000 to 5000 units/ml, between about 2000 to 20000 units/ml, between about 2000 to 15000 units/ml, between about 2000 to 10000 units/ml, or between about 2000 to 4000 units/ml. In alternative aspects, the formulations of the invention can comprise a water-based formulation, e.g., when no buffer is feasible; any water-based buffer system can be used.

For example, the invention provides formulations comprising at least one enzyme of the invention and comprising a buffer (formulation) of: pH 7, 35% glycerol, 0.1% sodium benzoate, 0.1% potassium sorbate; pH 7, 35% glycerol, 300 ppm proxel; pH 7, 10% sodium chloride, 25% glycerol, 0.1% sodium benzoate, 0.1% potassium sorbate; pH 7, 10% sodium chloride, 25% glycerol, 300 ppm proxel; pH 5.5, 35% glycerol, 0.1% sodium benzoate, 0.1% potassium sorbate; pH 5.5,

TABLE 5

PECTATE LYASE FORMULATION STABILITY STUDY PHASE II

| Formulation No. | pH | Buffer | ADDITIVES | | |
|---|---|---|---|---|---|
| 1 | pH 7.0 | NA | | | 0.1% sodium benzoate, 0.1% potassium sorbate |
| 2 | pH 7.0 | NA | | | 300 ppm proxel |
| 3 | pH 7.0 | NA | sodium chloride 15% | | 0.1% sodium benzoate, 0.1% potassium sorbate |
| 4 | pH 7.0 | NA | sodium chloride 15% | | 300 ppm proxel |
| 5 | pH 7.0 | NA | | glycerol 35% | 0.1% sodium benzoate, 0.1% potassium sorbate |
| 6 | pH 7.0 | NA | | glycerol 35% | 300 ppm proxel |
| 7 | pH 7.0 | NA | sodium chloride 10% | glycerol 25% | 0.1% sodium benzoate, 0.1% potassium sorbate |
| 8 | pH 7.0 | NA | sodium chloride 10% | glycerol 25% | 300 ppm proxel |
| 9 | pH 5.5 | NA | | | 0.1% sodium benzoate, 0.1% potassium sorbate |
| 10 | pH 5.5 | NA | | | 300 ppm proxel |
| 11 | pH 5.5 | NA | sodium chloride 15% | | 0.1% sodium benzoate, 0.1% potassium sorbate |
| 12 | pH 5.5 | NA | sodium chloride 15% | | 300 ppm proxel |
| 13 | pH 5.5 | NA | | glycerol 35% | 0.1% sodium benzoate, 0.1% potassium sorbate |
| 14 | pH 5.5 | NA | | glycerol 35% | 300 ppm proxel |
| 15 | pH 5.5 | NA | sodium chloride 10% | glycerol 25% | 0.1% sodium benzoate, 0.1% potassium sorbate |
| 16 | pH 5.5 | NA | sodium chloride 10% | glycerol 25% | 300 ppm proxel |
| CONTROLS | | | | | |
| 17 | pH 7.0 | TRIS | | glycerol 35% | 0.1% sodium benzoate, 0.1% potassium sorbate |
| 18 | pH 5.5 | TRIS | | glycerol 35% | 0.1% sodium benzoate, 0.1% potassium sorbate |
| 19 | pH 7.0 | Acetate | | glycerol 35% | 0.1% sodium benzoate, 0.1% potassium sorbate |
| 20 | pH 5.5 | Acetate | | glycerol 35% | 0.1% sodium benzoate, 0.1% potassium sorbate |

Additional buffers that can be used in a formulation of the invention: 20 mM MOPS, pH 7 or 25 mM MOPS, 50 mM NaCl, pH 7.5.

Best performing formulations (using SEQ ID NO:134 as an exemplary enzyme of the invention) based on physical appearance and retention of greater than 80% activity:

TABLE 6

| Formulation No | Details |
|---|---|
| 5 | pH 7, 35% glycerol, 0.1% sodium benzoate, 0.1% potassium sorbate |
| 6 | pH 7, 35% glycerol, 300 ppm proxel |
| 7 | pH 7, 10% sodium chloride, 25% glycerol, 0.1% sodium benzoate, 0.1% potassium sorbate |
| 8 | pH 7, 10% sodium chloride, 25% glycerol, 300 ppm proxel |
| 13 | pH 5.5, 35% glycerol, 0.1% sodium benzoate, 0.1% potassium sorbate |
| 14 | pH 5.5, 35% glycerol, 300 ppm proxel |
| 15 | pH 5.5, 10% sodium chloride, 25% glycerol, 0.1% sodium benzoate, 0.1% potassium sorbate |
| 20* | 20 mM acetate buffer, pH 5.5, 35% glycerol |

35% glycerol, 300 ppm proxel; pH 5.5, 10% sodium chloride, 25% glycerol, 0.1% sodium benzoate, 0.1% potassium sorbate; or, 20 mM acetate buffer, pH 5.5, 35% glycerol; 20 mM MOPS, pH 7 or 25 mM MOPS, 50 mM NaCl, pH 7.5; pH 5.0, 40 mM TRIS; pH 7.0, 40 mM TRIS; pH 8.0, 40 mM TRIS; pH 7.5, 50% glycerol; pH 7.5, 20% NaCl; pH 7.5, 30% propylene glycol; pH 7.5, 100 mM sodium sulfate; pH 5.5, 35% glycerol; or, any combination thereof, or, with equivalents thereof.

Exemplary Bioscouring Application

In one aspect, pH is pH 8.5 (bicarbonate buffer)

Non-ionic wetting agent (1 g/L) [e.g.: Apollowet NFW]

Liquor ratio in the enzyme bath: 10:1 to 50:1 (L liquor:kg fabric)

Enzyme dose: 0.137 ml of the concentrated extract per kg of fabric

Temperature range: between about 50° C. to 70° C.

Treatment time about 20 min

Chelants should be excluded from the enzyme bath, and should only be added after 20 minutes of enzyme treatment and retained for 10 minutes before discharging bath Thus, in the invention provides a bioscouring process using at least one enzyme of the invention comprising at least one, several or all of the following steps/limitations: pH is pH 8.5, in bicarbonate buffer, comprising a non-ionic wetting agent (at, e.g., 1 g/L), where the liquor ratio in the enzyme bath is between about 10:1 to 50:1 (L liquor:kg fabric), where the enzyme dose is between about 0.1 and 0.2 ml, e.g., at about 0.137 ml of the concentrated extract per kg of fabric, at a temperature range: between about 50° C. to 70° C.; with a treatment time about 20 min; and, in one aspect, comprising chelants, which should be excluded from the enzyme bath and should only be added after 20 minutes of enzyme treatment and retained for 10 minutes before discharging bath.

The enzyme SEQ ID NO:134 performed well in the range of 5 to 25 grams of pure enzyme per ton of treated fabric.

A number of embodiments of the invention have been described. Nevertheless, it will be understood that various modifications may be made without departing from the spirit and scope of the invention. Accordingly; other embodiments are within the scope of the following claims.

What is claimed is:

1. An isolated, synthetic or recombinant nucleic acid molecule comprising
    (a) a nucleic acid sequence having at least 95%, 96%, 97%, 98%, 99%, or more, or 100% sequence identity to SEQ ID NO:77 or SEQ ID NO:131 and encoding a polypeptide having pectate lyase (EC 4.2.2.2) activity, or enzymatically active fragments thereof;
    (b) a nucleic acid sequence comprising the sequence SEQ ID NO:77 or SEQ ID NO:131 and encoding a polypeptide having pectate lyase (EC 4.2.2.2) activity, or an enzymatically active fragment thereof;
    (c) a nucleic acid sequence encoding a polypeptide having pectate lyase (EC 4.2.2.2) activity, wherein the polypeptide has at least 95%, 96%, 97%, 98%, 99%, or more, or 100% sequence identity to SEQ ID NO:78 or SEQ ID NO:132, or an enzymatically active fragment thereof;
    (d) a nucleic acid sequence encoding a polypeptide having pectate lyase (EC 4.2.2.2) activity, wherein the polypeptide has the sequence SEQ ID NO:78 or SEQ ID NO:132, or an enzymatically active fragment thereof;
    (e) the nucleic acid sequence of (c) or (d) further comprising a heterologous sequence encoding a signal sequence, a catalytic domain, and/or prepro domain from a different pectate lyase operably linked to the nucleic acid sequence or encoding a signal sequence and/or prepro domain from a non-pectate lyase protein linked to the nucleic acid sequence;
(f) a sequence complementary to the full-length nucleic acid of (a), (b), (c), (d), or (e).

2. The isolated, synthetic or recombinant nucleic acid of claim 1, wherein the pectate lyase activity comprises the breakup or dissolution of a plant fiber or a plant cell wall; beta-elimination (trans-elimination) cleavage of pectin, polygalacturonic acid (pectate), 1,4-linked alpha-D-galacturonic acid, and/or methyl-esterified galacturonic acid; and/or catalyzes the random cleavage of alpha-1,4-glycosidic linkages in pectic acid (polygalacturonic acid).

3. An isolated, synthetic or recombinant nucleic acid, comprising:
(a) a polynucleotide sequence that hybridizes under stringent conditions to the complete complement of a nucleic acid comprising SEQ ID NO:77 or SEQ ID NO:131,
wherein the polynucleotide sequence encodes a polypeptide having a pectate lyase activity and,
wherein the stringent conditions include a wash step comprising a wash in 0.2.times SSC at a temperature of about 65 degrees C. for about 15 minutes, or
(b) a nucleic acid sequence complementary to the full-length sequence of (a).

4. A nucleic acid probe for identifying a nucleic acid encoding a polypeptide with a pectate lyase activity, wherein the probe comprises at least 75, 100, 150, 200, 300, 400 or 500 consecutive bases of SEQ ID NO:77 or SEQ ID NO:131,
wherein the probe identifies the nucleic acid by binding or hybridization under stringent conditions, wherein the stringent conditions include a wash step comprising a wash in 0.2 times SSC at a temperature of about 65 degrees C. for about 15 minutes.

5. An amplification primer sequence pair for amplifying a nucleic acid encoding a polypeptide having a pectate lyase activity, wherein the primer pair is capable of amplifying the nucleic acid molecule of claim 1 or claim 3, or a fragment thereof encoding a polypeptide with pectate lyase activity.

6. An expression cassette comprising a nucleic acid comprising the nucleic acid molecule as set forth in claim 1 or claim 3.

7. A vector or cloning vehicle comprising a nucleic acid comprising the nucleic acid molecule as set forth in claim 1 or claim 3.

8. A transformed cell comprising a nucleic acid comprising the nucleic acid molecule as set forth in claim 1 or claim 3.

9. An antisense oligonucleotide consisting of a nucleic acid sequence complementary to or capable of hybridizing under stringent conditions to the nucleic acid sequence of claim 1 or claim 3, or a fragment thereof
wherein the stringent conditions include a wash step comprising a wash in 0.2 times SSC at a temperature of about 65 degrees C. for about 15 minutes.

10. A double-stranded inhibitory RNA (RNAi) molecule comprising a fragment of the nucleic acid sequence of claim 1 or claim 3.

11. An array comprising the nucleic acid molecule of claim 1 or claim 3, wherein the nucleic acid molecule is immobilized.

12. A method of producing a recombinant polypeptide comprising the steps of:
(a) providing a nucleic acid operably linked to a promoter, wherein the nucleic acid comprises the nucleic acid molecule of claim 1 or claim 3; and
(b) expressing the nucleic acid of step (a) under conditions that allow expression of the encoded polypeptide, thereby producing the recombinant polypeptide.

13. A method for overexpressing a recombinant pectate lyase in a cell
wherein, the method comprises expressing a vector comprising the nucleic acid molecule of claim 1 or claim 3,
wherein, overexpression is achieved by use of a high activity promoter, a dicistronic vector, or by gene amplification of the vector.

14. The isolated, synthetic or recombinant nucleic acid molecule of claim 1, wherein the pectate lyase activity is exo-acting or endo-acting.

15. The isolated, synthetic or recombinant nucleic acid molecule of claim 1, wherein the pectate lyase activity is thermostable or thermotolerant.

16. The isolated, synthetic or recombinant nucleic acid molecule of claim 1, wherein the nucleic acid sequence has at least 95% sequence identity to SEQ ID NO: 77 or SEQ ID NO: 131 and encodes a polypeptide having pectate lyase activity.

17. The isolated, synthetic or recombinant nucleic acid molecule of claim 1, wherein the nucleic acid sequence has at least 97% sequence identity to SEQ ID NO: 77 or SEQ ID NO: 131 and encodes a polypeptide having pectate lyase activity.

18. The isolated, synthetic or recombinant nucleic acid molecule of claim 1, wherein the nucleic acid sequence has at least 98% sequence identity to SEQ ID NO: 77 or SEQ ID NO: 131 and encodes a polypeptide having pectate lyase activity.

19. The isolated, synthetic or recombinant nucleic acid molecule of claim 1, wherein the nucleic acid sequence has at least 99% sequence identity to SEQ ID NO: 77 or SEQ ID NO: 131 and encodes a polypeptide having pectate lyase activity.

* * * * *

SEQUENCE LISTING

<160> NUMBER OF SEQ ID NOS: 134

<210> SEQ ID NO 1
<211> LENGTH: 1917
<212> TYPE: DNA
<213> ORGANISM: Unknown
<220> FEATURE:
<223> OTHER INFORMATION: Obtained from an environmental sample

<400> SEQUENCE: 1

```
gtgtctctct ttagaaaact cgcactgctg gttctgtgcg gtctactgct ttctgtcgga      60
gcagaaaccc gagcgtcgaa gcgaattgtc gtggccgctg atggatcggg tgacgtcagg     120
acaattcaac aagcggtgga ccaggttccc aaagacaata cacacccggt cttgattcag     180
atcaaaccgg gtgtgtatca ggaacaggtg cgtgtcgccg ccggcaaacg ctttatcact     240
tttcgcggcg acgatgcgag caagaccgtc atcacctatc gattgagcgc actgcaagcg     300 ggaaatacccc ggctggcatt caccaccttc gttaatgcag acgactttcg cgccgagaac     360
ctgacgtttg aaaactcctt cggcaccggt tcacaagcgg ttgctttgtt tgtcgatgcg     420
gaccgcgcga cgtttgaaaa ctgccggttc ctcggttggc aggacacttt gtttgtgaac     480
ggcagccgcc acttcttcaa agactgctac gtcgaaggcc acgtcgattt cattttcggc     540
acggcctccg ccgtgtttga gaactgcacc attcacagca aaggcgaagg ttatgtgacc     600
gcacactatc gcaccagcga tgagatggat accggttttg tctttcatcg ttgtcgtttg     660
accggacgag acacgggccg cggagtttat ctcggaaggc cttggcgacc ttacgcgcgc     720
gtcgtcttta tcgattgctg gctggacgca cacatcagac ctgaaggctg ggataattgg     780
agagatcctg aacgagagaa gaccgcgtgg tttgccgagt acaagtcaaa agggcccggt     840
gctaatcccg tagctcgtgt cgcgtggtcc aggcagttga cgacagaaca agccgccgag     900
ttttcgcggg aacgcttttt cagccgcgct gttcgcgggc tctctgggca ggccaaccag     960
gcagtcggaa cgatcgcgtg ggacgatgcg cagaaaaaac cgaacgagtg gtatgcgagc    1020
gccgaggcgt tgcgcattgc cgacaacgtt gttctttatc aacgtgactc cggcggttgg    1080
cccaagaaca tcgacatggg gaagccgctc gacgaaaagg gtcgagccgg tcttctgcgc    1140
gtgcgtaaga agaacgattc cacgatcgac aatggcgcga cttacacgca actctcgttt    1200
ctggcgcggg tttacacggc gcaaaagcag gagcggcatc gcgagtcgtt tctgaaggga    1260
ctcgattacc tgttgaaggc gcagtatcca aacggaggct ggccgcagtt ctatcccaac    1320
ctcaacggct attacaaaca catcactttc aacgacaacg ccatgatcgg cgtgatgaaa    1380
ctgctgcgcg acgtagcgac agcgaaaccg gcgtatgcgt tcgtcgacga agcacgacgg    1440
acgagtgcgg cgaaggcggt cgaaaaagga atcgagtgca tactgaagac gcaggtggtt    1500
gtgaatggcc ggcgcaccgt gtggtgtgcg caacatgacg aagtcacgct cgcgcctgcc    1560
```

-continued

```
ccggcgagga cgtttgaatt agtttcgctg agtggtggtg aaagcgttga gatcgtgcgc    1620
tttttgatgt cgatcaagaa cccgtcgccg gcggttgtcg aggcgatcga gtcggcggtt    1680
gcgtggttcg agcaatcgca agtgaaagat cccgccggca aacctgcgtg ggcgcgattt    1740
tatgagatcg gcactaatcg tccgatcttc gccgggcgtg acggcgtcgt taagtatgat    1800
gtgaaacaga tcgatgagga acgacgaaag aattacgcat ggtacgttga cgacgcagcg    1860
aaactactga aaccgacta tcctgagtgg aaagaaaaga acgccaaaga tcaatga       1917
```

```
<210> SEQ ID NO 2
<211> LENGTH: 638
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(21)
<220> FEATURE:
<221> NAME/KEY: DOMAIN
<222> LOCATION: (28)...(308)
<223> OTHER INFORMATION: Pectin methyl esterase domain
<220> FEATURE:
<221> NAME/KEY: DOMAIN
<222> LOCATION: (309)...(638)
<223> OTHER INFORMATION: Catalytic domain

<400> SEQUENCE: 2
```

Met Ser Leu Phe Arg Lys Leu Ala Leu Leu Val Leu Cys Gly Leu Leu
 1               5                  10                  15

Leu Ser Val Gly Ala Glu Thr Arg Ala Ser Lys Arg Ile Val Val Ala
            20                  25                  30

Ala Asp Gly Ser Gly Asp Val Arg Thr Ile Gln Gln Ala Val Asp Gln
        35                  40                  45

Val Pro Lys Asp Asn Thr His Pro Val Leu Ile Gln Ile Lys Pro Gly
    50                  55                  60

Val Tyr Gln Glu Gln Val Arg Val Ala Ala Gly Lys Arg Phe Ile Thr
65                  70                  75                  80

Phe Arg Gly Asp Asp Ala Ser Lys Thr Val Ile Thr Tyr Arg Leu Ser
                85                  90                  95

Ala Leu Gln Ala Gly Asn Thr Arg Leu Ala Phe Thr Thr Phe Val Asn
            100                 105                 110

Ala Asp Asp Phe Arg Ala Glu Asn Leu Thr Phe Glu Asn Ser Phe Gly
        115                 120                 125

Thr Gly Ser Gln Ala Val Ala Leu Phe Val Asp Ala Asp Arg Ala Thr
    130                 135                 140

Phe Glu Asn Cys Arg Phe Leu Gly Trp Gln Asp Thr Leu Phe Val Asn
145                 150                 155                 160

Gly Ser Arg His Phe Lys Asp Cys Tyr Val Glu Gly His Val Asp
                165                 170                 175

Phe Ile Phe Gly Thr Ala Ser Ala Val Phe Glu Asn Cys Thr Ile His
            180                 185                 190

Ser Lys Gly Glu Gly Tyr Val Thr Ala His Tyr Arg Thr Ser Asp Glu
        195                 200                 205

Met Asp Thr Gly Phe Val Phe His Arg Cys Arg Leu Thr Gly Arg Asp
    210                 215                 220

Thr Gly Arg Gly Val Tyr Leu Gly Arg Pro Trp Arg Pro Tyr Ala Arg
225                 230                 235                 240

-continued

Val Val Phe Ile Asp Cys Trp Leu Asp Ala His Ile Arg Pro Glu Gly
            245                 250                 255

Trp Asp Asn Trp Arg Asp Pro Glu Arg Glu Lys Thr Ala Trp Phe Ala
            260                 265                 270

Glu Tyr Lys Ser Lys Gly Pro Gly Ala Asn Pro Val Ala Arg Val Ala
            275                 280                 285

Trp Ser Arg Gln Leu Thr Thr Glu Gln Ala Ala Glu Phe Ser Arg Glu
290                 295                 300

Arg Phe Phe Ser Arg Ala Val Arg Gly Leu Ser Gly Gln Ala Asn Gln
305                 310                 315                 320

Ala Val Gly Thr Ile Ala Trp Asp Asp Ala Gln Lys Lys Pro Asn Glu
            325                 330                 335

Trp Tyr Ala Ser Ala Glu Ala Leu Arg Ile Ala Asp Asn Val Val Leu
            340                 345                 350

Tyr Gln Arg Asp Ser Gly Gly Trp Pro Lys Asn Ile Asp Met Gly Lys
            355                 360                 365

Pro Leu Asp Glu Lys Gly Arg Ala Gly Leu Leu Arg Val Arg Lys Lys
370                 375                 380

Asn Asp Ser Thr Ile Asp Asn Gly Ala Thr Tyr Thr Gln Leu Ser Phe
385                 390                 395                 400

Leu Ala Arg Val Tyr Thr Ala Gln Lys Gln Glu Arg His Arg Glu Ser
            405                 410                 415

Phe Leu Lys Gly Leu Asp Tyr Leu Leu Lys Ala Gln Tyr Pro Asn Gly
            420                 425                 430

Gly Trp Pro Gln Phe Tyr Pro Asn Leu Asn Gly Tyr Tyr Lys His Ile
            435                 440                 445

Thr Phe Asn Asp Asn Ala Met Ile Gly Val Met Lys Leu Leu Arg Asp
450                 455                 460

Val Ala Thr Ala Lys Pro Ala Tyr Ala Phe Val Asp Glu Ala Arg Arg
465                 470                 475                 480

Thr Ser Ala Ala Lys Ala Val Glu Lys Gly Ile Glu Cys Ile Leu Lys
            485                 490                 495

Thr Gln Val Val Val Asn Gly Arg Arg Thr Val Trp Cys Ala Gln His
            500                 505                 510

Asp Glu Val Thr Leu Ala Pro Ala Pro Ala Arg Thr Phe Glu Leu Val
            515                 520                 525

Ser Leu Ser Gly Gly Glu Ser Val Glu Ile Val Arg Phe Leu Met Ser
530                 535                 540

Ile Lys Asn Pro Ser Pro Ala Val Val Glu Ala Ile Glu Ser Ala Val
545                 550                 555                 560

Ala Trp Phe Glu Gln Ser Gln Val Lys Asp Pro Ala Gly Lys Pro Ala
            565                 570                 575

Trp Ala Arg Phe Tyr Glu Ile Gly Thr Asn Arg Pro Ile Phe Ala Gly
            580                 585                 590

Arg Asp Gly Val Val Lys Tyr Asp Val Lys Gln Ile Asp Glu Glu Arg
            595                 600                 605

Arg Lys Asn Tyr Ala Trp Tyr Val Asp Asp Ala Lys Leu Leu Lys
            610                 615                 620

Thr Asp Tyr Pro Glu Trp Lys Glu Lys Asn Ala Lys Asp Gln
625                 630                 635

<210> SEQ ID NO 3
<211> LENGTH: 1416
<212> TYPE: DNA

```
<213> ORGANISM: Unknown
<220> FEATURE:
<223> OTHER INFORMATION: Obtained from an environmental sample

<400> SEQUENCE: 3
atgtcgtcac gacgcgagtt cattagagat ctgttgactg gcggcgcact gatcgccgtc      60
gcgccgcgtc tgtctgcgtt tgcagcggag gagaatccgt gggaaacggt gatgccttcg     120
atcgtgaaac gcatcaagcg acctcgtttc ccgatgcgca cgtttgatct cacggagttt     180
ggagcgaaag gtgatggacg aacagattgc acgttggctt ccgtcgcgc gatcgatcga      240 tgcacgaacg ccgtggtgg gagagtagtt gttccaccgg gttcgtatct cactggcgcc     300
attcatttga agagcaacgt cgaccttcat atctcagaag gtactacggt caagttcagc     360
cagaacccga agactacct gccgttgtt ttctcgcgtt gggaaggcgt cgaggtgttc       420
aactactcgc cttttatcta cgccttcgaa caaacgaaca ttgcgatcac tggcaagggc     480
acgctcaacg gtcaaagcga caacgaacac tggtggccct ggaacggacg tgccgcgtac     540
ggctggaaag aagggatgag caatcagcgt cccgatcgaa atgcgctgtt gcgatggcc      600 gaaaaaggtg tcccggttca ggagcgcatt tttggtgagg ccattacttt aaggccgcag     660
ttcattcaac cttatcgttg tgagaacgtg ctgatcgaag gtgtcactat tcgaaactcg     720
ccgatgtggg aaattcatcc ggtgctctgc cggaatgtca tcgtccaaaa tgtgatcatc     780
aacagtcatg gtccaaacaa cgacgggtgt aatcctgagt cgtgcacgga tgtgttgatt     840
aaggattgtg acttcgacac tggtgacgat tgtatcgcga tcaagtcagg ccgaaatgca     900
gatgggcggc gactgaaggc tcctactgaa acattatcg tgactggttg tcgcatgaaa     960
gatggtcacg gcgggattac ggtgggcagc gagatttcgg gtggggtgcg aaatcttttc    1020
gcatccaact gccggctcga cagtccgaac ctggaccatg cattgcgggt taagaataac    1080
gctatgcgtg gcgggctgtt ggagaatctg cacttccgaa atatcgacgt cgggcaagtg    1140
gcgcacgcgg tgatcacgat cgatttcaat tatgaggaag gcgcgaaggg atcgttcacg    1200
ccagtcgttc gtgattacac cgtcgatggc cttcgcagca cgaaaagtaa gtacgcgctc    1260
gatgtgcagg gcttggcgac ggcgccgatc gtgaatctgc gtctaaccaa ctgcatcttc    1320
gacaatgtcg ctgaaggaaa tgttgtgaag aacgtaaagg atgcaactat cgagaatgtc    1380
aaaatcaatg gaaaaagcgt tgatgcagtg ccgtag                              1416

<210> SEQ ID NO 4
<211> LENGTH: 471
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(28)
<220> FEATURE:
<221> NAME/KEY: DOMAIN
<222> LOCATION: (81)...(476)
<223> OTHER INFORMATION: Catalytic domain

<400> SEQUENCE: 4

Met Ser Ser Arg Arg Glu Phe Ile Arg Asp Leu Leu Thr Gly Gly Ala
 1               5                  10                  15

Leu Ile Ala Val Ala Pro Arg Leu Ser Ala Phe Ala Ala Glu Glu Asn
             20                  25                  30

Pro Trp Glu Thr Val Met Pro Ser Ile Val Lys Arg Ile Lys Arg Pro
         35                  40                  45
```

-continued

```
Arg Phe Pro Met Arg Thr Phe Asp Leu Thr Glu Phe Gly Ala Lys Gly
         50                  55                  60

Asp Gly Arg Thr Asp Cys Thr Leu Ala Phe Arg Arg Ala Ile Asp Arg
 65                  70                  75                  80

Cys Thr Asn Ala Gly Gly Arg Val Val Pro Pro Gly Ser Tyr
                 85                  90                  95

Leu Thr Gly Ala Ile His Leu Lys Ser Asn Val Asp Leu His Ile Ser
                100                 105                 110

Glu Gly Thr Thr Val Lys Phe Ser Gln Asn Pro Lys Asp Tyr Leu Pro
                115                 120                 125

Val Val Phe Ser Arg Trp Glu Gly Val Glu Val Phe Asn Tyr Ser Pro
        130                 135                 140

Phe Ile Tyr Ala Phe Glu Gln Thr Asn Ile Ala Ile Thr Gly Lys Gly
145                 150                 155                 160

Thr Leu Asn Gly Gln Ser Asp Asn Glu His Trp Trp Pro Trp Asn Gly
                165                 170                 175

Arg Ala Ala Tyr Gly Trp Lys Glu Gly Met Ser Asn Gln Arg Pro Asp
                180                 185                 190

Arg Asn Ala Leu Phe Ala Met Ala Glu Lys Gly Val Pro Val Gln Glu
                195                 200                 205

Arg Ile Phe Gly Glu Gly His Tyr Leu Arg Pro Gln Phe Ile Gln Pro
        210                 215                 220

Tyr Arg Cys Glu Asn Val Leu Ile Glu Gly Val Thr Ile Arg Asn Ser
225                 230                 235                 240

Pro Met Trp Glu Ile His Pro Val Leu Cys Arg Asn Val Ile Val Gln
                245                 250                 255

Asn Val Ile Ile Asn Ser His Gly Pro Asn Asn Asp Gly Cys Asn Pro
                260                 265                 270

Glu Ser Cys Thr Asp Val Leu Ile Lys Asp Cys Asp Phe Asp Thr Gly
        275                 280                 285

Asp Asp Cys Ile Ala Ile Lys Ser Gly Arg Asn Ala Asp Gly Arg Arg
290                 295                 300

Leu Lys Ala Pro Thr Glu Asn Ile Ile Val Thr Gly Cys Arg Met Lys
305                 310                 315                 320

Asp Gly His Gly Gly Ile Thr Val Gly Ser Glu Ile Ser Gly Gly Val
                325                 330                 335

Arg Asn Leu Phe Ala Ser Asn Cys Arg Leu Asp Ser Pro Asn Leu Asp
                340                 345                 350

His Ala Leu Arg Val Lys Asn Asn Ala Met Arg Gly Gly Leu Leu Glu
                355                 360                 365

Asn Leu His Phe Arg Asn Ile Asp Val Gly Gln Val Ala His Ala Val
        370                 375                 380

Ile Thr Ile Asp Phe Asn Tyr Glu Glu Gly Ala Lys Gly Ser Phe Thr
385                 390                 395                 400

Pro Val Val Arg Asp Tyr Thr Val Asp Gly Leu Arg Ser Thr Lys Ser
                405                 410                 415

Lys Tyr Ala Leu Asp Val Gln Gly Leu Ala Thr Ala Pro Ile Val Asn
                420                 425                 430

Leu Arg Leu Thr Asn Cys Ile Phe Asp Asn Val Ala Glu Gly Asn Val
        435                 440                 445

Val Lys Asn Val Lys Asp Ala Thr Ile Glu Asn Val Lys Ile Asn Gly
450                 455                 460
```

Lys Ser Val Asp Ala Val Pro
465                 470

<210> SEQ ID NO 5
<211> LENGTH: 1077
<212> TYPE: DNA
<213> ORGANISM: Unknown
<220> FEATURE:
<223> OTHER INFORMATION: Obtained from an environmental sample

<400> SEQUENCE: 5

```
ttggacgaca agtgggctga gcggacatcg cccgatttca atctcgtctc gtggaatgaa      60
attctaaagc agccgaaact tggtacgcg gtcgacgaag cgacgcggat cgcaaatcag     120
gtgatccttt atcaacgcga caacggtggt tggccgaaga atatcgacat ggccgccatg     180
ctcatgcagg cagaacgcga aaacttagt cgcgagaaga gcgagaccga cacgacaatc     240
gacaacggcg cgacgacaac ccagctcgcg tatctggcga aggtcatcac ggccaagaat     300
atcgaaagcc atcgcgtcgc gtttttcaaa ggcctcgatt ttcttttcgc catgcagtac     360
gggaatggcg gcttcccgca attttttcct ctgcgtgacg attattcgcg cgagattacg     420
ttcaacgaca acgcgatgat aaatgtgctt cggttgctcc gcgacatagc cgatcgaaag     480
aacgattatg tgtttgtcga tgaagagcgg cgagcgaagg ccgagcaggc tgtaaggcgt     540
gcgatcccgt tgatcctcag cacgcaggtc gtcgtcgatg aaagaaaac cgtctgggct     600
gcgcagtatg atgagaagac attgaagccg ccgcggcgc gaaagttcga gccggcatca     660
ttgaccgccg gcgagagcgt tggcatcgtc cggttttga tgctagaaaa accaacaccc     720
gagatcatta acgcgatcga atccgccatc gcttggtaca aggcgaacaa catctcggga     780
cttaggtggg agaggcgaaa cggcgagaac attgtgatca aagacaagaa cgcgccgccc     840
gtctgggcgc gcttttatca gatcgaaacg atgaggccga tcttcgccgg tcgcgatgcg     900
gtcatcagat acgatgtgat gcagatcgag tcggaacgtc gaaacggata tgcatggtac     960
gtatccgaac cgaatgagtt gttgaatgaa gattatccga agtggaggac aaggagtgcg    1020
aagcgtgccc agatctttca acgtccgcct cttggttcga gatttcggac cgtgtag      1077
```

<210> SEQ ID NO 6
<211> LENGTH: 358
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(358)
<223> OTHER INFORMATION: Catalytic domain

<400> SEQUENCE: 6

Met Asp Asp Lys Trp Ala Glu Arg Thr Ser Pro Asp Phe Asn Leu Val
 1               5                  10                  15

Ser Trp Asn Glu Ile Leu Lys Gln Pro Lys Leu Trp Tyr Ala Val Asp
             20                  25                  30

Glu Ala Thr Arg Ile Ala Asn Gln Val Ile Leu Tyr Gln Arg Asp Asn
         35                  40                  45

Gly Gly Trp Pro Lys Asn Ile Asp Met Ala Ala Met Leu Met Gln Ala
     50                  55                  60

Glu Arg Glu Lys Leu Ser Arg Glu Lys Ser Gly Thr Asp Thr Thr Ile
 65                  70                  75                  80

Asp Asn Gly Ala Thr Thr Thr Gln Leu Ala Tyr Leu Ala Lys Val Ile

```
                     85                  90                  95
Thr Ala Lys Asn Ile Glu Ser His Arg Val Ala Phe Phe Lys Gly Leu
                100                 105                 110

Asp Phe Leu Phe Ala Met Gln Tyr Gly Asn Gly Gly Phe Pro Gln Phe
            115                 120                 125

Phe Pro Leu Arg Asp Asp Tyr Ser Arg Glu Ile Thr Phe Asn Asp Asn
        130                 135                 140

Ala Met Ile Asn Val Leu Arg Leu Leu Arg Asp Ile Ala Asp Arg Lys
145                 150                 155                 160

Asn Asp Tyr Val Phe Val Asp Glu Glu Arg Arg Ala Lys Ala Glu Gln
                165                 170                 175

Ala Val Arg Arg Ala Ile Pro Leu Ile Leu Ser Thr Gln Val Val
            180                 185                 190

Asp Gly Lys Lys Thr Val Trp Ala Ala Gln Tyr Asp Glu Lys Thr Leu
        195                 200                 205

Lys Pro Ala Ala Ala Arg Lys Phe Glu Pro Ala Ser Leu Thr Ala Gly
    210                 215                 220

Glu Ser Val Gly Ile Val Arg Phe Leu Met Leu Glu Lys Pro Thr Pro
225                 230                 235                 240

Glu Ile Ile Asn Ala Ile Glu Ser Ala Ile Ala Trp Tyr Lys Ala Asn
                245                 250                 255

Asn Ile Ser Gly Leu Arg Trp Glu Arg Arg Asn Gly Glu Asn Ile Val
            260                 265                 270

Ile Lys Asp Lys Asn Ala Pro Pro Val Trp Ala Arg Phe Tyr Gln Ile
        275                 280                 285

Glu Thr Met Arg Pro Ile Phe Ala Gly Arg Asp Ala Val Ile Arg Tyr
    290                 295                 300

Asp Val Met Gln Ile Glu Ser Glu Arg Arg Asn Gly Tyr Ala Trp Tyr
305                 310                 315                 320

Val Ser Glu Pro Asn Glu Leu Leu Asn Glu Asp Tyr Pro Lys Trp Arg
                325                 330                 335

Thr Arg Ser Ala Lys Arg Ala Gln Ile Phe Gln Arg Pro Pro Leu Gly
            340                 345                 350

Ser Arg Phe Arg Thr Val
        355

<210> SEQ ID NO 7
<211> LENGTH: 1125
<212> TYPE: DNA
<213> ORGANISM: Unknown
<220> FEATURE:
<223> OTHER INFORMATION: Obtained from an environmental sample

<400> SEQUENCE: 7
gtgcatgcgg gcgcgaaaca cgtgagccga tggcgcgaag agttcctgcg cgacttcgcc      60
gcgcggctct cccgaaccat tccgtcctcg ccggcgcaga gcgctgcggt cagcggggtt     120
ccggcggcga tccgctgggg agcggacgtc ctgcggcaga agccggagtg gtatgcctcg     180
cgagaggcga ggacgatcgc cgacagcgtc atccagtacc aggcggcgga cggcggctgg     240
cccaagaaca ccgacctcgg gactccgccc acgcgctgaa tcacgcgcgg cgcggcggcc     300
gacgtgacgt cgagcaccat cgacaacaac ggcacgacga tgccgatgca gttccttgcg     360
ctggtggcgg acgcgaccgg cgaggctcgc tatcgcgcgt cgttcctccg ggcttcgac      420 tacctgctcg ccgcgcagta tcccaacggc ggctggccgc agttctttcc gctccgccgc     480
```

```
gggtattaca cccacatcac cttcaacgac aacgcgatgg tcaacgtgct gaccgtgctg      540
cgcgatgccg cggccggtca ggcgccatac gccttcgtgg acgagcccg  ccgcgcgaag     600 gcccgcgccg ccgtgtcccg ggggatcgac gtcatcctga agacccaagt gaaacagaac     660
ggcaagctga cggcgtggtg cgcgcagcac gacgagaaga ccctcgcgcc ggcgtgggcg     720
cgcgcttacg agccgccatc gctctccggc agcgaaaccg tcggcatcgt ccgcttcctg     780
atggagatcg agaagccgtc accggagatc gtcgccgcga tcgaagggc  cgtcgcctgg    840 ctgaagtccg tggcgattcc ggggctgcgc tacgagtcct tcaccggcgc ggacggacag     900
agggaccgcc gcgtcgttcc ggatccatcg gccggactcc tgtgggcgcg gttctacgag     960
ctcggcacca accggccgat cttcctcggc cgcgactccg tggttcgcgc cgcgctcagt    1020
gacatcgaac gcgagcgccg cgccggctac gcctactacg gtacgtgcc  ggcgagcctg   1080 attgctgcgg actacccgcg ctggcgttcg acgctccggc gctga                   1125
```

<210> SEQ ID NO 8
<211> LENGTH: 374
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(374)
<223> OTHER INFORMATION: Catalytic domain

<400> SEQUENCE: 8

```
Met His Ala Gly Ala Lys His Val Ser Arg Trp Arg Glu Glu Phe Leu
 1               5                  10                  15

Arg Asp Phe Ala Ala Arg Leu Ser Arg Thr Ile Pro Ser Ser Pro Ala
            20                  25                  30

Gln Ser Ala Ala Val Ser Gly Val Pro Ala Ala Ile Arg Trp Gly Ala
        35                  40                  45

Asp Val Leu Arg Gln Lys Pro Glu Trp Tyr Ala Ser Arg Glu Ala Arg
    50                  55                  60

Thr Ile Ala Asp Ser Val Ile Gln Tyr Gln Ala Asp Gly Gly Trp
65                  70                  75                  80

Pro Lys Asn Thr Asp Leu Gly Thr Pro Thr Ala Glu Ser Arg Ala
            85                  90                  95

Gly Ala Ala Ala Asp Val Thr Ser Ser Thr Ile Asp Asn Asn Gly Thr
        100                 105                 110

Thr Met Pro Met Gln Phe Leu Ala Leu Val Ala Asp Ala Thr Gly Glu
    115                 120                 125

Ala Arg Tyr Arg Ala Ser Phe Leu Arg Gly Phe Asp Tyr Leu Leu Ala
    130                 135                 140

Ala Gln Tyr Pro Asn Gly Gly Trp Pro Gln Phe Phe Pro Leu Arg Arg
145                 150                 155                 160

Gly Tyr Tyr Thr His Ile Thr Phe Asn Asp Asn Ala Met Val Asn Val
                165                 170                 175

Leu Thr Val Leu Arg Asp Ala Ala Gly Gln Ala Pro Tyr Ala Phe
            180                 185                 190

Val Asp Glu Pro Arg Arg Ala Lys Ala Arg Ala Val Ser Arg Gly
        195                 200                 205

Ile Asp Val Ile Leu Lys Thr Gln Val Lys Gln Asn Gly Lys Leu Thr
    210                 215                 220

Ala Trp Cys Ala Gln His Asp Glu Lys Thr Leu Ala Pro Ala Trp Ala
```

```
                225                 230                 235                 240
Arg Ala Tyr Glu Pro Pro Ser Leu Ser Gly Ser Glu Thr Val Gly Ile
            245                 250                 255
Val Arg Phe Leu Met Glu Ile Glu Lys Pro Ser Pro Glu Ile Val Ala
        260                 265                 270
Ala Ile Glu Gly Ala Val Ala Trp Leu Lys Ser Val Ala Ile Pro Gly
    275                 280                 285
Leu Arg Tyr Glu Ser Phe Thr Gly Ala Asp Gly Gln Arg Asp Arg Arg
    290                 295                 300
Val Val Pro Asp Pro Ser Ala Gly Leu Leu Trp Ala Arg Phe Tyr Glu
305                 310                 315                 320
Leu Gly Thr Asn Arg Pro Ile Phe Leu Gly Arg Asp Ser Val Val Arg
            325                 330                 335
Ala Ala Leu Ser Asp Ile Glu Arg Glu Arg Ala Gly Tyr Ala Tyr
        340                 345                 350
Tyr Gly Thr Trp Pro Ala Ser Leu Ile Ala Ala Asp Tyr Pro Arg Trp
    355                 360                 365
Arg Ser Thr Leu Arg Arg
    370
```

<210> SEQ ID NO 9
<211> LENGTH: 1116
<212> TYPE: DNA
<213> ORGANISM: Unknown
<220> FEATURE:
<223> OTHER INFORMATION: Obtained from an environmental sample

<400> SEQUENCE: 9

```
ttgatcggta gcatgaaaac gattctctca aatctgaacg cggcgctgct ttcatgcgcc      60
ctgctctttg cggcagccac acagggaacc aagccgcccg aagtgcggtg aatgagtgc     120
ctaaaccaaa aacctgcctg gtacggcagc ccggaagcgg tgcgcattgc tgacaacctg     180
ttgctttacc aacgcgacca cggcggctgg cacaagaata tcgaaatggc tgcggtcttg     240
accgaacagc aacaggcaga gttgaaagcg caaaaggcaa ccgacgattc gacgattgat     300
aacggcgcga cctataccca ggtgatttat ctggcgcgcg tcttcaatgc gacgaagcag     360
gagcgattca aaaccgcgtt tctcaaagga ttcgattatc tgctcaaggc tcagtatgcg     420
aacggcggct ggccgcagta ttacccgcgt ttgcagggtt attacaaaca catcacgttc     480
aacgatgacg cgatggtcgg cgtgcttgat cttctgcgcg atgttgcgcg cggcgattcc     540
ggttatcggt tcgtggacag cgaccggcgc gcccgcgcca gccaggccgt gcaaaaagga     600
attgagtgca tcttgaaatg ccagatcgtg gtcgccggga aaagaccgc ctggtgcgcg     660
caacacgatg aagtgacatt cgcccccgcg ccggcacgca cctacgagaa atttcgctg     720
agcggcagcg aatcggttgg cctgatccgc ttcctgatgg cattgaaca accgacgcg     780
cgtgtagttg aggcgattga gtccgccgtt gcctggctca gcaagccaa gctgaccggc     840
atcaaagtgg ttcagaaggc ggatgcttcg aagcccaatg gcttcgaccg ggtcgtcgtt     900
gaagatgcac aagccgggcc attgtgggcg cgcttttacg agatcggtac gggccgcccg     960
atcttttccg gacgtgacgg catcgtcaaa tacagcttgg cggaaatcga acacgaacgg    1020
cgcacgggct acggctggta cacgaatgcg cccgcgaaat tgctggaaca agattatccg    1080
gcctggcaaa tcaaacgcgg gggcaagaaa aagtaa                              1116
```

<210> SEQ ID NO 10

```
<211> LENGTH: 371
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(29)
<220> FEATURE:
<221> NAME/KEY: DOMAIN
<222> LOCATION: (30)...(371)
<223> OTHER INFORMATION: Catalytic domain

<400> SEQUENCE: 10
```

Met Ile Gly Ser Met Lys Thr Ile Leu Ser Asn Leu Asn Ala Ala Leu
 1               5                  10                  15

Leu Ser Cys Ala Leu Leu Phe Ala Ala Ala Thr Gln Gly Thr Lys Pro
            20                  25                  30

Pro Glu Val Arg Trp Asn Glu Cys Leu Asn Gln Lys Pro Ala Trp Tyr
        35                  40                  45

Gly Ser Pro Glu Ala Val Arg Ile Ala Asp Asn Leu Leu Leu Tyr Gln
    50                  55                  60

Arg Asp His Gly Gly Trp His Lys Asn Ile Glu Met Ala Ala Val Leu
65                  70                  75                  80

Thr Glu Gln Gln Gln Ala Glu Leu Lys Ala Gln Lys Ala Thr Asp Asp
                85                  90                  95

Ser Thr Ile Asp Asn Gly Ala Thr Tyr Thr Gln Val Ile Tyr Leu Ala
            100                 105                 110

Arg Val Phe Asn Ala Thr Lys Gln Glu Arg Phe Lys Thr Ala Phe Leu
        115                 120                 125

Lys Gly Phe Asp Tyr Leu Leu Lys Ala Gln Tyr Ala Asn Gly Gly Trp
    130                 135                 140

Pro Gln Tyr Tyr Pro Arg Leu Gln Gly Tyr Tyr Lys His Ile Thr Phe
145                 150                 155                 160

Asn Asp Asp Ala Met Val Gly Val Leu Asp Leu Leu Arg Asp Val Ala
                165                 170                 175

Arg Gly Asp Ser Gly Tyr Arg Phe Val Asp Ser Asp Arg Ala Arg
            180                 185                 190

Ala Ser Gln Ala Val Gln Lys Gly Ile Glu Cys Ile Leu Lys Cys Gln
        195                 200                 205

Ile Val Val Ala Gly Lys Lys Thr Ala Trp Cys Ala Gln His Asp Glu
    210                 215                 220

Val Thr Phe Ala Pro Ala Pro Ala Arg Thr Tyr Glu Lys Ile Ser Leu
225                 230                 235                 240

Ser Gly Ser Glu Ser Val Gly Leu Ile Arg Phe Leu Met Gly Ile Glu
                245                 250                 255

Gln Pro Asp Ala Arg Val Val Glu Ala Ile Glu Ser Ala Val Ala Trp
            260                 265                 270

Leu Lys Gln Ala Lys Leu Thr Gly Ile Lys Val Val Gln Lys Ala Asp
        275                 280                 285

Ala Ser Lys Pro Asn Gly Phe Asp Arg Val Val Glu Asp Ala Gln
    290                 295                 300

Ala Gly Pro Leu Trp Ala Arg Phe Tyr Glu Ile Gly Thr Gly Arg Pro
305                 310                 315                 320

Ile Phe Ser Gly Arg Asp Gly Ile Val Lys Tyr Ser Leu Ala Glu Ile
                325                 330                 335

Glu His Glu Arg Arg Thr Gly Tyr Gly Trp Tyr Thr Asn Ala Pro Ala

```
                340              345              350
    Lys Leu Leu Glu Gln Asp Tyr Pro Ala Trp Gln Ile Lys Arg Gly Gly
            355                  360                  365

Lys Lys Lys
        370

<210> SEQ ID NO 11
<211> LENGTH: 1167
<212> TYPE: DNA
<213> ORGANISM: Unknown
<220> FEATURE:
<223> OTHER INFORMATION: Obtained from an environmental sample

<400> SEQUENCE: 11
atgtcgttgg gaccaggtgc taatccgaaa gctcgcgttc cctggtccaa acaactatcg      60
ggtgttgagg caaagttgtt cgatcgcgag cggttcttca gcctcgctgc ggaacgaacc     120
tctaagaaga atgaccagca agtcggcgcc atcgcgtgga agatgcaca cggaaaggca      180 gatgagtggt atgcgagcgt tgaggcactt cgtatagccg ataacgtcgt tttctatcaa     240
cgtgactcag gtggctggcc caagaatatc gagatggcga agacgttgag cgatcgtgag     300
aaggctgcga ttctccgcga agaaaaaag aatgactcaa caatcgacaa tggcgcgact      360
cacactcagt tatcttttct ggcgcgcgtc tatacagcac aacagcagga gcgacatcgc     420
gagtcatttt taaaaggact ggattactta ctgaaggcgc agtattcaaa tggtggctgg     480
ccacagttct atccaaactt gaatggctac tacaaacgga tcacgtacaa cgatggcgcg     540
atgatcggtg tgatgaagct tctgcgtgat gttgcggcag cgaaacctga atacgcgttt     600
gtcgatgaaa ctcggcgtgc gaaggctgcg aacgcgtgg aaaaaggcat cgtgtgcatt      660
ttgaaaacgc aggtggttgt tgatgggcgt cgcactgttt ggtgtgcaca acacgacgaa     720
gtgacgtttg cgcccgcgcc tgcaagaaag tttgagttag cttcgttgag cggcggtgag    780
agcgtcgata ttgttcgatt tctaatgtcg ataaaggatc catcgcgtaa cgtggttgaa     840
tcgattgaat cggcagttaa atggtttgag cagtcggagc taaaaggcgt taagtgggtc     900
aagaaaaccg acgctactca acctaatggg ttcgattgtg tcgttgttaa agatccggag     960
agctctgttt gggcgcgctt ttacgagatt ggcacgaacc gcccgatctt tgccgggcgt    1020
gatggagtgc ctaagtatga cgtcgcgcag atcgaacacg agcgacgaac gggttacgaa   1080
tggtacgttg atgaggcagc aaaactgctg aaaaaagatt atccggcgtg gaagaaacga   1140
catgtcgtca cgacgcgagt tcattag                                        1167

<210> SEQ ID NO 12
<211> LENGTH: 388
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(388)
<223> OTHER INFORMATION: Catalytic domain

<400> SEQUENCE: 12

Met Ser Leu Gly Pro Gly Ala Asn Pro Lys Ala Arg Val Pro Trp Ser
 1               5                  10                  15

Lys Gln Leu Ser Gly Val Glu Ala Lys Leu Phe Asp Arg Glu Arg Phe
            20                  25                  30

Phe Ser Leu Ala Ala Glu Arg Thr Ser Lys Lys Asn Asp Gln Gln Val
```

```
            35                  40                  45
Gly Ala Ile Ala Trp Lys Asp Ala His Gly Lys Ala Asp Glu Trp Tyr
 50                  55                  60
Ala Ser Val Glu Ala Leu Arg Ile Ala Asp Asn Val Val Phe Tyr Gln
 65                  70                  75                  80
Arg Asp Ser Gly Gly Trp Pro Lys Asn Ile Glu Met Ala Lys Thr Leu
                 85                  90                  95
Ser Asp Arg Glu Lys Ala Ala Ile Leu Arg Glu Lys Lys Lys Asn Asp
            100                 105                 110
Ser Thr Ile Asp Asn Gly Ala Thr His Thr Gln Leu Ser Phe Leu Ala
            115                 120                 125
Arg Val Tyr Thr Ala Gln Gln Gln Glu Arg His Arg Glu Ser Phe Leu
130                 135                 140
Lys Gly Leu Asp Tyr Leu Leu Lys Ala Gln Tyr Ser Asn Gly Gly Trp
145                 150                 155                 160
Pro Gln Phe Tyr Pro Asn Leu Asn Gly Tyr Tyr Lys Arg Ile Thr Tyr
                165                 170                 175
Asn Asp Gly Ala Met Ile Gly Val Met Lys Leu Leu Arg Asp Val Ala
            180                 185                 190
Ala Ala Lys Pro Glu Tyr Ala Phe Val Asp Glu Thr Arg Arg Ala Lys
            195                 200                 205
Ala Ala Asn Ala Val Glu Lys Gly Ile Val Cys Ile Leu Lys Thr Gln
            210                 215                 220
Val Val Val Asp Gly Arg Arg Thr Val Trp Cys Ala Gln His Asp Glu
225                 230                 235                 240
Val Thr Phe Ala Pro Ala Pro Ala Arg Lys Phe Glu Leu Ala Ser Leu
                245                 250                 255
Ser Gly Gly Glu Ser Val Asp Ile Val Arg Phe Leu Met Ser Ile Lys
            260                 265                 270
Asp Pro Ser Arg Asn Val Val Glu Ser Ile Glu Ser Ala Val Lys Trp
            275                 280                 285
Phe Glu Gln Ser Glu Leu Lys Gly Val Lys Trp Val Lys Lys Thr Asp
290                 295                 300
Ala Thr Gln Pro Asn Gly Phe Asp Cys Val Val Lys Asp Pro Glu
305                 310                 315                 320
Ser Ser Val Trp Ala Arg Phe Tyr Glu Ile Gly Thr Asn Arg Pro Ile
                325                 330                 335
Phe Ala Gly Arg Asp Gly Val Pro Lys Tyr Asp Val Ala Gln Ile Glu
            340                 345                 350
His Glu Arg Arg Thr Gly Tyr Glu Trp Tyr Val Asp Glu Ala Ala Lys
            355                 360                 365
Leu Leu Lys Lys Asp Tyr Pro Ala Trp Lys Lys Arg His Val Val Thr
370                 375                 380
Thr Arg Val His
385

<210> SEQ ID NO 13
<211> LENGTH: 1065
<212> TYPE: DNA
<213> ORGANISM: Unknown
<220> FEATURE:
<223> OTHER INFORMATION: Obtained from an environmental sample

<400> SEQUENCE: 13
atgaaaacga tcagccttat ttgcctcgca atctctgctg ggattctgga ttcggttgcg     60
```

-continued

```
gcggcacgct ggaacgaatt cgcccagaag gcggatgatt ggtatcgagg tgacgaaggc    120
aggcgcgttg cttcgaatat tctttctcac caatcactgc aaggaagctg cccaagaat    180 accgatacca ccgcgagatt cttcaatgga gatctagcga agattcaggg cacgttcgac    240
aacggtgcga cgacggacga gttgcgtttc ctggcccgcg cgtttgtcgc cacgaaagaa    300
aaaaactacg agtcagcgtt ccgaaaaggc ttcgaacaca ttctcgcggc gcaatacgcg    360
aacggcggat ggccgcaata ttcgccgccg cccaaaagtt accaccgaca cattaccttc    420
aacgataatt cgatggtgcg gctgatgatt ttccttcgcg aggtcacgac ttcgaatctc    480
tactcgttcg tcgaagcgcc gctgcgaaca caagcccgcg aaagtttcga tcgcggtgtg    540
cggtgcattc ttaagtgcca gatcgtcgtg aacgggcaca agaccgcgtg gtgcgcgcaa    600
catgatgaaa cggatttcag cccccgatcc gcgcgtagtt acgaactgcc ttcgctgagc    660
ggttctgaat cagtcggcat tgtgcgcttg ctgatgagcc tcgatcagcc gagccgcgga    720
gtgatcgatg ccatcaccaa cgccgtagcg tggttcgaat cggcgaagct gcccgggatc    780
aaaaccgttc aagagaccga tccgaattcg cccaaaggct ggaatcgcgt cgtcgtaaaa    840
gatgaaagtg cccgaccgat gtgggcgcgt ttctacgaca tcaacaccaa caaaccgttc    900
ttttgtgatc gcgatggtgt gccaaagccg agtcttgccg agatcggtta tgaacggcgg    960
aacggttatg cgtggctcgg atactggcct gaagacttgc tcgcaagaga gtatccagcg   1020
tggaagatga agtggctgaa gcccaaagag cgcccagcat tttga                   1065
```

<210> SEQ ID NO 14
<211> LENGTH: 354
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(22)
<220> FEATURE:
<221> NAME/KEY: DOMAIN
<222> LOCATION: (23)...(354)
<223> OTHER INFORMATION: Catalytic domain

<400> SEQUENCE: 14

```
Met Lys Thr Ile Ser Leu Ile Cys Leu Ala Ile Ser Ala Gly Ile Leu
  1               5                  10                  15

Asp Ser Val Ala Ala Ala Arg Trp Asn Glu Phe Ala Gln Lys Ala Asp
             20                  25                  30

Asp Trp Tyr Arg Gly Asp Glu Gly Arg Arg Val Ala Ser Asn Ile Leu
         35                  40                  45

Ser His Gln Ser Leu Gln Gly Ser Trp Pro Lys Asn Thr Asp Thr Thr
     50                  55                  60

Ala Arg Phe Phe Asn Gly Asp Leu Ala Lys Ile Gln Gly Thr Phe Asp
 65                  70                  75                  80

Asn Gly Ala Thr Thr Asp Glu Leu Arg Phe Leu Ala Arg Ala Phe Val
                 85                  90                  95

Ala Thr Lys Glu Lys Asn Tyr Glu Ser Ala Phe Arg Lys Gly Phe Glu
            100                 105                 110

His Ile Leu Ala Ala Gln Tyr Ala Asn Gly Gly Trp Pro Gln Tyr Ser
        115                 120                 125

Pro Pro Lys Ser Tyr His Arg His Ile Thr Phe Asn Asp Asn Ser
    130                 135                 140
```

Met Val Arg Leu Met Ile Phe Leu Arg Glu Val Thr Thr Ser Asn Leu
145                 150                 155                 160

Tyr Ser Phe Val Glu Ala Pro Leu Arg Thr Gln Ala Arg Glu Ser Phe
            165                 170                 175

Asp Arg Gly Val Arg Cys Ile Leu Lys Cys Gln Ile Val Val Asn Gly
        180                 185                 190

His Lys Thr Ala Trp Cys Ala Gln His Asp Glu Thr Asp Phe Ser Pro
    195                 200                 205

Arg Ser Ala Arg Ser Tyr Glu Leu Pro Ser Leu Ser Gly Ser Glu Ser
210                 215                 220

Val Gly Ile Val Arg Leu Leu Met Ser Leu Asp Gln Pro Ser Arg Gly
225                 230                 235                 240

Val Ile Asp Ala Ile Thr Asn Ala Val Ala Trp Phe Glu Ser Ala Lys
                245                 250                 255

Leu Pro Gly Ile Lys Thr Val Gln Glu Thr Asp Pro Asn Ser Pro Lys
            260                 265                 270

Gly Trp Asn Arg Val Val Val Lys Asp Glu Ser Ala Arg Pro Met Trp
        275                 280                 285

Ala Arg Phe Tyr Asp Ile Asn Thr Asn Lys Pro Phe Phe Cys Asp Arg
    290                 295                 300

Asp Gly Val Pro Lys Pro Ser Leu Ala Glu Ile Gly Tyr Glu Arg Arg
305                 310                 315                 320

Asn Gly Tyr Ala Trp Leu Gly Tyr Trp Pro Glu Asp Leu Leu Ala Arg
                325                 330                 335

Glu Tyr Pro Ala Trp Lys Met Lys Trp Leu Lys Pro Lys Glu Arg Pro
            340                 345                 350

Ala Phe

<210> SEQ ID NO 15
<211> LENGTH: 1575
<212> TYPE: DNA
<213> ORGANISM: Bacteria

<400> SEQUENCE: 15

```
atgagacgac cagtcgcact ccggctccac gcggcactgg ccaccctggc cctggcggcc      60
gcgaccggcg tggtgctctc gatccccag gcatcggcgg cggccggcgg cgccaccggc     120
tacgccggcc agaacggcgg caccaccggc ggtgccggcg ccagaccgt acgggccacc     180 acgggcaccg ccatccacgc ggccctgtgc ggacgggcca gcagcagcac cccgatcacg     240
atcgaggtcg agggaacgat caaccacgcc aacaccgcca aggtgtccgg ccccagctgc     300
aacaccgccg ccggagtgat cgagctgaag cagatcagca cgtcacgct cgtcggggtc     360 ggctccggcg ccgtcttcga ccaactcggc atccacatcc gcgagtccag caacatcatc     420
atccagaacg tgacggtccg gaacgtcaag aagtcgggct cgccgctgtc aacggcggc     480 gacgccatcg gcatggagag cgacgtccgc aacgtctggg tcgaccactc caccctggag     540
gcctcgggcg cgagtccga gggctacgac ggcctcttcg acatgaagga caacaccgg     600 tacgtgaccc tgtcgtacag catcctgcgc aaatccgggc gcggcggcct cgtggggtcc     660
agcgagaccg aactctcgaa cagcttcatc acgtaccacc acaacctgta cgagaacatc     720
gactcgcgcg cgcccctgct gcgcggcggg accgcccaca tgtacaacaa ccactacctg     780
cggatcaacg agtccggcat caactcccgt gccggagccc acgccaaggt ggacaacaac     840
tacttcgagg actccaagga cgtcctcggc accttctaca ccgacgccgc cgggtactgg     900
```

-continued

```
caggtcagcg gcaacgtcta cgacaacgtg acctggtccg cccggggcac cgacaacaac    960
ccggcggggc cggacccgca gtccaacacc accgtctcca tccctacgc cttcagcctc    1020
gacccggcca cctgcgtgcc ggacgtcgtg agccgaacgg cggtgccgg caagggactt    1080
caggtgtcga acggcagctg ctccccgcag acacccacgc ccacgccgac gggcacgccg    1140
accacacccg cgccgacgac tcccaccccg agcccgacgc cctccacgcc cggaccgacc    1200
cagcccggcg ggacgaacct cagcatcggt gccgggtccg acggttcgag caaggccgac    1260
ggcaccagct acggcaacgt ccgggacggg gacctcggca cccactggtc tccggccggt    1320
tcgaccggct ccgtgtcgat caagtggggc agcgccacca cggtctcccg catcgtcatc    1380
cgcgaggcgg cgggcgcgac gggcgtcatc ggctcctggc tcgtcctgaa cggcgacacc    1440
ggcgccgtgc tgacctccgg cagcggggcg gggacgatct ccgtccccg gacggccctg    1500
aagaagatca ccttcgagat cacgggcgcg agcggcacgc cacggatcgc cgagttcgag    1560
acgtacgccg gctag                                                    1575
```

<210> SEQ ID NO 16
<211> LENGTH: 524
<212> TYPE: PRT
<213> ORGANISM: Bacteria
<220> FEATURE:
<221> NAME/KEY: SIGNAL
<222> LOCATION: (1)...(33)
<220> FEATURE:
<221> NAME/KEY: DOMAIN
<222> LOCATION: (34)...(359)
<223> OTHER INFORMATION: Catalytic domain

<400> SEQUENCE: 16

Met Arg Arg Pro Val Ala Leu Arg Leu His Ala Leu Ala Thr Leu
 1               5                  10                  15

Ala Leu Ala Ala Ala Thr Gly Val Val Leu Ser Ile Pro Gln Ala Ser
                 20                  25                  30

Ala Ala Ala Gly Gly Ala Thr Gly Tyr Ala Gly Gln Asn Gly Gly Thr
             35                  40                  45

Thr Gly Gly Ala Gly Gly Gln Thr Val Arg Ala Thr Thr Gly Thr Ala
         50                  55                  60

Ile His Ala Ala Leu Cys Gly Arg Ala Ser Ser Thr Pro Ile Thr
 65                  70                  75                  80

Ile Glu Val Glu Gly Thr Ile Asn His Ala Asn Thr Ala Lys Val Ser
                 85                  90                  95

Gly Pro Ser Cys Asn Thr Ala Ala Gly Val Ile Glu Leu Lys Gln Ile
             100                 105                 110

Ser Asn Val Thr Leu Val Gly Val Gly Ser Gly Ala Val Phe Asp Gln
         115                 120                 125

Leu Gly Ile His Ile Arg Glu Ser Ser Asn Ile Ile Gln Asn Val
     130                 135                 140

Thr Val Arg Asn Val Lys Lys Ser Gly Ser Pro Leu Ser Asn Gly Gly
145                 150                 155                 160

Asp Ala Ile Gly Met Glu Ser Asp Val Arg Asn Val Trp Val Asp His
                 165                 170                 175

Ser Thr Leu Glu Ala Ser Gly Gly Glu Ser Glu Gly Tyr Asp Gly Leu
             180                 185                 190

Phe Asp Met Lys Asp Asn Thr Arg Tyr Val Thr Leu Ser Tyr Ser Ile
         195                 200                 205

Leu Arg Lys Ser Gly Arg Gly Gly Leu Val Gly Ser Ser Glu Thr Glu

```
              210                 215                 220
Leu Ser Asn Ser Phe Ile Thr Tyr His His Asn Leu Tyr Glu Asn Ile
225                 230                 235                 240

Asp Ser Arg Ala Pro Leu Leu Arg Gly Gly Thr Ala His Met Tyr Asn
                245                 250                 255

Asn His Tyr Leu Arg Ile Asn Glu Ser Gly Ile Asn Ser Arg Ala Gly
                260                 265                 270

Ala His Ala Lys Val Asp Asn Tyr Phe Glu Asp Ser Lys Asp Val
                275                 280                 285

Leu Gly Thr Phe Tyr Thr Asp Ala Ala Gly Tyr Trp Gln Val Ser Gly
290                 295                 300

Asn Val Tyr Asp Asn Val Thr Trp Ser Ala Arg Gly Thr Asp Asn Asn
305                 310                 315                 320

Pro Ala Gly Pro Asp Pro Gln Ser Asn Thr Thr Val Ser Ile Pro Tyr
                325                 330                 335

Ala Phe Ser Leu Asp Pro Ala Thr Cys Val Pro Asp Val Val Ser Arg
                340                 345                 350

Thr Ala Gly Ala Gly Lys Gly Leu Gln Val Ser Asn Gly Ser Cys Ser
                355                 360                 365

Pro Gln Thr Pro Thr Pro Thr Pro Thr Gly Thr Pro Thr Thr Pro Ala
                370                 375                 380

Pro Thr Thr Pro Thr Pro Ser Pro Thr Pro Ser Thr Pro Gly Pro Thr
385                 390                 395                 400

Gln Pro Gly Gly Thr Asn Leu Ser Ile Gly Ala Gly Ser Asp Gly Ser
                405                 410                 415

Ser Lys Ala Asp Gly Thr Ser Tyr Gly Asn Val Arg Asp Gly Asp Leu
                420                 425                 430

Gly Thr His Trp Ser Pro Ala Gly Ser Thr Gly Ser Val Ser Ile Lys
                435                 440                 445

Trp Gly Ser Ala Thr Thr Val Ser Arg Ile Val Ile Arg Glu Ala Ala
                450                 455                 460

Gly Ala Thr Gly Val Ile Gly Ser Trp Leu Val Leu Asn Gly Asp Thr
465                 470                 475                 480

Gly Ala Val Leu Thr Ser Gly Ser Gly Ala Gly Thr Ile Ser Val Pro
                485                 490                 495

Arg Thr Ala Leu Lys Lys Ile Thr Phe Glu Ile Thr Gly Ala Ser Gly
                500                 505                 510

Thr Pro Arg Ile Ala Glu Phe Glu Thr Tyr Ala Gly
                515                 520

<210> SEQ ID NO 17
<211> LENGTH: 1047
<212> TYPE: DNA
<213> ORGANISM: Unknown
<220> FEATURE:
<223> OTHER INFORMATION: Obtained from an environmental sample

<400> SEQUENCE: 17
ttgccgcgtg cgcccggtgg tgagtcgtca tcgccagcgc agacgtcatc ggttgcggtc     60
tcctgggatc agatcctccg tcagcctgcg gcctggtacg gcggtgcgga ggcgttgcga    120
gtcgctgaga acgtgctctt gtatcagcgc gcggcaggag ggtggccgaa gaacatcaac    180
atggcggcgc cgatgaccgc cgctgaccgt gcgaaagtca cggacgagcg cgcgcagaac    240
gacgccacga tcgacaacac gtcaacgacg acgcagatcc gttttcttgc gctcgttctt    300
```

```
cgcggcaccg ccgacgcacg attcaaggac gcggcgctga agggcatcga cttcctgctg    360
gctgcgcaat acgcgaatgg aggctggcct cagtattttc ccctgcgcga cgactactcg    420
cggcgcatca cgttcaatga cgacgcgatg gtgaatgtga tgacgctgct gcgcgagact    480
tcgcagggcc agacgccgtt cgagttcgtc gacgcctcgc ggcgcggccg ggcggcgcag    540
tctgtctcac gcggcgtcga cgtcatgctg cgcacgcaga ttcgagtcaa cggcgtgctg    600
accggctggt gccagcagca cgacgagcgg aactttcagc cggtgaaggc gcgcgcgtac    660
gaacatccgt cgattgccag caaggaaacc gcgagcatcg caagattcct gatgggatt     720 gaacggccgt cgccggagat cgtgtccgcg gtggatggcg cagtcgcgtg gttgcgagcg    780
gcgcagattt caggtgtgcg gacggagcgc cggcccgacg gatcgaatcc gggcggcgac    840
gtcgtggcgg tgcaggactc cgccgcgccg ccaatctggg cccgcttcta cgagattggc    900
accaaccggc cgatgttttc gggtcgcgac ggcgtcatca agtacagcct cagcgagatc    960
gagatcgagc ggcgcgctgg atacagctgg tacggcgact acgccgccag actgctcaga   1020
gacgactatc cgaagtggaa gaaatga                                       1047

<210> SEQ ID NO 18
<211> LENGTH: 348
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(348)
<223> OTHER INFORMATION: Catalytic domain

<400> SEQUENCE: 18

Met Pro Arg Ala Pro Gly Gly Glu Ser Ser Pro Ala Gln Thr Ser
  1               5                  10                  15

Ser Val Ala Val Ser Trp Asp Gln Ile Leu Arg Gln Pro Ala Ala Trp
             20                  25                  30

Tyr Gly Gly Ala Glu Ala Leu Arg Val Ala Glu Asn Val Leu Leu Tyr
         35                  40                  45

Gln Arg Ala Ala Gly Gly Trp Pro Lys Asn Ile Asn Met Ala Ala Pro
     50                  55                  60

Met Thr Ala Ala Asp Arg Ala Lys Val Thr Asp Glu Arg Ala Gln Asn
 65                  70                  75                  80

Asp Ala Thr Ile Asp Asn Thr Ser Thr Thr Thr Gln Ile Arg Phe Leu
                 85                  90                  95

Ala Leu Val Leu Arg Gly Thr Ala Asp Ala Arg Phe Lys Asp Ala Ala
            100                 105                 110

Leu Lys Gly Ile Asp Phe Leu Leu Ala Ala Gln Tyr Ala Asn Gly Gly
        115                 120                 125

Trp Pro Gln Tyr Phe Pro Leu Arg Asp Asp Tyr Ser Arg Arg Ile Thr
    130                 135                 140

Phe Asn Asp Asp Ala Met Val Asn Val Met Thr Leu Leu Arg Glu Thr
145                 150                 155                 160

Ser Gln Gly Gln Thr Pro Phe Glu Phe Val Asp Ala Ser Arg Arg Gly
                165                 170                 175

Arg Ala Ala Gln Ser Val Ser Arg Gly Val Asp Val Met Leu Arg Thr
            180                 185                 190

Gln Ile Arg Val Asn Gly Val Leu Thr Gly Trp Cys Gln Gln His Asp
        195                 200                 205
```

```
Glu Arg Asn Phe Gln Pro Val Lys Ala Arg Ala Tyr Glu His Pro Ser
    210                 215                 220
Ile Ala Ser Lys Glu Thr Ala Ser Ile Ala Arg Phe Leu Met Gly Ile
225                 230                 235                 240
Glu Arg Pro Ser Pro Glu Ile Val Ser Ala Val Asp Gly Ala Val Ala
                245                 250                 255
Trp Leu Arg Ala Ala Gln Ile Ser Gly Val Arg Thr Glu Arg Arg Pro
            260                 265                 270
Asp Gly Ser Asn Pro Gly Gly Asp Val Val Ala Val Gln Asp Ser Ala
        275                 280                 285
Ala Pro Pro Ile Trp Ala Arg Phe Tyr Glu Ile Gly Thr Asn Arg Pro
    290                 295                 300
Met Phe Ser Gly Arg Asp Gly Val Ile Lys Tyr Ser Leu Ser Glu Ile
305                 310                 315                 320
Glu Ile Glu Arg Arg Ala Gly Tyr Ser Trp Tyr Gly Asp Tyr Ala Ala
                325                 330                 335
Arg Leu Leu Arg Asp Asp Tyr Pro Lys Trp Lys Lys
            340                 345
```

<210> SEQ ID NO 19
<211> LENGTH: 1122
<212> TYPE: DNA
<213> ORGANISM: Unknown
<220> FEATURE:
<223> OTHER INFORMATION: Obtained from an environmental sample

<400> SEQUENCE: 19

```
gtgaacaggt ggcgcgaaga cttcttgcgc gacttcgcgg cccgcatgct ccggtgcatg    60
gttcccggc cgcagatcca ctggggcggc ggtgtcatcc ggcaggaacc ggaatggtac    120
ggctcggccg aggcgcgtgc gatcgccgac agcgttcttc aataccagtc gaccgctggc    180
ggctggccca gaacaccga cttgacggtc tcgccaccgt ccgccgaatt ccttgcggat    240
gcggatggtc tcacgaacac gatcgacaac gacgccacca cgttgccgat gcgatttctc    300
gctctggtgg cgcacgcgac cggcggcatc aagtaccgcg ccgcgttcga acgcggtctg    360
gactacctgc tcgccgctca gtatcccaat ggcggctggc tcagtatttt ccctgcgt     420
gacggctatt actcgcacat cacctacaac gacaatgcga tggtcaacgt cctcaccgtt    480
ctgcgcgatg cggccgcggg ccggccccct tactcgttcg tcgacagggc ccggcgcgcc    540
agagcagaaa cggccatcgc tcgcggcatc gacatcatcg tgcgcactca ggtgagacgg    600
gccggcgtgc tgaccgcatg gtgcgcccag cacgacgaaa agacgctcga gccggcgtgg    660
gcgcgcaact acgaaccgcc gacactctcc gggcacgaaa gcgtcggcat cgtgcgcttt    720
ctcatgggaa tcgaaaagcc cacgccgagg atcgtcgcgg cggtgcaagg cgccgctgac    780
tggttgagag ccgtcgcgat cagcgggttg cgtctcgagg aattcaccga cgccgatggc    840
aggcgcgaca ggcgcgtcgt cgccgatccg gcagcgccgc tcctgtgggc gcgcttctac    900
gagcttggca cggaccgtcc cgtcttcacc ggccgcgaca aggtgatccg gtactcgctc    960
agcgaaatcg agcacgagcg ccggaacggg tatgcctact atggcacatg gccggccacg    1020
ctcctcagcg aggagtaccc ccgttggcgc gcgaaacacc tggctcgacg gagcgtcagg    1080
caggtagagg agggaatcgc gatacgcgtc cctaatccct ga                       1122
```

<210> SEQ ID NO 20
<211> LENGTH: 373
<212> TYPE: PRT

```
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(373)
<223> OTHER INFORMATION: Catalytic domain

<400> SEQUENCE: 20

Met Asn Arg Trp Arg Glu Asp Phe Leu Arg Asp Phe Ala Ala Arg Met
 1               5                  10                  15

Leu Arg Cys Met Val Pro Arg Pro Gln Ile His Trp Gly Gly Gly Val
            20                  25                  30

Ile Arg Gln Glu Pro Glu Trp Tyr Gly Ser Ala Glu Ala Arg Ala Ile
        35                  40                  45

Ala Asp Ser Val Leu Gln Tyr Gln Ser Thr Ala Gly Gly Trp Pro Lys
    50                  55                  60

Asn Thr Asp Leu Thr Val Ser Pro Pro Ser Ala Glu Phe Leu Ala Asp
65                  70                  75                  80

Ala Asp Gly Leu Thr Asn Thr Ile Asp Asn Asp Ala Thr Thr Leu Pro
                85                  90                  95

Met Arg Phe Leu Ala Leu Val Ala His Ala Thr Gly Gly Ile Lys Tyr
            100                 105                 110

Arg Ala Ala Phe Glu Arg Gly Leu Asp Tyr Leu Leu Ala Ala Gln Tyr
        115                 120                 125

Pro Asn Gly Gly Trp Pro Gln Tyr Phe Pro Leu Arg Asp Gly Tyr Tyr
    130                 135                 140

Ser His Ile Thr Tyr Asn Asp Asn Ala Met Val Asn Val Leu Thr Val
145                 150                 155                 160

Leu Arg Asp Ala Ala Gly Arg Pro Pro Tyr Ser Phe Val Asp Arg
                165                 170                 175

Ala Arg Arg Ala Arg Ala Glu Thr Ala Ile Ala Arg Gly Ile Asp Ile
            180                 185                 190

Ile Val Arg Thr Gln Val Arg Arg Ala Gly Val Leu Thr Ala Trp Cys
        195                 200                 205

Ala Gln His Asp Glu Lys Thr Leu Glu Pro Ala Trp Ala Arg Asn Tyr
    210                 215                 220

Glu Pro Pro Thr Leu Ser Gly His Glu Ser Val Gly Ile Val Arg Phe
225                 230                 235                 240

Leu Met Gly Ile Glu Lys Pro Thr Pro Arg Ile Val Ala Ala Val Gln
                245                 250                 255

Gly Ala Ala Asp Trp Leu Arg Ala Val Ala Ile Ser Gly Leu Arg Leu
            260                 265                 270

Glu Glu Phe Thr Asp Ala Asp Gly Arg Arg Asp Arg Arg Val Val Ala
        275                 280                 285

Asp Pro Ala Ala Pro Leu Leu Trp Ala Arg Phe Tyr Glu Leu Gly Thr
    290                 295                 300

Asp Arg Pro Val Phe Thr Gly Arg Asp Lys Val Ile Arg Tyr Ser Leu
305                 310                 315                 320

Ser Glu Ile Glu His Glu Arg Arg Asn Gly Tyr Ala Tyr Tyr Gly Thr
                325                 330                 335

Trp Pro Ala Thr Leu Leu Ser Glu Glu Tyr Pro Arg Trp Arg Ala Lys
            340                 345                 350

His Leu Ala Arg Arg Ser Val Arg Gln Val Glu Glu Gly Ile Ala Ile
        355                 360                 365
```

-continued

Arg Val Pro Asn Pro
    370

<210> SEQ ID NO 21
<211> LENGTH: 1269
<212> TYPE: DNA
<213> ORGANISM: Unknown
<220> FEATURE:
<223> OTHER INFORMATION: Obtained from an environmental sample

<400> SEQUENCE: 21

```
atgcgtaaat cgaactgggc cgtcacaacg gccatcctgc tcgcgctgag cgccgcaccg      60
ctggcggcaa agcccatcgg acagatcacc ctcgccgtgc cgctcagccc ggcgcgcctg     120
accgaaacgc cgcctgagca gcgggcgcaa tggcaggcct atctcgccac caccgaggca     180
cagcttaagg cagacaaggc ggcgctggct gccgagcgcg ccggtctggc cgaaatcccc     240
gccaagccga gaccggcag cgccaacacc atgccgctcg acaagccgct ggaatggtac     300
gcgtcgtccg aggcgcgtct ggtcgccgat aatatcgtca gctatcagac tccggcaggc     360
ggctggggca aaaatcaggc ccgcaacgaa cccacgcggt tgaaaggtca ggcctacact     420
atcgatgacg ccgatcccac cggttcgggc aaatggaact tcgtcggcac catcgacaac     480
gacgccacca tcgtggaaat tcgctttctc gcccgcgtag cggcggcggc cacgggcccg     540
gaaggcgacg tctatcgcgc ctccgccacg cgcggcatca cctacttgct ggcggcgcag     600
tacccccaatg gcggctggcc gcaggtctgg ccgcttcagg gcggctatca cgacgccatc     660
accctcaatg acgcgcgat gatccatgtg ctcgaactgt ttgacgacat cgccagcgga     720
cagggcgact tcgccttcct gcctgagccg ctgcgcgaca aggtcgaggc cgcacaggca     780
aagggtcaga aggtgcttct cgatcttcag cttaagcgca acggcgaacg cacccctgtg     840
gcgcagcagt acgatccgat taccctcttg cccagcgcgg cgcgtaacta cgagccgtcg     900
tcgatcagca ccggtgaaag cgccggtgtg ctgatctacc tcatgtccct gcccaaccc      960
tcgcctgaag tgcgcgacgc catcgaaaaa ggcgtggccc tgctgatcaa acttcagatc    1020
aacggcatgg catgggaaaa ggacggcatg cgcaaacgtc tggtcgccaa ggctgacgcc    1080
tcgccgctgt ggtcgcgcta tcacgactcg gaaacgctgc tgcccatctt cggtgaccgc    1140
gacatgcgca tcttcgacga cgtcaacgac atcagcgacg aacgcagccg cggctatgcc    1200
tggtatggca caagcccggc acgggccatc gccgaatacg aaaaatggaa acagggcaac    1260
ggcaaatga                                                           1269
```

<210> SEQ ID NO 22
<211> LENGTH: 422
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(23)
<220> FEATURE:
<221> NAME/KEY: DOMAIN
<222> LOCATION: (24)...(422)
<223> OTHER INFORMATION: Catalytic domain

<400> SEQUENCE: 22

Met Arg Lys Ser Asn Trp Ala Val Thr Thr Ala Ile Leu Leu Ala Leu
 1               5                  10                  15

Ser Ala Ala Pro Leu Ala Ala Lys Pro Ile Gly Gln Ile Thr Leu Ala
            20                  25                  30

```
Val Pro Leu Ser Pro Ala Arg Leu Thr Glu Thr Pro Pro Glu Gln Arg
         35                  40                  45

Ala Gln Trp Gln Ala Tyr Leu Ala Thr Thr Glu Ala Gln Leu Lys Ala
 50                  55                  60

Asp Lys Ala Ala Leu Ala Ala Glu Arg Ala Gly Leu Ala Glu Ile Pro
 65                  70                  75                  80

Ala Lys Pro Lys Thr Gly Ser Ala Asn Thr Met Pro Leu Asp Lys Pro
                 85                  90                  95

Leu Glu Trp Tyr Ala Ser Ser Glu Ala Arg Leu Val Ala Asp Asn Ile
                100                 105                 110

Val Ser Tyr Gln Thr Pro Ala Gly Gly Trp Gly Lys Asn Gln Ala Arg
        115                 120                 125

Asn Glu Pro Thr Arg Leu Lys Gly Gln Ala Tyr Thr Ile Asp Asp Ala
        130                 135                 140

Asp Pro Thr Gly Ser Gly Lys Trp Asn Phe Val Gly Thr Ile Asp Asn
145                 150                 155                 160

Asp Ala Thr Ile Val Glu Ile Arg Phe Leu Ala Arg Val Ala Ala Ala
                165                 170                 175

Ala Thr Gly Pro Glu Gly Asp Val Tyr Arg Ala Ser Ala Thr Arg Gly
                180                 185                 190

Ile Thr Tyr Leu Leu Ala Ala Gln Tyr Pro Asn Gly Gly Trp Pro Gln
        195                 200                 205

Val Trp Pro Leu Gln Gly Gly Tyr His Asp Ala Ile Thr Leu Asn Asp
    210                 215                 220

Gly Ala Met Ile His Val Leu Glu Leu Phe Asp Asp Ile Ala Ser Gly
225                 230                 235                 240

Gln Gly Asp Phe Ala Phe Leu Pro Glu Pro Leu Arg Asp Lys Val Glu
                245                 250                 255

Ala Ala Gln Ala Lys Gly Gln Lys Val Leu Leu Asp Leu Gln Leu Lys
        260                 265                 270

Arg Asn Gly Glu Arg Thr Leu Trp Ala Gln Gln Tyr Asp Pro Ile Thr
    275                 280                 285

Leu Leu Pro Ser Ala Ala Arg Asn Tyr Glu Pro Ser Ser Ile Ser Thr
        290                 295                 300

Gly Glu Ser Ala Gly Val Leu Ile Tyr Leu Met Ser Leu Pro Asn Pro
305                 310                 315                 320

Ser Pro Glu Val Arg Asp Ala Ile Glu Lys Gly Val Ala Leu Leu Ile
                325                 330                 335

Lys Leu Gln Ile Asn Gly Met Ala Trp Glu Lys Asp Gly Met Arg Lys
        340                 345                 350

Arg Leu Val Ala Lys Ala Asp Ala Ser Pro Leu Trp Ser Arg Tyr His
        355                 360                 365

Asp Ser Glu Thr Leu Leu Pro Ile Phe Gly Arg Asp Met Arg Ile
        370                 375                 380

Phe Asp Asp Val Asn Asp Ile Ser Asp Glu Arg Ser Arg Gly Tyr Ala
385                 390                 395                 400

Trp Tyr Gly Thr Ser Pro Ala Arg Ala Ile Ala Glu Tyr Glu Lys Trp
                405                 410                 415

Lys Gln Gly Asn Gly Lys
        420

<210> SEQ ID NO 23
<211> LENGTH: 1182
```

<212> TYPE: DNA
<213> ORGANISM: Unknown
<220> FEATURE:
<223> OTHER INFORMATION: Obtained from an environmental sample

<400> SEQUENCE: 23

```
atgaaccgtg gcgtgattgt tttgctggcg ccgctccag ctgcggcgca tggcgcagtg      60
ctggggtata tgacgcctgc gcagccgttg accgaggcgc gcattgccgc gctgccggcg    120
tcggagcagg gcgcctggcg gggctacctc gcccgctccc gcgcagccat ggacgccgac    180
aaggccgccc tggccgccga gcgcgccgcg ctcgccaccg taccgccggc gccgccgcat    240
ggcggtggtg atggcgggat ggcgcgcaac cgtccgacgg cttggtatgg gacgccggaa    300
gcgcggcaca tcgcggacaa tatcgtcagc ttccagacgc cgtccggcgg ctggggcaag    360
aacgtggacc gcacgggacc tgtgcgccag cgcggacagc attacgtttc cttcgatggc    420
aaggagtcct ggaacttcat cggcacgatc gacaacaacg ccacaacgag cgagctgaaa    480
ttcctggcgc gcgtgcaggc gcaaatgccc ggcgcggcgg gcgacgaata ccggaaggcc    540
gccctgcgcg catcagcta cctgttgaac tcacaatatc ccaacggcgg cttcccgcag    600
gtctatccgc tgcaaggcgg ctaccacgac gccatcacct caacgacga tgccttcgcc    660
aacgtgctgc aagtgctgct ggaagtggcg aaccgcaggg gcgactatgc cttcgtcccc    720
gaaaccgtgg caaccgatgc ccgcgcggcc gcggacaagg cgctccaagt cctgctggcg    780
agccagatca tcgtcggcgg cgtacgcacc gcctggtgcc agcagcacga tgcgatcacg    840
ctggcgcccg tcggcgcccg caatttcgaa ccggccgcgc tgaccagcac ggaaagcgcg    900
cgcctgctga tgctgttgat gctgctgccc gatccgagcc ggagctgag agcgtcaatc    960
catgcgggga tggcctggct gcagaaagcg cgctgccgg gggatgtctg gtcgcgctac   1020
tatgacctga acacgatgag gccgatcttt ggggatcgtg accgcagtat ccacgatgat   1080
gtgaaggaat tgagcgagga gaggcaaaaa ggctatggct ggttcagtaa cggaccagcc   1140
agagctaaac aggcttttga ggcctggacg cgcaaacctt ga                      1182
```

<210> SEQ ID NO 24
<211> LENGTH: 393
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(18)
<220> FEATURE:
<221> NAME/KEY: DOMAIN
<222> LOCATION: (19)...(393)
<223> OTHER INFORMATION: Catalytic domain

<400> SEQUENCE: 24

```
Met Asn Arg Gly Val Ile Val Leu Leu Ala Ala Pro Ala Ala Ala
 1               5                  10                  15

His Gly Ala Val Leu Gly Tyr Met Thr Pro Ala Gln Pro Leu Thr Glu
                20                  25                  30

Ala Arg Ile Ala Ala Leu Pro Ala Ser Glu Gln Gly Ala Trp Arg Gly
            35                  40                  45

Tyr Leu Ala Arg Ser Arg Ala Ala Met Asp Ala Asp Lys Ala Ala Leu
        50                  55                  60

Ala Ala Glu Arg Ala Ala Leu Ala Thr Val Pro Pro Ala Pro Pro His
65                  70                  75                  80
```

-continued

Gly Gly Gly Asp Gly Gly Met Ala Arg Asn Arg Pro Thr Ala Trp Tyr
            85                  90                  95

Gly Thr Pro Glu Ala Arg His Ile Ala Asp Asn Ile Val Ser Phe Gln
               100                 105                 110

Thr Pro Ser Gly Gly Trp Gly Lys Asn Val Asp Arg Thr Gly Pro Val
           115                 120                 125

Arg Gln Arg Gly Gln His Tyr Val Ser Phe Asp Gly Lys Glu Ser Trp
       130                 135                 140

Asn Phe Ile Gly Thr Ile Asp Asn Asn Ala Thr Thr Ser Glu Leu Lys
145                 150                 155                 160

Phe Leu Ala Arg Val Gln Ala Gln Met Pro Gly Ala Ala Gly Asp Glu
                165                 170                 175

Tyr Arg Lys Ala Ala Leu Arg Gly Ile Ser Tyr Leu Leu Asn Ser Gln
            180                 185                 190

Tyr Pro Asn Gly Gly Phe Pro Gln Val Tyr Pro Leu Gln Gly Gly Tyr
        195                 200                 205

His Asp Ala Ile Thr Phe Asn Asp Asp Ala Phe Ala Asn Val Leu Gln
    210                 215                 220

Val Leu Leu Glu Val Ala Asn Arg Arg Gly Asp Tyr Ala Phe Val Pro
225                 230                 235                 240

Glu Thr Val Ala Thr Asp Ala Arg Ala Ala Asp Lys Ala Leu Gln
                245                 250                 255

Val Leu Leu Ala Ser Gln Ile Ile Val Gly Val Arg Thr Ala Trp
            260                 265                 270

Cys Gln Gln His Asp Ala Ile Thr Leu Ala Pro Val Gly Ala Arg Asn
        275                 280                 285

Phe Glu Pro Ala Ala Leu Thr Ser Thr Glu Ser Ala Arg Leu Leu Met
290                 295                 300

Leu Leu Met Leu Leu Pro Asp Pro Ser Pro Glu Leu Arg Ala Ser Ile
305                 310                 315                 320

His Ala Gly Met Ala Trp Leu Gln Lys Ala Ala Leu Pro Gly Asp Val
                325                 330                 335

Trp Ser Arg Tyr Tyr Asp Leu Asn Thr Met Arg Pro Ile Phe Gly Asp
            340                 345                 350

Arg Asp Arg Ser Ile His Asp Asp Val Lys Glu Leu Ser Glu Glu Arg
        355                 360                 365

Gln Lys Gly Tyr Gly Trp Phe Ser Asn Gly Pro Ala Arg Ala Lys Gln
    370                 375                 380

Ala Phe Glu Ala Trp Thr Arg Lys Pro
385                 390

```
<210> SEQ ID NO 25
<211> LENGTH: 1194
<212> TYPE: DNA
<213> ORGANISM: Unknown
<220> FEATURE:
<223> OTHER INFORMATION: Obtained from an environmental sample

<400> SEQUENCE: 25
ttggtcgctg ccctattaag ctgcggcagc gccaatctct atgcagaatc aaccgcaaaa      60
tcggttacgc aatcagcagc cacaaatcaa ttgcaaaatg aaaaaagcag ttggacagc     120 tattacgccg catccaaaaa aatacatcag gcagaccagg attttctcgc cgctgaatta    180
aaaaaactcg gtcagaaaaa accaacattg cccgcacaca ccaaagattt tggttttgat    240
gttaagcagg taaatgcaga ttggtttaaa agtgacgaag gcaaacgtgt gatggagatt    300
```

```
attctctcct tccaaacccc gtccggcggt tggtcaaagc gtaccgacat ggccaaggcg      360
gtgcgacaac ctgggcaagc ctttggcgtt gaaaaaggct atatcccaac atttgataat      420
ggcgctacca gcactcaatt gatgttgctc gcgcaagcac accaagccac cggcgatcac      480
cgctttagcg acgcatttgg gcgcggcttg caattaattt tgactgcgca atacccgaat      540
ggtggctggc cacaaaactt tccactaacc ggtagctacc acgattacat cacctacaac      600
gacaatctta cgcgcgacct gatggtagtg ctgcacaaaa cagcgcaggc aaaaaatgat      660
tttgcattcg tgaccaaagc gcagcaaatc gcagcgtcag ctagcctcgc gcgtgcactt      720
gattgcgtat tgaaatcaca agttgtcgtc aatggcacac gcacactctg gggcgcacag      780
cacgatgtta aaacactgca accaaccaaa gcgcgcgcat ttgaaatggt gtcactcact      840
accactgaaa gcgcagccat gctcagtttt ctgatggata tcaaaaatcc cagcgcggat      900
attattcaat ccatacatgc agccatagcc tggtatgagc aaaataaaat cgtcggaaaa      960
acctggacac gtggtgatgc ggaattaaaa gataataaaa attcgcagcc actctgggcg     1020 cgttttatg agataggcac taataagcct atatttgggg atcgcgatga cactgtgtat       1080
tacgatttgg caaaagtgtc taaagagcgt cgcgaaggtt atgcgtggta ctccactgac      1140
ccgaataaga cgctaaaaaa atatgctgaa tggtctaaaa aatatcccaa ataa            1194
```

<210> SEQ ID NO 26
<211> LENGTH: 397
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(15)
<220> FEATURE:
<221> NAME/KEY: DOMAIN
<222> LOCATION: (16)...(397)
<223> OTHER INFORMATION: Catalytic domain

<400> SEQUENCE: 26

```
Met Val Ala Ala Leu Leu Ser Cys Gly Ser Ala Asn Leu Tyr Ala Glu
  1               5                  10                  15

Ser Thr Ala Lys Ser Val Thr Gln Ser Ala Ala Thr Asn Gln Leu Gln
             20                  25                  30

Asn Glu Lys Ser Ser Trp Asp Ser Tyr Tyr Ala Ala Ser Lys Lys Ile
         35                  40                  45

His Gln Ala Asp Gln Asp Phe Leu Ala Ala Glu Leu Lys Lys Leu Gly
     50                  55                  60

Gln Lys Lys Pro Thr Leu Pro Ala His Thr Lys Asp Phe Gly Phe Asp
 65                  70                  75                  80

Val Lys Gln Val Asn Ala Asp Trp Phe Lys Ser Asp Glu Gly Lys Arg
                 85                  90                  95

Val Met Glu Ile Ile Leu Ser Phe Gln Thr Pro Ser Gly Gly Trp Ser
            100                 105                 110

Lys Arg Thr Asp Met Ala Lys Ala Val Arg Gln Pro Gly Gln Ala Phe
        115                 120                 125

Gly Val Glu Lys Gly Tyr Ile Pro Thr Phe Asp Asn Gly Ala Thr Ser
    130                 135                 140

Thr Gln Leu Met Leu Leu Ala Gln Ala His Gln Ala Thr Gly Asp His
145                 150                 155                 160

Arg Phe Ser Asp Ala Phe Gly Arg Gly Leu Gln Leu Ile Leu Thr Ala
```

```
                        165                 170                 175
Gln Tyr Pro Asn Gly Gly Trp Pro Gln Asn Phe Pro Leu Thr Gly Ser
                180                 185                 190
Tyr His Asp Tyr Ile Thr Tyr Asn Asp Asn Leu Thr Arg Asp Leu Met
            195                 200                 205
Val Val Leu His Lys Thr Ala Gln Ala Lys Asn Asp Phe Ala Phe Val
        210                 215                 220
Thr Lys Ala Gln Gln Ile Ala Ala Ser Ala Ser Leu Ala Arg Ala Leu
225                 230                 235                 240
Asp Cys Val Leu Lys Ser Gln Val Val Asn Gly Thr Arg Thr Leu
                245                 250                 255
Trp Gly Ala Gln His Asp Val Lys Thr Leu Gln Pro Thr Lys Ala Arg
                260                 265                 270
Ala Phe Glu Met Val Ser Leu Thr Thr Thr Glu Ser Ala Ala Met Leu
            275                 280                 285
Ser Phe Leu Met Asp Ile Lys Asn Pro Ser Ala Asp Ile Ile Gln Ser
        290                 295                 300
Ile His Ala Ala Ile Ala Trp Tyr Glu Gln Asn Lys Ile Val Gly Lys
305                 310                 315                 320
Thr Trp Thr Arg Gly Asp Ala Glu Leu Lys Asp Asn Lys Asn Ser Gln
                325                 330                 335
Pro Leu Trp Ala Arg Phe Tyr Glu Ile Gly Thr Asn Lys Pro Ile Phe
                340                 345                 350
Gly Asp Arg Asp Asp Thr Val Tyr Tyr Asp Leu Ala Lys Val Ser Lys
            355                 360                 365
Glu Arg Arg Glu Gly Tyr Ala Trp Tyr Ser Thr Asp Pro Asn Lys Thr
        370                 375                 380
Leu Lys Lys Tyr Ala Glu Trp Ser Lys Lys Tyr Pro Lys
385                 390                 395

<210> SEQ ID NO 27
<211> LENGTH: 1917
<212> TYPE: DNA
<213> ORGANISM: Unknown
<220> FEATURE:
<223> OTHER INFORMATION: Obtained from an environmental sample

<400> SEQUENCE: 27
gtgtctctct ttagaaaact cgcactgccg gttctgtgcg gtctactgct ttctgtcgga     60
gcagaaaccc gagcgtcgaa gcgcattgtc gtggccgctg atggatcggg tgacgtcagg    120
acgattcaac aagcggtgga ccaggttccc aaagacaata cacaccccggt cttgattcag    180 atcaagccgg gtgtgtatca ggaacaagtg cgtgtcgccg ccggcaaacg ctttatcact    240
cttcgcggcg acgacgcgag caagaccgtc atcacctatc gattgagcgc actacaagcg    300 ggaaatacccc ggttggcatt caccacctta attaatgcag cgactttcg cgccgagaac    360 ctgacgtttg aaaactcctt cggcaccggt tcacaagcgg ttgctttgtt tgtcgatgcg    420
aaccgcgcga cgtttgaaaa ctgccggttc ctcgggtggc aggacacttt gtttgtgaac    480
ggcagccgcc acttcttcaa agactgctac gtcgaaggcc atgtcgattt cattttcggc    540
acggcctccg cagtgtttga aactgcacc attcacagca aaggcgaagg ttatgtgacc    600
gcgcactatc gcaccagcga tgagatggat accggttttg tctttcatcg ttgtcgtttg    660 accgacgag acacgggccg cggagtttat ctcggaaggc cgtggcgacc ttacgcgcgc    720
gtcgtcttta tcgattgctg gctggacgca cacatcagac ctgaaggctg ggataattgg    780
```

-continued

```
agagatcctg aacgagagaa gaccgcgtgg tttgccgagt acaagtcaaa agggcccggt      840
gctaatcccg tagctcgtgt cgcgtggtcc aggcagttga cgacagaaca agccgccgag      900
ttttcgcggg aacgcttttt cagccgcgct gttcgcgggc tctctgggca ggccaaccag      960
gcagtcggaa cgatcgcgtg ggacgatgcg cagaaaaaac cgaacgagtg gtatgcgagc     1020
gccgaggcgt tgcgcatcgc cgacaacgtt gttctttatc aacgtgactc cggcggctgg     1080
cccaagaaca tcgacatggg gaagccgctc gacgacaagg gtcgagccgg tcttctgcgc     1140
gtgcgtaaga agaacgattc caccatcgat aacggcgcga cttacacgca actctcgttt     1200
ctagcgcggg tttacacggc gcaaaagcag gagcggcatc gcgagtcgtt tctgaaggga     1260
ctcgattacc tgttgaaggc gcagtatcca acggaggct ggccgcagtt ctatcccaat      1320
ctcaacggct attacaaaca catcactttc aacgacaacg cgatgatcgg cgtgatgaaa     1380
ctgctgcgcg acgtagcggc agcgaaaccg gcgtatgcgc ttgtcgacga agcacgacga     1440
acgagtgcgg cgaaggcggt cgaaaaagga atcgagtgca tactgaagac gcaggtggtt     1500
gtgaatggcc ggcgcaccgt gtggtgtgcg caacatgacg aagtcacgct cgcgcctgcc     1560
ccggcgagga cgtttgaatt agtttcgctg agtggtggtg aaagcgttga gatcgtgcgc     1620
ttttgatgt cgatcaagaa cccgtcgccg gcggttgtcg aggcgatcga gtcggcggtt      1680
gcgtggttcg agcaatcgca agtgaaagat cccgccggca aacctgcgtg ggcgcgattt     1740
tatgagatcg gcactaatcg tccgatcttc gccgggcgtg acggcgtcgt taagtatgat     1800
gtgaaacaga tcgatgagga acgacgaaag aattacgcat ggtacgttga cgacgcagcg     1860
aaactactga agaccgacta tcctgagtgg aaagaaaaga acgccaaaga tcaatga       1917
```

<210> SEQ ID NO 28
<211> LENGTH: 638
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(21)
<220> FEATURE:
<221> NAME/KEY: DOMAIN
<222> LOCATION: (28)...(308)
<223> OTHER INFORMATION: Pectin methyl esterase domain
<220> FEATURE:
<221> NAME/KEY: DOMAIN
<222> LOCATION: (309)...(638)
<223> OTHER INFORMATION: Catalytic domain

<400> SEQUENCE: 28

```
Met Ser Leu Phe Arg Lys Leu Ala Leu Pro Val Leu Cys Gly Leu Leu
 1               5                  10                  15

Leu Ser Val Gly Ala Glu Thr Arg Ala Ser Lys Arg Ile Val Val Ala
             20                  25                  30

Ala Asp Gly Ser Gly Asp Val Arg Thr Ile Gln Gln Ala Val Asp Gln
         35                  40                  45

Val Pro Lys Asp Asn Thr His Pro Val Leu Ile Gln Ile Lys Pro Gly
     50                  55                  60

Val Tyr Gln Glu Gln Val Arg Val Ala Ala Gly Lys Arg Phe Ile Thr
 65                  70                  75                  80

Leu Arg Gly Asp Asp Ala Ser Lys Thr Val Ile Thr Tyr Arg Leu Ser
                 85                  90                  95

Ala Leu Gln Ala Gly Asn Thr Arg Leu Ala Phe Thr Thr Leu Ile Asn
```

-continued

```
                100                 105                 110
Ala Asp Asp Phe Arg Ala Glu Asn Leu Thr Phe Glu Asn Ser Phe Gly
            115                 120                 125

Thr Gly Ser Gln Ala Val Ala Leu Phe Val Asp Ala Asn Arg Ala Thr
130                 135                 140

Phe Glu Asn Cys Arg Phe Leu Gly Trp Gln Asp Thr Leu Phe Val Asn
145                 150                 155                 160

Gly Ser Arg His Phe Phe Lys Asp Cys Tyr Val Glu Gly His Val Asp
                165                 170                 175

Phe Ile Phe Gly Thr Ala Ser Ala Val Phe Glu Asn Cys Thr Ile His
            180                 185                 190

Ser Lys Gly Glu Gly Tyr Val Thr Ala His Tyr Arg Thr Ser Asp Glu
            195                 200                 205

Met Asp Thr Gly Phe Val Phe His Arg Cys Arg Leu Thr Gly Arg Asp
            210                 215                 220

Thr Gly Arg Gly Val Tyr Leu Gly Arg Pro Trp Arg Pro Tyr Ala Arg
225                 230                 235                 240

Val Val Phe Ile Asp Cys Trp Leu Asp Ala His Ile Arg Pro Glu Gly
                245                 250                 255

Trp Asp Asn Trp Arg Asp Pro Glu Arg Glu Lys Thr Ala Trp Phe Ala
            260                 265                 270

Glu Tyr Lys Ser Lys Gly Pro Gly Ala Asn Pro Val Ala Arg Val Ala
            275                 280                 285

Trp Ser Arg Gln Leu Thr Thr Glu Gln Ala Ala Glu Phe Ser Arg Glu
            290                 295                 300

Arg Phe Phe Ser Arg Ala Val Arg Gly Leu Ser Gly Gln Ala Asn Gln
305                 310                 315                 320

Ala Val Gly Thr Ile Ala Trp Asp Asp Ala Gln Lys Lys Pro Asn Glu
                325                 330                 335

Trp Tyr Ala Ser Ala Glu Ala Leu Arg Ile Ala Asp Asn Val Val Leu
            340                 345                 350

Tyr Gln Arg Asp Ser Gly Gly Trp Pro Lys Asn Ile Asp Met Gly Lys
            355                 360                 365

Pro Leu Asp Asp Lys Gly Arg Ala Gly Leu Leu Arg Val Arg Lys Lys
370                 375                 380

Asn Asp Ser Thr Ile Asp Asn Gly Ala Thr Tyr Thr Gln Leu Ser Phe
385                 390                 395                 400

Leu Ala Arg Val Tyr Thr Ala Gln Lys Gln Glu Arg His Arg Glu Ser
                405                 410                 415

Phe Leu Lys Gly Leu Asp Tyr Leu Leu Lys Ala Gln Tyr Pro Asn Gly
            420                 425                 430

Gly Trp Pro Gln Phe Tyr Pro Asn Leu Asn Gly Tyr Tyr Lys His Ile
            435                 440                 445

Thr Phe Asn Asp Asn Ala Met Ile Gly Val Met Lys Leu Leu Arg Asp
            450                 455                 460

Val Ala Ala Ala Lys Pro Ala Tyr Ala Phe Val Asp Glu Ala Arg Arg
465                 470                 475                 480

Thr Ser Ala Ala Lys Ala Val Glu Lys Gly Ile Glu Cys Ile Leu Lys
                485                 490                 495

Thr Gln Val Val Val Asn Gly Arg Arg Thr Val Trp Cys Ala Gln His
            500                 505                 510

Asp Glu Val Thr Leu Ala Pro Ala Pro Ala Arg Thr Phe Glu Leu Val
            515                 520                 525
```

```
Ser Leu Ser Gly Gly Glu Ser Val Glu Ile Val Arg Phe Leu Met Ser
    530                 535                 540

Ile Lys Asn Pro Ser Pro Ala Val Val Glu Ala Ile Glu Ser Ala Val
545                 550                 555                 560

Ala Trp Phe Glu Gln Ser Gln Val Lys Asp Pro Ala Gly Lys Pro Ala
                565                 570                 575

Trp Ala Arg Phe Tyr Glu Ile Gly Thr Asn Arg Pro Ile Phe Ala Gly
            580                 585                 590

Arg Asp Gly Val Val Lys Tyr Asp Val Lys Gln Ile Asp Glu Glu Arg
        595                 600                 605

Arg Lys Asn Tyr Ala Trp Tyr Val Asp Asp Ala Lys Leu Leu Lys
610                 615                 620

Thr Asp Tyr Pro Glu Trp Lys Glu Lys Asn Ala Lys Asp Gln
625                 630                 635
```

<210> SEQ ID NO 29
<211> LENGTH: 1398
<212> TYPE: DNA
<213> ORGANISM: Unknown
<220> FEATURE:
<223> OTHER INFORMATION: Obtained from an environmental sample

<400> SEQUENCE: 29

```
atgattaacc gtcgagattt cataaaagac ctcatcatca cctccgccgg agtcgcggtt    60
ctcccgcaac tggcgttcgg acaaaacgat ccctggaaaa ctcaataccc gcagatcctc   120
gcgcggatca aaccgccgaa atttccgaag cgcgatttcg tcatcacgaa gttcggcgcg   180
aaggcgggaa ccgatagcac gcaagcgatc gctaaagccc tcgacgcttg cgcgaaagcc   240
ggcggcggac gcgtcgtcgt acccgccggc gaatttctca ccggtgcgat ccatctcaag   300
tcgaacacca atctctacgt ctcaaaaggc gcgactctga agttttcgac cgaccccgaa   360
aaatatctgc cgatcgttca cacgcggtgg gaagggatgg agttgatgca tctctcgccg   420
ttcatctacg cgtacgagca gacgaacatc gcgatcaccg cgagggcac gctcgacggc   480
caaggcaaat cgttcttttg aagtggcac ggcaacccgc gatacggcgg caaccccgaa   540
gtgatcagtc agcaaaaagc gcgggcgcga ctttacgaga tgatggacaa gaacgtaccc   600
gtcgcggagc gcgtgttcgg tatcgggcac tatctccggc cgcagttcat ccagccgtac   660
aaatgtaaga acgtcttgat cgaaggcgtg acgatcatcg actcgccgat gtgggaagtt   720
catccggtgc tttgcgagaa tgtcaccgtc cgcaatcttc acatctcgtc gcacggtccg   780
aacaacgacg gctgcgatcc cgagtcgtgc aaagacgtcc tgatcgacaa ctgcttcttc   840
gacaccggtg acgactgcat cgcgatcaag tcgggtcgca ataacgacgg tcgtcgtctg   900
aacacaccga ccgagaacat catcgtccgc aactgcacga tgaaagacgg tcacggtggt   960
atcacggtcg gaagcgagat ctcgggcggc gtgcgaaact tgttcgcaca cgattgcaag  1020
atggacagtg cggatctgtg gaccgcgctc cgggtaaaga caacgcatc gcggggcggc  1080
atgctggaga atttctattt ccgcaacatc accgtcgggc aagtcgcgcg tgctgtggtc  1140
gagatcgatt tcaactatga gaaggcgcg aagggatcgt acacaccggt catgcgcaac  1200
tacgtggtcg aggatctgac gtgcaccagc gggaaccggc ccgtcgatct gcaaggatta  1260
gacaacgcgc caatttacga tgtgtcgctg cgtaacacga ccttcggcgc gatgaagaac  1320
aagagcgtcg tgaagaatgt ccgaggactg aagatcgaaa acgttaccgt cagcggcacg  1380
cgcgtggaga gtttatga                                                1398
```

<210> SEQ ID NO 30
<211> LENGTH: 465
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(27)
<220> FEATURE:
<221> NAME/KEY: DOMAIN
<222> LOCATION: (77)...(459)
<223> OTHER INFORMATION: Catalytic domain

<400> SEQUENCE: 30

```
Met Ile Asn Arg Arg Asp Phe Ile Lys Asp Leu Ile Ile Thr Ser Ala
 1               5                  10                  15

Gly Val Ala Val Leu Pro Gln Leu Ala Phe Gly Gln Asn Asp Pro Trp
            20                  25                  30

Lys Thr Gln Tyr Pro Gln Ile Leu Ala Arg Ile Lys Pro Pro Lys Phe
        35                  40                  45

Pro Lys Arg Asp Phe Val Ile Thr Lys Phe Gly Ala Lys Ala Gly Thr
50                  55                  60

Asp Ser Thr Gln Ala Ile Ala Lys Ala Leu Asp Ala Cys Ala Lys Ala
65                  70                  75                  80

Gly Gly Gly Arg Val Val Pro Ala Gly Glu Phe Leu Thr Gly Ala
            85                  90                  95

Ile His Leu Lys Ser Asn Thr Asn Leu Tyr Val Ser Lys Gly Ala Thr
            100                 105                 110

Leu Lys Phe Ser Thr Asp Pro Glu Lys Tyr Leu Pro Ile Val His Thr
        115                 120                 125

Arg Trp Glu Gly Met Glu Leu Met His Leu Ser Pro Phe Ile Tyr Ala
130                 135                 140

Tyr Glu Gln Thr Asn Ile Ala Ile Thr Gly Glu Gly Thr Leu Asp Gly
145                 150                 155                 160

Gln Gly Lys Ser Phe Phe Trp Lys Trp His Gly Asn Pro Arg Tyr Gly
            165                 170                 175

Gly Asn Pro Glu Val Ile Ser Gln Gln Lys Ala Arg Ala Arg Leu Tyr
            180                 185                 190

Glu Met Met Asp Lys Asn Val Pro Val Ala Glu Arg Val Phe Gly Ile
        195                 200                 205

Gly His Tyr Leu Arg Pro Gln Phe Ile Gln Pro Tyr Lys Cys Lys Asn
210                 215                 220

Val Leu Ile Glu Gly Val Thr Ile Ile Asp Ser Pro Met Trp Glu Val
225                 230                 235                 240

His Pro Val Leu Cys Glu Asn Val Thr Val Arg Asn Leu His Ile Ser
            245                 250                 255

Ser His Gly Pro Asn Asn Asp Gly Cys Asp Pro Glu Ser Cys Lys Asp
            260                 265                 270

Val Leu Ile Asp Asn Cys Phe Phe Asp Thr Gly Asp Asp Cys Ile Ala
        275                 280                 285

Ile Lys Ser Gly Arg Asn Asn Asp Gly Arg Arg Leu Asn Thr Pro Thr
290                 295                 300

Glu Asn Ile Ile Val Arg Asn Cys Thr Met Lys Asp Gly His Gly Gly
305                 310                 315                 320

Ile Thr Val Gly Ser Glu Ile Ser Gly Gly Val Arg Asn Leu Phe Ala
```

|  |  | 325 |  |  |  | 330 |  |  |  | 335 |  |
|---|---|---|---|---|---|---|---|---|---|---|---|
| His | Asp | Cys | Lys | Met | Asp | Ser | Ala | Asp | Leu | Trp | Thr | Ala | Leu | Arg | Val |
|  |  |  | 340 |  |  |  |  | 345 |  |  |  | 350 |

Lys Asn Asn Ala Ser Arg Gly Gly Met Leu Glu Asn Phe Tyr Phe Arg
            355                 360                 365

Asn Ile Thr Val Gly Gln Val Ala Arg Ala Val Val Glu Ile Asp Phe
        370                 375                 380

Asn Tyr Glu Glu Gly Ala Lys Gly Ser Tyr Thr Pro Val Met Arg Asn
385                 390                 395                 400

Tyr Val Val Glu Asp Leu Thr Cys Thr Ser Gly Asn Arg Pro Val Asp
                405                 410                 415

Leu Gln Gly Leu Asp Asn Ala Pro Ile Tyr Asp Val Ser Leu Arg Asn
                420                 425                 430

Thr Thr Phe Gly Ala Met Lys Asn Lys Ser Val Val Lys Asn Val Arg
            435                 440                 445

Gly Leu Lys Ile Glu Asn Val Thr Val Ser Gly Thr Arg Val Glu Ser
        450                 455                 460

Leu
465

<210> SEQ ID NO 31
<211> LENGTH: 1401
<212> TYPE: DNA
<213> ORGANISM: Unknown
<220> FEATURE:
<223> OTHER INFORMATION: Obtained from an environmental sample

<400> SEQUENCE: 31

```
atgatcaatc tttatggcgt ctttgacatc cggacctttg ggcccaacc ggacggagaa       60
acgccttcca ctgcggcgat tacggcggcc atcgaaactt gtgccgcggc cggggagga      120
gtggtctaca tcccggccgg acggttcctc accggtcccc tccgcctcaa agccacgtc      180
cggctccatc tcgaggccgg agcgcacttg ctctttagtc aggacccggc cgattatcct      240
gttctggaga cgaggtggga ggggaaggag gtcttgacct atgcacacca gatctacggc      300
gaggacctcg aaggggtcgc gattaccggt cggggaccca tcgacggccg ggcgagact      360
tggtggcgac tcttccgcgc caaagccttc acccatcccc gacccccgct catcgccttt      420
accccgctgca aggacatcct gatagaagga gtaaccctcg tcaattcacc ggcctggacc      480
atcaatcctg tgatgtgcga gcgggtgacc atcgataagg tgactatcat caacccgccc      540
gactcgccca caccgacgg gatcgacccc gattcctccc ggaacgtcta tatcactaac      600
tgctacattg acgtaggcga tgactgcatc gccatcaaag cgggccgaga ggactccctt      660
tatcggacgc cttgtgaaaa cattgtcatc gccaactgcc tcatgcgcca cggtcacggc      720
ggggtggtca tcggcagcga gaccagcggg gtattcgca aggtagtcat taccaactgc      780
atcttcgagg acaccgaccg gggcattaga cttaagtccc ggcgcggacg cggcgggttc      840
gtcgaggacc tccgggcgac gaatattatc atggaaaagg tgctctgtcc cttcgtcctc      900
aacatgtact atgataccgg gggaggcgtg atcgacgagc gcgcgcatga cttagaaccc      960
catccggtaa gcgaggctac acccctccttc cgccgcctct ccttcagtca cattactgcc     1020
cgggaagtgc aggccgccgc ggccttcctc tacggcctgc cgaacagcc tctggaggac     1080
gtcttatttg acgatatctg gatagagctg gccgccgacg cttctcctgc cgtccggcc     1140
atgatgcggg ccgtcccgcc catgagccaa ggtggtgtgc tctgctacgg tgcgcggcgg     1200
```

-continued

```
atctccttcc ggcacatgca cctccgcggg caccgcggtc cggccttcca gatcgaacgc    1260
gcggaggcgg tgcagttgat gggctgctcg accgacggca gtgaagaccc ccagcttgtc    1320
ttgggtcaag cggaggaggt caccatccgt gactgcacct ttaccgccca gcaggacccc    1380
gcaaaagaaa ggcaaaatta a                                              1401
```

<210> SEQ ID NO 32
<211> LENGTH: 466
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(348)
<223> OTHER INFORMATION: Catalytic domain

<400> SEQUENCE: 32

```
Met Ile Asn Leu Tyr Gly Val Phe Asp Ile Arg Thr Phe Gly Ala Gln
  1               5                  10                  15

Pro Asp Gly Glu Thr Pro Ser Thr Ala Ala Ile Thr Ala Ala Ile Glu
             20                  25                  30

Thr Cys Ala Ala Gly Gly Gly Val Val Tyr Ile Pro Ala Gly Arg
         35                  40                  45

Phe Leu Thr Gly Pro Leu Arg Leu Lys Ser His Val Arg Leu His Leu
     50                  55                  60

Glu Ala Gly Ala His Leu Leu Phe Ser Gln Asp Pro Ala Asp Tyr Pro
 65                  70                  75                  80

Val Leu Glu Thr Arg Trp Glu Gly Lys Glu Val Leu Thr Tyr Ala His
                 85                  90                  95

Gln Ile Tyr Gly Glu Asp Leu Glu Gly Val Ala Ile Thr Gly Arg Gly
            100                 105                 110

Thr Ile Asp Gly Arg Gly Glu Thr Trp Trp Arg Leu Phe Arg Ala Lys
        115                 120                 125

Ala Phe Thr His Pro Arg Pro Arg Leu Ile Ala Phe Thr Arg Cys Lys
    130                 135                 140

Asp Ile Leu Ile Glu Gly Val Thr Leu Val Asn Ser Pro Ala Trp Thr
145                 150                 155                 160

Ile Asn Pro Val Met Cys Glu Arg Val Thr Ile Asp Lys Val Thr Ile
                165                 170                 175

Ile Asn Pro Pro Asp Ser Pro Asn Thr Asp Gly Ile Asp Pro Asp Ser
            180                 185                 190

Ser Arg Asn Val Tyr Ile Thr Asn Cys Tyr Ile Asp Val Gly Asp Asp
        195                 200                 205

Cys Ile Ala Ile Lys Ala Gly Arg Glu Asp Ser Leu Tyr Arg Thr Pro
    210                 215                 220

Cys Glu Asn Ile Val Ile Ala Asn Cys Leu Met Arg His Gly His Gly
225                 230                 235                 240

Gly Val Val Ile Gly Ser Glu Thr Ser Gly Gly Ile Arg Lys Val Val
                245                 250                 255

Ile Thr Asn Cys Ile Phe Glu Asp Thr Asp Arg Gly Ile Arg Leu Lys
            260                 265                 270

Ser Arg Arg Gly Arg Gly Gly Phe Val Glu Asp Leu Arg Ala Thr Asn
        275                 280                 285

Ile Ile Met Glu Lys Val Leu Cys Pro Phe Val Leu Asn Met Tyr Tyr
    290                 295                 300
```

-continued

```
Asp Thr Gly Gly Gly Val Ile Asp Glu Arg Ala His Asp Leu Glu Pro
305                 310                 315                 320

His Pro Val Ser Glu Ala Thr Pro Ser Phe Arg Arg Leu Ser Phe Ser
            325                 330                 335

His Ile Thr Ala Arg Glu Val Gln Ala Ala Ala Phe Leu Tyr Gly
        340                 345                 350

Leu Pro Glu Gln Pro Leu Glu Asp Val Leu Phe Asp Asp Ile Trp Ile
    355                 360                 365

Glu Leu Ala Ala Asp Ala Ser Pro Ala Arg Pro Ala Met Met Arg Ala
370                 375                 380

Val Pro Pro Met Ser Gln Gly Val Leu Cys Tyr Gly Ala Arg Arg
385                 390                 395                 400

Ile Ser Phe Arg His Met His Leu Arg Gly His Arg Gly Pro Ala Phe
                405                 410                 415

Gln Ile Glu Arg Ala Glu Ala Val Gln Leu Met Gly Cys Ser Thr Asp
            420                 425                 430

Gly Ser Glu Asp Pro Gln Leu Val Leu Gly Gln Ala Glu Glu Val Thr
        435                 440                 445

Ile Arg Asp Cys Thr Phe Thr Ala Gln Gln Asp Pro Ala Lys Glu Arg
    450                 455                 460

Gln Asn
465
```

<210> SEQ ID NO 33
<211> LENGTH: 1041
<212> TYPE: DNA
<213> ORGANISM: Unknown
<220> FEATURE:
<223> OTHER INFORMATION: Obtained from an environmental sample

<400> SEQUENCE: 33

```
atgaaacttc gatgtctgat gctcaccctg cttctttgcg gcagcgcctt cgccgccgac      60
cggattacgg ccgacaagat caacaacaag cccgactcct ggcttaccag cgacgaaggc     120
atcaagctga tcgacaacat catcacctgg cagaaccccg agggtggctg gccaagtac      180
tacgacgcga ccaatccgca aaacaaggc gaagtctacg gcgactggga cggcgtcggc      240
accatcgaca cggctacac ctacaccgag ctgaatctcc tggcgcacgt ctacaccctc      300
accaagcgcc cggagatcct cgattcgttc aacaagggcc tggagtttct gctcaaagcc      360
caataccca gcggcggctg gccgcaacgg tttccggtgc ccaacaacta cggcaagtgc      420
atcacgctca cgacaacgc gatggtgaac gtgatgcagt cctgcagaa cgtcgcaaag      480
ggcaaggaag acttcgcttt cgtcgacgag cagcgtcgcg ccaaagcgaa ggaggcgttt      540
gaccgcggga tcgactgcct tctgaagctc cagattaccg tgaacggcaa gcttaccgcc      600
tgggcccagc agtatgaccc gaagacactc gccgcggcgc ccgcccgggc gtacgagctc      660
ccgggcctca gcggctgcga aagcgcgccc gtcatgcgct tgttcatgtc tttggagaac      720
cccagtcccg aagttcagcg cgccgtccac gcggcggcgg cttggtacga ggcgtcgaag      780
atcaccggca agaagctggt gcgcgagaac aacgacgtga cactggccga cgaccccaac      840
ggcgagccgc tttgggcgcg cttctacgac atcgaaacca accgcccgtt ctattgcggt      900
cgcgacggcg tgaagaagtg gtcgctggac gagatcgagc ccgaacgccg caagggctac      960
gcttgggtcc gcccctgggc gacgagcgta ctggagcagt atcgcaagtg ggcggcgaag     1020
cacccacccg tgaacagttg a                                               1041
```

```
<210> SEQ ID NO 34
<211> LENGTH: 346
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(18)
<220> FEATURE:
<221> NAME/KEY: DOMAIN
<222> LOCATION: (19)...(346)
<223> OTHER INFORMATION: Catalytic domain

<400> SEQUENCE: 34

Met Lys Leu Arg Cys Leu Met Leu Thr Leu Leu Cys Gly Ser Ala
 1               5                  10                  15

Phe Ala Ala Asp Arg Ile Thr Ala Asp Lys Ile Asn Asn Lys Pro Asp
             20                  25                  30

Ser Trp Leu Thr Ser Asp Glu Gly Ile Lys Leu Ile Asp Asn Ile Ile
             35                  40                  45

Thr Trp Gln Asn Pro Glu Gly Gly Trp Ala Lys Tyr Tyr Asp Ala Thr
 50                  55                  60

Asn Pro His Lys Gln Gly Glu Val Tyr Gly Asp Trp Asp Val Gly
65                   70                  75                  80

Thr Ile Asp Asn Gly Tyr Thr Tyr Thr Glu Leu Asn Leu Leu Ala His
                 85                  90                  95

Val Tyr Thr Leu Thr Lys Arg Pro Glu Ile Leu Asp Ser Phe Asn Lys
            100                 105                 110

Gly Leu Glu Phe Leu Leu Lys Ala Gln Tyr Pro Ser Gly Gly Trp Pro
        115                 120                 125

Gln Arg Phe Pro Val Pro Asn Asn Tyr Gly Lys Cys Ile Thr Leu Asn
    130                 135                 140

Asp Asn Ala Met Val Asn Val Met Gln Phe Leu Gln Asn Val Ala Lys
145                 150                 155                 160

Gly Lys Glu Asp Phe Ala Phe Val Asp Glu Gln Arg Arg Ala Lys Ala
                165                 170                 175

Lys Glu Ala Phe Asp Arg Gly Ile Asp Cys Leu Leu Lys Leu Gln Ile
            180                 185                 190

Thr Val Asn Gly Lys Leu Thr Ala Trp Ala Gln Gln Tyr Asp Pro Lys
        195                 200                 205

Thr Leu Ala Ala Ala Pro Ala Arg Ala Tyr Glu Leu Pro Gly Leu Ser
    210                 215                 220

Gly Cys Glu Ser Ala Pro Val Met Arg Leu Phe Met Ser Leu Glu Asn
225                 230                 235                 240

Pro Ser Pro Glu Val Gln Arg Ala Val His Ala Ala Ala Trp Tyr
                245                 250                 255

Glu Ala Ser Lys Ile Thr Gly Lys Lys Leu Val Arg Glu Asn Asn Asp
            260                 265                 270

Val Thr Leu Ala Asp Asp Pro Asn Gly Glu Pro Leu Trp Ala Arg Phe
        275                 280                 285

Tyr Asp Ile Glu Thr Asn Arg Pro Phe Tyr Cys Gly Arg Asp Gly Val
    290                 295                 300

Lys Lys Trp Ser Leu Asp Glu Ile Glu Pro Glu Arg Arg Lys Gly Tyr
305                 310                 315                 320

Ala Trp Val Arg Pro Trp Ala Thr Ser Val Leu Glu Gln Tyr Arg Lys
                325                 330                 335
```

Trp Ala Ala Lys His Pro Pro Val Asn Ser
    340       345

<210> SEQ ID NO 35
<211> LENGTH: 1071
<212> TYPE: DNA
<213> ORGANISM: Unknown
<220> FEATURE:
<223> OTHER INFORMATION: Obtained from an environmental sample

<400> SEQUENCE: 35

```
atgccaaaaa attccgacga cgcgtggcgg gaaaagactc cgcccgattg gagtcttgtc      60
acatggagcg acgtattcaa acagaagcct ctctggtacc aaaccgacga ggcggctcga     120
gtcgcggacc aactcctcat ctatcaaaaa gagaacggcg ggtttgagaa gaatgtcgac     180
atggcgttga tgctgacgca aaggaaaaa gaagagctca ccgcaaagcg gtcagacgtc      240
tccgaaacga cgatcgacaa ccggaccacg tatcctcagg tcgcgtatct cggtcgagta     300
atcaccgcaa gccttcttaa accttcgccg ccggcgaatc ttccgaaata caaagacgcc     360
ttcaacaaag gtcttgatta cctgcttgcc tcccagtatg agaacggagg atttccgcaa     420
ttctatccgt tgaaaaaagg ctattacaca cacatcacct tcaacgacga cgcgatgatc     480
ggcgtcctga aggtgcttcg cgacatcgca aataagaaag aggattacgt gttcgtggat     540
gaagcgcgaa gacttcgcgc cgagcaagcg gtcgccaaag cgctgcctct tattctgaag     600
cttcaggttg tcgtcgacgg aaagaaaacc gtctgggctg cgcagtatga cgagactacg     660
ctggcgcctg cagcggctcg caagtttgag cccgtgtcgt tgaccgctgg tgagagcgtc     720
ggcatcgtcc gatacctgat gcaggaaaaa ccgacgccgg agatcaccga tgcgatcgag     780
tctgcgatcg attggtatcg aaagaacaag atcgacggaa tacgttggga gcgcatcaaa     840
ggcgagaaca cggttgtgaa agacaaatcg gctcccccta tatgggcacg gttctatcag     900
atcgaaacga tgcgtccgat cttcatcgga cgtgattcgg ttatcaagta tgacgtgacg     960
caggtcgaag ccgagcgtcg gaatggttac gcctggtacg tcaccgcacc gaatgaattg    1020
gtgaacgagg attatttgaa gtggaagggg aaaagcgccg gagccaagta g            1071
```

<210> SEQ ID NO 36
<211> LENGTH: 356
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(356)
<223> OTHER INFORMATION: Catalytic domain

<400> SEQUENCE: 36

Met Pro Lys Asn Ser Asp Asp Ala Trp Arg Glu Lys Thr Pro Pro Asp
1     5       10       15

Trp Ser Leu Val Thr Trp Ser Asp Val Phe Lys Gln Lys Pro Leu Trp
      20       25       30

Tyr Gln Thr Asp Glu Ala Ala Arg Val Ala Asp Gln Leu Leu Ile Tyr
    35       40       45

Gln Lys Glu Asn Gly Gly Phe Glu Lys Asn Val Asp Met Ala Leu Met
  50       55       60

Leu Thr Gln Lys Glu Lys Glu Glu Leu Thr Ala Lys Arg Ser Asp Val
65       70       75       80

```
Ser Glu Thr Thr Ile Asp Asn Arg Thr Thr Tyr Pro Gln Val Ala Tyr
                85                  90                  95

Leu Gly Arg Val Ile Thr Ala Ser Leu Leu Lys Pro Ser Pro Pro Ala
            100                 105                 110

Asn Leu Pro Lys Tyr Lys Asp Ala Phe Asn Lys Gly Leu Asp Tyr Leu
        115                 120                 125

Leu Ala Ser Gln Tyr Glu Asn Gly Gly Phe Pro Gln Phe Tyr Pro Leu
    130                 135                 140

Lys Lys Gly Tyr Tyr Thr His Ile Thr Phe Asn Asp Ala Met Ile
145                 150                 155                 160

Gly Val Leu Lys Val Leu Arg Asp Ile Ala Asn Lys Lys Glu Asp Tyr
                165                 170                 175

Val Phe Val Asp Glu Ala Arg Arg Leu Arg Ala Glu Gln Ala Val Ala
            180                 185                 190

Lys Ala Leu Pro Leu Ile Leu Lys Leu Gln Val Val Asp Gly Lys
        195                 200                 205

Lys Thr Val Trp Ala Ala Gln Tyr Asp Glu Thr Thr Leu Ala Pro Ala
    210                 215                 220

Ala Ala Arg Lys Phe Glu Pro Val Ser Leu Thr Ala Gly Glu Ser Val
225                 230                 235                 240

Gly Ile Val Arg Tyr Leu Met Gln Glu Lys Pro Thr Pro Glu Ile Thr
                245                 250                 255

Asp Ala Ile Glu Ser Ala Ile Asp Trp Tyr Arg Lys Asn Lys Ile Asp
            260                 265                 270

Gly Ile Arg Trp Glu Arg Ile Lys Gly Glu Asn Thr Val Val Lys Asp
        275                 280                 285

Lys Ser Ala Pro Pro Ile Trp Ala Arg Phe Tyr Gln Ile Glu Thr Met
    290                 295                 300

Arg Pro Ile Phe Ile Gly Arg Asp Ser Val Ile Lys Tyr Asp Val Thr
305                 310                 315                 320

Gln Val Glu Ala Glu Arg Arg Asn Gly Tyr Ala Trp Tyr Val Thr Ala
                325                 330                 335

Pro Asn Glu Leu Val Asn Glu Asp Tyr Leu Lys Trp Lys Gly Lys Ser
            340                 345                 350

Ala Gly Ala Lys
        355

<210> SEQ ID NO 37
<211> LENGTH: 1860
<212> TYPE: DNA
<213> ORGANISM: Unknown
<220> FEATURE:
<223> OTHER INFORMATION: Obtained from an environmental sample

<400> SEQUENCE: 37
atgttcacta ctactggctc tcattgcgcc cggaattccg cgcgtttttc ccttactgcg      60
atagcagccg ctgttgcgtt gatggcaggc acttcagcat tgcagctgc gacgggtggc     120 ttctctacca ctgatggtgg caacgtatcg ggcgcccgtt cgtttactgc atcgacttac    180
cagcaaatca acaccattat tgccaacgca aaactggatg atgcaggtaa aaaagtcact    240
gggggtgctt acccgcttat cattacctac accggtaatg aagactcgct gattaaccag    300
atgatcaaag accacacggg gaattcatcg ggcaactgcc ctaacccgcg ttggagcgaa    360
gcctatcgct acgtggaaat taaagagttt accaagggta ttaccattca aggcgcgaat    420
ggttcttcag caaacttcgg cattgtgatt aataaatctg acaatgtgat tgtgcgtaat    480
```

-continued

```
atgaaaatcg gtgcgcttgc tggtgcgagt aacgatgcgg atatgattcg tatcgacacc    540
ggcgttaacg tgtggattga tcacaacgaa ttgtttgcgg taaataatga atgtaaaggt    600
tcacccgatg gtgacctgac atttgaaagt gcgattgata ttaaaaaagc atcgcaaaat    660
attacggtgt cctacaacat tatccgcgat agtaaaaaag tagggctcga tggttcgagt    720
agcagtgata ttgcaggtgg ccgtaagatt acgttccatc acaatattta tcgcaatgtt    780
ggtgcacgtt taccgttgca acgcggtggt tggacacaca tgtataacaa tctttacgac    840
ggagttacca gctcgggtat taacgttcgt caaggtggct acgcgctaat cgagaacaac    900
tggttccaaa atgctgtcaa cccggttacc tgccgttttg acagtagtaa ctgcggttac    960
tgggatctgc gcaacaacaa cgtgcgcaac cctggtgatt ctccaccta caacattacc   1020
tggaccagcg gtggcaccat cgacgccacc aactggacta ccactcaacc tttcccgatt   1080
agcattcctt acagctactc gcctgttagc ccgcagtgtg tcaaagacaa gttggcaaat   1140
tatgctggtg tcggtaaaaa caatgcgcaa ttaacggcgt ctgcgtgcag cggaaatact   1200
tcatcggtag caccttcatc agtgccagca tcatcggcgg caccttcaag ccgttcatcc   1260
agcagtgcag cgccatccag cacaccaact acatcaagct cgagttcagt tgccgcaacc   1320
ggttcaattt cgctcggtgc aacggcaacc aacaacagca ttgtgttgag ttggtcaccc   1380
aacaatgtga cgctcggttc gcaagaagtg tatcgcgata ccgacgctga tccatcgggg   1440
cgtgtgcgta tcgcatccct ggctgcttca gcgcgtatgt ataccgatag cacagcggca   1500
tcgggccaaa cctattacta ctggattaaa ataccactt ctggtgttgt caccaattcc    1560
aatgctgcat cagcgcgtat tggtagcacg gcgtccagtt ctgttgcatc aagcagctca   1620
agttcaagcg gcggcgcgcc cgtattaggt ggtactggtg attatccaag cggcttctcc   1680
aagtgcgctg atttgggcgg gacttgttca gtgtcatcgg gcgatggctg ggttgcgttt   1740
ggtcgcaaag gcaagtgggt taccaagaaa gtatcggtag gtagttcaat cgcctgtacc   1800
gttgcggcat ttggttcgga tccacagggc aaccctaaca agtgttctta caaacgttaa   1860
```

<210> SEQ ID NO 38
<211> LENGTH: 619
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(35)
<220> FEATURE:
<221> NAME/KEY: DOMAIN
<222> LOCATION: (36)...(387)
<223> OTHER INFORMATION: Catalytic domain

<400> SEQUENCE: 38

```
Met Phe Thr Thr Thr Gly Ser His Cys Ala Arg Asn Ser Ala Arg Phe
 1               5                  10                  15

Ser Leu Thr Ala Ile Ala Ala Val Ala Leu Met Ala Gly Thr Ser
            20                  25                  30

Ala Phe Ala Ala Ala Thr Gly Gly Phe Ser Thr Thr Asp Gly Gly Asn
        35                  40                  45

Val Ser Gly Ala Arg Ser Phe Thr Ala Ser Thr Tyr Gln Gln Ile Asn
    50                  55                  60

Thr Ile Ile Ala Asn Ala Lys Leu Asp Asp Ala Gly Lys Lys Val Thr
65                  70                  75                  80
```

```
Gly Gly Ala Tyr Pro Leu Ile Ile Thr Tyr Thr Gly Asn Glu Asp Ser
            85                  90                  95

Leu Ile Asn Gln Met Ile Lys Asp His Thr Val Asn Ser Ser Gly Asn
            100                 105                 110

Cys Pro Asn Pro Arg Trp Ser Glu Ala Tyr Arg Tyr Val Glu Ile Lys
            115                 120                 125

Glu Phe Thr Lys Gly Ile Thr Ile Gln Gly Ala Asn Gly Ser Ser Ala
    130                 135                 140

Asn Phe Gly Ile Val Ile Asn Lys Ser Asp Asn Val Ile Val Arg Asn
145                 150                 155                 160

Met Lys Ile Gly Ala Leu Ala Gly Ala Ser Asn Asp Ala Asp Met Ile
                165                 170                 175

Arg Ile Asp Thr Gly Val Asn Val Trp Ile Asp His Asn Glu Leu Phe
            180                 185                 190

Ala Val Asn Asn Glu Cys Lys Gly Ser Pro Asp Gly Asp Leu Thr Phe
            195                 200                 205

Glu Ser Ala Ile Asp Ile Lys Lys Ala Ser Gln Asn Ile Thr Val Ser
    210                 215                 220

Tyr Asn Ile Ile Arg Asp Ser Lys Lys Val Gly Leu Asp Gly Ser Ser
225                 230                 235                 240

Ser Ser Asp Ile Ala Gly Gly Arg Lys Ile Thr Phe His His Asn Ile
                245                 250                 255

Tyr Arg Asn Val Gly Ala Arg Leu Pro Leu Gln Arg Gly Gly Trp Thr
            260                 265                 270

His Met Tyr Asn Asn Leu Tyr Asp Gly Val Thr Ser Ser Gly Ile Asn
            275                 280                 285

Val Arg Gln Gly Gly Tyr Ala Leu Ile Glu Asn Asn Trp Phe Gln Asn
            290                 295                 300

Ala Val Asn Pro Val Thr Cys Arg Phe Asp Ser Ser Asn Cys Gly Tyr
305                 310                 315                 320

Trp Asp Leu Arg Asn Asn Asn Val Arg Asn Pro Gly Asp Phe Ser Thr
                325                 330                 335

Tyr Asn Ile Thr Trp Thr Ser Gly Gly Thr Ile Asp Ala Thr Asn Trp
            340                 345                 350

Thr Thr Thr Gln Pro Phe Pro Ile Ser Ile Pro Tyr Ser Tyr Ser Pro
            355                 360                 365

Val Ser Pro Gln Cys Val Lys Asp Lys Leu Ala Asn Tyr Ala Gly Val
    370                 375                 380

Gly Lys Asn Asn Ala Gln Leu Thr Ala Ser Ala Cys Ser Gly Asn Thr
385                 390                 395                 400

Ser Ser Val Ala Pro Ser Ser Val Pro Ala Ser Ser Ala Ala Pro Ser
                405                 410                 415

Ser Arg Ser Ser Ser Ser Ala Ala Pro Ser Ser Thr Pro Thr Thr Ser
            420                 425                 430

Ser Ser Ser Ser Val Ala Ala Thr Gly Ser Ile Ser Leu Gly Ala Thr
            435                 440                 445

Ala Thr Asn Asn Ser Ile Val Leu Ser Trp Ser Pro Asn Asn Val Thr
    450                 455                 460

Leu Gly Ser Gln Glu Val Tyr Arg Asp Thr Asp Ala Asp Pro Ser Gly
465                 470                 475                 480

Arg Val Arg Ile Ala Ser Leu Ala Ala Ser Ala Arg Met Tyr Thr Asp
                485                 490                 495

Ser Thr Ala Ala Ser Gly Gln Thr Tyr Tyr Tyr Trp Ile Lys Asn Thr
```

-continued

```
                       500                 505                 510
Thr Ser Gly Val Val Thr Asn Ser Asn Ala Ala Ser Ala Arg Ile Gly
            515                 520                 525
Ser Thr Ala Ser Ser Val Ala Ser Ser Ser Ser Ser Ser Gly
    530                 535                 540
Gly Ala Pro Val Leu Gly Gly Thr Gly Asp Tyr Pro Ser Gly Phe Ser
545                 550                 555                 560
Lys Cys Ala Asp Leu Gly Gly Thr Cys Ser Val Ser Ser Gly Asp Gly
                565                 570                 575
Trp Val Ala Phe Gly Arg Lys Gly Lys Trp Val Thr Lys Lys Val Ser
            580                 585                 590
Val Gly Ser Ser Ile Ala Cys Thr Val Ala Ala Phe Gly Ser Asp Pro
        595                 600                 605
Gln Gly Asn Pro Asn Lys Cys Ser Tyr Lys Arg
    610                 615

<210> SEQ ID NO 39
<211> LENGTH: 1077
<212> TYPE: DNA
<213> ORGANISM: Unknown
<220> FEATURE:
<223> OTHER INFORMATION: Obtained from an environmental sample

<400> SEQUENCE: 39
atggcgccga tcctccgacc caacctcctt tgcacttacg cgctctgcat gggcttgctc        60
gccgtggtga gctgcgcggc ggggccggtg tcagcgcagc agccggcgcc atggagcacg       120
gccatcgtgg agcaggagga gagcgcgttc gcctccccgt cgatgcgcag cgtcgccgac       180
aacgtcgtgc ccatcagtc ggccgaaggc ggctggccta agaacaccaa tctggcggcg       240
ccgccatcgg ggccggcgcc ggagggcgtc gccaatacga tcgacaatga tgcgacgacg       300
ctgccgatgg agtttctggc gcgtgtgatc cacgccggcg cgtccgata caagccggcc       360 ttcgagcgcg ggctggatta tctgcttgcg gctcagtacg cgaacggcgg ctggccgcag       420
ttctatccgc tgcgcggggg ctattacgat cacgtgacgt tcaacgacga cgccatgatc       480
cgggtgatga ttctgctcgg cgcagtggcg cgcggcgggg cgccctatga atttgtcgac       540
gccgggcggc gcgcgcgcgc tgcagccgcg gtcgagcggg gcctggcgct catcctgcgc       600
acgcagatcc ggcagggcgg ggcgctgacg gtctggtgcg cgcagtatga cagcgccacc       660
ttgcagcccg cctgggcgcg cgcctatgag ccgccgtccc tgtccggcgc ggaaagtgtg       720
gggatcgtgc gctatctcat gtcgatcgac catccctcgc ccgaagtcgt cgccgccgtc       780
gacggcgctg tggcatggct gcgcgcggcc gccattgccg cgtgcgcgt ggagaatttc       840 acggacgccg acggccgccc tgaccgccgc gccgtggccg acgcgggcgc gccgccgatc       900
tgggcgcggt tctacgagtt cggcgccaac cggccgatct tcctggggcg tgattccgtt       960
tttcactaca cgttcggaga aatcgagcgc gagcggcgcg caggctacaa ttattacgga      1020
tactgggcgc gctccgtgct ggaagactat ccggcctggc gcgcgcgcgt gcgatga       1077

<210> SEQ ID NO 40
<211> LENGTH: 358
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(32)
```

```
<220> FEATURE:
<221> NAME/KEY: DOMAIN
<222> LOCATION: (33)...(358)
<223> OTHER INFORMATION: Catalytic domain

<400> SEQUENCE: 40

Met Ala Pro Ile Leu Arg Pro Asn Leu Leu Cys Thr Tyr Ala Leu Cys
1               5                   10                  15

Met Gly Leu Leu Ala Val Val Ser Cys Ala Ala Gly Pro Val Ser Ala
            20                  25                  30

Gln Gln Pro Ala Pro Trp Ser Thr Ala Ile Val Glu Gln Glu Glu Ser
        35                  40                  45

Ala Phe Ala Ser Pro Ser Met Arg Ser Val Ala Asp Asn Val Val Arg
    50                  55                  60

His Gln Ser Ala Glu Gly Gly Trp Pro Lys Asn Thr Asn Leu Ala Ala
65                  70                  75                  80

Pro Pro Ser Gly Pro Ala Pro Glu Gly Val Ala Asn Thr Ile Asp Asn
                85                  90                  95

Asp Ala Thr Thr Leu Pro Met Glu Phe Leu Ala Arg Val Ile His Ala
            100                 105                 110

Gly Gly Val Arg Tyr Lys Pro Ala Phe Glu Arg Gly Leu Asp Tyr Leu
        115                 120                 125

Leu Ala Ala Gln Tyr Ala Asn Gly Gly Trp Pro Gln Phe Tyr Pro Leu
    130                 135                 140

Arg Gly Gly Tyr Tyr Asp His Val Thr Phe Asn Asp Asp Ala Met Ile
145                 150                 155                 160

Arg Val Met Ile Leu Leu Gly Ala Val Ala Arg Gly Gly Ala Pro Tyr
                165                 170                 175

Glu Phe Val Asp Ala Gly Arg Arg Arg Ala Ala Ala Ala Val Glu
            180                 185                 190

Arg Gly Leu Ala Leu Ile Leu Arg Thr Gln Ile Arg Gln Gly Gly Ala
        195                 200                 205

Leu Thr Val Trp Cys Ala Gln Tyr Asp Ser Ala Thr Leu Gln Pro Ala
    210                 215                 220

Trp Ala Arg Ala Tyr Glu Pro Pro Ser Leu Ser Gly Ala Glu Ser Val
225                 230                 235                 240

Gly Ile Val Arg Tyr Leu Met Ser Ile Asp His Pro Ser Pro Glu Val
                245                 250                 255

Val Ala Ala Val Asp Gly Ala Val Ala Trp Leu Arg Ala Ala Ala Ile
            260                 265                 270

Ala Gly Val Arg Val Glu Asn Phe Thr Asp Ala Asp Gly Arg Pro Asp
        275                 280                 285

Arg Arg Ala Val Ala Asp Ala Gly Ala Pro Pro Ile Trp Ala Arg Phe
    290                 295                 300

Tyr Glu Phe Gly Ala Asn Arg Pro Ile Phe Leu Gly Arg Asp Ser Val
305                 310                 315                 320

Phe His Tyr Thr Phe Gly Glu Ile Glu Arg Glu Arg Ala Gly Tyr
                325                 330                 335

Asn Tyr Tyr Gly Tyr Trp Ala Arg Ser Val Leu Glu Asp Tyr Pro Ala
            340                 345                 350

Trp Arg Ala Arg Val Arg
        355

<210> SEQ ID NO 41
<211> LENGTH: 1080
```

<212> TYPE: DNA
<213> ORGANISM: Unknown
<220> FEATURE:
<223> OTHER INFORMATION: Obtained from an environmental sample

<400> SEQUENCE: 41

```
atgaaaaatt taaaatacag tttagtttca tttgtactac tcattactat gaatgttttt    60
acgcaagaaa aaaagtaac ttggaaaagc atcacagaaa ataacgatga aaattggttt   120
gtaagcgaag aagccaaaaa aatagccgaa atgttttgt tatatcaacg cgatattggt   180
ggttggccaa aaacactga aattcaaaat gaactttcag aaaagaaaa actaacatta   240
aaagaattaa aatcggatcc aaaaggatgt accatcgaca atggtgcaac gtgtcaggaa   300
ttacttttct tatccaaaat atataaatcc aatccagatg agcgatataa aatggctttc   360
ttaaaaggtg tgatttacct gattacagct caatacaaaa atggtggttg gccacaatat   420
taccctttga gagaaggata ttacactcat attacttaca acgataatgc aatggtgaat   480
gttttaaagt tgttgaaaga agttaaagat aaatctgatt actactcaat tcaagcaccc   540
gatgaaattt ccaaaatggc tgaagtatca tttaataaag gagtcgattg catattaaaa   600
acacagtaca aacaaaatgg aatattaacc gcttggtgtg cacaacatga cagggaaaca   660
ttgaaacctg ctaaagcaag agcttatgaa ttgccttcgt taagcggaaa agaatcagcc   720
aaaattgtgt tgttattaat gtcaatcgaa aatccatcta agaagtaat tactgccgta   780
aattcagcag ttaattggtt tgaaaaaca aaaatcaacg gaattaaaat tgaaaccatt   840
tccaccggga aaaggatga aaaagataga attgttgttg aaagtcctga tgctccgccg   900
ctttgggcaa gatttatgga attaagtgac aacaaaccat ttttttgtga tcgtgacgga   960
aagaaaaaat acagcatgtc agaaattagt caagagcgta gaaccggcta tgcatggtac  1020
accaacgaac caaagaagt tttaaaaaaa tacgatgatt ggaagtcatc attaaactaa  1080
```

<210> SEQ ID NO 42
<211> LENGTH: 359
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(21)
<220> FEATURE:
<221> NAME/KEY: DOMAIN
<222> LOCATION: (22)...(359)
<223> OTHER INFORMATION: Catalytic domain

<400> SEQUENCE: 42

```
Met Lys Asn Leu Lys Tyr Ser Leu Val Ser Phe Val Leu Ile Thr
 1               5                  10                  15

Met Asn Val Phe Thr Gln Glu Lys Lys Val Thr Trp Lys Ser Ile Thr
            20                  25                  30

Glu Asn Asn Asp Glu Asn Trp Phe Val Ser Glu Ala Lys Lys Ile
        35                  40                  45

Ala Glu Asn Val Leu Leu Tyr Gln Arg Asp Ile Gly Gly Trp Pro Lys
    50                  55                  60

Asn Thr Glu Ile Gln Asn Glu Leu Ser Glu Lys Glu Lys Leu Thr Leu
65                  70                  75                  80

Lys Glu Leu Lys Ser Asp Pro Lys Gly Cys Thr Ile Asp Asn Gly Ala
                85                  90                  95

Thr Cys Gln Glu Leu Leu Phe Leu Ser Lys Ile Tyr Lys Ser Asn Pro
```

```
            100                 105                 110
Asp Glu Arg Tyr Lys Met Ala Phe Leu Lys Gly Val Ile Tyr Leu Ile
        115                 120                 125

Thr Ala Gln Tyr Lys Asn Gly Gly Trp Pro Gln Tyr Tyr Pro Leu Arg
    130                 135                 140

Glu Gly Tyr Tyr Thr His Ile Thr Tyr Asn Asp Asn Ala Met Val Asn
145                 150                 155                 160

Val Leu Lys Leu Leu Lys Glu Val Lys Asp Lys Ser Asp Tyr Tyr Ser
                165                 170                 175

Ile Gln Ala Pro Asp Glu Ile Ser Lys Met Ala Glu Val Ser Phe Asn
            180                 185                 190

Lys Gly Val Asp Cys Ile Leu Lys Thr Gln Tyr Lys Gln Asn Gly Ile
        195                 200                 205

Leu Thr Ala Trp Cys Ala Gln His Asp Arg Glu Thr Leu Lys Pro Ala
    210                 215                 220

Lys Ala Arg Ala Tyr Glu Leu Pro Ser Leu Ser Gly Lys Glu Ser Ala
225                 230                 235                 240

Lys Ile Val Leu Leu Leu Met Ser Ile Glu Asn Pro Ser Lys Glu Val
                245                 250                 255

Ile Thr Ala Val Asn Ser Ala Val Asn Trp Phe Glu Lys Thr Lys Ile
            260                 265                 270

Asn Gly Ile Lys Ile Glu Thr Ile Ser Thr Gly Lys Lys Asp Glu Lys
        275                 280                 285

Asp Arg Ile Val Val Glu Ser Pro Asp Ala Pro Leu Trp Ala Arg
    290                 295                 300

Phe Met Glu Leu Ser Asp Asn Lys Pro Phe Phe Cys Asp Arg Asp Gly
305                 310                 315                 320

Lys Lys Lys Tyr Ser Met Ser Glu Ile Ser Gln Glu Arg Arg Thr Gly
                325                 330                 335

Tyr Ala Trp Tyr Thr Asn Glu Pro Lys Glu Val Leu Lys Lys Tyr Asp
            340                 345                 350

Asp Trp Lys Ser Ser Leu Asn
        355

<210> SEQ ID NO 43
<211> LENGTH: 1902
<212> TYPE: DNA
<213> ORGANISM: Unknown
<220> FEATURE:
<223> OTHER INFORMATION: Obtained from an environmental sample

<400> SEQUENCE: 43
gtggatccaa agaattgggg cagcggattt accggcgaaa tcaaagtaac taacaacaca      60
agccaaacag tcaatagctg gtctgtgtca tggcaagagg caggagccag tgtaactaat     120
tcctggaatg caaccttggg agggacgaat ccttataccg caaccgggtt aggatggaac     180
tcaaccctgg cgcccggagc ctctgccagt tttggttttc aagcaaacgg cactgcgggg     240
gcaccaaagg taaatggcag tttgtgtggt gcgactgcat catctgcagc gaccagcaaa     300
tccagtgcga gtgttgcgag ttcaaagatt gcaagttcaa ttcaatcaag tgcaactagc     360
agttcaaaat cgtccagttc tgctgcacct tcaagcacgc aaaatccag tagctctgct     420 ccaacggctg catcattcac tattcaagaa gagcaagccg ttttttgccg tgtagacggt     480
attgcaacga aaagtaccaa caccggattc accggcaacg gctacaccaa ttccaataat     540
gtacaaggtg ctgccattgt gtgggcggta aatgcaacta ccagtgcacg ccatacaatt     600
```

-continued

```
actttccgct tcgctaatgg tggcactgcg aatcgcaatg gctcgctagt cattaacggc     660
ggcagcaatg gtaattacac ggtgcaatta ccacgcaccg cgagctgggc tgactggcaa     720
acagtaagtc tggaaattga tttggtacaa ggcaataaca atttgcaact caccgcattg     780
actgcagatg gcctcgcaaa tatcgacttc atcaaaattg aaggagcatc aaccaaagcg     840
ggaacctgtg caggtgcggt cagcagtagc agtgttgcct cttcggtaaa atccagtgct     900
agcgcggcaa gcagttctgt accaacgaac accggcgcca tgctaacttt ggatggcaac     960
cctgccgcaa gctggcttaa caaatcgcgt acaaagtgga gcgcatcgcg cgctgacatt    1020
gttgcctctt atcaacagtc caacggcggc tggccaaaaa atctggatta caattcagtg    1080
agcgctggta tggcggcag tgcaagcggc accatcgata tggtgcaac tattactgaa      1140 atggtttatc tcgctgaggt ttacaaaacc ggaaacaata ccaagtaccg cgatgcagtt    1200
cgccgtgcag caaactttat cgtgagttcg caatatagca ctggcgcgtt gccgcaattt    1260
tatccgctca aggtggcta tgcagaccac gccacctta atgataacgg catggcttac      1320
gcattaactg tattggattt cgctgcaaac aagcgcgcgc tttttgatac ggatgtcttt    1380
aatgacacag accgcgcaaa atttaaaaca gcggtaacca aaggtgttga ttacatttta    1440
aaagcgcaat ggaaacaaaa tggaaaatta acagcctggt gcgcacaaca tggcgcgact    1500
gactatcaac taaaaaagc acgcgcttat gaattggaat cactgagtgg tagcgagtct    1560
gttggtgtaa ttgcattttt aatgacgcag ccgcagacag cacaaatcca acggccgtt     1620 aaagcaggcc tcaactggtt caatagcccg agcacctatt tggaaggtta cacctacgat    1680
tcatccaaag cgtccactaa tcccatagtg cagaaagcgg gaagtagaat gtggtatcgc    1740
ttttacgatt taaataccaa ccgtggtttt ttcagcgacc gggacggcag caaattctat    1800
gacattacca aaatgtctga gaacgtcgc acgggttata gttggggtgg cgcttatggt      1860
gagagcatca tcgcctttgg caaaaaagtg ggctatctat aa                        1902
```

<210> SEQ ID NO 44
<211> LENGTH: 633
<212> TYPE: PRT
<213> ORGANISM: Unknown
<220> FEATURE:
<223> OTHER INFORMATION: Obtained from an environmental sample
<220> FEATURE:
<221> NAME/KEY: BINDING
<222> LOCATION: (4)...(89)
<223> OTHER INFORMATION: Carbohydrate binding module
<220> FEATURE:
<221> NAME/KEY: BINDING
<222> LOCATION: (152)...(275)
<223> OTHER INFORMATION: Carbohydrate binding module
<220> FEATURE:
<221> NAME/KEY: DOMAIN
<222> LOCATION: (277)...(633)
<223> OTHER INFORMATION: Catalytic domain

<400> SEQUENCE: 44

```
Met Asp Pro Lys Asn Trp Gly Ser Gly Phe Thr Gly Glu Ile Lys Val
 1               5                  10                  15

Thr Asn Asn Thr Ser Gln Thr Val Asn Ser Trp Ser Val Ser Trp Gln
                20                  25                  30

Glu Ala Gly Ala Ser Val Thr Asn Ser Trp Asn Ala Thr Leu Gly Gly
            35                  40                  45

Thr Asn Pro Tyr Thr Ala Thr Gly Leu Gly Trp Asn Ser Thr Leu Ala
        50                  55                  60
```

-continued

```
Pro Gly Ala Ser Ala Ser Phe Gly Phe Gln Ala Asn Gly Thr Ala Gly
 65                  70                  75                  80

Ala Pro Lys Val Asn Gly Ser Leu Cys Gly Ala Thr Ala Ser Ser Ala
                 85                  90                  95

Ala Thr Ser Lys Ser Ser Ala Ser Val Ala Ser Ser Lys Ile Ala Ser
            100                 105                 110

Ser Ile Gln Ser Ser Ala Thr Ser Ser Ser Lys Ser Ser Ser Ser Ala
            115                 120                 125

Ala Pro Ser Ser Thr Pro Lys Ser Ser Ser Ala Pro Thr Ala Ala
        130                 135                 140

Ser Phe Thr Ile Gln Glu Glu Gln Ala Gly Phe Cys Arg Val Asp Gly
145                 150                 155                 160

Ile Ala Thr Glu Ser Thr Asn Thr Gly Phe Thr Gly Asn Gly Tyr Thr
                165                 170                 175

Asn Ser Asn Asn Val Gln Gly Ala Ala Ile Val Trp Ala Val Asn Ala
            180                 185                 190

Thr Thr Ser Ala Arg His Thr Ile Thr Phe Arg Phe Ala Asn Gly Gly
            195                 200                 205

Thr Ala Asn Arg Asn Gly Ser Leu Val Ile Asn Gly Gly Ser Asn Gly
210                 215                 220

Asn Tyr Thr Val Gln Leu Pro Arg Thr Ala Ser Trp Ala Asp Trp Gln
225                 230                 235                 240

Thr Val Ser Leu Glu Ile Asp Leu Val Gln Gly Asn Asn Leu Gln
                245                 250                 255

Leu Thr Ala Leu Thr Ala Asp Gly Leu Ala Asn Ile Asp Phe Ile Lys
            260                 265                 270

Ile Glu Gly Ala Ser Thr Lys Ala Gly Thr Cys Ala Gly Ala Val Ser
            275                 280                 285

Ser Ser Ser Val Ala Ser Ser Val Lys Ser Ser Ala Ser Ala Ala Ser
        290                 295                 300

Ser Ser Val Pro Thr Asn Thr Gly Ala Met Leu Thr Leu Asp Gly Asn
305                 310                 315                 320

Pro Ala Ala Ser Trp Leu Asn Lys Ser Arg Thr Lys Trp Ser Ala Ser
                325                 330                 335

Arg Ala Asp Ile Val Ala Ser Tyr Gln Gln Ser Asn Gly Gly Trp Pro
            340                 345                 350

Lys Asn Leu Asp Tyr Asn Ser Val Ser Ala Gly Asn Gly Gly Ser Ala
            355                 360                 365

Ser Gly Thr Ile Asp Asn Gly Ala Thr Ile Thr Glu Met Val Tyr Leu
        370                 375                 380

Ala Glu Val Tyr Lys Thr Gly Asn Asn Thr Lys Tyr Arg Asp Ala Val
385                 390                 395                 400

Arg Arg Ala Ala Asn Phe Ile Val Ser Ser Gln Tyr Ser Thr Gly Ala
                405                 410                 415

Leu Pro Gln Phe Tyr Pro Leu Lys Gly Gly Tyr Ala Asp His Ala Thr
            420                 425                 430

Phe Asn Asp Asn Gly Met Ala Tyr Ala Leu Thr Val Leu Asp Phe Ala
            435                 440                 445

Ala Asn Lys Arg Ala Pro Phe Asp Thr Asp Val Phe Asn Asp Thr Asp
        450                 455                 460

Arg Ala Lys Phe Lys Thr Ala Val Thr Lys Gly Val Asp Tyr Ile Leu
465                 470                 475                 480

Lys Ala Gln Trp Lys Gln Asn Gly Lys Leu Thr Ala Trp Cys Ala Gln
```

```
                     485               490                495
His Gly Ala Thr Asp Tyr Gln Pro Lys Lys Ala Arg Ala Tyr Glu Leu
                500                 505                510

Glu Ser Leu Ser Gly Ser Glu Ser Val Gly Val Ile Ala Phe Leu Met
            515                 520                 525

Thr Gln Pro Gln Thr Ala Gln Ile Gln Thr Ala Val Lys Ala Gly Leu
        530                 535                 540

Asn Trp Phe Asn Ser Pro Ser Thr Tyr Leu Glu Gly Tyr Thr Tyr Asp
545                 550                 555                 560

Ser Ser Lys Ala Ser Thr Asn Pro Ile Val Gln Lys Ala Gly Ser Arg
                565                 570                 575

Met Trp Tyr Arg Phe Tyr Asp Leu Asn Thr Asn Arg Gly Phe Phe Ser
            580                 585                 590

Asp Arg Asp Gly Ser Lys Phe Tyr Asp Ile Thr Lys Met Ser Glu Glu
        595                 600                 605

Arg Arg Thr Gly Tyr Ser Trp Gly Gly Ala Tyr Gly Glu Ser Ile Ile
    610                 615                 620

Ala Phe Gly Lys Lys Val Gly Tyr Leu
625                 630
```

<210> SEQ ID NO 45
<211> LENGTH: 987
<212> TYPE: DNA
<213> ORGANISM: Unknown
<220> FEATURE:
<223> OTHER INFORMATION: Obtained from an environmental sample

<400> SEQUENCE: 45

```
atgactagac gcgccttcat cgcggttatc tgtttcttcg cggccgtctg cgcgcacgcg     60
cagtccaccg tgcgctggaa ggacgtgctc gagcagtccg agggctggta ttccacgacc    120
gccgcgcacg tcgtcgccga cacggtgctg ctgtatcaac gtccatccgg tggatggccg    180
aaggacatcg acatgacggc gccgccggcg gaccgcactc ctcccgcgcg tccagacgcg    240
accatcgaca acgcgccac gaccacgcag atccgcctgc tcgctcgtgc ggcctcgggc    300
gcaccggcgg ctgccgccca cctacacg gcggcggcgc ttcgcgggat cgattacctg     360
ctcgaggcg agtatcccaa cggcggctgg ccgcagttct tccccctgcg caaggactat    420
tcgcgctacg tcacgttcaa cgacgacgcg atgatgaacg tgatgttcct gctggacgag    480
gtctcggcgg gagatgcgcc gttcacgttc gtggacgaac aacgccgcga ccgcgcgcgc    540
gctgccgtcg ccaaggggt ctccgtcatc ctgaagtcgc aggtccggat cgacgggacg    600
ctgaccgcct ggtgcgcgca acacgacgag atcaccctgg caccgcgtcc ggcgcgcacc    660
ttcgagcacg cgtcgctcag cggcaacgag tctgtcgcga tcgtgcgctt cctgatgacc    720
cgtccgccga cgccagcgat cgtcgccgcg gtcgatgcgg cggtcgcctg gctcagacgc    780
gtccgcctcc ctgacggacg gtgggcccga ttctacgagt tcggtaccaa tcgtccgatc    840
ttctcggggc gagacagtgt cgtgcgctac aaactgagg agatcgaaca ggaacgtcag    900
gagggctacg cgtggtacgg cacgtggccg aggacgcttg ttgagaagat gtaccctgca    960
tggaagtcgc ggcttccggg caagtag                                         987
```

<210> SEQ ID NO 46
<211> LENGTH: 328
<212> TYPE: PRT
<213> ORGANISM: Unknown
<220> FEATURE:

<223> OTHER INFORMATION: Obtained from an environmental sample
<220> FEATURE:
<221> NAME/KEY: SIGNAL
<222> LOCATION: (1)...(20)
<220> FEATURE:
<221> NAME/KEY: DOMAIN
<222> LOCATION: (21)...(328)
<223> OTHER INFORMATION: Catalytic domain

<400> SEQUENCE: 46

```
Met Thr Arg Arg Ala Phe Ile Ala Val Ile Cys Phe Phe Ala Ala Val
 1               5                  10                  15

Cys Ala His Ala Gln Ser Thr Val Arg Trp Lys Asp Val Leu Glu Gln
            20                  25                  30

Ser Glu Gly Trp Tyr Ser Thr Thr Ala Ala His Val Val Ala Asp Thr
        35                  40                  45

Val Leu Leu Tyr Gln Arg Pro Ser Gly Gly Trp Pro Lys Asp Ile Asp
    50                  55                  60

Met Thr Ala Pro Pro Ala Asp Arg Thr Pro Ala Arg Pro Asp Ala
65                  70                  75                  80

Thr Ile Asp Asn Gly Ala Thr Thr Thr Gln Ile Arg Leu Leu Ala Arg
                85                  90                  95

Ala Ala Ser Gly Ala Pro Ala Ala Ala His Thr Tyr Thr Ala Ala
            100                 105                 110

Ala Leu Arg Gly Ile Asp Tyr Leu Leu Glu Ala Gln Tyr Pro Asn Gly
        115                 120                 125

Gly Trp Pro Gln Phe Phe Pro Leu Arg Lys Asp Tyr Ser Arg Tyr Val
    130                 135                 140

Thr Phe Asn Asp Asp Ala Met Met Asn Val Met Phe Leu Leu Asp Glu
145                 150                 155                 160

Val Ser Ala Gly Asp Ala Pro Phe Thr Phe Val Asp Glu Gln Arg Arg
                165                 170                 175

Asp Arg Ala Arg Ala Ala Val Ala Lys Gly Val Ser Val Ile Leu Lys
            180                 185                 190

Ser Gln Val Arg Ile Asp Gly Thr Leu Thr Ala Trp Cys Ala Gln His
        195                 200                 205

Asp Glu Ile Thr Leu Ala Pro Arg Pro Ala Arg Thr Phe Glu His Ala
    210                 215                 220

Ser Leu Ser Gly Asn Glu Ser Val Ala Ile Val Arg Phe Leu Met Thr
225                 230                 235                 240

Arg Pro Pro Thr Pro Ala Ile Val Ala Val Asp Ala Ala Val Ala
                245                 250                 255

Trp Leu Arg Arg Val Arg Leu Pro Asp Gly Arg Trp Ala Arg Phe Tyr
            260                 265                 270

Glu Phe Gly Thr Asn Arg Pro Ile Phe Ser Gly Arg Asp Ser Val Val
        275                 280                 285

Arg Tyr Lys Leu Glu Glu Ile Glu Gln Glu Arg Gln Glu Gly Tyr Ala
    290                 295                 300

Trp Tyr Gly Thr Trp Pro Arg Thr Leu Val Glu Lys Met Tyr Pro Ala
305                 310                 315                 320

Trp Lys Ser Arg Leu Pro Gly Lys
                325
```

<210> SEQ ID NO 47
<211> LENGTH: 1077
<212> TYPE: DNA
<213> ORGANISM: Unknown

<220> FEATURE:
<223> OTHER INFORMATION: Obtained from an environmental sample

<400> SEQUENCE: 47

```
atgaaaaatt ttaaaaatat tgtaggagcg ttacttatat ctgtaacgtt ttgtgtgcac      60
gggcaggtaa acaaaaaatc ctggcgggct attacacagt ctaacgacga tgcatggttt     120
gcatctgatg gagctgcaca gattgcagat aatgtattac tctatcagcg caatgttggc     180
ggatggccta aaatattga atgcaggaa ccgcttagtg aggccgacaa aaaaaagctg       240
atagatctta agtctacggc caaagaaagt actacagata tgggggctac gtgtcaggaa    300
atggtattcc tctctaagat atataaacaa agcccgaag agaagtataa agaggctttt      360
ttaaaaggac ttaattattt gcttgaagca cagtataaaa atggtggatg ccacagttc     420
taccctttaa aaaaaggtta ttatacccac attacctata tgacgattc tatggtaaac     480
attcttatga tcttaaagaa tattaaggaa gatgccaact attacagtat tacgccaagc    540
gataaagttt taaagcaggt atcgacagct tttgacagag cattgactg cattctaaaa    600
acacagtaca agcaaaaggg tgtgcttaca agctggtgtg cccagcacga tgaggttaca    660
ttagaacctg caaatgcaag ggcttttgag ttggcatcac taagtggtaa agaatctgct    720
aaaataacgt tgttgctaat gtctgtaaaa aatccgtcta aagaggttgt tgctgctgta    780
gatgctgctg tggcgtggtt tgaaaaaaca aaaattgaag gcattaaagt agaagaagta    840
accggagctg atggcaaaaa ggatagggta gtagtacaaa gggctgatgc cgaaccattg    900
tgggcgcgtt ttatggaact ggataccaac aggccatttt tttgcgacag ggacggtata    960
aaaaaatatt cgcttgctga gataggtcat gaacgccgta acggatatgg ctggtacacc   1020
aacgaaccaa agaagttttt aagaaatac accaaatgga aaacagtct taaatag        1077
```

<210> SEQ ID NO 48
<211> LENGTH: 358
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(21)
<220> FEATURE:
<221> NAME/KEY: DOMAIN
<222> LOCATION: (22)...(358)
<223> OTHER INFORMATION: Catalytic domain

<400> SEQUENCE: 48

```
Met Lys Asn Phe Lys Asn Ile Val Gly Ala Leu Leu Ile Ser Val Thr
  1               5                  10                  15

Phe Cys Val His Gly Gln Val Asn Lys Lys Ser Trp Arg Ala Ile Thr
                 20                  25                  30

Gln Ser Asn Asp Asp Ala Trp Phe Ala Ser Asp Gly Ala Ala Gln Ile
             35                  40                  45

Ala Asp Asn Val Leu Leu Tyr Gln Arg Asn Val Gly Gly Trp Pro Lys
         50                  55                  60

Asn Ile Glu Met Gln Glu Pro Leu Ser Glu Ala Asp Lys Lys Lys Leu
 65                  70                  75                  80

Ile Asp Leu Lys Ser Thr Ala Lys Glu Ser Thr Thr Asp Asn Gly Ala
                 85                  90                  95

Thr Cys Gln Glu Met Val Phe Leu Ser Lys Ile Tyr Lys Gln Lys Pro
            100                 105                 110
```

```
Glu Glu Lys Tyr Lys Glu Ala Phe Leu Lys Gly Leu Asn Tyr Leu Leu
            115                 120                 125

Glu Ala Gln Tyr Lys Asn Gly Gly Trp Pro Gln Phe Tyr Pro Leu Lys
130                 135                 140

Lys Gly Tyr Tyr Thr His Ile Thr Tyr Asn Asp Asp Ser Met Val Asn
145                 150                 155                 160

Ile Leu Met Ile Leu Lys Asn Ile Lys Glu Asp Ala Asn Tyr Tyr Ser
                165                 170                 175

Ile Thr Pro Ser Asp Lys Val Leu Lys Gln Val Ser Thr Ala Phe Asp
            180                 185                 190

Arg Gly Ile Asp Cys Ile Leu Lys Thr Gln Tyr Lys Gln Lys Gly Val
            195                 200                 205

Leu Thr Ser Trp Cys Ala Gln His Asp Glu Val Thr Leu Glu Pro Ala
            210                 215                 220

Asn Ala Arg Ala Phe Glu Leu Ala Ser Leu Ser Gly Lys Glu Ser Ala
225                 230                 235                 240

Lys Ile Thr Leu Leu Leu Met Ser Val Lys Asn Pro Ser Lys Glu Val
                245                 250                 255

Val Ala Ala Val Asp Ala Ala Val Ala Trp Phe Glu Lys Thr Lys Ile
            260                 265                 270

Glu Gly Ile Lys Val Glu Glu Val Thr Gly Ala Asp Gly Lys Lys Asp
            275                 280                 285

Arg Val Val Val Gln Arg Ala Asp Ala Glu Pro Leu Trp Ala Arg Phe
            290                 295                 300

Met Glu Leu Asp Thr Asn Arg Pro Phe Phe Cys Asp Arg Asp Gly Ile
305                 310                 315                 320

Lys Lys Tyr Ser Leu Ala Glu Ile Gly His Glu Arg Arg Asn Gly Tyr
                325                 330                 335

Gly Trp Tyr Thr Asn Glu Pro Lys Glu Val Leu Lys Lys Tyr Thr Lys
            340                 345                 350

Trp Lys Asn Ser Leu Lys
            355

<210> SEQ ID NO 49
<211> LENGTH: 1023
<212> TYPE: DNA
<213> ORGANISM: Unknown
<220> FEATURE:
<223> OTHER INFORMATION: Obtained from an environmental sample

<400> SEQUENCE: 49
atgttaagtt tcatcgcggt atcagtgttt cataattact gcacagggca gacagcgtcc      60
accaaaaatt cagtggccga aaagatgctt cagtaccagt tgtcaaatgg cgcctggccc     120
aaacagttgg tagacaaaag tgtcgttgat tacagtcttc cattaacgaa agagcgccta     180
cagcagatca agaaaacaga tattgatcat gctacgctcg acaacagtgc gacaacccgg     240
gaaataactg aattgatcaa ggcttttaag gacactaaaa ataaggcata tttgactgct     300
gtagaaaagg ggattgcata tatttatcg gctcaatatg agaatggcgg atttccacaa     360
tactacccaa ataaattata ctatagagct gagataacat acaacgatga tgcgatgatc     420
aatgcattac tagtgcttta caagtagcc aataagcgag aggggtttga ggctatcaat     480
cccatatttg tgtcaaaagc gcaaaaagca gttgaaaagg gtataacctg tatcctaaaa     540
acacaggtca tacaagacgg aaaaaggagt atttgggctg cgcaatacga tcagaacact     600
ttacaacctg ctcaggcaag aaagtttgaa ccagcttcat tgagcacaag tgaatctgtt     660
```

```
tccatcgttc gctttctcat gctacagcct gcaaccactg aaattaagca agcgatcgaa    720
catgcaatac aatggttcga acagcatgat attgaaggtt accgtttcga ccgcatacaa    780
gataggtgta ctggaaaata tcaacggcaa cttgtcgcag atcggacttc cacgatttgg    840
gcgcgatttt ataatctcga agacaaccgc ccattgtttg gagatcggga caatacaatc    900
aaatacaact ttgaggaggt ttcagaggag cgtagaaatg gctatgcttg gttcggcaac    960
tggccggaaa agctgatcca aaaggactat ccaaaatgga aaaacaata caaaattaaa   1020 taa                                                                 1023
```

<210> SEQ ID NO 50
<211> LENGTH: 340
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(16)
<220> FEATURE:
<221> NAME/KEY: DOMAIN
<222> LOCATION: (17)...(340)
<223> OTHER INFORMATION: Catalytic domain

<400> SEQUENCE: 50

```
Met Leu Ser Phe Ile Ala Val Ser Val Phe His Asn Tyr Cys Thr Gly
 1               5                  10                  15

Gln Thr Ala Ser Thr Lys Asn Ser Val Ala Glu Lys Met Leu Gln Tyr
            20                  25                  30

Gln Leu Ser Asn Gly Ala Trp Pro Lys Gln Leu Val Asp Lys Ser Val
        35                  40                  45

Val Asp Tyr Ser Leu Pro Leu Thr Lys Glu Arg Leu Gln Gln Ile Lys
    50                  55                  60

Lys Thr Asp Ile Asp His Ala Thr Leu Asp Asn Ser Ala Thr Thr Arg
65                  70                  75                  80

Glu Ile Thr Glu Leu Ile Lys Ala Phe Lys Asp Thr Lys Asn Lys Ala
                85                  90                  95

Tyr Leu Thr Ala Val Glu Lys Gly Ile Ala Tyr Ile Leu Ser Ala Gln
            100                 105                 110

Tyr Glu Asn Gly Gly Phe Pro Gln Tyr Tyr Pro Asn Lys Leu Tyr Tyr
        115                 120                 125

Arg Ala Glu Ile Thr Tyr Asn Asp Asp Ala Met Ile Asn Ala Leu Leu
    130                 135                 140

Val Leu Tyr Lys Val Ala Asn Lys Arg Glu Gly Phe Glu Ala Ile Asn
145                 150                 155                 160

Pro Ile Phe Val Ser Lys Ala Gln Lys Ala Val Glu Lys Gly Ile Thr
                165                 170                 175

Cys Ile Leu Lys Thr Gln Val Ile Gln Asp Gly Lys Arg Ser Ile Trp
            180                 185                 190

Ala Ala Gln Tyr Asp Gln Asn Thr Leu Gln Pro Ala Gln Ala Arg Lys
        195                 200                 205

Phe Glu Pro Ala Ser Leu Ser Thr Ser Glu Ser Val Ser Ile Val Arg
    210                 215                 220

Phe Leu Met Leu Gln Pro Ala Thr Thr Glu Ile Lys Gln Ala Ile Glu
225                 230                 235                 240

His Ala Ile Gln Trp Phe Glu Gln His Asp Ile Glu Gly Tyr Arg Phe
                245                 250                 255
```

Asp Arg Ile Gln Asp Arg Val Thr Gly Lys Tyr Gln Arg Gln Leu Val
            260                 265                 270

Ala Asp Arg Thr Ser Thr Ile Trp Ala Arg Phe Tyr Asn Leu Glu Asp
        275                 280                 285

Asn Arg Pro Leu Phe Gly Asp Arg Asp Asn Thr Ile Lys Tyr Asn Phe
    290                 295                 300

Glu Glu Val Ser Glu Glu Arg Arg Asn Gly Tyr Ala Trp Phe Gly Asn
305                 310                 315                 320

Trp Pro Glu Lys Leu Ile Gln Lys Asp Tyr Pro Lys Trp Lys Lys Gln
            325                 330                 335

Tyr Lys Ile Lys
            340

<210> SEQ ID NO 51
<211> LENGTH: 1131
<212> TYPE: DNA
<213> ORGANISM: Unknown
<220> FEATURE:
<223> OTHER INFORMATION: Obtained from an environmental sample

<400> SEQUENCE: 51
gtgacgtggg atcagatcct tcgtcagcct gccgcctggt acggcggtcc ggaagcgcga      60
cggatcgcga atctggtcct gctgtaccag cgcgcgacgg ggggctggcc caagaacatc     120
gacatggcgc ggtcgttgtc tccggacgat cgcacgacgc tcgcggcgga acgggccctc     180
accgactcga cgatcgacaa tggatcgacg acgacgcagt gcggtttcct cgcgatggtg     240
cagcacgccc agcaggcacc cgtgcgcgac gccatcacgc acggcctgga ctatctgctg     300
aacgcgcaat actcgaacgg cggatggccg cagtactttc cgctccgaga cgactactcg     360
cgtcacatca cgttcaacga cgacgcgatg atcaatgtaa tgacggtgct acgcgatgtc     420
gcagaagctc gcatgcccct cgaagggatc gacgcggtcc gtcgggaccg ggcgcgtgtc     480
gccatcacgc gtggcatcga cgtgattctc gggacgcaaa tccgcgtcgg gaccgtctg      540 acgggctggt gccagcagca tgacgagcgc tccctcgccc ccaccaaggc tcgcgcctac     600
gagcacccat cgatcgccag caaggaaacg gtaaccatca cgcgcttcct catgaccctc     660
gatcgcccga gtcagcagat catcgcggcg atcgaggcgg ctgtcgagtg gttgcgcgtg     720
gcgaccctgt cgggtgtgcg agttgagcgt cggccggacc cggcgagtcc gaccggatat     780
gacgtcgtcg ccgcgccgga tgccgccgca cctccgacct gggcacggtt ctacgagatc     840
ggcacgaacc gcccaatgtt ttccggccgc gacggcgtga tcagattccg gctcgcggac     900
atcgagattg agcgccgcac cggctacagc tggatgggcg actatgccgc gaggttgctg     960
aacgaggagt atccggcgtg gcgaggcta cgccgggcga gctttcagaa cgccgagctg    1020
cacaaggagt ccggtgaagt cgtacacacg gcgatcgtgc acgatcttgc cttccttgat    1080
gtcgaagaca agaccagcc gcagccgaaa gtgcttttcg ctgggcggta g             1131

<210> SEQ ID NO 52
<211> LENGTH: 376
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(376)
<223> OTHER INFORMATION: Catalytic domain

```
<400> SEQUENCE: 52

Met Thr Trp Asp Gln Ile Leu Arg Gln Pro Ala Ala Trp Tyr Gly Gly
  1               5                  10                  15

Pro Glu Ala Arg Arg Ile Ala Asn Leu Val Leu Leu Tyr Gln Arg Ala
             20                  25                  30

Thr Gly Gly Trp Pro Lys Asn Ile Asp Met Ala Arg Ser Leu Ser Pro
         35                  40                  45

Asp Asp Arg Thr Thr Leu Ala Ala Glu Arg Ala Leu Thr Asp Ser Thr
     50                  55                  60

Ile Asp Asn Gly Ser Thr Thr Thr Gln Leu Arg Phe Leu Ala Met Val
 65                  70                  75                  80

Gln His Ala Gln Gln Ala Pro Val Arg Asp Ala Ile Thr His Gly Leu
                 85                  90                  95

Asp Tyr Leu Leu Asn Ala Gln Tyr Ser Asn Gly Gly Trp Pro Gln Tyr
            100                 105                 110

Phe Pro Leu Arg Asp Asp Tyr Ser Arg His Ile Thr Phe Asn Asp Asp
            115                 120                 125

Ala Met Ile Asn Val Met Thr Val Leu Arg Asp Val Ala Glu Ala Arg
        130                 135                 140

Met Pro Phe Glu Gly Ile Asp Ala Val Arg Arg Asp Arg Ala Arg Val
145                 150                 155                 160

Ala Ile Thr Arg Gly Ile Asp Val Ile Leu Gly Thr Gln Ile Arg Val
                165                 170                 175

Gly Asp Arg Leu Thr Gly Trp Cys Gln Gln His Asp Glu Arg Ser Leu
            180                 185                 190

Ala Pro Thr Lys Ala Arg Ala Tyr Glu His Pro Ser Ile Ala Ser Lys
        195                 200                 205

Glu Thr Val Thr Ile Thr Arg Phe Leu Met Thr Leu Asp Arg Pro Ser
210                 215                 220

Gln Gln Ile Ile Ala Ala Ile Glu Ala Ala Val Glu Trp Leu Arg Val
225                 230                 235                 240

Ala Thr Leu Ser Gly Val Arg Val Glu Arg Arg Pro Asp Pro Ala Ser
                245                 250                 255

Pro Thr Gly Tyr Asp Val Val Ala Ala Pro Asp Ala Ala Ala Pro Pro
            260                 265                 270

Thr Trp Ala Arg Phe Tyr Glu Ile Gly Thr Asn Arg Pro Met Phe Ser
        275                 280                 285

Gly Arg Asp Gly Val Ile Arg Phe Arg Leu Ala Asp Ile Glu Ile Glu
    290                 295                 300

Arg Arg Thr Gly Tyr Ser Trp Met Gly Asp Tyr Ala Ala Arg Leu Leu
305                 310                 315                 320

Asn Glu Glu Tyr Pro Ala Trp Ala Arg Leu Arg Arg Ala Ser Phe Gln
                325                 330                 335

Asn Ala Glu Leu His Lys Glu Ser Gly Val Val His Thr Ala Ile
            340                 345                 350

Val His Asp Leu Ala Phe Leu Asp Val Glu Asp Lys Asp Gln Pro Gln
        355                 360                 365

Pro Lys Val Leu Phe Ala Gly Arg
    370                 375

<210> SEQ ID NO 53
<211> LENGTH: 1977
<212> TYPE: DNA
<213> ORGANISM: Unknown
```

<220> FEATURE:
<223> OTHER INFORMATION: Obtained from an environmental sample

<400> SEQUENCE: 53

```
atgaataact caacaaaaaa aatgattcgg ccactcaagg catcttttgc cttgggcgct      60
ctcgcactgg caatcgcatc accctcatgg gcggcttgct cttacagcgt aaccaataat     120
tggggctctg gctttaccgg agaaattaaa gtaaccaacg atacaacatc gactgtaaat     180
aattggtctg tgtcttggca ggaatcaggc gtgaccgtca ctaacgcatg gaatgcaaca     240
ctgagcggat caaatcctta taccgcaaca tcactcgggt ggaacggaac tctcgctcca     300
aaagcttcag caagttttgg ttttcaagca aatggaacag cgggcgcacc gaaagtaaat     360
ggaaccttgt gtggtaccag cacatcatca acaggtacat cctcagttgc accttcatcc     420
gtagcgagta gcgttgctgt atcaagcagt aaatcatcaa gctctgttgc aaccatcagt     480
agctctaaat ccagcagcag tgtgccgaca gtttcatcat tcactattca ggaagagcaa     540
gccggtttct gccgtgtaga tggcattgca actgaaagta ctaacactgg ctatacaggt     600
aatggctaca ccaacaccac taatgcgcaa ggcgctgcaa ttgaatgggc aattaatgct     660
cccaacagca gccgctacac cctcaccttc cgttatgcca atgctggtac cgctaatcgc     720
aatggttcgt tattaattaa cgacggaagc aatggtaact acacagtgca attgccaagt     780
accggcgcat gggcaacctg gcaaaccgtc agtgttgaag tggatttggt gcaaggcaat     840
aatattttga aactcgcttc gcttactgct gatggccttg cgaatataga ttcattaaaa     900
attgaaggcg cacaagccaa agctggtgta tgcagcacta cggtaagtag cagctcttcg     960
tcaattaaat caagttccag ttcatcatcg tccagctcaa ctgcagcagt aaaaacatta    1020
acactggatg gtaaccctgc tgcaaactgg tttaataaat ccagaaccaa gtggaatgtc    1080
agcagagctg acatcgtact ttcgtatcag caatcaaatg gtggctggcc aaaaaatttg    1140
gactacaact cggtaggctc aggtaatggt ggtagcgaca cgcgcactat tgataatggt    1200
gcaaccataa ccgaaatggt gtacctcgct gaagtgtata aaaatggcgg aataccaaaa    1260
taccgcgacg ccgtgcgcag agcagcgaat tttattgtga gttcacaata cagcactggt    1320
gctttaccgc agttttatcc gctgaaaggt ggttacgcag atcacgctac ctttaatgat    1380
aatggtatgg cttacgcgtt gactgttctg gatttcgcgg taaataaacg cgcgccattt    1440
gataacgata ttttctctga ctctgaccgc agcaaattta aaactgctgt taccaaaggc    1500
gtcgattaca tattaaaagc gcaatggaaa cagaatggaa aattaaccgt atggtgcgca    1560
caacacggtg ctaatgatta tcaaccgaaa aaagcgcgtg cttacgagtt agaatcattg    1620
agtggtagtg aatctgtcgg tgtactcgct ttcttaatga ctcaaccaca aaccacgcaa    1680
attgaagcag ctgtgcgtgc aggtgtggcc tggtttaata gcccaagcac ctacttgaat    1740
aattacactt acgattcttc caaagcttcg accaatccaa tcgtgccaaa atccggaagc    1800
aaaatgtggt atcgctttta tgacctgaat accaaccgcg gtttcttcag tgatcgtgac    1860
ggcagcaagt tctacgacat cacccaaatg tcagaagagc gtcgcactgg ttacagttgg    1920
ggtggtgact acggcagctc gattatcagc ttcgcacaaa aagtgggata tctctaa      1977
```

<210> SEQ ID NO 54
<211> LENGTH: 658
<212> TYPE: PRT
<213> ORGANISM: Unknown
<220> FEATURE:
<223> OTHER INFORMATION: Obtained from an environmental sample
<220> FEATURE:

```
<221> NAME/KEY: SIGNAL
<222> LOCATION: (1)...(31)
<220> FEATURE:
<221> NAME/KEY: BINDING
<222> LOCATION: (32)...(124)
<223> OTHER INFORMATION: Carbohydrate binding module
<220> FEATURE:
<221> NAME/KEY: BINDING
<222> LOCATION: (180)...(303)
<223> OTHER INFORMATION: Carbohydrate binding module
<220> FEATURE:
<221> NAME/KEY: DOMAIN
<222> LOCATION: (304)...(658)
<223> OTHER INFORMATION: Catalytic domain

<400> SEQUENCE: 54
```

Met Asn Asn Ser Thr Lys Lys Met Ile Arg Pro Leu Lys Ala Ser Phe
1               5                   10                  15

Ala Leu Gly Ala Leu Ala Leu Ala Ile Ala Ser Pro Ser Trp Ala Ala
            20                  25                  30

Cys Ser Tyr Ser Val Thr Asn Asn Trp Gly Ser Gly Phe Thr Gly Glu
            35                  40                  45

Ile Lys Val Thr Asn Asp Thr Thr Ser Thr Val Asn Asn Trp Ser Val
50                  55                  60

Ser Trp Gln Glu Ser Gly Val Thr Val Thr Asn Ala Trp Asn Ala Thr
65                  70                  75                  80

Leu Ser Gly Ser Asn Pro Tyr Thr Ala Thr Ser Leu Gly Trp Asn Gly
                85                  90                  95

Thr Leu Ala Pro Lys Ala Ser Ala Ser Phe Gly Phe Gln Ala Asn Gly
            100                 105                 110

Thr Ala Gly Ala Pro Lys Val Asn Gly Thr Leu Cys Gly Thr Ser Thr
            115                 120                 125

Ser Ser Thr Gly Thr Ser Ser Val Ala Pro Ser Ser Val Ala Ser Ser
        130                 135                 140

Val Ala Val Ser Ser Ser Lys Ser Ser Ser Ser Val Ala Thr Ile Ser
145                 150                 155                 160

Ser Ser Lys Ser Ser Ser Ser Val Pro Thr Val Ser Ser Phe Thr Ile
                165                 170                 175

Gln Glu Glu Gln Ala Gly Phe Cys Arg Val Asp Gly Ile Ala Thr Glu
            180                 185                 190

Ser Thr Asn Thr Gly Tyr Thr Gly Asn Gly Tyr Thr Asn Thr Thr Asn
            195                 200                 205

Ala Gln Gly Ala Ala Ile Glu Trp Ala Ile Asn Ala Pro Asn Ser Ser
        210                 215                 220

Arg Tyr Thr Leu Thr Phe Arg Tyr Ala Asn Ala Gly Thr Ala Asn Arg
225                 230                 235                 240

Asn Gly Ser Leu Leu Ile Asn Asp Gly Ser Asn Gly Asn Tyr Thr Val
                245                 250                 255

Gln Leu Pro Ser Thr Gly Ala Trp Ala Thr Trp Gln Thr Val Ser Val
            260                 265                 270

Glu Val Asp Leu Val Gln Gly Asn Asn Ile Leu Lys Leu Ala Ser Leu
            275                 280                 285

Thr Ala Asp Gly Leu Ala Asn Ile Asp Ser Leu Lys Ile Glu Gly Ala
            290                 295                 300

Gln Ala Lys Ala Gly Val Cys Ser Thr Thr Val Ser Ser Ser Ser Ser
305                 310                 315                 320

Ser Ile Lys Ser Ser Ser Ser Ser Ser Ser Ser Ser Thr Ala Ala
                325                 330                 335

Val Lys Thr Leu Thr Leu Asp Gly Asn Pro Ala Ala Asn Trp Phe Asn
            340                 345                 350

Lys Ser Arg Thr Lys Trp Asn Val Ser Arg Ala Asp Ile Val Leu Ser
        355                 360                 365

Tyr Gln Gln Ser Asn Gly Gly Trp Pro Lys Asn Leu Asp Tyr Asn Ser
    370                 375                 380

Val Gly Ser Gly Asn Gly Gly Ser Asp Ser Gly Thr Ile Asp Asn Gly
385                 390                 395                 400

Ala Thr Ile Thr Glu Met Val Tyr Leu Ala Glu Val Tyr Lys Asn Gly
                405                 410                 415

Gly Asn Thr Lys Tyr Arg Asp Ala Val Arg Ala Ala Asn Phe Ile
            420                 425                 430

Val Ser Ser Gln Tyr Ser Thr Gly Ala Leu Pro Gln Phe Tyr Pro Leu
        435                 440                 445

Lys Gly Gly Tyr Ala Asp His Ala Thr Phe Asn Asp Asn Gly Met Ala
    450                 455                 460

Tyr Ala Leu Thr Val Leu Asp Phe Ala Val Asn Lys Arg Ala Pro Phe
465                 470                 475                 480

Asp Asn Asp Ile Phe Ser Asp Ser Arg Ser Lys Phe Lys Thr Ala
                485                 490                 495

Val Thr Lys Gly Val Asp Tyr Ile Leu Lys Ala Gln Trp Lys Gln Asn
        500                 505                 510

Gly Lys Leu Thr Val Trp Cys Ala Gln His Gly Ala Asn Asp Tyr Gln
    515                 520                 525

Pro Lys Lys Ala Arg Ala Tyr Glu Leu Glu Ser Leu Ser Gly Ser Glu
530                 535                 540

Ser Val Gly Val Leu Ala Phe Leu Met Thr Gln Pro Gln Thr Thr Gln
545                 550                 555                 560

Ile Glu Ala Ala Val Arg Ala Gly Val Ala Trp Phe Asn Ser Pro Ser
                565                 570                 575

Thr Tyr Leu Asn Asn Tyr Thr Tyr Asp Ser Ser Lys Ala Ser Thr Asn
        580                 585                 590

Pro Ile Val Pro Lys Ser Gly Ser Lys Met Trp Tyr Arg Phe Tyr Asp
    595                 600                 605

Leu Asn Thr Asn Arg Gly Phe Phe Ser Asp Arg Asp Gly Ser Lys Phe
610                 615                 620

Tyr Asp Ile Thr Gln Met Ser Glu Glu Arg Arg Thr Gly Tyr Ser Trp
625                 630                 635                 640

Gly Gly Asp Tyr Gly Ser Ser Ile Ile Ser Phe Ala Gln Lys Val Gly
                645                 650                 655

Tyr Leu

<210> SEQ ID NO 55
<211> LENGTH: 1125
<212> TYPE: DNA
<213> ORGANISM: Unknown
<220> FEATURE:
<223> OTHER INFORMATION: Obtained from an environmental sample

<400> SEQUENCE: 55
gtggtcctag gtaataacgg cggcagcttg agttgcgtcc aatatattgt gattgtgaaa    60
ggacccggtg gacctcgacc gccggtgaaa ccggccgtcc aggcgcccgt tagggttacc   120
tggagcgcat gcctagtcca gcggcccgaa tggtacggga gtgacgaagc gatccgcatc   180

```
gcggacaacg tcctcctcta ccagcgcaac accggcgggt ggccgaagga catagatatg    240
gccgagccca tcccggaaca caggaagtcc ttttcctca ccgagaagga gcggaccgat     300
gactcgacca tcgacaacgg tgccaccgtg acccagctca gtatctcgc ccgcgtctac     360 aaggcgacca ggctggaacg gttcaaggag ggcttcctca aggtctcga ctacctcttg     420 gccgcccagt acccgaacgg cggctggccc cagtattatc ctaacttgag gggctactac    480
gccaacatca cttataacga caatgccatg gtgaacgtgc tcaccctcct ccagagcatc    540
gccaaaaagg ccccggagta cgacttcgtc gacccggcgc gccgggagaa ggccgcccgg    600
gccgtggcga aagggatcga ctgcatcctc aagacccaga tccgtgtcaa tggaaaactt    660
accgcctggt gcgcccagca tgaccccaag cgctggcgc ccgcgccggc ccgttcgtat     720
gagcttgagt ccatcagcgg tttcgagagc gtcgggatcg tccggttctt aatgagcctc    780
gagaatccga gcccgaaggt catcgaggcg gtagaggccg ccgtgaaatg gttcgaggag    840
gtcaagctta ccgggatcaa ggtggtcgag aaacccgacc cgtccttcc gggcggttac     900 gaccgcgtgg tggtcgaaga ccccaacgcg ccgcccatct gggcccggtt ctacgagatc    960
ggcaccaacc gtcccttctt ctgcggccgc gatggtatca aaaatacag cctggcggag     1020 atcgaacacg aacgccgggt cggttactcc tggtacacca tgccccggc ctacctcatc     1080 gagaaggagt atccgctctg gcgggccaaa caccctacca agtaa                    1125
```

```
<210> SEQ ID NO 56
<211> LENGTH: 374
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(374)
<223> OTHER INFORMATION: Catalytic domain

<400> SEQUENCE: 56
```

Met Val Leu Gly Asn Asn Gly Gly Ser Leu Ser Cys Val Gln Tyr Ile
 1               5                  10                  15

Val Ile Val Lys Gly Pro Gly Pro Arg Pro Val Lys Pro Ala
             20                  25                  30

Val Gln Ala Pro Val Arg Val Thr Trp Ser Ala Cys Leu Val Gln Arg
         35                  40                  45

Pro Glu Trp Tyr Gly Ser Asp Glu Ala Ile Arg Ile Ala Asp Asn Val
     50                  55                  60

Leu Leu Tyr Gln Arg Asn Thr Gly Gly Trp Pro Lys Asp Ile Asp Met
65                  70                  75                  80

Ala Glu Pro Ile Pro Glu His Arg Lys Ser Phe Phe Leu Thr Glu Lys
                 85                  90                  95

Glu Arg Thr Asp Asp Ser Thr Ile Asp Asn Gly Ala Thr Val Thr Gln
            100                 105                 110

Leu Lys Tyr Leu Ala Arg Val Tyr Lys Ala Thr Arg Leu Glu Arg Phe
        115                 120                 125

Lys Glu Gly Phe Leu Lys Gly Leu Asp Tyr Leu Leu Ala Ala Gln Tyr
    130                 135                 140

Pro Asn Gly Gly Trp Pro Gln Tyr Tyr Pro Asn Leu Arg Gly Tyr Tyr
145                 150                 155                 160

Ala Asn Ile Thr Tyr Asn Asp Asn Ala Met Val Asn Val Leu Thr Leu
                165                 170                 175

-continued

```
Leu Gln Ser Ile Ala Lys Lys Ala Pro Glu Tyr Asp Phe Val Asp Pro
            180                 185                 190
Ala Arg Arg Glu Lys Ala Ala Arg Ala Val Ala Lys Gly Ile Asp Cys
        195                 200                 205
Ile Leu Lys Thr Gln Ile Arg Val Asn Gly Lys Leu Thr Ala Trp Cys
    210                 215                 220
Ala Gln His Asp Pro Lys Thr Leu Ala Pro Ala Pro Ala Arg Ser Tyr
225                 230                 235                 240
Glu Leu Glu Ser Ile Ser Gly Phe Glu Ser Val Gly Ile Val Arg Phe
                245                 250                 255
Leu Met Ser Leu Glu Asn Pro Ser Pro Lys Val Ile Glu Ala Val Glu
            260                 265                 270
Ala Ala Val Lys Trp Phe Glu Glu Val Lys Leu Thr Gly Ile Lys Val
        275                 280                 285
Val Glu Lys Pro Asp Pro Ser Leu Pro Gly Gly Tyr Asp Arg Val Val
    290                 295                 300
Val Glu Asp Pro Asn Ala Pro Pro Ile Trp Ala Arg Phe Tyr Glu Ile
305                 310                 315                 320
Gly Thr Asn Arg Pro Phe Phe Cys Gly Arg Asp Gly Ile Lys Lys Tyr
                325                 330                 335
Ser Leu Ala Glu Ile Glu His Glu Arg Arg Val Gly Tyr Ser Trp Tyr
            340                 345                 350
Thr Asn Ala Pro Ala Tyr Leu Ile Glu Lys Glu Tyr Pro Leu Trp Arg
        355                 360                 365
Ala Lys His Pro Thr Lys
    370
```

<210> SEQ ID NO 57
<211> LENGTH: 1170
<212> TYPE: DNA
<213> ORGANISM: Unknown
<220> FEATURE:
<223> OTHER INFORMATION: Obtained from an environmental sample

<400> SEQUENCE: 57

```
atggacaaac gcgtcaaatg gattcatcag ctttcaaaag aagaagcaaa gcagttcgag        60
cccgaaaatt tcctcaaagg caaagacggc tggaatccga aaaaggcgga tgaccgctgg       120
ctcgaaaaaa caaaacctga ctggcagctc gttacgtgga cgacgcgtt acgccaggcg        180
ccgctctggt atcaaccga tgaagcggcg cgcattgccg accaggtgat tttgtaccag       240
aaagacaacg gcggctggga aaaaaatctc gatatgacgg cgatgctcac gcaagccgaa       300
cgcgaaaagc tcgccaaaga aaatcgaac acgtcggaaa cgacgatcga caaccgcacg       360
acctacacgc aagtcgcttt tctcgccaaa gtcattacgg gcagcttgca gaaaacgact       420
ccgccgacca atttcccgaa acataaggaa gcttttttca agggcttgga ttacctgctc       480
gcgtcgcagt acgaatcggg cggctttccg cagttttatc cgctcaaaaa aggttattac       540
acgcacatca cgttcaacga cgatgcgatg attggcgttt tgaaggtttt gcgcgaaatc       600
gccaaaaaga aggaagacta tcttttttgtt gacgaagaac gccgcctgaa agcggaaaaa       660
tcggtcgaaa aagcgctgcc gctgattctg aaattgcagg ttgaagtcgg cggcaaaaaa       720
acggtttggg cggcgcagta tgacgaaaac actttaaaac ccgcagcggc gcgaaagttt       780
gaaccggttt cttaacggc gggcgaatcg gtcggcatcg tccggttttt aatgtacgat       840
tcaaagcccg accaggcgac gattgacgcg attgaatctg ccattcagtg gtatcgcgcg       900
```

-continued

```
aacaaaatcg aaggcattcg atgggtgcgc gaaaacggcg aaaaccgcgt cgtcaaggac    960
aaaaacgcgc cgccgatttg gcgcgggttt tacgaaatcg aaacgatgaa gccgattttc   1020
atcgggcgcg acgccatcat tcgttacgac gtgtctgaaa tcgaagccga gcgccgcaac   1080
ggctacgcgt ggtacgtctc ggagccgaac gagctgcttg aaaagatta cccgaaatgg    1140 ctggaaaaaa ttaaaaaatc agtaaagtaa                                   1170
```

<210> SEQ ID NO 58
<211> LENGTH: 389
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(389)
<223> OTHER INFORMATION: Catalytic domain

<400> SEQUENCE: 58

```
Met Asp Lys Arg Val Lys Trp Ile His Gln Leu Ser Lys Glu Glu Ala
 1               5                  10                  15

Lys Gln Phe Glu Pro Glu Asn Phe Leu Lys Gly Lys Asp Gly Trp Asn
            20                  25                  30

Pro Lys Lys Ala Asp Asp Arg Trp Leu Glu Lys Thr Lys Pro Asp Trp
        35                  40                  45

Gln Leu Val Thr Trp Asn Asp Ala Leu Arg Gln Ala Pro Leu Trp Tyr
    50                  55                  60

Gln Thr Asp Glu Ala Ala Arg Ile Ala Asp Gln Val Ile Leu Tyr Gln
65                  70                  75                  80

Lys Asp Asn Gly Gly Trp Glu Lys Asn Leu Asp Met Thr Ala Met Leu
                85                  90                  95

Thr Gln Ala Glu Arg Glu Lys Leu Ala Lys Glu Lys Ser Asn Thr Ser
            100                 105                 110

Glu Thr Thr Ile Asp Asn Arg Thr Thr Tyr Thr Gln Val Ala Phe Leu
        115                 120                 125

Ala Lys Val Ile Thr Gly Ser Leu Gln Lys Thr Thr Pro Pro Thr Asn
    130                 135                 140

Phe Pro Lys His Lys Glu Ala Phe Phe Lys Gly Leu Asp Tyr Leu Leu
145                 150                 155                 160

Ala Ser Gln Tyr Glu Ser Gly Gly Phe Pro Gln Phe Tyr Pro Leu Lys
                165                 170                 175

Lys Gly Tyr Tyr Thr His Ile Thr Phe Asn Asp Asp Ala Met Ile Gly
            180                 185                 190

Val Leu Lys Val Leu Arg Glu Ile Ala Lys Lys Glu Asp Tyr Leu
        195                 200                 205

Phe Val Asp Glu Glu Arg Arg Leu Lys Ala Glu Lys Ser Val Glu Lys
    210                 215                 220

Ala Leu Pro Leu Ile Leu Lys Leu Gln Val Glu Val Gly Gly Lys Lys
225                 230                 235                 240

Thr Val Trp Ala Ala Gln Tyr Asp Glu Asn Thr Phe Lys Pro Ala Ala
                245                 250                 255

Ala Arg Lys Phe Glu Pro Val Ser Leu Thr Ala Gly Glu Ser Val Gly
            260                 265                 270

Ile Val Arg Phe Leu Met Tyr Asp Ser Lys Pro Asp Gln Ala Thr Ile
        275                 280                 285

Asp Ala Ile Glu Ser Ala Ile Gln Trp Tyr Arg Ala Asn Lys Ile Glu
```

```
                  290                 295                 300
Gly Ile Arg Trp Val Arg Glu Asn Gly Glu Asn Arg Val Val Lys Asp
305                 310                 315                 320

Lys Asn Ala Pro Pro Ile Trp Ala Arg Phe Tyr Glu Ile Glu Thr Met
                325                 330                 335

Lys Pro Ile Phe Ile Gly Arg Asp Ala Ile Ile Arg Tyr Asp Val Ser
                340                 345                 350

Glu Ile Glu Ala Glu Arg Arg Asn Gly Tyr Ala Trp Tyr Val Ser Glu
                355                 360                 365

Pro Asn Glu Leu Leu Glu Lys Asp Tyr Pro Lys Trp Leu Glu Lys Ile
370                 375                 380

Lys Lys Ser Val Lys
385

<210> SEQ ID NO 59
<211> LENGTH: 1080
<212> TYPE: DNA
<213> ORGANISM: Unknown
<220> FEATURE:
<223> OTHER INFORMATION: Obtained from an environmental sample

<400> SEQUENCE: 59
atgagaatcc ggtcctcttc aatcgcgttc ggcctgattt gcagtctggc gctaagggtg      60
cctgcgcaag cgcaggtcac cgtgcgctgg gcggacgtcc tgaaccagcc cgccgcctgg     120
tatggcaccg atgaagcccg tcgaattgcc gaccacgtgc tcgagcatca acgagcggaa     180
ggcggatggc caaagaacac ggacatgacc gcagcgcccg atccggcggt gctcacagcc     240
gcgcgagtga agccagactc gacgatcgat aacggcgcga ccgtcactga aatgcgcgtc     300
ctcgcgcgcg tctaccgttc atcacccgat ccccgttatc gcgatgcgct gctcaagggt     360
ctcgactatc tgttggcagc gcagtatgcc aacggcggct ggccgcagtt ctacccgctc     420
cggcaggact attcgcgcta tatcacgttc aacgacaacg cgatgatcaa tgtcgtgacg     480
ctgctctcag acgtcgctgc cggaaatggc gactgggcgt tgctgatgc cagcggcgc      540
gagaaaagcc ggacggctgt agagaaggcc gtagaagtca tcctgcgcgc gcaggtgaga     600
gttgacggcc ggctgaccgc gtggtgcgcc caacacgacg aggtgacact cgagccgcgc     660
aaggcccgcg cctacgaaca tccgtcgctg agcggacagg agacggtggg gatcatccgg     720
tttctcatga cccgcgataa accggatcag agagtcgtcg atgcaatcga ggcgtcagtg     780
gcatggctga aggcggtgca gctcaaagga cttcgcgtcg accagcgccg cgatccctcg     840
ctgccggagg ggcgtgacgt ggtgaccgtc gctgacccgt cggcgccgcc gctctgggcg     900
cgcttctacg aaatcgggac caatcgcccg atcttctctg acgcgacgg cgtgatccga     960
tactcgctgg cagagatcga gcacgaacgc cggatagggt acgcctggct cggaacctgg    1020
cccgcgaagc tgctcgatac cgaatacccs tcctggcgac ggactcaaca aaggccgtga    1080

<210> SEQ ID NO 60
<211> LENGTH: 359
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(24)
<220> FEATURE:
<221> NAME/KEY: DOMAIN
<222> LOCATION: (25)...(359)
```

<223> OTHER INFORMATION: Catalytic domain

<400> SEQUENCE: 60

```
Met Arg Ile Arg Ser Ser Ile Ala Phe Gly Leu Ile Cys Ser Leu
 1               5                  10                  15

Ala Leu Arg Val Pro Ala Gln Ala Gln Val Thr Val Arg Trp Ala Asp
            20                  25                  30

Val Leu Asn Gln Pro Ala Ala Trp Tyr Gly Thr Asp Glu Ala Arg Arg
        35                  40                  45

Ile Ala Asp His Val Leu Glu His Gln Arg Ala Glu Gly Gly Trp Pro
    50                  55                  60

Lys Asn Thr Asp Met Thr Ala Ala Pro Asp Pro Ala Val Leu Thr Ala
65                  70                  75                  80

Ala Arg Val Lys Pro Asp Ser Thr Ile Asp Asn Gly Ala Thr Val Thr
                85                  90                  95

Glu Met Arg Val Leu Ala Arg Val Tyr Arg Ser Ser Pro Asp Pro Arg
            100                 105                 110

Tyr Arg Asp Ala Leu Leu Lys Gly Leu Asp Tyr Leu Leu Ala Ala Gln
        115                 120                 125

Tyr Ala Asn Gly Gly Trp Pro Gln Phe Tyr Pro Leu Arg Gln Asp Tyr
    130                 135                 140

Ser Arg Tyr Ile Thr Phe Asn Asp Asn Ala Met Ile Asn Val Val Thr
145                 150                 155                 160

Leu Leu Ser Asp Val Ala Ala Gly Asn Gly Asp Trp Ala Phe Ala Asp
                165                 170                 175

Ala Ser Arg Arg Glu Lys Ser Arg Thr Ala Val Glu Lys Ala Val Glu
            180                 185                 190

Val Ile Leu Arg Ala Gln Val Arg Val Asp Gly Arg Leu Thr Ala Trp
        195                 200                 205

Cys Ala Gln His Asp Glu Val Thr Leu Glu Pro Arg Lys Ala Arg Ala
    210                 215                 220

Tyr Glu His Pro Ser Leu Ser Gly Gln Glu Thr Val Gly Ile Ile Arg
225                 230                 235                 240

Phe Leu Met Thr Arg Asp Lys Pro Asp Gln Arg Val Val Asp Ala Ile
                245                 250                 255

Glu Ala Ser Val Ala Trp Leu Lys Ala Val Gln Leu Lys Gly Leu Arg
            260                 265                 270

Val Asp Gln Arg Arg Asp Pro Ser Leu Pro Glu Gly Arg Asp Val Val
        275                 280                 285

Thr Val Ala Asp Pro Ser Ala Pro Pro Leu Trp Ala Arg Phe Tyr Glu
    290                 295                 300

Ile Gly Thr Asn Arg Pro Ile Phe Ser Gly Arg Asp Gly Val Ile Arg
305                 310                 315                 320

Tyr Ser Leu Ala Glu Ile Glu His Glu Arg Arg Ile Gly Tyr Ala Trp
                325                 330                 335

Leu Gly Thr Trp Pro Ala Lys Leu Leu Asp Thr Glu Tyr Pro Ser Trp
            340                 345                 350

Arg Arg Thr Gln Gln Arg Pro
        355
```

<210> SEQ ID NO 61
<211> LENGTH: 1224
<212> TYPE: DNA
<213> ORGANISM: Unknown
<220> FEATURE:

<223> OTHER INFORMATION: Obtained from an environmental sample

<400> SEQUENCE: 61

```
gtggaattac cagtaaccgg cgcatgggca acctggcaaa ccgcaactgt tgaaattgat      60
ttggtgcaag gtaacaacct gttaaaactt tctgcgatca cggctgatgg tttggcaaat     120
atcgattcgt tgaaaattga cggcgcacaa accaaagccg gcgtgtgcag cactgtggca     180
agcagcagct cttcatccgt tgcttcatcg attaaatcaa gctccagttc atcctcttcc     240
agttcaacga cgacggtaaa aacattaaca ctggatggca accccgcagc aaactggttt     300
aacaaatcca gaaccaaatg gaataccagc agagccgatg ttgtactttc ctatcaacaa     360
tccaacggcg gctggccaaa aaatctcgat tacaattcag taagcgcagg taatggcggc     420
agcgatagcg gcaccatcga taacggtgca accattactg aaatggttta tctcgcggaa     480
gtttacaaaa atggcaacaa caccaagtat cgcgatgcgg tgcgcagagc cgcaaatttt     540
attgtcagct cgcaatacag cactggtgca ttaccacaat tttatccatt gaaaggcggc     600
tatgcagacc acgccacctt taacgataac ggcatggcat atgcattaac ggtattggat     660
tttgcagtca acaaacgcgc cccatttgat actgatgttt ctccgattc tgatcgcgcg      720
aaattcaaaa ccgctgttgc caaaggtgtg gattacattt tgaaagcgca gtggaaacaa     780
aacgaaaaat taaccgtgtg gtgtgcacaa catggtgcta ccgattatca accgaaaaaa     840
gcgcgcgcct atgaattgga atcactgagt ggcagcgaat ctgttggtgt actcgctttc     900
ttgatgaccc aaccgcaaac cgcacaaatt gaagccgctg taaaagccgg tgtagcctgg     960
ttcaatagcc ccaacacgta tttgaacaat tacacttacg actcttcaaa agcgtcaact    1020
aatccaatag ttgccaagtc tggaagcaaa atgtggtatc gcttttacga tttaaatacc    1080
aatcgtggct tcttcagtga tcgcgatggc agcaaattct atgacatcac ccagatgtca    1140
gaagagcgtc gcactggata tagctggggt ggtgattacg gcacgtcgat tatttccttc    1200
gcgcaaaaag tgggatatct gtaa                                           1224
```

<210> SEQ ID NO 62
<211> LENGTH: 407
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (0)...(407)
<223> OTHER INFORMATION: Catalytic domain

<400> SEQUENCE: 62

```
Met Glu Leu Pro Val Thr Gly Ala Trp Ala Thr Trp Gln Thr Ala Thr
  1               5                  10                  15

Val Glu Ile Asp Leu Val Gln Gly Asn Asn Leu Leu Lys Leu Ser Ala
                 20                  25                  30

Ile Thr Ala Asp Gly Leu Ala Asn Ile Asp Ser Leu Lys Ile Asp Gly
             35                  40                  45

Ala Gln Thr Lys Ala Gly Val Cys Ser Thr Val Ala Ser Ser Ser Ser
         50                  55                  60

Ser Ser Val Ala Ser Ser Ile Lys Ser Ser Ser Ser Ser Ser Ser Ser
 65                  70                  75                  80

Ser Ser Thr Thr Thr Val Lys Thr Leu Thr Leu Asp Gly Asn Pro Ala
                 85                  90                  95

Ala Asn Trp Phe Asn Lys Ser Arg Thr Lys Trp Asn Thr Ser Arg Ala
```

```
              100                 105                 110
Asp Val Val Leu Ser Tyr Gln Gln Ser Asn Gly Gly Trp Pro Lys Asn
            115                 120                 125

Leu Asp Tyr Asn Ser Val Ser Ala Gly Asn Gly Gly Ser Asp Ser Gly
        130                 135                 140

Thr Ile Asp Asn Gly Ala Thr Ile Thr Glu Met Val Tyr Leu Ala Glu
145                 150                 155                 160

Val Tyr Lys Asn Gly Asn Asn Thr Lys Tyr Arg Asp Ala Val Arg Arg
                165                 170                 175

Ala Ala Asn Phe Ile Val Ser Ser Gln Tyr Ser Thr Gly Ala Leu Pro
            180                 185                 190

Gln Phe Tyr Pro Leu Lys Gly Gly Tyr Ala Asp His Ala Thr Phe Asn
        195                 200                 205

Asp Asn Gly Met Ala Tyr Ala Leu Thr Val Leu Asp Phe Ala Val Asn
    210                 215                 220

Lys Arg Ala Pro Phe Asp Thr Asp Val Phe Ser Asp Ser Asp Arg Ala
225                 230                 235                 240

Lys Phe Lys Thr Ala Val Ala Lys Gly Val Asp Tyr Ile Leu Lys Ala
                245                 250                 255

Gln Trp Lys Gln Asn Gly Lys Leu Thr Val Trp Cys Ala Gln His Gly
            260                 265                 270

Ala Thr Asp Tyr Gln Pro Lys Lys Ala Arg Ala Tyr Glu Leu Glu Ser
        275                 280                 285

Leu Ser Gly Ser Glu Ser Val Gly Val Leu Ala Phe Leu Met Thr Gln
    290                 295                 300

Pro Gln Thr Ala Gln Ile Glu Ala Ala Val Lys Ala Gly Val Ala Trp
305                 310                 315                 320

Phe Asn Ser Pro Asn Thr Tyr Leu Asn Asn Tyr Thr Tyr Asp Ser Ser
                325                 330                 335

Lys Ala Ser Thr Asn Pro Ile Val Ala Lys Ser Gly Ser Lys Met Trp
            340                 345                 350

Tyr Arg Phe Tyr Asp Leu Asn Thr Asn Arg Gly Phe Phe Ser Asp Arg
        355                 360                 365

Asp Gly Ser Lys Phe Tyr Asp Ile Thr Gln Met Ser Glu Glu Arg Arg
    370                 375                 380

Thr Gly Tyr Ser Trp Gly Gly Asp Tyr Gly Thr Ser Ile Ile Ser Phe
385                 390                 395                 400

Ala Gln Lys Val Gly Tyr Leu
                405

<210> SEQ ID NO 63
<211> LENGTH: 1023
<212> TYPE: DNA
<213> ORGANISM: Unknown
<220> FEATURE:
<223> OTHER INFORMATION: Obtained from an environmental sample

<400> SEQUENCE: 63
atgttaagtt tcatcgcggt atcagtgttt cataattact gtacagggca gactgcgtcc        60
accaaaaatt cagtggccga aaagatgctt cagtaccagt tgtcaaatgg cgcctggccc       120
aaacagttgg tagacaaaag tgtcgttgat tacagtcttc cattaacgaa agagctccta       180
cagcagatca agaaaacaga tattgatcat gctacgctcg acaacagtgc gacaaccccgg      240 gaaataactg aattgatcaa ggcttttaag gacactaaaa ataaggcata tttgactgct       300
```

-continued

```
gcagaaaagg ggattgcata tattttatcg gctcaatatg agaatggcgg atttccacaa    360
tactacccaa ataaattata ctatagagct gagataacat acaacgatga tgcgatgatc    420
aatgcattac tagtgcttta caaagtagcc aataagcgag aggggtttga ggctatcaat    480
cccatatttg tgtcaaaagc gcaaaaagca gttgaaaagg gtataacctg tatcctaaaa    540
acacaggtca tacaagacgg aaaaaggagt atttgggctg cgcaatacga tcagaacact    600
ttacaacctg ctcaggcaag aaagtttgaa ccagcttcat tgagcacaag tgaatctgtt    660
tccatcgttc gctttctcat gctacagcct gcaaccactg aaattaagca agcgatcgaa    720
catgcaatac aatggttcga acagcatgat attgaaggtt accgtttcga ccgcatacaa    780 gataggtga ctggaaaata tcaacggcag cttgtcgctg atcggacttc cacgatttgg    840
gcgcgatttt ataatctcga agacaaccgt ccattgtttg gagatcggga caatacaatc    900
aaatacaact tgaggaggt ttcagaggag cgtagaaatg gctatgcttg gttcggcaac    960
tggccggaaa agctgatcca aaaggactat ccaaaatgga aaaacaata caaaattcaa   1020 taa                                                                 1023
```

<210> SEQ ID NO 64
<211> LENGTH: 340
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(16)
<220> FEATURE:
<221> NAME/KEY: DOMAIN
<222> LOCATION: (17)...(340)
<223> OTHER INFORMATION: Catalytic domain

<400> SEQUENCE: 64

```
Met Leu Ser Phe Ile Ala Val Ser Val Phe His Asn Tyr Cys Thr Gly
  1               5                  10                  15

Gln Thr Ala Ser Thr Lys Asn Ser Val Ala Glu Lys Met Leu Gln Tyr
             20                  25                  30

Gln Leu Ser Asn Gly Ala Trp Pro Lys Gln Leu Val Asp Lys Ser Val
         35                  40                  45

Val Asp Tyr Ser Leu Pro Leu Thr Lys Glu Leu Gln Gln Ile Lys
     50                  55                  60

Lys Thr Asp Ile Asp His Ala Thr Leu Asp Asn Ser Ala Thr Arg
 65                  70                  75                  80

Glu Ile Thr Glu Leu Ile Lys Ala Phe Lys Asp Thr Lys Asn Lys Ala
                 85                  90                  95

Tyr Leu Thr Ala Ala Glu Lys Gly Ile Ala Tyr Ile Leu Ser Ala Gln
            100                 105                 110

Tyr Glu Asn Gly Gly Phe Pro Gln Tyr Pro Asn Lys Leu Tyr Tyr
        115                 120                 125

Arg Ala Glu Ile Thr Tyr Asn Asp Asp Ala Met Ile Asn Ala Leu Leu
    130                 135                 140

Val Leu Tyr Lys Val Ala Asn Lys Arg Glu Gly Phe Glu Ala Ile Asn
145                 150                 155                 160

Pro Ile Phe Val Ser Lys Ala Gln Lys Ala Val Glu Lys Gly Ile Thr
                165                 170                 175

Cys Ile Leu Lys Thr Gln Val Ile Gln Asp Gly Lys Arg Ser Ile Trp
            180                 185                 190
```

```
Ala Ala Gln Tyr Asp Gln Asn Thr Leu Gln Pro Ala Gln Ala Arg Lys
        195                 200                 205

Phe Glu Pro Ala Ser Leu Ser Thr Ser Glu Ser Val Ser Ile Val Arg
210                 215                 220

Phe Leu Met Leu Gln Pro Ala Thr Thr Glu Ile Lys Gln Ala Ile Glu
225                 230                 235                 240

His Ala Ile Gln Trp Phe Glu Gln His Asp Ile Glu Gly Tyr Arg Phe
                245                 250                 255

Asp Arg Ile Gln Asp Arg Val Thr Gly Lys Tyr Gln Arg Gln Leu Val
            260                 265                 270

Ala Asp Arg Thr Ser Thr Ile Trp Ala Arg Phe Tyr Asn Leu Glu Asp
        275                 280                 285

Asn Arg Pro Leu Phe Gly Asp Arg Asp Asn Thr Ile Lys Tyr Asn Phe
    290                 295                 300

Glu Glu Val Ser Glu Gly Arg Arg Asn Gly Tyr Ala Trp Phe Gly Asn
305                 310                 315                 320

Trp Pro Glu Lys Leu Ile Gln Lys Asp Tyr Pro Lys Trp Lys Gln
                325                 330                 335

Tyr Lys Ile Gln
        340

<210> SEQ ID NO 65
<211> LENGTH: 1311
<212> TYPE: DNA
<213> ORGANISM: Bacteria

<400> SEQUENCE: 65
gtgaaccgac gtacccgcct gggagcggtc gccgcgaccg ccctcgccct gacggtcacc      60
gcccccgccg ccggtgccca cgccgccgct ccccacgccg cgccacgccc ggtcgccgat     120
ccggctcgcg ccacgctgcc cgccggcgac ggctgggcgt ccgagggac cggcacgacc      180 ggtgggcgcg ccgccgaggc ctcccgggtc ttcaccgtcg ccacctggga ggagttccgg     240
gccgcgctcg cggtgcccgg ctccgagccc aggatcgtca aggtggtggg cacgctgaac     300
gccaccgccg ccggctgcgg cgccttcgag gcgccgggct acgacttcgc cgctacctc     360 gccgactacg acccgccgt gtggggtac gagaaggagg tcagcggccc gcaggaggag      420
ctgcgggcgg cgtccgcgac cgcgcagggc caggccatca aggtcaaggt gccggcgaac     480
accacgatcg tcggggtcgg caggcacgcg gggatcacgg gcggcagcct ccaggtgcag     540
ggcgtcgaca acgtcgtggt ccgcaacctg acgctggaga gcccgctcga ctgcttcccg     600
cagtgggacc cgaccgacgg cgcgaccggg cgtggaact ccgagtacga cagcctcgtc      660
gtgtacggct ccacccatgt ctggatcgac cacaacacct tcaccgacgg cgcccacccg     720
gacagttcgc tgccctcgta ctacggcgag gtctaccagc agcacgacgg cgaactggac     780
gtcgtgcggg gcgcggacct cgtcacggtc tcgtggaacg ccttcaccga ccacgacaag     840
accctgatga tcggcaacag cgacagcgcg ggcgccaccg accggggcaa gctgcgggtc     900
accctgcacc acaacctgtt cgagaacgtc gtcgagcggg cgccccgggt caggttcggg     960
caggtcgacg cgtacaacaa ccacttcgtc gtgccgagtt cggcctacgc gtacagcctg    1020
ggcgtcgggc aggagtccca gctcttcgcg gagaagaacg cgttcaccct cgccgggggc    1080
gtgccggccg ggaagatcct caagaagtgg aaggacgcgc ccgtcaccac cgtcggcaac    1140
tacgtgaacg gcaggccggt cgacctgctc gccgtccaca acacccagtt cccggaggag    1200
cagttgcggg ccgacgcggg ctggaccccc gtcctgcgca ccagggtcga ccacccgagg    1260
```

-continued gccgtccccg cgctcgtcga ccaccgcgcg ggcgccggcc gctcctgctg a    1311

<210> SEQ ID NO 66
<211> LENGTH: 436
<212> TYPE: PRT
<213> ORGANISM: Bacteria
<220> FEATURE:
<221> NAME/KEY: SIGNAL
<222> LOCATION: (1)...(28)
<220> FEATURE:
<221> NAME/KEY: DOMAIN
<222> LOCATION: (29)...(436)
<223> OTHER INFORMATION: Catalytic domain

<400> SEQUENCE: 66

```
Met Asn Arg Arg Thr Arg Leu Gly Ala Val Ala Ala Thr Ala Leu Ala
 1               5                  10                  15

Leu Thr Val Thr Ala Pro Ala Ala Gly Ala His Ala Ala Ala Pro His
             20                  25                  30

Ala Ala Pro Arg Pro Val Ala Asp Pro Ala Arg Ala Thr Leu Pro Ala
         35                  40                  45

Gly Asp Gly Trp Ala Ser Glu Gly Thr Gly Thr Thr Gly Gly Ala Ala
     50                  55                  60

Ala Glu Ala Ser Arg Val Phe Thr Val Ala Thr Trp Glu Glu Phe Arg
 65                  70                  75                  80

Ala Ala Leu Ala Val Pro Gly Ser Glu Pro Arg Ile Val Lys Val Val
                 85                  90                  95

Gly Thr Leu Asn Ala Thr Ala Ala Gly Cys Gly Ala Phe Glu Ala Pro
            100                 105                 110

Gly Tyr Asp Phe Ala Arg Tyr Leu Ala Asp Tyr Asp Pro Ala Val Trp
        115                 120                 125

Gly Tyr Glu Lys Glu Val Ser Gly Pro Gln Glu Glu Leu Arg Ala Ala
    130                 135                 140

Ser Ala Thr Ala Gln Gly Gln Ala Ile Lys Val Lys Val Pro Ala Asn
145                 150                 155                 160

Thr Thr Ile Val Gly Val Gly Arg His Ala Gly Ile Thr Gly Gly Ser
                165                 170                 175

Leu Gln Val Gln Gly Val Asp Asn Val Val Arg Asn Leu Thr Leu
            180                 185                 190

Glu Ser Pro Leu Asp Cys Phe Pro Gln Trp Asp Pro Thr Asp Gly Ala
        195                 200                 205

Thr Gly Ala Trp Asn Ser Glu Tyr Asp Ser Leu Val Val Tyr Gly Ser
    210                 215                 220

Thr His Val Trp Ile Asp His Asn Thr Phe Thr Asp Gly Ala His Pro
225                 230                 235                 240

Asp Ser Ser Leu Pro Ser Tyr Tyr Gly Glu Val Tyr Gln Gln His Asp
                245                 250                 255

Gly Glu Leu Asp Val Val Arg Gly Ala Asp Leu Val Thr Val Ser Trp
            260                 265                 270

Asn Ala Phe Thr Asp His Asp Lys Thr Leu Met Ile Gly Asn Ser Asp
        275                 280                 285

Ser Ala Gly Ala Thr Asp Arg Gly Lys Leu Arg Val Thr Leu His His
    290                 295                 300

Asn Leu Phe Glu Asn Val Val Glu Arg Ala Pro Arg Val Arg Phe Gly
305                 310                 315                 320

Gln Val Asp Ala Tyr Asn Asn His Phe Val Val Pro Ser Ser Ala Tyr
```

|  |  |  | 325 |  |  |  | 330 |  |  |  | 335 |
|---|---|---|---|---|---|---|---|---|---|---|---|

Ala Tyr Ser Leu Gly Val Gly Gln Glu Ser Gln Leu Phe Ala Glu Lys
        340                345                350

Asn Ala Phe Thr Leu Ala Gly Gly Val Pro Ala Gly Lys Ile Leu Lys
        355                360              365

Lys Trp Lys Asp Ala Pro Val Thr Thr Val Gly Asn Tyr Val Asn Gly
    370                  375              380

Arg Pro Val Asp Leu Leu Ala Val His Asn Thr Gln Phe Pro Glu Glu
385                390              395            400

Gln Leu Arg Ala Asp Ala Gly Trp Thr Pro Val Leu Arg Thr Arg Val
        405                410              415

Asp His Pro Arg Ala Val Pro Ala Leu Val Asp His Arg Ala Gly Ala
        420                425              430

Gly Arg Ser Cys
        435

<210> SEQ ID NO 67
<211> LENGTH: 1995
<212> TYPE: DNA
<213> ORGANISM: Unknown
<220> FEATURE:
<223> OTHER INFORMATION: Obtained from an environmental sample

<400> SEQUENCE: 67

```
atgaaaaatt caaaaactgt ttttactgca caaaaaaaac tcatgcactc ttgcattgcc      60
gccgctatcg gcttggcgat aagttcaggt gcttggtcag cttgtactta cactgtcacc     120
aataattggg gttctggctt caccggtgaa atcaaagtta ccaacaacac atcatcggct     180
gtaaatggtt ggtctgtgtc ttggcaggaa tcaggcgcat cagtcaccaa ctcatggaac     240
gcaactctga gcggatcaaa tccttatacg gcagccgcct taggttggaa tgcaactctc     300
gcacccggtg cttctgccag ttttggcttt caagcaaatg gcactgctag cgcacctaaa     360
gtgaatggca ctttatgtgg aacagctact tcatcaacac ctgcgtcatc cagcagtgtt     420
gcgagttcgg ttaaatcaag cgcacccgtt tcgtccagca gtaaatcatc cagctcaatc     480
actgtgagta gtagttctat cgccagcagc agcgcaccaa gtgtttcttc attaacaatt     540
caggaagagc aagctggctt ctgtcgtgtt gatggcattg caacagaaag caccaacacc     600
ggctttaccg gcaacggcta ccaatgca acaacgcac aaggtgcagc gattgaatgg        660
gcggtaaatg caccgagcag tggccgctac acactcacat ccgtttttgc aaatggcggc     720
actgcagcac gcaatggttc actgttaatt aacggcggta gcaatggtaa ctacaccgtg     780
gatttaccac taaccggcgc atgggcgact tggcaaacag cgactgtaga atcgatttg     840
gtacaaggca ccaacacgct gaaactttct gcattaaccg cagatggctt agctaatatc     900
gattcattaa aaattgatgg caaccaaccg aaagcaggca cttgcagcaa tacatcaagc     960
agtgttgcca gcagttcttc atccgttaaa tccagttcaa gttcttcatc aagctcatcc    1020
accactgcaa aaatgctgac tcttgatggc aaccccgccg caagttggtt caacaaatcc    1080
agaaccaaat ggaatagcag tcgtgcggac attgtgttgt cttaccagca agctaacggc    1140
ggctggccaa aaaatctgga ttacaactca gtaagcgcag gtaatggtgg tagcgacagc    1200
ggcactatcg acaacggcgc aaccatcacg gaaatggttt atctcgcaga agtttataaa    1260
aacgggggca atacaaaata tcgcgatgca gtacgtaaag cggcaaactt tattgtgagt    1320
tcgcaataca gcactggtgc gttaccacaa tttacccat tgaaaggtgg ttatgcagat    1380
```

-continued

```
cacgccacct ttaacgataa cggcatggct tacgcattaa cggtattgga ttttgcggtg   1440
aacaaacgtg cgccgtttga taacgatgta ttttctgatg cagaccgcgc aaaattcaaa   1500
actgccgtga ccaaaggtat tgattacatt ttgaaagccc aatggaaaca aaatggaaaa   1560
ctcaccgcat ggtgtgcgca acacggagca aacgactatc aaccaaaagc ggcgcgtgct   1620
tatgagttag tatctttaag cggcagcgaa tccgttggca tcatcgcttt cctgatgacc   1680
caaccacaaa ctgcgcaaat cgaagcagcg gttaaagccg gtgtaaactg gttcgctagc   1740
ccgaatacat acttggctaa ttacacctac gactcgtcaa agcctctac caatccgatt    1800 gtgtacaaat ccggcagcag aatgtggtat cgcttctacg atctgaacac caatcgcgga   1860
ttctttagtg atcgcgatgg cagcaaattc tatgacatca ctcaaatgtc tgaagaacgt   1920
cgcaccggct acagctgggg cggttcttac ggtgaatcga ttatcagctt cgcgcaaaaa   1980
gtgggttatc tctaa                                                     1995
```

<210> SEQ ID NO 68
<211> LENGTH: 664
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(32)
<220> FEATURE:
<221> NAME/KEY: BINDING
<222> LOCATION: (33)...(126)
<223> OTHER INFORMATION: Carbohydrate binding module
<220> FEATURE:
<221> NAME/KEY: BINDING
<222> LOCATION: (184)...(307)
<223> OTHER INFORMATION: Carbohydrate binding module
<220> FEATURE:
<221> NAME/KEY: DOMAIN
<222> LOCATION: (308)...(664)
<223> OTHER INFORMATION: Catalytic domain

<400> SEQUENCE: 68

```
Met Lys Asn Ser Lys Thr Val Phe Thr Ala Gln Lys Lys Leu Met His
 1               5                  10                  15

Ser Cys Ile Ala Ala Ala Ile Gly Leu Ala Ile Ser Ser Gly Ala Trp
                20                  25                  30

Ser Ala Cys Thr Tyr Thr Val Thr Asn Asn Trp Gly Ser Gly Phe Thr
            35                  40                  45

Gly Glu Ile Lys Val Thr Asn Asn Thr Ser Ala Val Asn Gly Trp
        50                  55                  60

Ser Val Ser Trp Gln Glu Ser Gly Ala Ser Val Thr Asn Ser Trp Asn
65                  70                  75                  80

Ala Thr Leu Ser Gly Ser Asn Pro Tyr Thr Ala Ala Leu Gly Trp
                85                  90                  95

Asn Ala Thr Leu Ala Pro Gly Ala Ser Ala Ser Phe Gly Phe Gln Ala
            100                 105                 110

Asn Gly Thr Ala Ser Ala Pro Lys Val Asn Gly Thr Leu Cys Gly Thr
        115                 120                 125

Ala Thr Ser Ser Thr Pro Ala Ser Ser Ser Val Ala Ser Ser Val
    130                 135                 140

Lys Ser Ser Ala Pro Val Ser Ser Ser Ser Lys Ser Ser Ser Ile
145                 150                 155                 160

Thr Val Ser Ser Ser Ile Ala Ser Ser Ser Ala Pro Ser Val Ser
                165                 170                 175
```

-continued

```
Ser Leu Thr Ile Gln Glu Glu Gln Ala Gly Phe Cys Arg Val Asp Gly
            180                 185                 190

Ile Ala Thr Glu Ser Thr Asn Thr Gly Phe Thr Gly Asn Gly Tyr Thr
        195                 200                 205

Asn Ala Asn Asn Ala Gln Gly Ala Ala Ile Glu Trp Ala Val Asn Ala
    210                 215                 220

Pro Ser Ser Gly Arg Tyr Thr Leu Thr Phe Arg Phe Ala Asn Gly Gly
225                 230                 235                 240

Thr Ala Ala Arg Asn Gly Ser Leu Leu Ile Asn Gly Gly Ser Asn Gly
                245                 250                 255

Asn Tyr Thr Val Asp Leu Pro Leu Thr Gly Ala Trp Ala Thr Trp Gln
            260                 265                 270

Thr Ala Thr Val Glu Ile Asp Leu Val Gln Gly Thr Asn Thr Leu Lys
        275                 280                 285

Leu Ser Ala Leu Thr Ala Asp Gly Leu Ala Asn Ile Asp Ser Leu Lys
    290                 295                 300

Ile Asp Gly Asn Gln Pro Lys Ala Gly Thr Cys Ser Asn Thr Ser Ser
305                 310                 315                 320

Ser Val Ala Ser Ser Ser Ser Val Lys Ser Ser Ser Ser Ser
                325                 330                 335

Ser Ser Ser Ser Thr Thr Ala Lys Met Leu Thr Leu Asp Gly Asn Pro
            340                 345                 350

Ala Ala Ser Trp Phe Asn Lys Ser Arg Thr Lys Trp Asn Ser Ser Arg
        355                 360                 365

Ala Asp Ile Val Leu Ser Tyr Gln Gln Ala Asn Gly Gly Trp Pro Lys
    370                 375                 380

Asn Leu Asp Tyr Asn Ser Val Ser Ala Gly Asn Gly Ser Asp Ser
385                 390                 395                 400

Gly Thr Ile Asp Asn Gly Ala Thr Ile Thr Glu Met Val Tyr Leu Ala
                405                 410                 415

Glu Val Tyr Lys Asn Gly Gly Asn Thr Lys Tyr Arg Asp Ala Val Arg
            420                 425                 430

Lys Ala Ala Asn Phe Ile Val Ser Ser Gln Tyr Ser Thr Gly Ala Leu
        435                 440                 445

Pro Gln Phe Tyr Pro Leu Lys Gly Gly Tyr Ala Asp His Ala Thr Phe
    450                 455                 460

Asn Asp Asn Gly Met Ala Tyr Ala Leu Thr Val Leu Asp Phe Ala Val
465                 470                 475                 480

Asn Lys Arg Ala Pro Phe Asp Asn Asp Val Phe Ser Asp Ala Asp Arg
                485                 490                 495

Ala Lys Phe Lys Thr Ala Val Thr Lys Gly Ile Asp Tyr Ile Leu Lys
            500                 505                 510

Ala Gln Trp Lys Gln Asn Gly Lys Leu Thr Ala Trp Cys Ala Gln His
        515                 520                 525

Gly Ala Asn Asp Tyr Gln Pro Lys Ala Ala Arg Ala Tyr Glu Leu Val
    530                 535                 540

Ser Leu Ser Gly Ser Glu Ser Val Gly Ile Ile Ala Phe Leu Met Thr
545                 550                 555                 560

Gln Pro Gln Thr Ala Gln Ile Glu Ala Val Lys Ala Gly Val Asn
                565                 570                 575

Trp Phe Ala Ser Pro Asn Thr Tyr Leu Ala Asn Tyr Thr Tyr Asp Ser
            580                 585                 590
```

```
Ser Lys Ala Ser Thr Asn Pro Ile Val Tyr Lys Ser Gly Ser Arg Met
        595                 600                 605

Trp Tyr Arg Phe Tyr Asp Leu Asn Thr Asn Arg Gly Phe Phe Ser Asp
610                 615                 620

Arg Asp Gly Ser Lys Phe Tyr Asp Ile Thr Gln Met Ser Glu Glu Arg
625                 630                 635                 640

Arg Thr Gly Tyr Ser Trp Gly Gly Ser Tyr Gly Glu Ser Ile Ile Ser
                645                 650                 655

Phe Ala Gln Lys Val Gly Tyr Leu
            660
```

<210> SEQ ID NO 69
<211> LENGTH: 1035
<212> TYPE: DNA
<213> ORGANISM: Unknown
<220> FEATURE:
<223> OTHER INFORMATION: Obtained from an environmental sample

<400> SEQUENCE: 69

```
atggcgcgtt tgttccggtg cgtgtgtgcc agcctgggag gatgggccgc ggttctggcc      60
gccgcggcgg gcccggattg gtcccgcctg ctcgcgcaac cggacccttg gtttcgcagt     120
ccggcgggc aacaggcggt gacgaacgtt ttgtcctggc agagcgcgac aggcgcctgg     180
ccgaaaaacc tggacaccac ccgcgagccg cgtcggcagg attccgcccc gcccgagggc     240
actttcgaca cggcgccac caccggcgag ttgcggtttc tggcgcgggc gtttgcggcc     300
accggcgatc cgcgctgcga agccgcgtg ctccgggggc tggacggcat cctcgcggcc     360
cagcttccca gcggcggctg gccgcagtgt catcctccgc gcgcgcctta tcagcgccac     420
atcaccttca cgacggtgt catggtgcgc atcctggagc tgctgcgcga gatagaccgc     480
gcgccggagt ttcgctgggt ggacgaggcg cggcgcgcgc gggtgcgcgc ggccttcact     540
cgcgggctgg agtgcctcct cgctgccag gtggtcgtcg agggcagact caccgtgtgg     600
tgtgcccagc atgacgcgga gaactttcaa ccgcgaccgg cacgcgccta cgaactggaa     660
tcgctcagcg cgcgcgaaag cgccggcatc ctggtgttcc tcatgagcct ggagccgcca     720
accccggaga tcgcgcgcgc ggtcgaggcc ggggcggcct ggttttcggc ggtaaagctt     780
gaagggttcc gtctcgaacg aacgccgac gacgcgcggg tggtggaaga gccgggcgcg     840
ccgccgctct gggcgcggtt ctacgagatc gggaccaatc gccccatctt tgccggtcgc     900
gacggtgtca agaagtacgc cctgagcgag atcgagcggg aacgccgggt cggctatgcg     960
tggtacggcg cctggggtga accggtcgcc cgccattatg cccagtggcg ggagcgttac    1020
gggacgcaga aatga                                                    1035
```

<210> SEQ ID NO 70
<211> LENGTH: 344
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(22)
<220> FEATURE:
<221> NAME/KEY: DOMAIN
<222> LOCATION: (23)...(344)
<223> OTHER INFORMATION: Catalytic domain

<400> SEQUENCE: 70

Met Ala Arg Leu Phe Arg Cys Val Cys Ala Ser Leu Gly Gly Trp Ala

```
                1               5                  10                 15
            Ala Val Leu Ala Ala Ala Gly Pro Asp Trp Ser Arg Leu Leu Ala
                            20                 25                 30

Gln Pro Asp Pro Trp Phe Arg Ser Pro Ala Gly Gln Gln Ala Val Thr
                            35                 40                 45

Asn Val Leu Ser Trp Gln Ser Ala Thr Gly Ala Trp Pro Lys Asn Leu
                50                 55                 60

Asp Thr Thr Arg Glu Pro Arg Arg Gln Asp Ser Ala Pro Pro Glu Gly
            65                 70                 75                 80

Thr Phe Asp Asn Gly Ala Thr Thr Gly Glu Leu Arg Phe Leu Ala Arg
                            85                 90                 95

Ala Phe Ala Ala Thr Gly Asp Pro Arg Cys Glu Ala Ala Val Leu Arg
                            100                105                110

Gly Leu Asp Gly Ile Leu Ala Ala Gln Leu Pro Ser Gly Gly Trp Pro
                            115                120                125

Gln Cys His Pro Pro Arg Ala Pro Tyr Gln Arg His Ile Thr Phe Asn
                            130                135                140

Asp Gly Val Met Val Arg Ile Leu Glu Leu Leu Arg Glu Ile Asp Arg
            145                150                155                160

Ala Pro Glu Phe Arg Trp Val Asp Glu Ala Arg Ala Arg Val Arg
                            165                170                175

Ala Ala Phe Thr Arg Gly Leu Glu Cys Leu Leu Arg Cys Gln Val Val
                            180                185                190

Val Glu Gly Arg Leu Thr Val Trp Cys Ala Gln His Asp Ala Glu Asn
                            195                200                205

Phe Gln Pro Arg Pro Ala Arg Ala Tyr Glu Leu Glu Ser Leu Ser Gly
                            210                215                220

Ala Glu Ser Ala Gly Ile Leu Val Phe Leu Met Ser Leu Glu Pro Pro
            225                230                235                240

Thr Pro Glu Ile Ala Arg Ala Val Glu Ala Gly Ala Ala Trp Phe Ser
                            245                250                255

Ala Val Lys Leu Glu Gly Phe Arg Leu Glu Arg Thr Ala Asp Asp Ala
                            260                265                270

Arg Val Val Glu Glu Pro Gly Ala Pro Pro Leu Trp Ala Arg Phe Tyr
                            275                280                285

Glu Ile Gly Thr Asn Arg Pro Ile Phe Ala Gly Arg Asp Gly Val Lys
                            290                295                300

Lys Tyr Ala Leu Ser Glu Ile Glu Arg Glu Arg Val Gly Tyr Ala
            305                310                315                320

Trp Tyr Gly Ala Trp Gly Glu Pro Val Ala Arg His Tyr Ala Gln Trp
                            325                330                335

Arg Glu Arg Tyr Gly Thr Gln Lys
                            340

<210> SEQ ID NO 71
<211> LENGTH: 1038
<212> TYPE: DNA
<213> ORGANISM: Unknown
<220> FEATURE:
<223> OTHER INFORMATION: Obtained from an environmental sample

<400> SEQUENCE: 71
gtgactcgtg tcgcccttgc gatggggctt gttgcatggg ttccggcgct cgcttcagct      60
gggcccgctg catatttgca gaagccggac gactggttcg ccagtcccga ggccagggca     120
```

-continued

```
atcgccgcga acgtactcgc gcatcaggcc gatctcggcg ggtggccgaa gaacatcgac    180
acaacgaagc cgttcaccgg cgaccggacg caaatcaaac cgaccttcga taacagcgcg    240
acaaccgacg agctccggtt tctggcgcgc atccacaacg cgactcgcga cgagaagtac    300
cgcaccgcgt tcgagaaggg gctcgattac atcttgaaag cacaatacgc aaacggcggt    360
tggccgcagt cgcaccccgcc cggcaccggc taccaccggc acatcacctt caacgacaat    420
gccatggtcc gtttgatgga gctcgtgcgc gaagtcgcga cctcgaatcg gtacgacttc    480
ctggacgccg accgccgcaa ggcctgccgc gccgctttcg atcgcggcat cgaatgcatc    540
ctgaagtgcc agatcaaggt cgacagtaag ctgacggcat ggtgcgccca gcacgacgag    600
aaggacctcg ctccccggcc ggcgcggacc tacgagctcg tctcactcag cggctcggag    660
tcggtcggga tcgtccgcct actcatgagc ctcgatcgac caagcccgga ggtcgctcgg    720
gccatcgacg gcgcggtcgc gtggttccag tcggcgaagc tcgaaggcac caaggtcgtt    780
gtcgagcgcg acccgaagta tccgggcggc cgggaacgcg tggtggtgaa ggatccaaag    840
gcaccgccac tctgggcgcg cttctacgaa atcggcacga atcgcccat cttctccgac    900 cgcgacggca tcaagaagta cgcgctcgcc gagatcggcc ccgaacggcg gaatggctat    960
gcctggtatg gcacctggcc gcgcgacctg ctggagaagg aatacccagg gtggaaaaag    1020
aagctggccc ggccgtga                                                 1038
```

<210> SEQ ID NO 72
<211> LENGTH: 345
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(20)
<220> FEATURE:
<221> NAME/KEY: DOMAIN
<222> LOCATION: (21)...(345)
<223> OTHER INFORMATION: Catalytic domain

<400> SEQUENCE: 72

```
Met Thr Arg Val Ala Leu Ala Met Gly Leu Val Ala Trp Val Pro Ala
  1               5                  10                  15

Leu Ala Ser Ala Gly Pro Ala Ala Tyr Leu Gln Lys Pro Asp Asp Trp
             20                  25                  30

Phe Ala Ser Pro Glu Ala Arg Ala Ile Ala Ala Asn Val Leu Ala His
         35                  40                  45

Gln Ala Asp Leu Gly Gly Trp Pro Lys Asn Ile Asp Thr Thr Lys Pro
     50                  55                  60

Phe Thr Gly Asp Arg Thr Gln Ile Lys Pro Thr Phe Asp Asn Ser Ala
 65                  70                  75                  80

Thr Thr Asp Glu Leu Arg Phe Leu Ala Arg Ile His Asn Ala Thr Arg
                 85                  90                  95

Asp Glu Lys Tyr Arg Thr Ala Phe Glu Lys Gly Leu Asp Tyr Ile Leu
            100                 105                 110

Lys Ala Gln Tyr Ala Asn Gly Gly Trp Pro Gln Ser His Pro Pro Gly
        115                 120                 125

Thr Gly Tyr His Arg His Ile Thr Phe Asn Asp Asn Ala Met Val Arg
    130                 135                 140

Leu Met Glu Leu Val Arg Glu Val Ala Thr Ser Asn Arg Tyr Asp Phe
145                 150                 155                 160

Leu Asp Ala Asp Arg Arg Lys Ala Cys Arg Ala Ala Phe Asp Arg Gly
```

```
                     165                 170                 175
Ile Glu Cys Ile Leu Lys Cys Gln Ile Lys Val Asp Ser Lys Leu Thr
            180                 185                 190
Ala Trp Cys Ala Gln His Asp Glu Lys Asp Leu Ala Pro Arg Pro Ala
        195                 200                 205
Arg Thr Tyr Glu Leu Val Ser Leu Ser Gly Ser Glu Ser Val Gly Ile
    210                 215                 220
Val Arg Leu Leu Met Ser Leu Asp Arg Pro Ser Pro Glu Val Ala Arg
225                 230                 235                 240
Ala Ile Asp Gly Ala Val Ala Trp Phe Gln Ser Ala Lys Leu Glu Gly
                245                 250                 255
Thr Lys Val Val Val Glu Arg Asp Pro Lys Tyr Pro Gly Gly Arg Glu
            260                 265                 270
Arg Val Val Val Lys Asp Pro Lys Ala Pro Pro Leu Trp Ala Arg Phe
        275                 280                 285
Tyr Glu Ile Gly Thr Asn Arg Pro Ile Phe Ser Asp Arg Asp Gly Ile
    290                 295                 300
Lys Lys Tyr Ala Leu Ala Glu Ile Gly Pro Glu Arg Arg Asn Gly Tyr
305                 310                 315                 320
Ala Trp Tyr Gly Thr Trp Pro Arg Asp Leu Leu Glu Lys Glu Tyr Pro
                325                 330                 335
Gly Trp Lys Lys Lys Leu Ala Arg Pro
            340                 345

<210> SEQ ID NO 73
<211> LENGTH: 1221
<212> TYPE: DNA
<213> ORGANISM: Unknown
<220> FEATURE:
<223> OTHER INFORMATION: Obtained from an environmental sample

<400> SEQUENCE: 73
atgctcacca aaacatcact acttattgca ttgctaggca gttgttgtat cgcaccatta      60
catgcggaca caccagcaag caatgcaccg acaaccaatg catcaattcc gctacagcaa     120
actgcgagcg atgctgccgc ctggaaaaat tatctcgcca atccaacga gttgcgcaaa      180
gcagaccagg cgcagctcaa agccgagctg aaaaaactcg gcaaaaaac cgcgagtttg     240
cctgagtaca ccaaagaatt tggttttgaa gtgaagcagt catctgagtg gtttaaaagc     300
actgaaggta acgagtgat ggatattatc ctatcgtttc aaactccttc tggcggctgg      360
tcaaaacgca ctgacatgag caaagcgccg cgcaaacccg gccaggcatt tggtgttgaa     420
aaaaattaca tccccacctt tgataatggc gcgaccagca cacaattaat gctactggca     480
caggcgcatc aagccactgg cgataaacgc tacagcgatg catttgcgcg cgggcttgaa     540
tttatcatca ccgctcaata tcccaatggc ggctggccac aaaattttcc attggttggc     600
aagtatcacg atcacatcac ttacaacgat gccctgatgc gcgatttaat ggtagtgcta     660
cacaaggttg ccatggccaa ggatgaattt gcctttgtat ccaaggcgca gcaacaggcc     720
gcacaagcga gcctcgaacg cgcgctggac tgcgtttga aaacccaggt gatggccaat     780
ggccaattaa ctatatgggg tgcgcagcac gatgccaaaa ccttaaaacc cgccaaagcg     840
cgcgcctatg aaatgatttc actcaccagt tctgaaagcg tgtggatgct cgattttta      900
atggatttgc aacagcccag cgctgacatt attaaatccg tgcacgcggc tgccgcttgg     960
tatgagcaaa ataaaattat cggaaaaacc tggacccggg cgacacagt tctgaaagac   1020
```

-continued

```
gataaggatg caccgccaat ctgggcgcgt ttttatgaga taggtacgaa caaaccctg      1080 tttggcgacc gcgatgactc tgtccattac gatctgcaa aggtatcgga agagcgccgc      1140
acgggttatg cctggtacac aacctcaccc aatcaggtat taaaaaagta cgcgcgctgg    1200
gctaaacaat atccgcaata a                                                1221
```

```
<210> SEQ ID NO 74
<211> LENGTH: 406
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(22)
<220> FEATURE:
<221> NAME/KEY: DOMAIN
<222> LOCATION: (23)...(406)
<223> OTHER INFORMATION: Catalytic domain
```

<400> SEQUENCE: 74

| | | | | | | | | | | | | | | | |
|---|---|---|---|---|---|---|---|---|---|---|---|---|---|---|---|
| Met | Leu | Thr | Lys | Thr | Ser | Leu | Leu | Ile | Ala | Leu | Leu | Gly | Ser | Cys | Cys |
| 1 | | | | 5 | | | | | 10 | | | | | 15 | |

| Ile | Ala | Pro | Leu | His | Ala | Asp | Thr | Pro | Ala | Ser | Asn | Ala | Pro | Thr | Thr |
|---|---|---|---|---|---|---|---|---|---|---|---|---|---|---|---|
| | | | 20 | | | | | 25 | | | | | 30 | | |

| Asn | Ala | Ser | Ile | Pro | Leu | Gln | Gln | Thr | Ala | Ser | Asp | Ala | Ala | Ala | Trp |
|---|---|---|---|---|---|---|---|---|---|---|---|---|---|---|---|
| | | 35 | | | | | 40 | | | | | 45 | | | |

| Lys | Asn | Tyr | Leu | Ala | Lys | Ser | Asn | Glu | Leu | Arg | Lys | Ala | Asp | Gln | Ala |
|---|---|---|---|---|---|---|---|---|---|---|---|---|---|---|---|
| | 50 | | | | | 55 | | | | | 60 | | | | |

| Gln | Leu | Lys | Ala | Glu | Leu | Lys | Lys | Leu | Gly | Gln | Lys | Thr | Ala | Ser | Leu |
|---|---|---|---|---|---|---|---|---|---|---|---|---|---|---|---|
| 65 | | | | | 70 | | | | | 75 | | | | | 80 |

| Pro | Glu | Tyr | Thr | Lys | Glu | Phe | Gly | Phe | Glu | Val | Lys | Gln | Ser | Ser | Glu |
|---|---|---|---|---|---|---|---|---|---|---|---|---|---|---|---|
| | | | | 85 | | | | | 90 | | | | | 95 | |

| Trp | Phe | Lys | Ser | Thr | Glu | Gly | Lys | Arg | Val | Met | Asp | Ile | Ile | Leu | Ser |
|---|---|---|---|---|---|---|---|---|---|---|---|---|---|---|---|
| | | | 100 | | | | | 105 | | | | | 110 | | |

| Phe | Gln | Thr | Pro | Ser | Gly | Gly | Trp | Ser | Lys | Arg | Thr | Asp | Met | Ser | Lys |
|---|---|---|---|---|---|---|---|---|---|---|---|---|---|---|---|
| | | 115 | | | | | 120 | | | | | 125 | | | |

| Ala | Pro | Arg | Lys | Pro | Gly | Gln | Ala | Phe | Gly | Val | Glu | Lys | Asn | Tyr | Ile |
|---|---|---|---|---|---|---|---|---|---|---|---|---|---|---|---|
| | 130 | | | | | 135 | | | | | 140 | | | | |

| Pro | Thr | Phe | Asp | Asn | Gly | Ala | Thr | Ser | Thr | Gln | Leu | Met | Leu | Leu | Ala |
|---|---|---|---|---|---|---|---|---|---|---|---|---|---|---|---|
| 145 | | | | | 150 | | | | | 155 | | | | | 160 |

| Gln | Ala | His | Gln | Ala | Thr | Gly | Asp | Lys | Arg | Tyr | Ser | Asp | Ala | Phe | Ala |
|---|---|---|---|---|---|---|---|---|---|---|---|---|---|---|---|
| | | | | 165 | | | | | 170 | | | | | 175 | |

| Arg | Gly | Leu | Glu | Phe | Ile | Ile | Thr | Ala | Gln | Tyr | Pro | Asn | Gly | Gly | Trp |
|---|---|---|---|---|---|---|---|---|---|---|---|---|---|---|---|
| | | | 180 | | | | | 185 | | | | | 190 | | |

| Pro | Gln | Asn | Phe | Pro | Leu | Val | Gly | Lys | Tyr | His | Asp | His | Ile | Thr | Tyr |
|---|---|---|---|---|---|---|---|---|---|---|---|---|---|---|---|
| | | 195 | | | | | 200 | | | | | 205 | | | |

| Asn | Asp | Ala | Leu | Met | Arg | Asp | Leu | Met | Val | Val | Leu | His | Lys | Val | Ala |
|---|---|---|---|---|---|---|---|---|---|---|---|---|---|---|---|
| | 210 | | | | | 215 | | | | | 220 | | | | |

| Met | Ala | Lys | Asp | Glu | Phe | Ala | Phe | Val | Ser | Lys | Ala | Gln | Gln | Gln | Ala |
|---|---|---|---|---|---|---|---|---|---|---|---|---|---|---|---|
| 225 | | | | | 230 | | | | | 235 | | | | | 240 |

| Ala | Gln | Ala | Ser | Leu | Glu | Arg | Ala | Leu | Asp | Cys | Val | Leu | Lys | Thr | Gln |
|---|---|---|---|---|---|---|---|---|---|---|---|---|---|---|---|
| | | | | 245 | | | | | 250 | | | | | 255 | |

| Val | Met | Ala | Asn | Gly | Gln | Leu | Thr | Ile | Trp | Gly | Ala | Gln | His | Asp | Ala |
|---|---|---|---|---|---|---|---|---|---|---|---|---|---|---|---|
| | | | 260 | | | | | 265 | | | | | 270 | | |

| Lys | Thr | Leu | Lys | Pro | Ala | Lys | Ala | Arg | Ala | Tyr | Glu | Met | Ile | Ser | Leu |
|---|---|---|---|---|---|---|---|---|---|---|---|---|---|---|---|
| | | 275 | | | | | 280 | | | | | 285 | | | |

-continued

```
Thr Ser Ser Glu Ser Val Trp Met Leu Asp Phe Leu Met Asp Leu Gln
    290                 295                 300

Gln Pro Ser Ala Asp Ile Ile Lys Ser Val His Ala Ala Ala Ala Trp
305                 310                 315                 320

Tyr Glu Gln Asn Lys Ile Ile Gly Lys Thr Trp Thr Arg Gly Asp Thr
                325                 330                 335

Val Leu Lys Asp Asp Lys Asp Ala Pro Pro Ile Trp Ala Arg Phe Tyr
            340                 345                 350

Glu Ile Gly Thr Asn Lys Pro Leu Phe Gly Asp Arg Asp Asp Ser Val
        355                 360                 365

His Tyr Asp Leu Ala Lys Val Ser Glu Glu Arg Arg Thr Gly Tyr Ala
    370                 375                 380

Trp Tyr Thr Thr Ser Pro Asn Gln Val Leu Lys Lys Tyr Ala Arg Trp
385                 390                 395                 400

Ala Lys Gln Tyr Pro Gln
                405
```

<210> SEQ ID NO 75
<211> LENGTH: 1767
<212> TYPE: DNA
<213> ORGANISM: Unknown
<220> FEATURE:
<223> OTHER INFORMATION: Obtained from an environmental sample

<400> SEQUENCE: 75

```
atgaccacaa cccgccgcac tatcctgaaa gccgccgcca gcgccggcgc gatcgccagc      60
accggctggc cgccttggcc cgccgcacag gccgcgcaag ccgccgaccc gtgggcccgc     120
gcccagcaga tcatcgaccg cttcgccaag ccgctcagct tcccgaacag ggacttcccg     180
atcaccgagt tcggcgccaa accctgcaag ctggtcaaag cccagggcct ggtcgaagta     240
agagtcaaag gcgaactcga aacgccagca ccgcaagcgc cggacgccta cccggcaatc     300
aaagccgcca tcgccgcagc gagcaaggcc ggaggagggc gcgtgctgat cccggccggc     360
aactggtact gcaagggccc tatcgtgctg ctgtcgaacg tgcacgtgca ccttgccaag     420
ggcgcgcaag tctacttcag cgccaacgcc aaggacttcg cccgcgacgg cgactacgac     480
tgcggcgcca acggcaagct ggtgctctcg cgctggcaag caacgattg cctgaacttc      540
tcgcccatgg tctacgcgcg cgggcaaaag aatatcgcca ttaccggcga agactggacc     600
agcatcctga acggcaggc cggcgtggcg ttcgaagacg gcagcggcaa tggctggtgg     660
ggcatgaacc ccgccggcgc gccgcccggc agcaccacgc accagggcgc agccaatccg     720
aacaacgccg aggagccaat cgccagactg cccacgcgcc acgcgaactg gagcgccgac     780
gacaagtacc tgccgctgct gtccgaagcc ggcgtgcccg ccgagcgccg cgtgttcggt     840
ctggggcact acctgcggcc gtcgatggtc gaattcgtcg actgcgggga tgtgctgatg     900
cagggctacc aggtcatcaa cacgccgttc tggattcatc acccggtcaa ctcacgcaac     960
attcacttct ccaaagtgcg catggaaagc atcggcccga attcggacgg tttcgatccc    1020
gagtcctgcg acaccatcct ggtggacggc tgcctgttca taccggcga cgactgcatc     1080
gccatcaaat ccggcaagaa ccgagactcg caatacggcc caacgcgcaa tatggtggtc    1140
cagaactgca tcatgaaccg cggccacggc ggcgttacgc tgggcagcga atggcgggt    1200
ggcatcgagc atatctacgc gcagaaaatc gaattccgca acgcgttctg ggaccacgac    1260
ccgctgggca cggccatccg aatgaagacg aacatgaacc gcggcggcta ccttcgtcat    1320
ttctacgtgc gcgacgtgac gctgccgaat ggcgtgcgta ccaagagcgg cttctacaag    1380
```

-continued

```
acgctgccgg gatctccgct ggcaggcaag gtctccacca gcggcggcgc tgttatcact    1440
atcgactgcg attacgcgcc gaatgacgac agcgtgcgcg tgcggccgcc gcaggtgtcg    1500
gacgtgcata tctcgaacgt ccgcgtcagc aatgtgaaaa cggccgaagg ctcgttctcc    1560
tgctaccagg ccatggtgct gctcgggccc gtggcggcca gcttcaacgg cgcgcctggc    1620
acggccatcc tgccgatcac gaatgtcacc gtcagcgatt cggacttcgg cacgccgcgc    1680
aacagcgcag agccctggtt cgcgttcaac gtgcagggac tcaagctgcg caacgtgcgc    1740
atcgatggca aggagtacaa cgtatga                                        1767
```

<210> SEQ ID NO 76
<211> LENGTH: 588
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(34)
<220> FEATURE:
<221> NAME/KEY: DOMAIN
<222> LOCATION: (110)...(555)
<223> OTHER INFORMATION: Catalytic domain

<400> SEQUENCE: 76

```
Met Thr Thr Thr Arg Thr Ile Leu Lys Ala Ala Ala Ser Ala Gly
 1               5                  10                  15

Ala Ile Ala Ser Thr Gly Trp Pro Ala Leu Ala Ala Gln Ala Ala
                20                  25                  30

Gln Ala Ala Asp Pro Trp Ala Arg Ala Gln Gln Ile Ile Asp Arg Phe
            35                  40                  45

Ala Lys Pro Leu Ser Phe Pro Asn Arg Asp Phe Pro Ile Thr Glu Phe
        50                  55                  60

Gly Ala Lys Pro Cys Lys Leu Val Lys Ala Gln Gly Leu Val Glu Val
 65                  70                  75                  80

Arg Val Lys Gly Glu Leu Glu Thr Pro Ala Pro Gln Ala Pro Asp Ala
                85                  90                  95

Tyr Pro Ala Ile Lys Ala Ala Ile Ala Ala Ala Ser Lys Ala Gly Gly
            100                 105                 110

Gly Arg Val Leu Ile Pro Ala Gly Asn Trp Tyr Cys Lys Gly Pro Ile
        115                 120                 125

Val Leu Leu Ser Asn Val His Val His Leu Ala Lys Gly Ala Gln Val
    130                 135                 140

Tyr Phe Ser Ala Asn Ala Lys Asp Phe Ala Arg Asp Gly Asp Tyr Asp
145                 150                 155                 160

Cys Gly Ala Asn Gly Lys Leu Val Leu Ser Arg Trp Gln Gly Asn Asp
                165                 170                 175

Cys Leu Asn Phe Ser Pro Met Val Tyr Ala Arg Gly Gln Lys Asn Ile
            180                 185                 190

Ala Ile Thr Gly Glu Asp Trp Thr Ser Ile Leu Asn Gly Gln Ala Gly
        195                 200                 205

Val Ala Phe Glu Asp Gly Ser Gly Asn Gly Trp Trp Gly Met Asn Pro
    210                 215                 220

Ala Gly Ala Pro Pro Gly Ser Thr Thr His Gln Gly Ala Ala Asn Pro
225                 230                 235                 240

Asn Asn Ala Glu Glu Pro Ile Ala Arg Leu Pro Thr Arg His Ala Asn
                245                 250                 255
```

Trp Ser Ala Asp Asp Lys Tyr Leu Pro Leu Ser Glu Ala Gly Val
            260                 265                 270

Pro Ala Glu Arg Arg Val Phe Gly Leu Gly His Tyr Leu Arg Pro Ser
        275                 280                 285

Met Val Glu Phe Val Asp Cys Gly Asp Val Leu Met Gln Gly Tyr Gln
        290                 295                 300

Val Ile Asn Thr Pro Phe Trp Ile His Pro Val Asn Ser Arg Asn
305                 310                 315                 320

Ile His Phe Ser Lys Val Arg Met Glu Ser Ile Gly Pro Asn Ser Asp
                325                 330                 335

Gly Phe Asp Pro Glu Ser Cys Asp Thr Ile Leu Val Asp Gly Cys Leu
            340                 345                 350

Phe Asn Thr Gly Asp Asp Cys Ile Ala Ile Lys Ser Gly Lys Asn Arg
        355                 360                 365

Asp Ser Gln Tyr Gly Pro Thr Arg Asn Met Val Val Gln Asn Cys Ile
    370                 375                 380

Met Asn Arg Gly His Gly Gly Val Thr Leu Gly Ser Glu Met Ala Gly
385                 390                 395                 400

Gly Ile Glu His Ile Tyr Ala Gln Lys Ile Glu Phe Arg Asn Ala Phe
                405                 410                 415

Trp Asp His Asp Pro Leu Gly Thr Ala Ile Arg Met Lys Thr Asn Met
            420                 425                 430

Asn Arg Gly Gly Tyr Leu Arg His Phe Tyr Val Arg Asp Val Thr Leu
        435                 440                 445

Pro Asn Gly Val Arg Thr Lys Ser Gly Phe Tyr Lys Thr Leu Pro Gly
    450                 455                 460

Ser Pro Leu Ala Gly Lys Val Ser Thr Ser Gly Gly Ala Val Ile Thr
465                 470                 475                 480

Ile Asp Cys Asp Tyr Ala Pro Asn Asp Ser Val Arg Val Arg Pro
                485                 490                 495

Pro Gln Val Ser Asp Val His Ile Ser Asn Val Arg Val Ser Asn Val
            500                 505                 510

Lys Thr Ala Glu Gly Ser Phe Ser Cys Tyr Gln Ala Met Val Leu Leu
        515                 520                 525

Gly Pro Val Ala Ala Ser Phe Asn Gly Ala Pro Gly Thr Ala Ile Leu
    530                 535                 540

Pro Ile Thr Asn Val Thr Val Ser Asp Ser Asp Phe Gly Thr Pro Arg
545                 550                 555                 560

Asn Ser Ala Glu Pro Trp Phe Ala Phe Asn Val Gln Gly Leu Lys Leu
                565                 570                 575

Arg Asn Val Arg Ile Asp Gly Lys Glu Tyr Asn Val
            580                 585

<210> SEQ ID NO 77
<211> LENGTH: 2043
<212> TYPE: DNA
<213> ORGANISM: Unknown
<220> FEATURE:
<223> OTHER INFORMATION: Obtained from an environmental sample

<400> SEQUENCE: 77
atgaaaacct ccagagcaat ttttactaca tcaacacttt taccgcgcgc gcttatcgcg    60
gctagtgtca gcatggcaat gagttctgcc gcatgggcgg ttgtaccta taccgtcacc    120 aataattggg gctcaggatt taccggcgaa atcaaagtga ccaacaacac caccgccagc    180

-continued

```
gtgaacaatt ggtctgtgtc atggcaggaa tccggtgcgg ctatcaccaa cgcctggaat    240
gcaacgctca gtggctcaaa cccttacaca gccgtatccg ctggttggaa tggcacactt    300
gcccccaatg catcggccac ttttggtttc caggcaaacg gttctgccgg tgcacctaaa    360
gtgaatggca gcttgtgcgg caccaacact tcatcaacac cggcatccag cagtgttgcc    420
agctcggtta aatcaagcgc gcccgtatcg tccagcagca gatcatccag ttcaatcgct    480
atcactagca gctctttagc gagaagttct attgcctcca gcagctcact agttagtagc    540
tccagagcga gcagtagtgc gccaagcgtt ttctctttta cgatccagga agagcaagcg    600
ggcttctgtc gtgttgatgg cattgcgaca gaaagcacca acaccggttt taccggcaat    660
ggctacacca atgcgaacaa cgcgcaaggc gcagcgattg aatgggcagt cagcgcacct    720
agcagtggcc gttatacagt agccttccgc ttcgccaatg gcggcacagc agcgcgcaac    780
ggctcgttgt taatcaatgg cggtagcaat ggtaattaca ctgtggagtt accctgacc     840
ggcgcatggg caacctggca aattgccagc gtggaaattg atttagtgca aggcaataat    900
atttaaaac tctcggcgtt aaccgctgac ggtttggcca atatcgactc attaaaaata    960
gacggcgcgc aaaccaaagc aggtacttgc agcactacat caagcagcag cgttgccagc    1020
agctcgtcgt ccgttaaatc cagcgcaagt tcttcttcga gttcatccac cgctgcaaaa    1080
atactgacat tagacggtaa cccggccgcc agctggttca caaatccag gaccaagtgg    1140
aatagcagcc gcgccgatat tgtgttgtct taccagcaat ccaacggcgg ttggccaaaa    1200
aacctggatt acaactcagt gagcgcaggc aatggcggga gcgacagcgg caccatcgac    1260
aatggtgcaa ccattaccga aatggtttac ctcgctgaaa tttataaaaa cggcggcaac    1320
accaaatatc gcgatgcagt gcgcagagca gcaaactttt tagtgagctc gcaatacagc    1380
acaggcgcct tgccacaatt ttatccgttg aaaggcggct atgcggatca tgcgaccttt    1440
aacgataacg gcatggcgta cgcgttgacg gtattggatt tcgcagtaaa caaacgcgca    1500
ccgtttgata cgacattttt ctctgattct gatcgggcga aattcaaaac cgctgttgcc    1560
aaaggtgtgg attacatttt aaaagcgcag tggaaacaaa atggaaaact cactgcatgg    1620
tgtgcacaac acggtgctac ggattaccaa ccgaaaaaag cgcgcgctta tgaattggaa    1680
tcattgagtg gtagcgagtc ggtcggcatt ctcgccttct tgatgaccca accacaaacc    1740
gcgcaaatcg aagcggcggt caaggcgggt gtcaactggt tcgccagtcc aaatacttat    1800
ttggctaact acacttacga ttcatcaaaa gcgtctacca acccgattgt gtataaatcc    1860
ggaagcagaa tgtggtatcg cttctatgac ctgaacacca accgtggttt ctttagtgat    1920
cgcgatggca gcaaattcta tgatatcacc caaatgtcag aagagcgtcg caccggttat    1980
agctggggtg gctcttacgg tgaatctatt atttccttcg cgcaaaaagt gggttatctg    2040
taa                                                                   2043
```

<210> SEQ ID NO 78
<211> LENGTH: 680
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(33)
<220> FEATURE:
<221> NAME/KEY: BINDING
<222> LOCATION: (34)...(126)
<223> OTHER INFORMATION: Carbohydrate binding module

```
<220> FEATURE:
<221> NAME/KEY: BINDING
<222> LOCATION: (199)...(322)
<223> OTHER INFORMATION: Carbohydrate binding module
<220> FEATURE:
<221> NAME/KEY: DOMAIN
<222> LOCATION: (323)...(680)
<223> OTHER INFORMATION: Catalytic domain

<400> SEQUENCE: 78
```

Met Lys Thr Ser Arg Ala Ile Phe Thr Thr Ser Thr Leu Leu His Arg
 1               5                  10                  15

Ala Leu Ile Ala Ala Ser Val Ser Met Ala Met Ser Ser Ala Ala Trp
             20                  25                  30

Ala Gly Cys Thr Tyr Thr Val Thr Asn Asn Trp Gly Ser Gly Phe Thr
         35                  40                  45

Gly Glu Ile Lys Val Thr Asn Asn Thr Thr Ala Ser Val Asn Asn Trp
 50                  55                  60

Ser Val Ser Trp Gln Glu Ser Gly Ala Ala Ile Thr Asn Ala Trp Asn
 65                  70                  75                  80

Ala Thr Leu Ser Gly Ser Asn Pro Tyr Thr Ala Val Ser Ala Gly Trp
                 85                  90                  95

Asn Gly Thr Leu Ala Pro Asn Ala Ser Ala Thr Phe Gly Phe Gln Ala
            100                 105                 110

Asn Gly Ser Ala Gly Ala Pro Lys Val Asn Gly Ser Leu Cys Gly Thr
        115                 120                 125

Asn Thr Ser Ser Thr Pro Ala Ser Ser Val Ala Ser Ser Val Lys
    130                 135                 140

Ser Ser Ala Pro Val Ser Ser Ser Arg Ser Ser Ser Ser Ile Ala
145                 150                 155                 160

Ile Thr Ser Ser Ser Leu Ala Arg Ser Ser Ile Ala Ser Ser Ser Ser
                165                 170                 175

Leu Val Ser Ser Ser Arg Ala Ser Ser Ser Ala Pro Ser Val Phe Ser
            180                 185                 190

Phe Thr Ile Gln Glu Glu Gln Ala Gly Phe Cys Arg Val Asp Gly Ile
        195                 200                 205

Ala Thr Glu Ser Thr Asn Thr Gly Phe Thr Gly Asn Gly Tyr Thr Asn
210                 215                 220

Ala Asn Asn Ala Gln Gly Ala Ala Ile Glu Trp Ala Val Ser Ala Pro
225                 230                 235                 240

Ser Ser Gly Arg Tyr Thr Val Ala Phe Arg Phe Ala Asn Gly Gly Thr
                245                 250                 255

Ala Ala Arg Asn Gly Ser Leu Leu Ile Asn Gly Gly Ser Asn Gly Asn
            260                 265                 270

Tyr Thr Val Glu Leu Pro Leu Thr Gly Ala Trp Ala Thr Trp Gln Ile
        275                 280                 285

Ala Ser Val Glu Ile Asp Leu Val Gln Gly Asn Asn Ile Leu Lys Leu
290                 295                 300

Ser Ala Leu Thr Ala Asp Gly Leu Ala Asn Ile Asp Ser Leu Lys Ile
305                 310                 315                 320

Asp Gly Ala Gln Thr Lys Ala Gly Thr Cys Ser Thr Thr Ser Ser Ser
                325                 330                 335

Ser Val Ala Ser Ser Ser Ser Val Lys Ser Ser Ala Ser Ser Ser
            340                 345                 350

Ser Ser Ser Ser Thr Ala Ala Lys Ile Leu Thr Leu Asp Gly Asn Pro
        355                 360                 365

```
Ala Ala Ser Trp Phe Asn Lys Ser Arg Thr Lys Trp Asn Ser Ser Arg
    370                 375                 380

Ala Asp Ile Val Leu Ser Tyr Gln Gln Ser Asn Gly Gly Trp Pro Lys
385                 390                 395                 400

Asn Leu Asp Tyr Asn Ser Val Ser Ala Gly Asn Gly Gly Ser Asp Ser
                405                 410                 415

Gly Thr Ile Asp Asn Gly Ala Thr Ile Thr Glu Met Val Tyr Leu Ala
            420                 425                 430

Glu Ile Tyr Lys Asn Gly Gly Asn Thr Lys Tyr Arg Asp Ala Val Arg
        435                 440                 445

Arg Ala Ala Asn Phe Leu Val Ser Ser Gln Tyr Ser Thr Gly Ala Leu
    450                 455                 460

Pro Gln Phe Tyr Pro Leu Lys Gly Gly Tyr Ala Asp His Ala Thr Phe
465                 470                 475                 480

Asn Asp Asn Gly Met Ala Tyr Ala Leu Thr Val Leu Asp Phe Ala Val
                485                 490                 495

Asn Lys Arg Ala Pro Phe Asp Asn Asp Ile Phe Ser Asp Ser Asp Arg
            500                 505                 510

Ala Lys Phe Lys Thr Ala Val Ala Lys Gly Val Asp Tyr Ile Leu Lys
        515                 520                 525

Ala Gln Trp Lys Gln Asn Gly Lys Leu Thr Ala Trp Cys Ala Gln His
    530                 535                 540

Gly Ala Thr Asp Tyr Gln Pro Lys Lys Ala Arg Ala Tyr Glu Leu Glu
545                 550                 555                 560

Ser Leu Ser Gly Ser Glu Ser Val Gly Ile Leu Ala Phe Leu Met Thr
                565                 570                 575

Gln Pro Gln Thr Ala Gln Ile Glu Ala Ala Val Lys Ala Gly Val Asn
            580                 585                 590

Trp Phe Ala Ser Pro Asn Thr Tyr Leu Ala Asn Tyr Thr Tyr Asp Ser
        595                 600                 605

Ser Lys Ala Ser Thr Asn Pro Ile Val Tyr Lys Ser Gly Ser Arg Met
    610                 615                 620

Trp Tyr Arg Phe Tyr Asp Leu Asn Thr Asn Arg Gly Phe Phe Ser Asp
625                 630                 635                 640

Arg Asp Gly Ser Lys Phe Tyr Asp Ile Thr Gln Met Ser Glu Glu Arg
                645                 650                 655

Arg Thr Gly Tyr Ser Trp Gly Gly Ser Tyr Gly Glu Ser Ile Ile Ser
            660                 665                 670

Phe Ala Gln Lys Val Gly Tyr Leu
        675                 680

<210> SEQ ID NO 79
<211> LENGTH: 1746
<212> TYPE: DNA
<213> ORGANISM: Unknown
<220> FEATURE:
<223> OTHER INFORMATION: Obtained from an environmental sample

<400> SEQUENCE: 79
atgacgacac gacgcgaatt catcaaaggc tttctactta ccggagcagc cgtggccgtc      60
gctccgcgtt taattgcgtt cggcgcggag gcaagtccgt gggaaacgat gatgccttcg     120
atcctcgcac gcatcacacc acctcgtttt ccgaaacgca ccttctatct caatcgattc     180
ggcgccaagg gcgatggagt cacagactgc accgcggctt tcatcgcgc gatcgatgaa     240
```

```
tgcaccaaag ccggcggtgg gaaagtcgtc gtgccggcgg gcacttatct caccggcgcg      300
attcatttga agagcaacgt caacctcgaa gtctcggaag gcgcgacgat caagttcagt      360
caggacccga aacactacct gcctgttgtc ttctcgcgtt gggaaggtgt cgaagtcttc      420
aactactcgc ctttcattta cgcgttcgaa cagcgaaaca tcgcgatcac cggcaaaggc      480
acgctcgacg gacagagtga ttcggaacac tggtggccgt ggaacggccg tccgcagtac      540
ggatggaatg aagggatgaa acagcagcgt cccgatcgca acgcgttgtt cacaatggcg      600
gagaaaggcg tgccggtgcg cgagcgcatc tttggcgaag gtcattattt gaggccgcag      660
ttcattcagc cgtaccgctg ccagaacgtg ctgatccagg gcgtgacgat tcggaactcg      720
ccgatgtggg agattcatcc ggtgttgtgc cgcaacgtga ctattcacga cgtgcacatc      780
gatagtcatg gaccaaacaa cgacggctgc aatcccgaat cgtgcagcga cgtgttgatt      840
aaggatagct acttcgatac cggcgacgac tgcatcgcga tcaaatcggg acgcaacgcc      900
gacgggcggc ggcttaaagc gccgactgag aacatcatcg ttcaaggatg tcgcatgaaa      960
gacggccacg gtggaatcac ggtcggcagc gagatctcgg gcggcgtgcg aaacctgttt     1020
gccgagaatt gccggctcga cagtccaaac ctcgatcacg ccctgcgcgt gaagaacaat     1080
gccatgcgcg gcggattact cgagaacttc cacttccgta acatcgaagt cgggcaggtg     1140
gcccatgccg tgattacgat cgacttcaac tacgaagagg gcgcgaaagg gtcgttcacg     1200
ccggtcgttc gcgattacac ggtcgatcgt ttgcgcagca cgaagagcaa gcacgcactc     1260
gacgtccagg gtctgcccgg cgcgccggtc atcaacctgc gattgacaaa ctgcacattc     1320
aacgatgtgc agcaaccgaa cattctcaag aacgtcgaac aatcaacctt tgagaacgtc     1380
acgattaacg gaaagacgat cacacaaaca ggatccatct cagaaagagc ggccacgaca     1440
gcaatgaccg cgctttggcg cgacgcgtcg aggaaagaaa acggttatcc cgcgaagtgg     1500
acctatgatc atgggctggt cctgaaagga atcgagcgcg tttggaacaa taccggcgat     1560
aagaagtatc tgaagttcat ccaggacagc atggaccact tcgtcaacga cgacggctcc     1620
attcgcacct acacgatcga cgagtacaac atcgatcacg ttcttcccgg acgaaacctc     1680
ctgttccttt acaaaactac cggtcaggaa aagtatcgca aagccgccgc gttcttgcgc     1740
gaacaa                                                               1746
```

<210> SEQ ID NO 80
<211> LENGTH: 582
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(28)
<220> FEATURE:
<221> NAME/KEY: DOMAIN
<222> LOCATION: (81)...(458)
<223> OTHER INFORMATION: Catalytic domain

<400> SEQUENCE: 80

Met Thr Thr Arg Arg Glu Phe Ile Lys Gly Phe Leu Leu Thr Gly Ala
 1               5                  10                  15

Ala Val Ala Val Ala Pro Arg Leu Ile Ala Phe Gly Ala Glu Ala Ser
            20                  25                  30

Pro Trp Glu Thr Met Met Pro Ser Ile Leu Ala Arg Ile Thr Pro Pro
        35                  40                  45

Arg Phe Pro Lys Arg Thr Phe Tyr Leu Asn Arg Phe Gly Ala Lys Gly

-continued

```
            50                  55                  60
Asp Gly Val Thr Asp Cys Thr Ala Ala Phe His Arg Ala Ile Asp Glu
65                  70                  75                  80
Cys Thr Lys Ala Gly Gly Lys Val Val Pro Ala Gly Thr Tyr
                85                  90                  95
Leu Thr Gly Ala Ile His Leu Lys Ser Asn Val Asn Leu Glu Val Ser
                100                 105                 110
Glu Gly Ala Thr Ile Lys Phe Ser Gln Asp Pro Lys His Tyr Leu Pro
                115                 120                 125
Val Val Phe Ser Arg Trp Glu Gly Val Glu Val Phe Asn Tyr Ser Pro
130                 135                 140
Phe Ile Tyr Ala Phe Glu Gln Arg Asn Ile Ala Ile Thr Gly Lys Gly
145                 150                 155                 160
Thr Leu Asp Gly Gln Ser Asp Ser Glu His Trp Trp Pro Trp Asn Gly
                165                 170                 175
Arg Pro Gln Tyr Gly Trp Asn Glu Gly Met Lys Gln Gln Arg Pro Asp
                180                 185                 190
Arg Asn Ala Leu Phe Thr Met Ala Glu Lys Gly Val Pro Val Arg Glu
                195                 200                 205
Arg Ile Phe Gly Glu Gly His Tyr Leu Arg Pro Gln Phe Ile Gln Pro
                210                 215                 220
Tyr Arg Cys Gln Asn Val Leu Ile Gln Gly Val Thr Ile Arg Asn Ser
225                 230                 235                 240
Pro Met Trp Glu Ile His Pro Val Leu Cys Arg Asn Val Thr Ile His
                245                 250                 255
Asp Val His Ile Asp Ser His Gly Pro Asn Asn Asp Gly Cys Asn Pro
                260                 265                 270
Glu Ser Cys Ser Asp Val Leu Ile Lys Asp Ser Tyr Phe Asp Thr Gly
                275                 280                 285
Asp Asp Cys Ile Ala Ile Lys Ser Gly Arg Asn Ala Asp Gly Arg Arg
                290                 295                 300
Leu Lys Ala Pro Thr Glu Asn Ile Ile Val Gln Gly Cys Arg Met Lys
305                 310                 315                 320
Asp Gly His Gly Gly Ile Thr Val Gly Ser Glu Ile Ser Gly Gly Val
                325                 330                 335
Arg Asn Leu Phe Ala Glu Asn Cys Arg Leu Asp Ser Pro Asn Leu Asp
                340                 345                 350
His Ala Leu Arg Val Lys Asn Asn Ala Met Arg Gly Gly Leu Leu Glu
                355                 360                 365
Asn Phe His Phe Arg Asn Ile Glu Val Gly Gln Val Ala His Ala Val
                370                 375                 380
Ile Thr Ile Asp Phe Asn Tyr Glu Glu Gly Ala Lys Gly Ser Phe Thr
385                 390                 395                 400
Pro Val Val Arg Asp Tyr Thr Val Asp Arg Leu Arg Ser Thr Lys Ser
                405                 410                 415
Lys His Ala Leu Asp Val Gln Gly Leu Pro Gly Ala Pro Val Ile Asn
                420                 425                 430
Leu Arg Leu Thr Asn Cys Thr Phe Asn Asp Val Gln Gln Pro Asn Ile
                435                 440                 445
Leu Lys Asn Val Glu Gln Ser Thr Phe Glu Asn Val Thr Ile Asn Gly
                450                 455                 460
Lys Thr Ile Thr Gln Thr Gly Ser Ile Ser Glu Arg Ala Ala Thr Thr
465                 470                 475                 480
```

Ala Met Thr Ala Leu Trp Arg Asp Ala Ser Arg Lys Glu Asn Gly Tyr
            485                 490                 495

Pro Ala Lys Trp Thr Tyr Asp His Gly Leu Val Leu Lys Gly Ile Glu
        500                 505                 510

Arg Val Trp Asn Asn Thr Gly Asp Lys Lys Tyr Leu Lys Phe Ile Gln
            515                 520                 525

Asp Ser Met Asp His Phe Val Asn Asp Gly Ser Ile Arg Thr Tyr
        530                 535                 540

Thr Ile Asp Glu Tyr Asn Ile Asp His Val Leu Pro Gly Arg Asn Leu
545                 550                 555                 560

Leu Phe Leu Tyr Lys Thr Thr Gly Gln Glu Lys Tyr Arg Lys Ala Ala
                565                 570                 575

Ala Phe Leu Arg Glu Gln
            580

<210> SEQ ID NO 81
<211> LENGTH: 1065
<212> TYPE: DNA
<213> ORGANISM: Unknown
<220> FEATURE:
<223> OTHER INFORMATION: Obtained from an environmental sample

<400> SEQUENCE: 81

```
atgacgctac ccgttgtttc cctgcgcgtg ctgctggcgc tgctggccac gttgccggtc      60
gcctgcgcgg gcgctgcggt atccgcggca gcgaccgacc cggtcgccga gaacatgctg     120
ctgctgcaga ccgcctccgg tggctggtcc aagcactacc gcgggaagaa ggtcgactac     180
acgcgcaatt acgacaccgc cgagcgcgcc gcgctgcgcg cgcccggccg gcatgacgac     240
gcgacgatcg acaacaaggc cacgaccagc gagatcgcct acctggtgca ggcacatgcc     300
aggacgggca acccggcgta cctcgacggt gcccgccgcg gggtcgaata cctgctgcgc     360
gcgcagtacc cgaatggtgg ctggccgcag ttctacccccg accactcgtc ctaccggcac     420
cagatcacgc tcaacgacga cgcgatggtg catgccatca ccgtgctgca ggacatcgcc     480
gccggccgcg acggcatgca ggcgttgacg cccgagttcg gcgtccgcgc cgccgccgcc     540
gcgcagcgcg gcatcggaaa cctgctcgag ttgcaggtgc ggatcgacgg cgagccgacc     600
atctgggccg cgcagtacga cgagcatagc ctgcagccgg ccaaggcccg cgcctatgaa     660
ctgccctcgc tggccgtggc cgaatcggtc ggcgtggtgc gcctgctgat gcgccagccg     720
aggccggatg cccggaccgt cgccgcgatc gaatcggcgg cccgctggct ggaggcgcat     780
cgcctgcatg acctggcgct cgaacgcgtc gacgcaccgg ccgaggaaac gggcaaggac     840
gtgcgggtcg tgacccggcc cggcgcctcg ctgtgggcgc gcttctacga cctggatgga     900
cagcagcctc tgttcgtcga ccgcgacagc aagcccgtcc cgttcgccag cctgcccaac     960 gagccgcca ccggctatgc ctggtacggc acctggccgg agaagctgct ggcgcaggaa    1020
ctcccgcgct ggcgcgaggt ccatgccgcc ggcgccgcgc cctga                    1065
```

<210> SEQ ID NO 82
<211> LENGTH: 354
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(30)
<220> FEATURE:

-continued

```
<221> NAME/KEY: DOMAIN
<222> LOCATION: (31)...(354)
<223> OTHER INFORMATION: Catalytic domain

<400> SEQUENCE: 82

Met Thr Leu Pro Val Val Ser Leu Arg Val Leu Leu Ala Leu Leu Ala
 1               5                   10                  15

Thr Leu Pro Val Ala Cys Ala Gly Ala Ala Val Ser Ala Ala Ala Thr
            20                  25                  30

Asp Pro Val Ala Glu Asn Met Leu Leu Gln Thr Ala Ser Gly Gly
        35                  40                  45

Trp Ser Lys His Tyr Arg Gly Lys Lys Val Asp Tyr Thr Arg Asn Tyr
    50                  55                  60

Asp Thr Ala Glu Arg Ala Ala Leu Arg Ala Pro Gly Arg His Asp Asp
65                  70                  75                  80

Ala Thr Ile Asp Asn Lys Ala Thr Thr Ser Glu Ile Ala Tyr Leu Val
                85                  90                  95

Gln Ala His Ala Arg Thr Gly Asn Pro Ala Tyr Leu Asp Gly Ala Arg
            100                 105                 110

Arg Gly Val Glu Tyr Leu Leu Arg Ala Gln Tyr Pro Asn Gly Gly Trp
        115                 120                 125

Pro Gln Phe Tyr Pro Asp His Ser Ser Tyr Arg His Gln Ile Thr Leu
    130                 135                 140

Asn Asp Asp Ala Met Val His Ala Ile Thr Val Leu Gln Asp Ile Ala
145                 150                 155                 160

Ala Gly Arg Asp Gly Met Gln Ala Leu Thr Pro Glu Phe Gly Val Arg
                165                 170                 175

Ala Ala Ala Ala Gln Arg Gly Ile Gly Asn Leu Leu Glu Leu Gln
            180                 185                 190

Val Arg Ile Asp Gly Glu Pro Thr Ile Trp Ala Ala Gln Tyr Asp Glu
        195                 200                 205

His Ser Leu Gln Pro Ala Lys Ala Arg Ala Tyr Glu Leu Pro Ser Leu
    210                 215                 220

Ala Val Ala Glu Ser Val Gly Val Val Arg Leu Leu Met Arg Gln Pro
225                 230                 235                 240

Arg Pro Asp Ala Arg Thr Val Ala Ala Ile Glu Ser Ala Ala Arg Trp
                245                 250                 255

Leu Glu Ala His Arg Leu His Asp Leu Ala Leu Glu Arg Val Asp Ala
            260                 265                 270

Pro Ala Glu Glu Thr Gly Lys Asp Val Arg Val Thr Arg Pro Gly
        275                 280                 285

Ala Ser Leu Trp Ala Arg Phe Tyr Asp Leu Asp Gly Gln Gln Pro Leu
    290                 295                 300

Phe Val Asp Arg Asp Ser Lys Pro Val Pro Phe Ala Ser Leu Pro Asn
305                 310                 315                 320

Glu Arg Arg Thr Gly Tyr Ala Trp Tyr Gly Thr Trp Pro Glu Lys Leu
                325                 330                 335

Leu Ala Gln Glu Leu Pro Arg Trp Arg Glu Val His Ala Gly Ala
            340                 345                 350

Ala Pro

<210> SEQ ID NO 83
<211> LENGTH: 3618
<212> TYPE: DNA
<213> ORGANISM: Unknown
```

<220> FEATURE:
<223> OTHER INFORMATION: Obtained from an environmental sample

<400> SEQUENCE: 83

```
ttgactgctc tttcaagaaa cagtcaggtt gatgtaagct gggaaccgag ttccgcccaa      60
caggtaacct acaatctaaa acgcagtacc acgaaggagg gtccttatca gaccattgct     120
gaaaaaatgg cagaaaccga cttccgggat acagggttag agaatggcca gaagtattac     180
tatgttgtat ctgccgaaac gagtagcggt gagagtgcag attcacaagc tataacggct     240
gtgcctgtag cgccattgca agctccgacc ggcctttcag caagtcatgg caatggcggg     300
gtaaccattc attgggaatc cgtcaatggt gccgagtctt accaagtctt gcgcagtaaa     360
caaaagggca tcggctatga agtcatcaaa aacggtgtaa cggaaaccag ttatacagat     420
accgggattc ccgatggcga gaagtactat tatgtcgtat ccgccaagaa cgatacagct     480
gaaagtgcaa attcccaacc gattaacggt gctgctgtat cgacgagtgg tgtaccagcc     540
attccaaacg gtatgaacgc tactgccggt gatggcagag ctgccttaac ctggtccgct     600
gtatccggcg cagattccta tagcatcaag cgcggtgagt ttaacagtgg tcaatatgag     660
gtcattgcta aaaatataca ctctaccggt tatcaagata taggccttac aaacggtgat     720
acctatgatt atgtgatttc cgctgtcaat gagcaagggg aaagtttagg ctccgaaccc     780
atcgccgtta ctcctgcgaa agtaacggtt gtagcgaaag aaggcggaga ctttaaaacg     840
attcaagaag ccattgatgc tgcacctgat aacagtacga aacggcatgt tatttttata     900
aaaaatggtc aatatcgtga aaagcttacg atccctaaga gcaaaaccaa tctgagtttt     960
gtagggaaa gtaaggaagg gaccgtgctt gttttttaatg ataatgcaaa tacgcctggg    1020
ccagacggca aaccattagg cacttccaat agttcaagta tctttatcta tgccaatgat    1080
tttattgccc aaaatttaac catccagaac gactctggtc aaggaacagg tcaagcagtt    1140
gccgcttatg taagggccga tcgtctctac tttgaaaacg tgcagttttt aggataccag    1200
gatacattat atgcccatac gggaagacag tattataaaa actgctacgt agaaggggat    1260
gtggatttca ttttttggcgg agccacagcc ttgtttgata cctgtcacct tcatagcaag    1320
cgtacaggca gtaagttaac cgcagctagt accgatcaag tcacaccgta tgggtatgtt    1380
tttttagatt caaaaatcac ctcagatgaa ggcgtgacca atgtgcatct cgggcgacct    1440
tggcgtcctt attcagctgt cacctatatc aacaccgaaa tggatgcatc gattgttcct    1500
gacggatggg ataactgggg gaaagttgaa acgagaaaa cagccagata ttcagaatac    1560
aataacatgg ggccaggggc agacccgaaa aagcgggatc catggaccac acaattaacg    1620
ccggaggaag cgaatcaata cactgtgcaa aatgtgatga aggatctgac ggctggggat    1680
cctgagagaa tcgggattat cccattatca ccactgtcag caccgattat ttcacttgat    1740
caacgagatt ccattgtcaa tacaccaagc tttacaatta caggtcaagt ggataaagaa    1800
gcagccgttt ctgtcaatgg gaaggaaatt tccttacaaa aggatggcag cttcagcacg    1860
acggtggtgc tgaatgacgg tttgaacact attacagtgg gagctgtaga tgcagcaggg    1920
aatcaggcta ttcctgcagt gttaaaaatt gtttatgatc atgagaaacc tgtcgtatcc    1980
atcgatgatc ttaaaggaga aaaaacgggg aatcactaca atgtaatcta caatccgctg    2040
ccgattacag ggaagctgaa cgaagcagga acagttatgg tgaatggtga aaagtaaat    2100
gtatcggaaa agttgacgtt tagtacaaaa gtcattttaa agccggggtt aaataacatt    2160
acgattaccg ctgttgatca ggcagggaat gaagccgaat ctatcactat caatgtggtt    2220
```

-continued

```
ccaaaaggga atgctgttcc agacggtccc gtcaagatta tcaaaagtga acaacaaat    2280
gcaaataccg ttgaggttac ttttaatagc aagctagaaa aatttgattc tagtgatatt    2340
gcattgcaaa cggctacgaa cgtttgggca gctctcaatc ctggtttgaa acaattgatg    2400
acagtggaaa gcattaccac aaaagtgaat aaggataacc aaaccgtagc ggtgatcaaa    2460
acgaaggaag cctttcaaga agatggaacc attacgctcc caaaagttga agatccgttt    2520
catattcaat atttgaatgc cgattattat accggggatc gtacgcagga cattaagcat    2580
gcggatgccc tcttaacctg cagatggat catggcggct ggtttaaaaa ctgggtggaa     2640
aaatataaac ggccatggga tgggaaagaa ccaaaatctg aatggtattc gactaatcat    2700
ggtgaactag gacgattga taatgacgca acaacaaacg agattctctt tttagctctg     2760
atgtataaag aaacaggtga tgctcgttat aaggattccg ttttaaaagg aattgatttt    2820
ttactagaga tgcaggttga ttccggcggc tggccgcagg tctatcctgc aagaagcggt    2880
tactcagatt atgtgaccttt aatgataat gcgatggttc gcgttatgag tgtattaacg    2940
atggttaaag aaaagaagta tccgtttaat tccaacctag gtgacgagca actttctgag    3000
cagattgatg atgcattggg ccgtgggctg gattatatgt taaaatcgca aattaaggta    3060
gacggtgaag taaccgcatg gtgtgctcag catgaccctg tgacgtatga accgaaaggg    3120
gctcgtgcgt atgaacatcc ttcaatctct ggttcggaat ctgtagggat tgtccagtat    3180
ttgatgtcac tgccgaatcc ttcaactgag gttcaggctg ccattcatgg agctctaaat    3240
tggtttgaag aggcaaaatt ggcgggaacg aagtatgtat caggcgatcc aaatgggcaa    3300
tatttctacc cggacgccaa cagcaatacg tggtaccgct tctatgaaat tggcaccaat    3360
cgcccgattt tctcaggaag agacggtgtc attaaacaca acatcttaga gattgaaaaa    3420
gaaagaagag acggctaccg ctgggcagga gaatggccgc aaaaattatt aaatatcgcc    3480
aacacaactg gctactacga aaacagagta tacgtgaag tcgttgggga tcagtctaaa    3540
aacgccgctg gcgaatcttt ggaaatagga aacttatata gaatagaggc ctcggcttcc    3600
ggttctacaa gcaagtaa                                                  3618
```

<210> SEQ ID NO 84
<211> LENGTH: 1205
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (268)...(556)
<223> OTHER INFORMATION: Pectin methyl esterase domain
<220> FEATURE:
<221> NAME/KEY: DOMAIN
<222> LOCATION: (782)...(1164)
<223> OTHER INFORMATION: Catalytic domain

<400> SEQUENCE: 84

```
Met Thr Ala Leu Ser Arg Asn Ser Gln Val Asp Val Ser Trp Glu Pro
 1               5                  10                  15

Ser Ser Ala Gln Gln Val Thr Tyr Asn Leu Lys Arg Ser Thr Thr Lys
            20                  25                  30

Glu Gly Pro Tyr Gln Thr Ile Ala Glu Lys Met Ala Glu Thr Asp Phe
        35                  40                  45

Arg Asp Thr Gly Leu Glu Asn Gly Gln Lys Tyr Tyr Tyr Val Val Ser
    50                  55                  60

Ala Glu Thr Ser Ser Gly Glu Ser Ala Asp Ser Gln Ala Ile Thr Ala
```

```
            65                  70                  75                  80
Val Pro Val Ala Pro Leu Gln Ala Pro Thr Gly Leu Ser Ala Ser His
                85                  90                  95
Gly Asn Gly Gly Val Thr Ile His Trp Glu Ser Val Asn Gly Ala Glu
                100                 105                 110
Ser Tyr Gln Val Leu Arg Ser Lys Gln Lys Gly Ile Gly Tyr Glu Val
                115                 120                 125
Ile Lys Asn Gly Val Thr Glu Thr Ser Tyr Thr Asp Thr Gly Ile Pro
            130                 135                 140
Asp Gly Glu Lys Tyr Tyr Val Val Ser Ala Lys Asn Asp Thr Ala
145                 150                 155                 160
Glu Ser Ala Asn Ser Gln Pro Ile Asn Gly Ala Ala Val Ser Thr Ser
                165                 170                 175
Gly Val Pro Ala Ile Pro Asn Gly Met Asn Ala Thr Ala Gly Asp Gly
                180                 185                 190
Arg Ala Ala Leu Thr Trp Ser Ala Val Ser Gly Ala Asp Ser Tyr Ser
                195                 200                 205
Ile Lys Arg Gly Glu Phe Asn Ser Gly Gln Tyr Glu Val Ile Ala Lys
            210                 215                 220
Asn Ile His Ser Thr Gly Tyr Gln Asp Ile Gly Leu Thr Asn Gly Asp
225                 230                 235                 240
Thr Tyr Asp Tyr Val Ile Ser Ala Val Asn Glu Gln Gly Glu Ser Leu
                245                 250                 255
Gly Ser Glu Pro Ile Ala Val Thr Pro Ala Lys Val Thr Val Val Ala
                260                 265                 270
Lys Glu Gly Gly Asp Phe Lys Thr Ile Gln Glu Ala Ile Asp Ala Ala
                275                 280                 285
Pro Asp Asn Ser Thr Lys Arg His Val Ile Phe Ile Lys Asn Gly Gln
            290                 295                 300
Tyr Arg Glu Lys Leu Thr Ile Pro Lys Ser Lys Thr Asn Leu Ser Phe
305                 310                 315                 320
Val Gly Glu Ser Lys Glu Gly Thr Val Leu Val Phe Asn Asp Asn Ala
                325                 330                 335
Asn Thr Pro Gly Pro Asp Gly Lys Pro Leu Gly Thr Ser Asn Ser Ser
                340                 345                 350
Ser Ile Phe Ile Tyr Ala Asn Asp Phe Ile Ala Gln Asn Leu Thr Ile
            355                 360                 365
Gln Asn Asp Ser Gly Gln Gly Thr Gly Gln Ala Val Ala Ala Tyr Val
            370                 375                 380
Arg Ala Asp Arg Leu Tyr Phe Glu Asn Val Gln Phe Leu Gly Tyr Gln
385                 390                 395                 400
Asp Thr Leu Tyr Ala His Thr Gly Arg Gln Tyr Tyr Lys Asn Cys Tyr
                405                 410                 415
Val Glu Gly Asp Val Asp Phe Ile Phe Gly Gly Ala Thr Ala Leu Phe
                420                 425                 430
Asp Thr Cys His Leu His Ser Lys Arg Thr Gly Ser Lys Leu Thr Ala
                435                 440                 445
Ala Ser Thr Asp Gln Val Thr Pro Tyr Gly Tyr Val Phe Leu Asp Ser
            450                 455                 460
Lys Ile Thr Ser Asp Glu Gly Val Thr Asn Val His Leu Gly Arg Pro
465                 470                 475                 480
Trp Arg Pro Tyr Ser Ala Val Thr Tyr Ile Asn Thr Glu Met Asp Ala
                485                 490                 495
```

```
Ser Ile Val Pro Asp Gly Trp Asp Asn Trp Gly Lys Val Glu Asn Glu
            500                 505                 510

Lys Thr Ala Arg Tyr Ser Glu Tyr Asn Asn Met Gly Pro Gly Ala Asp
        515                 520                 525

Pro Lys Lys Arg Asp Pro Trp Thr Thr Gln Leu Thr Pro Glu Glu Ala
    530                 535                 540

Asn Gln Tyr Thr Val Gln Asn Val Met Lys Gly Ser Asp Gly Trp Asp
545                 550                 555                 560

Pro Glu Arg Ile Gly Ile Ile Pro Leu Ser Pro Leu Ser Ala Pro Ile
                565                 570                 575

Ile Ser Leu Asp Gln Arg Asp Ser Ile Val Asn Thr Pro Ser Phe Thr
            580                 585                 590

Ile Thr Gly Gln Val Asp Lys Glu Ala Ala Val Ser Val Asn Gly Lys
        595                 600                 605

Glu Ile Ser Leu Gln Lys Asp Gly Ser Phe Ser Thr Thr Val Val Leu
    610                 615                 620

Asn Asp Gly Leu Asn Thr Ile Thr Val Gly Ala Val Asp Ala Ala Gly
625                 630                 635                 640

Asn Gln Ala Ile Pro Ala Val Leu Lys Ile Val Tyr Asp His Glu Lys
                645                 650                 655

Pro Val Ser Ile Asp Asp Leu Lys Gly Lys Asn Gly Asn His
            660                 665                 670

Tyr Asn Val Ile Tyr Asn Pro Leu Pro Ile Thr Gly Lys Leu Asn Glu
        675                 680                 685

Ala Gly Thr Val Met Val Asn Gly Glu Lys Val Asn Val Ser Glu Lys
    690                 695                 700

Leu Thr Phe Ser Thr Lys Val Ile Leu Lys Pro Gly Leu Asn Asn Ile
705                 710                 715                 720

Thr Ile Thr Ala Val Asp Gln Ala Gly Asn Glu Ala Glu Ser Ile Thr
                725                 730                 735

Ile Asn Val Val Pro Lys Gly Asn Ala Val Pro Asp Gly Pro Val Lys
            740                 745                 750

Ile Ile Lys Ser Glu Thr Thr Asn Ala Asn Thr Val Glu Val Thr Phe
        755                 760                 765

Asn Ser Lys Leu Glu Lys Phe Asp Ser Asp Ile Ala Leu Gln Thr
    770                 775                 780

Ala Thr Asn Val Trp Ala Ala Leu Asn Pro Gly Leu Lys Gln Leu Met
785                 790                 795                 800

Thr Val Glu Ser Ile Thr Thr Lys Val Asn Lys Asp Asn Gln Thr Val
                805                 810                 815

Ala Val Ile Lys Thr Lys Glu Ala Phe Gln Glu Asp Gly Thr Ile Thr
            820                 825                 830

Leu Pro Lys Val Glu Asp Pro Phe His Ile Gln Tyr Leu Asn Ala Asp
        835                 840                 845

Tyr Tyr Thr Gly Asp Arg Thr Gln Asp Ile Lys His Ala Asp Ala Leu
    850                 855                 860

Leu Thr Trp Gln Met Asp His Gly Gly Trp Phe Lys Asn Trp Val Glu
865                 870                 875                 880

Lys Tyr Lys Arg Pro Trp Asp Gly Lys Glu Pro Lys Ser Glu Trp Tyr
                885                 890                 895

Ser Thr Asn His Gly Glu Leu Gly Thr Ile Asp Asn Asp Ala Thr Thr
            900                 905                 910
```

```
Asn Glu Ile Leu Phe Leu Ala Leu Met Tyr Lys Glu Thr Gly Asp Ala
        915                 920                 925
Arg Tyr Lys Asp Ser Val Leu Lys Gly Ile Asp Phe Leu Leu Glu Met
        930                 935                 940
Gln Val Asp Ser Gly Gly Trp Pro Gln Val Tyr Pro Ala Arg Ser Gly
945                 950                 955                 960
Tyr Ser Asp Tyr Val Thr Phe Asn Asp Asn Ala Met Val Arg Val Met
            965                 970                 975
Ser Val Leu Thr Met Val Lys Glu Lys Lys Tyr Pro Phe Asn Ser Asn
                980                 985                 990
Leu Gly Asp Glu Gln Leu Ser Glu Gln Ile Asp Asp Ala Leu Gly Arg
            995                1000                1005
Gly Leu Asp Tyr Met Leu Lys Ser Gln Ile Lys Val Asp Gly Glu Val
       1010                1015                1020
Thr Ala Trp Cys Ala Gln His Asp Pro Val Thr Tyr Glu Pro Lys Gly
1025                1030                1035                1040
Ala Arg Ala Tyr Glu His Pro Ser Ile Ser Gly Ser Glu Ser Val Gly
            1045                1050                1055
Ile Val Gln Tyr Leu Met Ser Leu Pro Asn Pro Ser Thr Glu Val Gln
            1060                1065                1070
Ala Ala Ile His Gly Ala Leu Asn Trp Phe Glu Glu Ala Lys Leu Ala
            1075                1080                1085
Gly Thr Lys Tyr Val Ser Gly Asp Pro Asn Gly Gln Tyr Phe Tyr Pro
       1090                1095                1100
Asp Ala Asn Ser Asn Thr Trp Tyr Arg Phe Tyr Glu Ile Gly Thr Asn
1105                1110                1115                1120
Arg Pro Ile Phe Ser Gly Arg Asp Gly Val Ile Lys His Asn Ile Leu
            1125                1130                1135
Glu Ile Glu Lys Glu Arg Arg Asp Gly Tyr Arg Trp Ala Gly Glu Trp
            1140                1145                1150
Pro Gln Lys Leu Leu Asn Ile Ala Asn Thr Thr Gly Tyr Tyr Glu Asn
            1155                1160                1165
Arg Val Tyr Val Glu Val Val Gly Asp Gln Ser Lys Asn Ala Ala Gly
       1170                1175                1180
Glu Ser Leu Glu Ile Gly Asn Leu Tyr Arg Ile Glu Ala Ser Ala Ser
1185                1190                1195                1200
Gly Ser Thr Ser Lys
            1205

<210> SEQ ID NO 85
<211> LENGTH: 1152
<212> TYPE: DNA
<213> ORGANISM: Unknown
<220> FEATURE:
<223> OTHER INFORMATION: Obtained from an environmental sample

<400> SEQUENCE: 85
atgtcggttg gaccaggtgc taatccgaaa gctcgtgttc catggtccaa acagttatcg     60
ggtgttgagg caaagctgtt tcagcgcgag cggttcttca gcctcgctgc ggagcacact    120
tctaagaaaa atgatcagga agtcggcgcg atcgcgtgga agatgcaca tggaaagccg     180 gatgagtggt atgcgagtgt tgaggcactg cggatggccg ataacgtcgt tctctatcaa    240
cgcgactcag gtggttggcc caagaacatc gacatggcga aggcactcaa cgatcgtgag    300
caggctgcga tcctccgcca gaagaaaaag aacgactcca cgatcgacaa tggtgcgact    360
```

-continued

| | |
|---|---|
| cacacacagt tatcctttct ggcgcgcgtc tatacagcac agcgtcagga gcgacatcgc | 420 |
| gagtcgtttt tcaaaggatt ggattactta ctgaatgcgc agtatccaaa tggaggctgg | 480 |
| ccgcagtttt atccgaaccc gacgggctat cacaagcaca ttacttacaa cgacggtgcg | 540 |
| atgattggtg tgatgaaggt gctgcgcgat atcgctgcgg cgaagccttt gtacgctttt | 600 |
| gtcgacgaag ctcggcgcgc gaaggcgacg agtgcagttg aaaaagggat cgagtgcatt | 660 |
| ttgaaaacgc aggtggtggt agatgggcgt cgcactgtgt ggagtgcgca acatgatgaa | 720 |
| gtaacgttag cgccagctcc tgcgcgaacc ttcgagttaa cttcgttgag cggcggtgag | 780 |
| agcgtagata tcgttcgatt tttaatgtcg atcaaggatc cgtcgcctaa agtagttgat | 840 |
| gcggttgaat cggcggttaa gtggtttgag caatcggagt taaaaggcgt gaagtgggtt | 900 |
| aagaaggcgg acgcttctaa acctggcggg tttgattgcg tcgtagttaa ggatccggag | 960 |
| agctcggttt gggcgcgctt ttatgagatt ggcacgaacc ggccgatctt ttccgggcgc | 1020 |
| gatggagtgg tcaaatacga cgtggcgcag atcgaacacg agcggcggac gaattatgag | 1080 |
| tggtacgttg atgaagcagc caagctgctg aagaaagagt atccggcctg gcggaaaaga | 1140 |
| acatctctgt ga | 1152 |

<210> SEQ ID NO 86
<211> LENGTH: 383
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(383)
<223> OTHER INFORMATION: Catalytic domain

<400> SEQUENCE: 86

```
Met Ser Val Gly Pro Gly Ala Asn Pro Lys Ala Arg Val Pro Trp Ser
 1               5                  10                  15

Lys Gln Leu Ser Gly Val Glu Ala Lys Leu Phe Gln Arg Glu Arg Phe
            20                  25                  30

Phe Ser Leu Ala Ala Glu His Thr Ser Lys Lys Asn Asp Gln Glu Val
        35                  40                  45

Gly Ala Ile Ala Trp Lys Asp Ala His Gly Lys Pro Asp Glu Trp Tyr
    50                  55                  60

Ala Ser Val Glu Ala Leu Arg Met Ala Asp Asn Val Val Leu Tyr Gln
65                  70                  75                  80

Arg Asp Ser Gly Gly Trp Pro Lys Asn Ile Asp Met Ala Lys Ala Leu
                85                  90                  95

Asn Asp Arg Glu Gln Ala Ala Ile Leu Arg Gln Lys Lys Lys Asn Asp
            100                 105                 110

Ser Thr Ile Asp Asn Gly Ala Thr His Thr Gln Leu Ser Phe Leu Ala
        115                 120                 125

Arg Val Tyr Thr Ala Gln Arg Gln Glu Arg His Arg Glu Ser Phe Phe
    130                 135                 140

Lys Gly Leu Asp Tyr Leu Leu Asn Ala Gln Tyr Pro Asn Gly Gly Trp
145                 150                 155                 160

Pro Gln Phe Tyr Pro Asn Pro Thr Gly Tyr His Lys His Ile Thr Tyr
                165                 170                 175

Asn Asp Gly Ala Met Ile Gly Val Met Lys Val Leu Arg Asp Ile Ala
            180                 185                 190

Ala Ala Lys Pro Leu Tyr Ala Phe Val Asp Glu Ala Arg Arg Ala Lys
```

```
                195                 200                 205
Ala Thr Ser Ala Val Glu Lys Gly Ile Glu Cys Ile Leu Lys Thr Gln
    210                 215                 220

Val Val Val Asp Gly Arg Arg Thr Val Trp Ser Ala Gln His Asp Glu
225                 230                 235                 240

Val Thr Leu Ala Pro Ala Pro Ala Arg Thr Phe Glu Leu Thr Ser Leu
            245                 250                 255

Ser Gly Gly Glu Ser Val Asp Ile Val Arg Phe Leu Met Ser Ile Lys
        260                 265                 270

Asp Pro Ser Pro Lys Val Asp Ala Val Glu Ser Ala Val Lys Trp
    275                 280                 285

Phe Glu Gln Ser Glu Leu Lys Gly Val Lys Trp Val Lys Lys Ala Asp
290                 295                 300

Ala Ser Lys Pro Gly Gly Phe Asp Cys Val Val Lys Asp Pro Glu
305                 310                 315                 320

Ser Ser Val Trp Ala Arg Phe Tyr Glu Ile Gly Thr Asn Arg Pro Ile
            325                 330                 335

Phe Ser Gly Arg Asp Gly Val Val Lys Tyr Asp Val Ala Gln Ile Glu
        340                 345                 350

His Glu Arg Arg Thr Asn Tyr Glu Trp Tyr Val Asp Glu Ala Ala Lys
    355                 360                 365

Leu Leu Lys Lys Glu Tyr Pro Ala Trp Arg Lys Arg Thr Ser Leu
370                 375                 380
```

<210> SEQ ID NO 87
<211> LENGTH: 1698
<212> TYPE: DNA
<213> ORGANISM: Unknown
<220> FEATURE:
<223> OTHER INFORMATION: Obtained from an environmental sample

<400> SEQUENCE: 87

```
atgtctacta caaaatgttt taacacagcc ccaggtttta ccctgaaagc agtcgcagca      60
gcagtggcga tgtttgcagg ttcttcagta ttcgcagcgg ctacaggtgg tttttccacg    120
actgatggcg gtgcggcaag cggctcgcaa tccttcacgg cggccaacct tgaccagctc    180
aacaccattg ttgccaatgc gaagagtggc ggttacccgg ttgtgattac ctataccggt    240
aatgaagaca gcttgattaa ccagatgatc aaagaccaca ccgtggattc ttcaggcaac    300
tgcccgaacc cacgctggag tgaaacctac cgcaaggtag aaattaagga gatgaccaaa    360
ggtgtcacca tcatcggtgc caatggttct tcggcaaact tcggtattgt ggtgaacaag    420
tccagcaatg tgattatccg caacatgaaa atcggtgcgc tggccggtgc agcaacgac    480
gcggatatga ttcgtatcga tagcggcact aacgtatggg ttgaccacaa cgaattgttc    540
gcggtgaaca acgaatgtaa aggttcaccg gatggcgatt tgaccttcga agcgccatc    600
gacatcaaga agattcaca caacatcacc gtgtcttaca acctgattcg cgacagcaaa    660
aaagtgggcc ttgatggttc agcagcagc gatatcgccg gtggccgcga gatcactttc    720
caccacaaca tttacaaaaa cgtgaatgca cgcttgccgt tgcaacgcgg tggctggacg    780
cacatgtata caacctgta cgacggcatt accggttccg gtatcaacgt acgtcaggcc    840
ggttatgcgt tgattgaaag caactggttc caaaatgcgg ttaacccggt gacttgccgt    900
tacgacagca gcaactgcgg tttctgggat ctgcgcaata caacgtgaa gtcgccagca    960
gatttcgcga cctataacat cacctggacc agcggcggca ctattgatgc aaccaactgg   1020
```

-continued

```
acgaccaccg ctccgttccc gatcagcatt ccttacagct actcgccggt gtctccacag    1080
tgcgtgaagg acaagttggc cagcgttgcg ggtgtgggta aaaacggtgc agttctgaac    1140
tcatcagtgt gtggtggaag cagctctgtt ccatcatcaa gctcagtcgc tactacttcc    1200
aaatcatcca gctcggtagc aaccagcaag tccagctccg tcgctacgac gtccagtaag    1260
tcatccagct cggtagtgcc atcatcatca agctcaagtt cagtggttaa taacggcagc    1320
atcgcgttaa ccgccactgc taccggcaat agcattgtcc tgagctggtc gccgaacaac    1380
ctgacactgg gcacccagga ggtgtatcgc gataccgatt cagacccaag tggccgtgtg    1440
cgtattgctg ccctgagttc cagcactcgc atgtacaccg atgccactgc atcggcgggc    1500
caaacgttct actactggat caaaaacacc accaacggtg taaccaccaa ttccaatgcg    1560
gcttcggcgg caattggcga tgcagctcgc gccattcgcg catgcgcagg aaaccgagga    1620
agtggcgctc gcaccagtcg cgcagtttcg actgggtcaa atcctcgtgg gcctgccggt    1680
agccatccca gagcttga                                                  1698
```

<210> SEQ ID NO 88
<211> LENGTH: 565
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(32)
<220> FEATURE:
<221> NAME/KEY: DOMAIN
<222> LOCATION: (33)...(375)
<223> OTHER INFORMATION: Catalytic domain

<400> SEQUENCE: 88

```
Met Ser Thr Thr Lys Cys Phe Asn Thr Ala Pro Gly Phe Thr Leu Lys
  1               5                  10                  15

Ala Val Ala Ala Val Ala Met Phe Ala Gly Ser Ser Val Phe Ala
             20                  25                  30

Ala Ala Thr Gly Gly Phe Ser Thr Thr Asp Gly Gly Ala Ala Ser Gly
         35                  40                  45

Ser Gln Ser Phe Thr Ala Ala Asn Leu Asp Gln Leu Asn Thr Ile Val
     50                  55                  60

Ala Asn Ala Lys Ser Gly Gly Tyr Pro Val Val Ile Thr Tyr Thr Gly
 65                  70                  75                  80

Asn Glu Asp Ser Leu Ile Asn Gln Met Ile Lys Asp His Thr Val Asp
                 85                  90                  95

Ser Ser Gly Asn Cys Pro Asn Pro Arg Trp Ser Glu Thr Tyr Arg Lys
            100                 105                 110

Val Glu Ile Lys Glu Met Thr Lys Gly Val Thr Ile Ile Gly Ala Asn
        115                 120                 125

Gly Ser Ser Ala Asn Phe Gly Ile Val Val Asn Lys Ser Ser Asn Val
    130                 135                 140

Ile Ile Arg Asn Met Lys Ile Gly Ala Leu Ala Gly Ala Ser Asn Asp
145                 150                 155                 160

Ala Asp Met Ile Arg Ile Asp Ser Gly Thr Asn Val Trp Val Asp His
                165                 170                 175

Asn Glu Leu Phe Ala Val Asn Asn Glu Cys Lys Gly Ser Pro Asp Gly
            180                 185                 190

Asp Leu Thr Phe Glu Ser Ala Ile Asp Ile Lys Lys Asp Ser His Asn
        195                 200                 205
```

```
Ile Thr Val Ser Tyr Asn Leu Ile Arg Asp Ser Lys Lys Val Gly Leu
    210                 215                 220

Asp Gly Ser Ser Ser Asp Ile Ala Gly Gly Arg Glu Ile Thr Phe
225                 230                 235                 240

His His Asn Ile Tyr Lys Asn Val Asn Ala Arg Leu Pro Leu Gln Arg
                245                 250                 255

Gly Gly Trp Thr His Met Tyr Asn Asn Leu Tyr Asp Gly Ile Thr Gly
                260                 265                 270

Ser Gly Ile Asn Val Arg Gln Ala Gly Tyr Ala Leu Ile Glu Ser Asn
                275                 280                 285

Trp Phe Gln Asn Ala Val Asn Pro Val Thr Cys Arg Tyr Asp Ser Ser
290                 295                 300

Asn Cys Gly Phe Trp Asp Leu Arg Asn Asn Val Lys Ser Pro Ala
305                 310                 315                 320

Asp Phe Ala Thr Tyr Asn Ile Thr Trp Thr Ser Gly Gly Thr Ile Asp
                325                 330                 335

Ala Thr Asn Trp Thr Thr Thr Ala Pro Phe Pro Ile Ser Ile Pro Tyr
                340                 345                 350

Ser Tyr Ser Pro Val Ser Pro Gln Cys Val Lys Asp Lys Leu Ala Ser
                355                 360                 365

Val Ala Gly Val Gly Lys Asn Gly Ala Val Leu Asn Ser Ser Val Cys
                370                 375                 380

Gly Gly Ser Ser Ser Val Pro Ser Ser Ser Val Ala Thr Thr Ser
385                 390                 395                 400

Lys Ser Ser Ser Val Ala Thr Ser Lys Ser Ser Val Ala Thr
                405                 410                 415

Thr Ser Ser Lys Ser Ser Ser Val Val Pro Ser Ser Ser Ser
                420                 425                 430

Ser Ser Val Val Asn Asn Gly Ser Ile Ala Leu Thr Ala Thr
                435                 440                 445

Gly Asn Ser Ile Val Leu Ser Trp Ser Pro Asn Asn Leu Thr Leu Gly
450                 455                 460

Thr Gln Glu Val Tyr Arg Asp Thr Asp Ser Asp Pro Ser Gly Arg Val
465                 470                 475                 480

Arg Ile Ala Ala Leu Ser Ser Ser Thr Arg Met Tyr Thr Asp Ala Thr
                485                 490                 495

Ala Ser Ala Gly Gln Thr Phe Tyr Tyr Trp Ile Lys Asn Thr Thr Asn
                500                 505                 510

Gly Val Thr Thr Asn Ser Asn Ala Ala Ser Ala Ile Gly Asp Ala
                515                 520                 525

Ala Arg Ala Ile Arg Ala Cys Ala Gly Asn Arg Gly Ser Gly Ala Arg
                530                 535                 540

Thr Ser Arg Ala Val Ser Thr Gly Ser Asn Pro Arg Gly Pro Ala Gly
545                 550                 555                 560

Ser His Pro Arg Ala
                565

<210> SEQ ID NO 89
<211> LENGTH: 1377
<212> TYPE: DNA
<213> ORGANISM: Unknown
<220> FEATURE:
<223> OTHER INFORMATION: Obtained from an environmental sample

<400> SEQUENCE: 89
```

```
atgacgacgc gacgcgaatt cattcgagat cttttggttg gcggcgtagt ggtcgctgtt      60
gcaccgcgtt tcctggcgtt ttcttcggtg gcgagtccgt gggaaacggt gatgccttcg     120
atcctcgaac gcatcaagcc accgcgtttt ccgaaacgca cgtgctatct caaccggttt     180
ggagcaaaag gcgacgggca aactgattgc acttcagctt ttcgacgcgc aatcgatcag     240
tgttcgaaag cgggcggtgg caaagtgatc gttccgcagg gaatgtatct caccggcgca     300
attcacttga agagcaacgt caatctcgag atctccgaag gcgcgacgat caagttcagt     360
caaaacccga agactatct cccggtggtt ttttcgcgtt gggaaggcgt cgaagtattc     420
aactactcac ctttcatcta cgcatttgaa cagcagaaca tcgcgatcac gggcaagggc     480
acgctcgatg gcagagtga taacgaacac tggtggccat ggaacggacg cgccaggtac     540
ggttggaaag aagggatgag ccaccagcgt ccggatcgaa acgcgctctt tgcgatggcg     600
gaaaaaggtg tttcggttcg cgaacgtgtt tcggcgagg gtcattactt aaggccgcag     660
ttcattcagc cgtatcgctg ccagaacgta ttgatcgacg gagttacgat acgaaactcg     720
ccgatgtggg aaattcatcc ggtgctgtgc cggaatgtca tcgtgcaaaa cgtgcacatt     780
aacagtcatg gaccaaacaa cgatggctgc aatcccgagt cgtgcactga tgtgctgatt     840
aagaactgtt acttcgacac tggcgacgac tgtatcgcgg tcaaatcagg acgcaacgcg     900
gacggccggc ggcttaaagc gccgacagag aacgtgatcg tgcaagactg tcaaatgaaa     960
gatggacacg gcgggatcac tgtcggcagt gagatctcag gcggtgtgag aaatctgttt    1020
gcggagaact gccggcttga tagtccaaac ctggaccatg ctttgcgggt taagaacaac    1080
gcgatgcgtg gagggctgct cgagaatttg cacttccgaa acatcgaagt tggtcaggtg    1140
gcgcatgcag tgatcacgat cgattttaat tacgaggaag gcgcgaaagg atcgttcacg    1200
ccggtggttc gtgactacac tgtcgatggt ttgcgcagca cgcgaagcaa atacgcgctc    1260
gacgttcaag gtctgtcggg gcgcgccgatc gtaaatctgc gtctgacgaa ttgcacgttc    1320
gacaatgttg ccgaagggaa cgtcgtgaag aatgttaagg acgcgacaat tcaaaaa      1377
```

<210> SEQ ID NO 90
<211> LENGTH: 459
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(31)
<220> FEATURE:
<221> NAME/KEY: DOMAIN
<222> LOCATION: (32)...(459)
<223> OTHER INFORMATION: Catalytic domain

<400> SEQUENCE: 90

Met Thr Thr Arg Arg Glu Phe Ile Arg Asp Leu Leu Val Gly Val
 1               5                  10                  15

Val Val Ala Val Ala Pro Arg Phe Leu Ala Phe Ser Ser Val Ala Ser
            20                  25                  30

Pro Trp Glu Thr Val Met Pro Ser Ile Leu Glu Arg Ile Lys Pro Pro
        35                  40                  45

Arg Phe Pro Lys Arg Thr Cys Tyr Leu Asn Arg Phe Gly Ala Lys Gly
    50                  55                  60

Asp Gly Gln Thr Asp Cys Thr Ser Ala Phe Arg Arg Ala Ile Asp Gln
65                  70                  75                  80

-continued

Cys Ser Lys Ala Gly Gly Lys Val Ile Val Pro Gln Gly Met Tyr
            85                  90                  95

Leu Thr Gly Ala Ile His Leu Lys Ser Asn Val Asn Leu Glu Ile Ser
            100                 105                 110

Glu Gly Ala Thr Ile Lys Phe Ser Gln Asn Pro Lys Asp Tyr Leu Pro
            115                 120                 125

Val Val Phe Ser Arg Trp Glu Gly Val Glu Val Phe Asn Tyr Ser Pro
130                 135                 140

Phe Ile Tyr Ala Phe Glu Gln Gln Asn Ile Ala Ile Thr Gly Lys Gly
145                 150                 155                 160

Thr Leu Asp Gly Gln Ser Asp Asn Glu His Trp Trp Pro Trp Asn Gly
            165                 170                 175

Arg Ala Arg Tyr Gly Trp Lys Glu Gly Met Ser His Gln Arg Pro Asp
            180                 185                 190

Arg Asn Ala Leu Phe Ala Met Ala Glu Lys Gly Val Ser Val Arg Glu
            195                 200                 205

Arg Val Phe Gly Glu Gly His Tyr Leu Arg Pro Gln Phe Ile Gln Pro
            210                 215                 220

Tyr Arg Cys Gln Asn Val Leu Ile Asp Gly Val Thr Ile Arg Asn Ser
225                 230                 235                 240

Pro Met Trp Glu Ile His Pro Val Leu Cys Arg Asn Val Ile Val Gln
            245                 250                 255

Asn Val His Ile Asn Ser His Gly Pro Asn Asn Asp Gly Cys Asn Pro
            260                 265                 270

Glu Ser Cys Thr Asp Val Leu Ile Lys Asn Cys Tyr Phe Asp Thr Gly
            275                 280                 285

Asp Asp Cys Ile Ala Val Lys Ser Gly Arg Asn Ala Asp Gly Arg Arg
290                 295                 300

Leu Lys Ala Pro Thr Glu Asn Val Ile Val Gln Asp Cys Gln Met Lys
305                 310                 315                 320

Asp Gly His Gly Gly Ile Thr Val Gly Ser Glu Ile Ser Gly Val
            325                 330                 335

Arg Asn Leu Phe Ala Glu Asn Cys Arg Leu Asp Ser Pro Asn Leu Asp
            340                 345                 350

His Ala Leu Arg Val Lys Asn Asn Ala Met Arg Gly Gly Leu Leu Glu
            355                 360                 365

Asn Leu His Phe Arg Asn Ile Glu Val Gly Gln Val Ala His Ala Val
            370                 375                 380

Ile Thr Ile Asp Phe Asn Tyr Glu Glu Gly Ala Lys Gly Ser Phe Thr
385                 390                 395                 400

Pro Val Val Arg Asp Tyr Thr Val Asp Gly Leu Arg Ser Thr Arg Ser
                405                 410                 415

Lys Tyr Ala Leu Asp Val Gln Gly Leu Ser Gly Ala Pro Ile Val Asn
                420                 425                 430

Leu Arg Leu Thr Asn Cys Thr Phe Asp Asn Val Ala Glu Gly Asn Val
            435                 440                 445

Val Lys Asn Val Lys Asp Ala Thr Ile Gln Lys
450                 455

<210> SEQ ID NO 91
<211> LENGTH: 1125
<212> TYPE: DNA
<213> ORGANISM: Unknown
<220> FEATURE:
<223> OTHER INFORMATION: Obtained from an environmental sample

<400> SEQUENCE: 91

```
gtggtcctag gtaataacgg cggcagcttg agttgcgtcc aatatattgt gattgtgaaa      60
ggacccggtg gacctcgacc gccggtgaaa ccggccgtcc aggcgcccgt tagggttacc    120
tggagcgcat ccctagtcca gcggcccgaa tggtacggga gtgacgaagc gatccgcatc    180
gcggacaacg tcctcctcta ccagcgcaac accggcgggt ggccgaagga catagatatg    240
gccgagccca tcccggaaca caggaagtcc tttttcctca ccgagaagga gcggaccgat    300
gactcgacca tcgacaacgg tgccaccgtg acccagctca gtatctcgcc cgcgtctac     360
aaggcgacca ggctggaacg gttcaaggag ggcttcctca aggtctcga ctacctcttg     420
gccgcccagt acccgaacgg cggctggccc cagtattatc ctaacttgag gggctactac    480
gccaacatca cttataacga caatgccatg gtgaacgtgc tcaccctcct ccagagcatc    540
gccaaaaagg ccccggagta cgacttcgtc gacccggcgc gccgggagaa ggccgcccgg    600
gccgtggcga aagggatcga ctgcatcctc aagacccaga tccgtgtcaa tggaaaactt    660
accgcctggt gcgcccagca tgacgccaag acgctggcgc ccgcgccggc ccgttcgtat    720
gagcttgagt ccatcagcgg tttcgagagc gtcgggatcg tccggttctt aatgagcctc    780
gagaatccga gcccgaaggt catcgaggcg gtagaggccg ccgtgaaatg gttcgaggag    840
gtcaagctta ccgggatcaa ggtggtcgag aaacccgacc cgtcccttcc gggcggttac    900
gaccgcgtgg tggtcgaaga ccccaacgcg ccgcccatct gggcccggtt ctacgagatc    960
ggcaccaacc gtcccttctt ctgcggccgc gatggtatca aaaaatacag cctggcggag   1020
atcgaacacg aacgccgggt cggttactcc tggtacacca tgccccggc ctacctcatc    1080
gagaaggagt atccgctctg gcgggccaaa caccctacca gtaa                    1125
```

<210> SEQ ID NO 92
<211> LENGTH: 374
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(374)

<400> SEQUENCE: 92

```
Met Val Leu Gly Asn Asn Gly Gly Ser Leu Ser Cys Val Gln Tyr Ile
  1               5                  10                  15

Val Ile Val Lys Gly Pro Gly Pro Arg Pro Val Lys Pro Ala
                 20                  25                  30

Val Gln Ala Pro Val Arg Val Thr Trp Ser Ala Ser Leu Val Gln Arg
             35                  40                  45

Pro Glu Trp Tyr Gly Ser Asp Glu Ala Ile Arg Ile Ala Asp Asn Val
         50                  55                  60

Leu Leu Tyr Gln Arg Asn Thr Gly Gly Trp Pro Lys Asp Ile Asp Met
 65                  70                  75                  80

Ala Glu Pro Ile Pro Glu His Arg Lys Ser Phe Phe Leu Thr Glu Lys
                 85                  90                  95

Glu Arg Thr Asp Asp Ser Thr Ile Asp Asn Gly Ala Thr Val Thr Gln
            100                 105                 110

Leu Lys Tyr Leu Ala Arg Val Tyr Lys Ala Thr Arg Leu Glu Arg Phe
        115                 120                 125

Lys Glu Gly Phe Leu Lys Gly Leu Asp Tyr Leu Leu Ala Ala Gln Tyr
```

```
              130                 135                 140
Pro Asn Gly Gly Trp Pro Gln Tyr Tyr Pro Asn Leu Arg Gly Tyr Tyr
145                 150                 155                 160

Ala Asn Ile Thr Tyr Asn Asp Asn Ala Met Val Asn Val Leu Thr Leu
                165                 170                 175

Leu Gln Ser Ile Ala Lys Lys Ala Pro Glu Tyr Asp Phe Val Asp Pro
            180                 185                 190

Ala Arg Arg Glu Lys Ala Ala Arg Ala Val Ala Lys Gly Ile Asp Cys
        195                 200                 205

Ile Leu Lys Thr Gln Ile Arg Val Asn Gly Lys Leu Thr Ala Trp Cys
210                 215                 220

Ala Gln His Asp Ala Lys Thr Leu Ala Pro Ala Pro Ala Arg Ser Tyr
225                 230                 235                 240

Glu Leu Glu Ser Ile Ser Gly Phe Glu Ser Val Gly Ile Val Arg Phe
                245                 250                 255

Leu Met Ser Leu Glu Asn Pro Ser Pro Lys Val Ile Glu Ala Val Glu
            260                 265                 270

Ala Ala Val Lys Trp Phe Glu Glu Val Lys Leu Thr Gly Ile Lys Val
        275                 280                 285

Val Glu Lys Pro Asp Pro Ser Leu Pro Gly Gly Tyr Asp Arg Val Val
290                 295                 300

Val Glu Asp Pro Asn Ala Pro Pro Ile Trp Ala Arg Phe Tyr Glu Ile
305                 310                 315                 320

Gly Thr Asn Arg Pro Phe Phe Cys Gly Arg Asp Gly Ile Lys Lys Tyr
                325                 330                 335

Ser Leu Ala Glu Ile Glu His Glu Arg Arg Val Gly Tyr Ser Trp Tyr
            340                 345                 350

Thr Asn Ala Pro Ala Tyr Leu Ile Glu Lys Glu Tyr Pro Leu Trp Arg
        355                 360                 365

Ala Lys His Pro Thr Lys
    370
```

<210> SEQ ID NO 93
<211> LENGTH: 1062
<212> TYPE: DNA
<213> ORGANISM: Unknown
<220> FEATURE:
<223> OTHER INFORMATION: Obtained from an environmental sample

<400> SEQUENCE: 93

```
gtggatccaa agaattggaa cccgaaaaaa gccgacgatt catggctcga aaagacgaaa      60
cccgattacc ggctggtctc ctggcgcgac gttttagatc aaactcagct ctggtacgcg     120
gtcgacgaag cgacgcgcat cgccaaccag gttttgctct ttcagcgcga taacggcggc     180
tgggaaaaaa acgtcgacat ggcggcgatg ctcactcaag ccgaacgaga aaaactcgtc     240
aaagaaaaat ctcacaccga tacgaccatc gacaacggcg cgacgaccac gcagctgcgt     300
tatctggcaa aagtcatcac ggcgaaaaac atcgaagctc ataaacagtc gtttctcaag     360
ggattggatt ttctgctcgc gatgcagtat gaaaacggag gatttccgca atattatcct     420
ttgaaaaacg attattcgcg cgagattact ttcaacgacg acgcgatgat caatgttctt     480
aaattgctgc gcgacgtggc aaaaaagaag gaagattatt tattcgtcga cgaagaccgg     540
cgcgccagag cggaaggcgc ggtcgaaaaa ggcgtccgcc tgatcttgaa acacacaggtc    600
gccatcgacg gcaaaaaaac gatctgggcg gcgcagtacg acgaaaacac tttgaaaccg     660
```

```
gcaaatgcga gaaagtttga gcccgcctcg ctcgcttcgc gcgaatcggt cagcgtggtc    720
agatttttga tgctcgacgc caaacccgac gaggaaaaaa tcggagcgat cgaatcggcg    780
atcgaatggt ttcaaaaaaa caaactgagc ggcattcgct gggaatcgaa aagcggagaa    840
aacctggtcg tcaaagacaa agcggcgccg ccgatctggg gaaggtttta tcaattcgaa    900
accatgcgcc ccattttat cgggcgcgac gcggtgattc gctacgatgt catgcaaatc    960
gaagccgaac gccgcaacgg ctacggctgg tacacgaacg agccgaacga gcttttggac   1020
aaagattatc cgaaatggaa agagaaaatt aagaaaaatt ag                       1062
```

<210> SEQ ID NO 94
<211> LENGTH: 353
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(353)

<400> SEQUENCE: 94

```
Met Asp Pro Lys Asn Trp Asn Pro Lys Lys Ala Asp Asp Ser Trp Leu
 1               5                  10                  15

Glu Lys Thr Lys Pro Asp Tyr Arg Leu Val Ser Trp Arg Asp Val Leu
            20                  25                  30

Asp Gln Thr Gln Leu Trp Tyr Ala Val Asp Glu Ala Thr Arg Ile Ala
        35                  40                  45

Asn Gln Val Leu Leu Phe Gln Arg Asp Asn Gly Gly Trp Glu Lys Asn
    50                  55                  60

Val Asp Met Ala Ala Met Leu Thr Gln Ala Glu Arg Glu Lys Leu Val
65                  70                  75                  80

Lys Glu Lys Ser His Thr Asp Thr Thr Ile Asp Asn Gly Ala Thr Thr
                85                  90                  95

Thr Gln Leu Arg Tyr Leu Ala Lys Val Ile Thr Ala Lys Asn Ile Glu
            100                 105                 110

Ala His Lys Gln Ser Phe Leu Lys Gly Leu Asp Phe Leu Leu Ala Met
        115                 120                 125

Gln Tyr Glu Asn Gly Gly Phe Pro Gln Tyr Tyr Pro Leu Lys Asn Asp
    130                 135                 140

Tyr Ser Arg Glu Ile Thr Phe Asn Asp Asp Ala Met Ile Asn Val Leu
145                 150                 155                 160

Lys Leu Leu Arg Asp Val Ala Lys Lys Lys Glu Asp Tyr Leu Phe Val
                165                 170                 175

Asp Glu Asp Arg Arg Ala Arg Ala Glu Gly Ala Val Glu Lys Gly Val
            180                 185                 190

Arg Leu Ile Leu Lys Thr Gln Val Ala Ile Asp Gly Lys Lys Thr Ile
        195                 200                 205

Trp Ala Ala Gln Tyr Asp Glu Asn Thr Leu Lys Pro Ala Asn Ala Arg
    210                 215                 220

Lys Phe Glu Pro Ala Ser Leu Ala Ser Arg Glu Ser Val Ser Val Val
225                 230                 235                 240

Arg Phe Leu Met Leu Asp Ala Lys Pro Asp Glu Glu Lys Ile Gly Ala
                245                 250                 255

Ile Glu Ser Ala Ile Glu Trp Phe Gln Lys Asn Lys Leu Ser Gly Ile
            260                 265                 270

Arg Trp Glu Ser Lys Ser Gly Glu Asn Leu Val Val Lys Asp Lys Ala
```

-continued

```
              275                 280                 285
Ala Pro Pro Ile Trp Gly Arg Phe Tyr Gln Phe Glu Thr Met Arg Pro
    290                 295                 300

Ile Phe Ile Gly Arg Asp Ala Val Ile Arg Tyr Asp Val Met Gln Ile
305                 310                 315                 320

Glu Ala Glu Arg Arg Asn Gly Tyr Gly Trp Tyr Thr Asn Glu Pro Asn
                325                 330                 335

Glu Leu Leu Asp Lys Asp Tyr Pro Lys Trp Lys Glu Lys Ile Lys Lys
            340                 345                 350

Asn
```

<210> SEQ ID NO 95
<211> LENGTH: 1074
<212> TYPE: DNA
<213> ORGANISM: Unknown
<220> FEATURE:
<223> OTHER INFORMATION: Obtained from an environmental sample

<400> SEQUENCE: 95

| | | | | | |
|---|---|---|---|---|---|
| atgacgctac | ccgttgtttc | cctgcgcgta | ctgctggcgc | tgctggccac | gtcgccggtc | 60 |
| gcctgcgcgg | gcgccgcggc | acccgcgact | gcgaccgatc | cggtcgccga | gaacatgctg | 120 |
| cttctgcaga | ccgcctccgg | cggctggtcc | aagcactacc | gcgagaagaa | ggtcgactac | 180 |
| gcgcgcgact | acgacgccgc | cgagcgcgcc | cgctgcgcg | cgcccgaccg | gcatgacgat | 240 |
| gcgacgatcg | acaacaaggc | cacgaccacc | gagatcgcct | acctggtgca | ggcacatgcc | 300 |
| aggacgggca | atccggccta | cctcgacggc | gcgcgccgcg | gcgtcgagta | cctgctgcgc | 360 |
| gcccagtacc | cgaacggcgg | ctggccgcag | ttctaccccg | accattcgtc | ctaccggcac | 420 |
| cagatcacgc | tcaacgacga | tgcgatggtg | cacgccatca | ccgtgctgca | ggacatcgcc | 480 |
| gcgggccgca | acggcatgca | ggtgctggcc | cggagttcg | gcgtccgcgc | cgccgcggcc | 540 |
| gcgcagcgcg | gcatcggaaa | cctgctcgag | ttgcaggtgc | ggatcgccgg | ggtgccgacg | 600 |
| atatgggccg | cgcagtacga | cgagaccagc | ctgcaaccgg | ccaaggcccg | cgcgtacgaa | 660 |
| ctgccttcgc | tggccgtggc | cgaatcggtc | ggcgtggtgc | gcctgctgat | gccgcagccg | 720 |
| gcgcctgatg | cgcgcacggt | cgccgcgatc | gaggcggcgg | ccgactggct | ggaggcgcac | 780 |
| cgcctgccgg | acctcgccct | ggaacgcatc | gaagcccccg | ccgaggaaac | cggcaaggac | 840 |
| gtccgcgtcg | tggccagacc | gggcgcgtcg | ttgtgggcgc | gcttctacga | cctcgagcgg | 900 |
| caggtgccgc | tgttcgtcga | tcgcaacagc | cgtccggtgc | ccttcgccga | gcttcccaac | 960 |
| gagcgtcgta | ccggctatgg | ctggtatggc | acctggccgg | aaaagctgct | ggcacaggaa | 1020 |
| ctcccgcgct | ggcgcaaggt | ccatgcggcc | agcgcgggcg | ctccggcccg | ttga | 1074 |

<210> SEQ ID NO 96
<211> LENGTH: 357
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(31)
<220> FEATURE:
<221> NAME/KEY: DOMAIN
<222> LOCATION: (32)...(357)
<223> OTHER INFORMATION: Catalytic domain

<400> SEQUENCE: 96

```
Met Thr Leu Pro Val Val Ser Leu Arg Val Leu Ala Leu Leu Ala
 1               5                  10                  15

Thr Ser Pro Val Ala Cys Ala Gly Ala Ala Pro Ala Thr Ala Thr
            20                  25                  30

Asp Pro Val Ala Glu Asn Met Leu Leu Gln Thr Ala Ser Gly Gly
            35                  40                  45

Trp Ser Lys His Tyr Arg Glu Lys Lys Val Asp Tyr Ala Arg Asp Tyr
     50                  55                  60

Asp Ala Ala Glu Arg Ala Ala Leu Arg Ala Pro Asp Arg His Asp Asp
 65                  70                  75                  80

Ala Thr Ile Asp Asn Lys Ala Thr Thr Thr Glu Ile Ala Tyr Leu Val
                 85                  90                  95

Gln Ala His Ala Arg Thr Gly Asn Pro Ala Tyr Leu Asp Gly Ala Arg
                100                 105                 110

Arg Gly Val Glu Tyr Leu Leu Arg Ala Gln Tyr Pro Asn Gly Gly Trp
            115                 120                 125

Pro Gln Phe Tyr Pro Asp His Ser Ser Tyr Arg His Gln Ile Thr Leu
        130                 135                 140

Asn Asp Asp Ala Met Val His Ala Ile Thr Val Leu Gln Asp Ile Ala
145                 150                 155                 160

Ala Gly Arg Asn Gly Met Gln Val Leu Ala Pro Glu Phe Gly Val Arg
                165                 170                 175

Ala Ala Ala Ala Ala Gln Arg Gly Ile Gly Asn Leu Leu Glu Leu Gln
            180                 185                 190

Val Arg Ile Ala Gly Val Pro Thr Ile Trp Ala Ala Gln Tyr Asp Glu
        195                 200                 205

Thr Ser Leu Gln Pro Ala Lys Ala Arg Ala Tyr Glu Leu Pro Ser Leu
    210                 215                 220

Ala Val Ala Glu Ser Val Gly Val Val Arg Leu Leu Met Arg Gln Pro
225                 230                 235                 240

Ala Pro Asp Ala Arg Thr Val Ala Ala Ile Glu Ala Ala Asp Trp
                245                 250                 255

Leu Glu Ala His Arg Leu Pro Asp Leu Ala Leu Glu Arg Ile Glu Ala
                260                 265                 270

Pro Ala Glu Glu Thr Gly Lys Asp Val Arg Val Ala Arg Pro Gly
                275                 280                 285

Ala Ser Leu Trp Ala Arg Phe Tyr Asp Leu Glu Arg Gln Val Pro Leu
    290                 295                 300

Phe Val Asp Arg Asn Ser Arg Pro Val Pro Phe Ala Glu Leu Pro Asn
305                 310                 315                 320

Glu Arg Arg Thr Gly Tyr Gly Trp Tyr Gly Thr Trp Pro Glu Lys Leu
                325                 330                 335

Leu Ala Gln Glu Leu Pro Arg Trp Arg Lys Val His Ala Ala Ser Ala
                340                 345                 350

Gly Ala Pro Ala Arg
                355

<210> SEQ ID NO 97
<211> LENGTH: 2097
<212> TYPE: DNA
<213> ORGANISM: Unknown
<220> FEATURE:
<223> OTHER INFORMATION: Obtained from an environmental sample

<400> SEQUENCE: 97
```

-continued

```
ttgaacgccg ccggcagccg gcggttcgcg caactcgtcg tcgcggatct gcggcggctg    60
gtgcccgcgc tggcgcccct cttcgcgac gagccgctgg cgggaggagt cgccgcgctc    120
cagcgcagcg tcgatgcgat cgtcgccgcg gacggcaccg gacagtttgc gacggtgcag    180
gaggcgatca acgccgcgcc gcagaacacc agcacgacca gccgctggat catcctcgtc    240
aaaccaggca cgtatcgcga ggtcgtctac gtgcagcgtg agaagcgctt cgtcacgctg    300
atcggcgaag acccggcacg gacgacgatc acgtaccacc tcaaagcgtc tgacgtgggg    360
ctcgacggca agcccatcgg cacgtttcgc acgccgacga tggtggtgga tgccgacgat    420
ttcacgatcg agaacctcac catcgagaac ggggcagggc cggtcggtca agcgctggcc    480 tgcgagtgg acggcgatcg cgtgacggtg aggaacagcc gcctgctggg ctggcaggac    540
acgatctttc tcaaccgtgg gcgccactac ttcgaggact cgttcatcgg cgggcacgtg    600
gatttcattt tcggcggcgc gacggcggtg ttcgagcgat gccatcttcg cgcctggcgg    660
gacggctacc tcacggccgc gtccacgccc gcggagcaac gattcggctt cgtgttcctg    720
aacagcatcg tcagtggaga agctggcgcc cgcacgtacc tcggtcgacc gtggcgggcg    780
ttcgcgcacg tggccttcat caagacgacg atgggcgagg tggtgcgccc ggtgggctgg    840
aacaactggg accggccgga gcgtgagaag accgtgcgtt ttctcgaagc aggcaccagc    900
ggcgcgggcg gcagcgtcgc tgccgcgcgt cgcctgggcg cgtcgccac gccagccgag    960 ctcgctgatc tgacgaccga ggtggtgctt ggcggcaccg acggctggga cccgcgtcgc   1020
gtcgccccgt accgtcggc cgttcgcgcc aacgcggcgc cgctgccgcg ccgcccggg    1080 cccgacgtcg ctggcccgca gagcccgccc gccttgacgt gggaccaggt cgcgcgccag   1140
ccagcgtcgt ggctggccac acccgaagcg ctgcggattg ccgagaacgt gcgcctctat   1200
caacggcaca ctggcggctg gcccaaaaac ctcgacatgg cgcagccgtt gacggacgcc   1260
gatcgcgcgc gtctcacggc cgatcgcgcg ctcgacgact cgaccatcga caatggcgcc   1320
acgacgcggc agatcgagtt tctcgcccgg atcgccgccg ccaaccgcga cgagcgcgcg   1380
caggcgtcga tgctggctgg gatcgactac ctgctcgcgg cccagtatcc aaacggcggc   1440
tggccgcagt atttcccgct ccgcaacgac tactcgcgcc acatcacgtt caacgacgac   1500
gcgatgatcg cggccgcgac gatcctgcag tcggtcgcgc tggcccgtcc gccgttcgcc   1560
ggcgtcgacg cgactcgccg ccggcggggcg gcggaggccg tcgcgcgcgc ccatcgcgtg   1620
attctggcct cgcagattcg cgtcaacggc cagctcactg gctggtgcca gcagcacgat   1680
gcacgcacgc tggagccagc gcgcgggcgc acctacgagc atccatcgat cagtggccgc   1740
gaaaccgtga cgatcgtcaa ttttcctgcgg tcgatcgaac cgcgcgaccg ccagacccaa   1800
gccgccatcg atgccgcgat ggagtggctc aaggccgtgc agatccgcgg ctggcgcacg   1860
gagcggcggc ccgatccctc aggaccgggc ggttacgacg tggtgatggt ggaggacccc   1920
aacgcggcgc cgctctgggc ccgcttctac gagattggca ccaatcgtcc gatctactcg   1980
ggccgggacg gcgtcatcaa gtaccggctc gccgagatcg aaattgaacg gcggaccggc   2040
tacagctggg tcgaccgta cgcgcaggcg ctgctcgatg aagagcgcag gaagtaa      2097
```

<210> SEQ ID NO 98
<211> LENGTH: 698
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN

```
<222> LOCATION: (45)...(333)
<223> OTHER INFORMATION: Pectin methyl esterase domain
<220> FEATURE:
<221> NAME/KEY: DOMAIN
<222> LOCATION: (336)...(698)
<223> OTHER INFORMATION: Catalytic domain

<400> SEQUENCE: 98
```

| | | | | | | | | | | | | | | |
|---|---|---|---|---|---|---|---|---|---|---|---|---|---|---|
| Met | Asn | Ala | Ala | Gly | Ser | Arg | Arg | Phe | Ala | Gln | Leu | Val | Val | Ala | Asp |
| 1 | | | | 5 | | | | | 10 | | | | | 15 | |
| Leu | Arg | Arg | Leu | Val | Pro | Ala | Leu | Ala | Pro | Phe | Phe | Arg | Asp | Glu | Pro |
| | | | 20 | | | | | 25 | | | | | 30 | | |
| Leu | Ala | Gly | Gly | Val | Ala | Ala | Leu | Gln | Arg | Ser | Val | Asp | Ala | Ile | Val |
| | | | 35 | | | | | 40 | | | | | 45 | | |
| Ala | Ala | Asp | Gly | Thr | Gly | Gln | Phe | Ala | Thr | Val | Gln | Glu | Ala | Ile | Asn |
| | 50 | | | | | 55 | | | | | 60 | | | | |
| Ala | Ala | Pro | Gln | Asn | Thr | Ser | Thr | Thr | Ser | Arg | Trp | Ile | Ile | Leu | Val |
| 65 | | | | | 70 | | | | | 75 | | | | | 80 |
| Lys | Pro | Gly | Thr | Tyr | Arg | Glu | Val | Val | Tyr | Val | Gln | Arg | Glu | Lys | Arg |
| | | | | 85 | | | | | 90 | | | | | 95 | |
| Phe | Val | Thr | Leu | Ile | Gly | Glu | Asp | Pro | Ala | Arg | Thr | Thr | Ile | Thr | Tyr |
| | | | 100 | | | | | 105 | | | | | 110 | | |
| His | Leu | Lys | Ala | Ser | Asp | Val | Gly | Leu | Asp | Gly | Lys | Pro | Ile | Gly | Thr |
| | | | 115 | | | | | 120 | | | | | 125 | | |
| Phe | Arg | Thr | Pro | Thr | Met | Val | Val | Asp | Ala | Asp | Phe | Thr | Ile | Glu |
| | 130 | | | | | 135 | | | | | 140 | | | | |
| Asn | Leu | Thr | Ile | Glu | Asn | Gly | Ala | Gly | Pro | Val | Gly | Gln | Ala | Leu | Ala |
| 145 | | | | | 150 | | | | | 155 | | | | | 160 |
| Leu | Arg | Val | Asp | Gly | Asp | Arg | Val | Thr | Val | Arg | Asn | Ser | Arg | Leu | Leu |
| | | | | 165 | | | | | 170 | | | | | 175 | |
| Gly | Trp | Gln | Asp | Thr | Ile | Phe | Leu | Asn | Arg | Gly | Arg | His | Tyr | Phe | Glu |
| | | | 180 | | | | | 185 | | | | | 190 | | |
| Asp | Ser | Phe | Ile | Gly | Gly | His | Val | Asp | Phe | Ile | Phe | Gly | Gly | Ala | Thr |
| | | | 195 | | | | | 200 | | | | | 205 | | |
| Ala | Val | Phe | Glu | Arg | Cys | His | Leu | Arg | Ala | Trp | Arg | Asp | Gly | Tyr | Leu |
| | 210 | | | | | 215 | | | | | 220 | | | | |
| Thr | Ala | Ala | Ser | Thr | Pro | Ala | Glu | Gln | Arg | Phe | Gly | Phe | Val | Phe | Leu |
| 225 | | | | | 230 | | | | | 235 | | | | | 240 |
| Asn | Ser | Ile | Val | Ser | Gly | Glu | Ala | Gly | Ala | Arg | Thr | Tyr | Leu | Gly | Arg |
| | | | | 245 | | | | | 250 | | | | | 255 | |
| Pro | Trp | Arg | Ala | Phe | Ala | His | Val | Ala | Phe | Ile | Lys | Thr | Thr | Met | Gly |
| | | | 260 | | | | | 265 | | | | | 270 | | |
| Glu | Val | Val | Arg | Pro | Val | Gly | Trp | Asn | Asn | Trp | Asp | Arg | Pro | Glu | Arg |
| | | | 275 | | | | | 280 | | | | | 285 | | |
| Glu | Lys | Thr | Val | Arg | Phe | Leu | Glu | Ala | Gly | Thr | Ser | Gly | Ala | Gly | Gly |
| | 290 | | | | | 295 | | | | | 300 | | | | |
| Ser | Val | Ala | Ala | Arg | Val | Ala | Trp | Ala | Arg | Val | Ala | Thr | Pro | Ala | Glu |
| 305 | | | | | 310 | | | | | 315 | | | | | 320 |
| Leu | Ala | Asp | Leu | Thr | Thr | Glu | Val | Val | Leu | Gly | Gly | Thr | Asp | Gly | Trp |
| | | | | 325 | | | | | 330 | | | | | 335 | |
| Asp | Pro | Arg | Arg | Val | Ala | Pro | Tyr | Pro | Ser | Ala | Val | Arg | Ala | Asn | Ala |
| | | | 340 | | | | | 345 | | | | | 350 | | |
| Ala | Pro | Leu | Pro | Arg | Pro | Pro | Gly | Pro | Asp | Val | Ala | Gly | Pro | Gln | Ser |
| | | | 355 | | | | | 360 | | | | | 365 | | |
| Pro | Pro | Ala | Leu | Thr | Trp | Asp | Gln | Val | Ala | Arg | Gln | Pro | Ala | Ser | Trp |

Leu Ala Thr Pro Glu Ala Leu Arg Ile Ala Glu Asn Val Arg Leu Tyr
385                 390                 395                 400

Gln Arg His Thr Gly Gly Trp Pro Lys Asn Leu Asp Met Ala Gln Pro
            405                 410                 415

Leu Thr Asp Ala Asp Arg Ala Arg Leu Thr Ala Asp Arg Ala Leu Asp
        420                 425                 430

Asp Ser Thr Ile Asp Asn Gly Ala Thr Thr Arg Gln Ile Glu Phe Leu
        435                 440                 445

Ala Arg Ile Ala Ala Ala Asn Arg Asp Glu Arg Ala Gln Ala Ser Met
450                 455                 460

Leu Ala Gly Ile Asp Tyr Leu Leu Ala Ala Gln Tyr Pro Asn Gly Gly
465                 470                 475                 480

Trp Pro Gln Tyr Phe Pro Leu Arg Asn Asp Tyr Ser Arg His Ile Thr
                485                 490                 495

Phe Asn Asp Asp Ala Met Ile Ala Ala Thr Ile Leu Gln Ser Val
            500                 505                 510

Ala Leu Ala Arg Pro Pro Phe Ala Gly Val Asp Ala Thr Arg Arg
        515                 520                 525

Arg Ala Ala Glu Ala Val Ala Arg Ala His Arg Val Ile Leu Ala Ser
530                 535                 540

Gln Ile Arg Val Asn Gly Gln Leu Thr Gly Trp Cys Gln His Asp
545                 550                 555                 560

Ala Arg Thr Leu Glu Pro Ala Arg Gly Arg Thr Tyr Glu His Pro Ser
            565                 570                 575

Ile Ser Gly Arg Glu Thr Val Thr Ile Val Asn Phe Leu Arg Ser Ile
                580                 585                 590

Glu Pro Arg Asp Arg Gln Thr Gln Ala Ala Ile Asp Ala Ala Met Glu
            595                 600                 605

Trp Leu Lys Ala Val Gln Ile Arg Gly Trp Arg Thr Glu Arg Arg Pro
        610                 615                 620

Asp Pro Ser Gly Pro Gly Gly Tyr Asp Val Val Met Val Glu Asp Pro
625                 630                 635                 640

Asn Ala Ala Pro Leu Trp Ala Arg Phe Tyr Glu Ile Gly Thr Asn Arg
                645                 650                 655

Pro Ile Tyr Ser Gly Arg Asp Gly Val Ile Lys Tyr Arg Leu Ala Glu
            660                 665                 670

Ile Glu Ile Glu Arg Arg Thr Gly Tyr Ser Trp Val Gly Pro Tyr Ala
            675                 680                 685

Gln Ala Leu Leu Asp Glu Glu Arg Arg Lys
690                 695

<210> SEQ ID NO 99
<211> LENGTH: 1782
<212> TYPE: DNA
<213> ORGANISM: Unknown
<220> FEATURE:
<223> OTHER INFORMATION: Obtained from an environmental sample

<400> SEQUENCE: 99
atgttcacta ctaacagctc tatttgcgcc cggaaatccg cgcgttttc actgactgcc      60 atggctgctg cggtggctat gatcgcgggc acctctgcct ttgcggcctc taccggtggc    120
ttttcgacca cggatggcgg caatgtgtca gggtcaaaat cctttaccgc ctcaagccac    180
acccaaatcc agcaaatcct tgaggatgcc aaagatggca attatccggt ggtgatcacc    240

-continued

```
tacaccggca atgaggattc actgattaac caagtcgtcc gggatcacac cgtcgattct     300
tcaggcaact gccctaaagc gcgttggaat gatgcctacc gcaaagtcga atcaaagaa      360 atgaccaagg gtgtcaccat tcagggtgcc aatggttcgt cggcgaattt cggaatcgtg     420
gtgaataaat ccagcaacgt gattattcgc aacatgaaga ttggtgcact gggcggcgct     480
aataacgatg cggatatgat ccgtgtggac agcggtgtga acgtctggat cgatcacaac     540
gaattattcg ccgtgaacaa cgagtgtaag ggttcacccg atggcgatct gacctttgaa     600
agcgcgattg atatcaaaaa agcctcgcaa gatatcaccg tgtcctacaa cgtgattcgc     660
gacagtaaaa aagtcggttt ggatggctcc agcagcagcg atatcgccgg cggccgcaaa     720
attactttcc accacaatat ctaccgcaac gtaggtgcgc gcttacccttt gcagcgcggc     780 ggttggacgc acatgtacaa caacctgtac gacggcatta ccagctcggg catcaacgtg     840
cgccaaaacg gttatgcgtt aattgaaagc aactggttcc aaaacgcggt taacccggtc     900
acctgccgtt ttgacagcag caactgcggc aagtgggatc tgcgcaacaa taacatccgc     960
aacccgggtg attttgcgac ttacaacatc acctggacca gtggcggcac catcgacgcc    1020
accaactgga ccaccactgc gcccttccct atcagcattc cctacagcta ttcaccggtt    1080
actccgcaat gtgtgaaaga tcgtctggcg agttacgcgg gtgtgggtaa aaacggcgcg    1140
cagctgactg cctcggcctg cggtggtgcg gcatcgtcca cctgcatc gtccacacct      1200 gcaagttcca gctctgcggc aaacagttcc gctgcatcag gcagtgtgag tttgggtggc    1260
agtgccggta atgcatcggt tgcacttaac tggaccgtga atgccaacat taatgcgctg    1320
gaaatttatc aggatacgga ttctgatccc gccggacgtg tgcgcattgc gtcgctgcca    1380
accagcgcga ccaactacac cgcaacaggt ctgagcaacg gcactaccta ttacttctgg    1440
gtgaaatatc gcaccaccaa taatgtgtgg agcaactcca atgtgttcag cgccaagcca    1500
agttcaggta caacccccgtc atcatccagc agcgcggctt catcaacgcc aagtggtgca    1560
ccggtgttaa gtggtacagg tgattaccca agcggcttct ccaagtgtgc tgatctgggt    1620
ggcacctgct cagtcgcctc gggcgatggt tgggttgcct ttggtcgcaa aggcaagtgg    1680
gtcaccaaaa aagtgtcagt cggtagctct attgcctgta ccgttgccgc gtttggatct    1740
gatccacaag caatcccaa taagtgttct tataaaaagt aa                         1782
```

<210> SEQ ID NO 100
<211> LENGTH: 593
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(35)
<220> FEATURE:
<221> NAME/KEY: DOMAIN
<222> LOCATION: (36)...(593)
<223> OTHER INFORMATION: Catalytic domain

<400> SEQUENCE: 100

```
Met Phe Thr Thr Asn Ser Ser Ile Cys Ala Arg Lys Ser Ala Arg Phe
  1               5                  10                  15

Ser Leu Thr Ala Met Ala Ala Val Ala Met Ile Ala Gly Thr Ser
             20                  25                  30

Ala Phe Ala Ala Ser Thr Gly Gly Phe Ser Thr Thr Asp Gly Gly Asn
         35                  40                  45
```

-continued

Val Ser Gly Ser Lys Ser Phe Thr Ala Ser Ser His Thr Gln Ile Gln
 50                  55                  60

Gln Ile Leu Glu Asp Ala Lys Asp Gly Asn Tyr Pro Val Val Ile Thr
 65                  70                  75                  80

Tyr Thr Gly Asn Glu Asp Ser Leu Ile Asn Gln Val Val Arg Asp His
                 85                  90                  95

Thr Val Asp Ser Ser Gly Asn Cys Pro Lys Ala Arg Trp Asn Asp Ala
            100                 105                 110

Tyr Arg Lys Val Glu Ile Lys Glu Met Thr Lys Gly Val Thr Ile Gln
        115                 120                 125

Gly Ala Asn Gly Ser Ser Ala Asn Phe Gly Ile Val Val Asn Lys Ser
130                 135                 140

Ser Asn Val Ile Ile Arg Asn Met Lys Ile Gly Ala Leu Gly Gly Ala
145                 150                 155                 160

Asn Asn Asp Ala Asp Met Ile Arg Val Asp Ser Gly Val Asn Val Trp
                165                 170                 175

Ile Asp His Asn Glu Leu Phe Ala Val Asn Asn Glu Cys Lys Gly Ser
            180                 185                 190

Pro Asp Gly Asp Leu Thr Phe Glu Ser Ala Ile Asp Ile Lys Lys Ala
        195                 200                 205

Ser Gln Asp Ile Thr Val Ser Tyr Asn Val Ile Arg Asp Ser Lys Lys
210                 215                 220

Val Gly Leu Asp Gly Ser Ser Ser Asp Ile Ala Gly Gly Arg Lys
225                 230                 235                 240

Ile Thr Phe His His Asn Ile Tyr Arg Asn Val Gly Ala Arg Leu Pro
                245                 250                 255

Leu Gln Arg Gly Gly Trp Thr His Met Tyr Asn Asn Leu Tyr Asp Gly
        260                 265                 270

Ile Thr Ser Ser Gly Ile Asn Val Arg Gln Asn Gly Tyr Ala Leu Ile
        275                 280                 285

Glu Ser Asn Trp Phe Gln Asn Ala Val Asn Pro Val Thr Cys Arg Phe
290                 295                 300

Asp Ser Ser Asn Cys Gly Lys Trp Asp Leu Arg Asn Asn Asn Ile Arg
305                 310                 315                 320

Asn Pro Gly Asp Phe Ala Thr Tyr Asn Ile Thr Trp Thr Ser Gly Gly
                325                 330                 335

Thr Ile Asp Ala Thr Asn Trp Thr Thr Thr Ala Pro Phe Pro Ile Ser
        340                 345                 350

Ile Pro Tyr Ser Tyr Ser Pro Val Thr Pro Gln Cys Val Lys Asp Arg
        355                 360                 365

Leu Ala Ser Tyr Ala Gly Val Gly Lys Asn Gly Ala Gln Leu Thr Ala
370                 375                 380

Ser Ala Cys Gly Gly Ala Ala Ser Ser Thr Pro Ala Ser Ser Thr Pro
385                 390                 395                 400

Ala Ser Ser Ser Ala Ala Asn Ser Ala Ala Ser Gly Ser Val
                405                 410                 415

Ser Leu Gly Gly Ser Ala Gly Asn Ala Ser Val Ala Leu Asn Trp Thr
        420                 425                 430

Val Asn Ala Asn Ile Asn Ala Leu Glu Ile Tyr Gln Asp Thr Asp Ser
            435                 440                 445

Asp Pro Ala Gly Arg Val Arg Ile Ala Ser Leu Pro Thr Ser Ala Thr
        450                 455                 460

Asn Tyr Thr Ala Thr Gly Leu Ser Asn Gly Thr Thr Tyr Tyr Phe Trp

```
                465                 470                 475                 480
            Val Lys Tyr Arg Thr Thr Asn Asn Val Trp Ser Asn Ser Asn Val Phe
                                485                 490                 495

Ser Ala Lys Pro Ser Ser Gly Thr Thr Pro Ser Ser Ser Ser Ser Ala
                            500                 505                 510

Ala Ser Ser Thr Pro Ser Gly Ala Pro Val Leu Ser Gly Thr Gly Asp
                        515                 520                 525

Tyr Pro Ser Gly Phe Ser Lys Cys Ala Asp Leu Gly Gly Thr Cys Ser
                    530                 535                 540

Val Ala Ser Gly Asp Gly Trp Val Ala Phe Gly Arg Lys Gly Lys Trp
            545                 550                 555                 560

Val Thr Lys Lys Val Ser Val Gly Ser Ser Ile Ala Cys Thr Val Ala
                                565                 570                 575

Ala Phe Gly Ser Asp Pro Gln Gly Asn Pro Asn Lys Cys Ser Tyr Lys
                            580                 585                 590

Lys

<210> SEQ ID NO 101
<211> LENGTH: 1404
<212> TYPE: DNA
<213> ORGANISM: Unknown
<220> FEATURE:
<223> OTHER INFORMATION: Obtained from an environmental sample

<400> SEQUENCE: 101
atgactatag accgtcgaga attccttata gacctcatta tcggcaccgc cggcttcgca         60
atcgcaccga gtgatgcgtt cggccaagct gatccatgga aaaccgtcta tccgcaaatc        120
ctcgctcgca tacggccacc gaaatttccg aagcgagatt tcatcatcac tagattcggc        180
gcaaagccgg gaaccgacag cgccgctgcg atcgcaaaag ctatcaccgc gtgcagcaag        240
gcaggcggag gacgtgttct cgttcccgca ggagagtttc tcaccggagc gatccatctg        300
aaatcgaacg taaactttca cgtgtcaaaa ggcgcgacgc tgaaattctc gaccgacccg        360
aaggcatatc tcccgattgt acatacgcga tgggaaggaa tggagctgat gcatctgtca        420
ccgttcatct acgcttatga gcagacgaac atcgctatca cgggtcaggg aacgctcgac        480
ggccagggaa aatcattctt ctggaaatgg catggcaatc cggcttatgg cggcgatccg        540
aacacgctca gccaacggcc cgctcgtgcg cggctttacg agatgatgga taagaatgtg        600
ccggtcgccg aacgtgtctt cggtctcgga cattatctgc ggccgcagtt tattcagccg        660
tacaaatgca ggaacgtttt gatcgaagat gtgacgatcg tcgattcgcc gatgtgggaa        720
gttcatccgg tgctttgcga gaacgtcacg gtccgaaatg ttcacatttc atcgcatggt        780
ccgaacaatg acggatgcga tccggagtcg tgcaaggacg tactgatcga caactgtttt        840
ttcgacaccg cgacgattg catcgcgatc aagtccggcc gcaacaatga cggtcgtcgg        900
atcaatgtcc cgaccgagaa catcatcgtc cgcaactgca caatgaaaga cggtcatggc        960
ggcatcacgg tcgcagtga gatttcggga ggcgtgcgaa atcttttttgc gcacgattgt       1020 cgactcgaca gtgcggatct ctggaccgcg cttcgcgtca gaacaatgc gtcgcgaggc       1080 ggcaagctcg agaattttta ttttcggaat ataacggtcg gccaggtcgc acgcgctgtg       1140
gtcgagatcg atttttaatta cgaggaaggt gcgaaaggct cgtatattcc tgtcgttcga       1200
aattatgttg ttgaaggact gacatgcgcc acaggcaatc gcgccgtcga tctgcaagga       1260
ttggacaacg cgccgatcta caatgtaacg ctgcgaaact gtacgtttgg ttctgtccga       1320
```

```
aatcgtagtg ttgtgaaaaa cgttcgtgga cttcggctcg agaatgtgaa gatcggcggc   1380
aggatcgtaa acgaactggt atga                                          1404
```

```
<210> SEQ ID NO 102
<211> LENGTH: 467
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(28)
<220> FEATURE:
<221> NAME/KEY: DOMAIN
<222> LOCATION: (78)...(459)
<223> OTHER INFORMATION: Catalytic domain
```

<400> SEQUENCE: 102

| Met | Thr | Ile | Asp | Arg | Arg | Glu | Phe | Leu | Ile | Asp | Leu | Ile | Ile | Gly | Thr |
|---|---|---|---|---|---|---|---|---|---|---|---|---|---|---|---|
| 1 | | | | 5 | | | | | 10 | | | | | 15 | |

| Ala | Gly | Phe | Ala | Ile | Ala | Pro | Ser | Asp | Ala | Phe | Gly | Gln | Ala | Asp | Pro |
|---|---|---|---|---|---|---|---|---|---|---|---|---|---|---|---|
| | | | 20 | | | | | 25 | | | | | 30 | | |

| Trp | Lys | Thr | Val | Tyr | Pro | Gln | Ile | Leu | Ala | Arg | Ile | Arg | Pro | Pro | Lys |
|---|---|---|---|---|---|---|---|---|---|---|---|---|---|---|---|
| | | 35 | | | | | 40 | | | | | 45 | | | |

| Phe | Pro | Lys | Arg | Asp | Phe | Ile | Ile | Thr | Arg | Phe | Gly | Ala | Lys | Pro | Gly |
|---|---|---|---|---|---|---|---|---|---|---|---|---|---|---|---|
| 50 | | | | | 55 | | | | | 60 | | | | | |

| Thr | Asp | Ser | Ala | Ala | Ala | Ile | Ala | Lys | Ala | Ile | Thr | Ala | Cys | Ser | Lys |
|---|---|---|---|---|---|---|---|---|---|---|---|---|---|---|---|
| 65 | | | | | 70 | | | | | 75 | | | | | 80 |

| Ala | Gly | Gly | Gly | Arg | Val | Leu | Val | Pro | Ala | Gly | Glu | Phe | Leu | Thr | Gly |
|---|---|---|---|---|---|---|---|---|---|---|---|---|---|---|---|
| | | | | 85 | | | | | 90 | | | | | 95 | |

| Ala | Ile | His | Leu | Lys | Ser | Asn | Val | Asn | Phe | His | Val | Ser | Lys | Gly | Ala |
|---|---|---|---|---|---|---|---|---|---|---|---|---|---|---|---|
| | | | 100 | | | | | 105 | | | | | 110 | | |

| Thr | Leu | Lys | Phe | Ser | Thr | Asp | Pro | Lys | Ala | Tyr | Leu | Pro | Ile | Val | His |
|---|---|---|---|---|---|---|---|---|---|---|---|---|---|---|---|
| | | 115 | | | | | 120 | | | | | 125 | | | |

| Thr | Arg | Trp | Glu | Gly | Met | Glu | Leu | Met | His | Leu | Ser | Pro | Phe | Ile | Tyr |
|---|---|---|---|---|---|---|---|---|---|---|---|---|---|---|---|
| 130 | | | | | 135 | | | | | 140 | | | | | |

| Ala | Tyr | Glu | Gln | Thr | Asn | Ile | Ala | Ile | Thr | Gly | Gln | Gly | Thr | Leu | Asp |
|---|---|---|---|---|---|---|---|---|---|---|---|---|---|---|---|
| 145 | | | | | 150 | | | | | 155 | | | | | 160 |

| Gly | Gln | Gly | Lys | Ser | Phe | Phe | Trp | Lys | Trp | His | Gly | Asn | Pro | Ala | Tyr |
|---|---|---|---|---|---|---|---|---|---|---|---|---|---|---|---|
| | | | | 165 | | | | | 170 | | | | | 175 | |

| Gly | Gly | Asp | Pro | Asn | Thr | Leu | Ser | Gln | Arg | Pro | Ala | Arg | Ala | Arg | Leu |
|---|---|---|---|---|---|---|---|---|---|---|---|---|---|---|---|
| | | | 180 | | | | | 185 | | | | | 190 | | |

| Tyr | Glu | Met | Met | Asp | Lys | Asn | Val | Pro | Val | Ala | Glu | Arg | Val | Phe | Gly |
|---|---|---|---|---|---|---|---|---|---|---|---|---|---|---|---|
| | | 195 | | | | | 200 | | | | | 205 | | | |

| Leu | Gly | His | Tyr | Leu | Arg | Pro | Gln | Phe | Ile | Gln | Pro | Tyr | Lys | Cys | Arg |
|---|---|---|---|---|---|---|---|---|---|---|---|---|---|---|---|
| | | 210 | | | | | 215 | | | | | 220 | | | |

| Asn | Val | Leu | Ile | Glu | Asp | Val | Thr | Ile | Val | Asp | Ser | Pro | Met | Trp | Glu |
|---|---|---|---|---|---|---|---|---|---|---|---|---|---|---|---|
| 225 | | | | | 230 | | | | | 235 | | | | | 240 |

| Val | His | Pro | Val | Leu | Cys | Glu | Asn | Val | Thr | Val | Arg | Asn | Val | His | Ile |
|---|---|---|---|---|---|---|---|---|---|---|---|---|---|---|---|
| | | | | 245 | | | | | 250 | | | | | 255 | |

| Ser | Ser | His | Gly | Pro | Asn | Asn | Asp | Gly | Cys | Asp | Pro | Glu | Ser | Cys | Lys |
|---|---|---|---|---|---|---|---|---|---|---|---|---|---|---|---|
| | | | 260 | | | | | 265 | | | | | 270 | | |

| Asp | Val | Leu | Ile | Asp | Asn | Cys | Phe | Phe | Asp | Thr | Gly | Asp | Asp | Cys | Ile |
|---|---|---|---|---|---|---|---|---|---|---|---|---|---|---|---|
| | | | 275 | | | | | 280 | | | | | 285 | | |

| Ala | Ile | Lys | Ser | Gly | Arg | Asn | Asn | Asp | Gly | Arg | Arg | Ile | Asn | Val | Pro |
|---|---|---|---|---|---|---|---|---|---|---|---|---|---|---|---|
| | | 290 | | | | | 295 | | | | | 300 | | | |

| Thr | Glu | Asn | Ile | Ile | Val | Arg | Asn | Cys | Thr | Met | Lys | Asp | Gly | His | Gly |
|---|---|---|---|---|---|---|---|---|---|---|---|---|---|---|---|

```
             305                 310                 315                 320
Gly Ile Thr Val Gly Ser Glu Ile Ser Gly Val Arg Asn Leu Phe
                325                 330                 335

Ala His Asp Cys Arg Leu Asp Ser Ala Asp Leu Trp Thr Ala Leu Arg
                340                 345                 350

Val Lys Asn Asn Ala Ser Arg Gly Gly Lys Leu Glu Asn Phe Tyr Phe
                355                 360                 365

Arg Asn Ile Thr Val Gly Gln Val Ala Arg Ala Val Val Glu Ile Asp
                370                 375                 380

Phe Asn Tyr Glu Glu Gly Ala Lys Gly Ser Tyr Ile Pro Val Val Arg
385                 390                 395                 400

Asn Tyr Val Val Glu Gly Leu Thr Cys Ala Thr Gly Asn Arg Ala Val
                405                 410                 415

Asp Leu Gln Gly Leu Asp Asn Ala Pro Ile Tyr Asn Val Thr Leu Arg
                420                 425                 430

Asn Cys Thr Phe Gly Ser Val Arg Asn Arg Ser Val Val Lys Asn Val
                435                 440                 445

Arg Gly Leu Arg Leu Glu Asn Val Lys Ile Gly Gly Arg Ile Val Asn
    450                 455                 460

Glu Leu Val
465

<210> SEQ ID NO 103
<211> LENGTH: 1101
<212> TYPE: DNA
<213> ORGANISM: Unknown
<220> FEATURE:
<223> OTHER INFORMATION: Obtained from an environmental sample

<400> SEQUENCE: 103
atgaacaccg cactgcaccg cgtcatccgc ctgccgctgc tgctggcgct gtgcctgccc     60
gcgctgcagg cacaggccac gcagaccgag cccgtcgccg agaacatgct gctgctgcag    120
accgcgtccg gcggctggtc caagcaccac cagggcaagg cggtcgacta cggccacacg    180
ttcaccgatg ccgaacgtgc ggcgctgcgc gcgcccgacc gcagggacga tgcgacgatc    240
gacaacaagg cgaccacgct tgagatcgtc gcgctgctgg aagcccacca gcgcaccggc    300
aatgccgcct atctggcggc tgcgcagcgc ggcgtggact acctgctggc cgcgcagtac    360
ccgaacggcg gctggccgca gtactacccg gaccgttcgc tgtaccggca ccaggtcacc    420
ttcaacgatg atgcgatgac ccgcgtgctg gagctgctgc aggacatcgt cgagggcaag    480
ggcgcgctgg cgcagctgac acccacgcat ggcgaacgcg ccagggccgc gctcgacagg    540
ggcatcgcct gcgtgctcgc cacccaggta cggatcgatg gcgagctcac gctctgggcc    600
gcgcagtacg acgaagccac gctgcagccg gcgaaggcgc gctcctacga gctgccatcg    660
ctggcggtcg ccgaatcggt cggggtgatg cggctgctga tgcgccagcc acagccgtcg    720
ccgcaggtgc tgacggcggt cgaggccggc gcacgctggc tggaggcgca ccgcatgcgc    780
gacctggccc ggcgaaagat cgacgcgccc ggcgaagaaa ccggccagga cgtggtgatc    840
gtcgccgagc ccggcgcgtc gctgtgggca cgcttctacg acctgcagca ccagcagccg    900
atgttcgtga accgcgaagg cgagcaggtg gcccgcttcg ccgacatgcc caacgaacgc    960
cgcgtcggct acgcctggta tggcgtgtgg ccggagaagc tgctgcagca ggagctgcca   1020
cgctggtaca cacccatgc cgaggcattg cgcgcgatta cgcctgcgca tgccgagcca   1080
aggccgccga agcggccctg a                                             1101
```

```
<210> SEQ ID NO 104
<211> LENGTH: 366
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(26)
<220> FEATURE:
<221> NAME/KEY: DOMAIN
<222> LOCATION: (27)...(366)
<223> OTHER INFORMATION: Catalytic domain

<400> SEQUENCE: 104

Met Asn Thr Ala Leu His Arg Val Ile Arg Leu Pro Leu Leu Ala
 1               5                  10                  15

Leu Cys Leu Pro Ala Leu Gln Ala Gln Ala Thr Gln Thr Glu Pro Val
                20                  25                  30

Ala Glu Asn Met Leu Leu Leu Gln Thr Ala Ser Gly Gly Trp Ser Lys
            35                  40                  45

His His Gln Gly Lys Ala Val Asp Tyr Gly His Thr Phe Thr Asp Ala
        50                  55                  60

Glu Arg Ala Ala Leu Arg Ala Pro Asp Arg Arg Asp Asp Ala Thr Ile
65                  70                  75                  80

Asp Asn Lys Ala Thr Thr Leu Glu Ile Val Ala Leu Leu Glu Ala His
                85                  90                  95

Gln Arg Thr Gly Asn Ala Ala Tyr Leu Ala Ala Gln Arg Gly Val
            100                 105                 110

Asp Tyr Leu Leu Ala Ala Gln Tyr Pro Asn Gly Gly Trp Pro Gln Tyr
        115                 120                 125

Tyr Pro Asp Arg Ser Leu Tyr Arg His Gln Val Thr Phe Asn Asp Asp
        130                 135                 140

Ala Met Thr Arg Val Leu Glu Leu Leu Gln Asp Ile Val Glu Gly Lys
145                 150                 155                 160

Gly Ala Leu Ala Gln Leu Thr Pro Thr His Gly Glu Arg Ala Arg Ala
                165                 170                 175

Ala Leu Asp Arg Gly Ile Ala Cys Val Leu Ala Thr Gln Val Arg Ile
            180                 185                 190

Asp Gly Glu Leu Thr Leu Trp Ala Ala Gln Tyr Asp Glu Ala Thr Leu
        195                 200                 205

Gln Pro Ala Lys Ala Arg Ser Tyr Glu Leu Pro Ser Leu Ala Val Ala
        210                 215                 220

Glu Ser Val Gly Val Met Arg Leu Leu Met Arg Gln Pro Gln Pro Ser
225                 230                 235                 240

Pro Gln Val Leu Thr Ala Val Glu Ala Gly Ala Arg Trp Leu Glu Ala
                245                 250                 255

His Arg Met Arg Asp Leu Ala Arg Arg Lys Ile Asp Ala Pro Gly Glu
            260                 265                 270

Glu Thr Gly Gln Asp Val Val Ile Val Ala Glu Pro Gly Ala Ser Leu
        275                 280                 285

Trp Ala Arg Phe Tyr Asp Leu Gln His Gln Pro Met Phe Val Asn
        290                 295                 300

Arg Glu Gly Glu Gln Val Ala Arg Phe Ala Asp Met Pro Asn Glu Arg
305                 310                 315                 320

Arg Val Gly Tyr Ala Trp Tyr Gly Val Trp Pro Glu Lys Leu Leu Gln
```

```
            325                 330                 335
Gln Glu Leu Pro Arg Trp Tyr Asn Thr His Ala Glu Ala Leu Arg Ala
        340                 345                 350

Ile Thr Pro Ala His Ala Glu Pro Arg Pro Pro Lys Arg Pro
        355                 360                 365

<210> SEQ ID NO 105
<211> LENGTH: 1203
<212> TYPE: DNA
<213> ORGANISM: Unknown
<220> FEATURE:
<223> OTHER INFORMATION: Obtained from an environmental sample

<400> SEQUENCE: 105
atgcaattca tcgaaacaca gcaattgggg accgccgcga aacccgtggc gggacgagga      60
ggcgacaggc gctttccgcg ggtcatgccc gccgtttgcg cgggccttgc cctcgccgtg     120
tcgtcggccg agccggtccg ggcgcagggc gcggatgcgg atgcggatgg cccactgccc     180
aggtggaaca ggaggctggt ggatcgcccc gaggactggt tcgcctccga cgagggacag     240
cgcgttgccg ccaacgtcct ccgctaccaa tcggcggaag gagcctggcc caaaaacacc     300
aatctggccg ccactcccct tcgccccgag gacattccct cctcgacctc cggggtggcc     360
aacacgatcg acaatgaagc caccaccgtg cccattcggt ttttggcccg tttcgcgcaa     420
atcaacgagg acacggccag ccgcgaggcg gtccagcgcg gattggacta tctcctcaag     480
gcgcaatatc cgaacggtgg ctggccgcag tatttcccgc tccgccgcgg ctaccactcg     540
cacatcacct acaacgacga cgccatggtg aatgtgctcg acctgctgct ggacgtgtcg     600
ctgggcgagg agccgttcga ttttgtggac gaggatcgcc gccagcgggc cgcgaccgcc     660
gtggagcggg ggatcgaatg catcctccgc acccaaatcc ggcaggagga ccaacccacc     720
ggctggtgcg cgcagtatga ccccgaaacc ttggccccgg cgtggggacg ggcgtacgag     780
ccgccgtcga tttccggagc cgagaccgtc ggcgtggcgc ggtttctgat gcggctggag     840
tcgccatcgc cggaagccgt cgaagccatc gagggcgcca tcgcctggct cgacacggtg     900
ggcatcgagg aattgcgtct cgaatggttc accaacagcg agggcaagcg tgaccggcgc     960
gtggtcgagg acgcttccgt gggcacccct tgggcgcgct tttacgaact cgaaacgaac    1020
cgccccttgt tcgtggaccg cgacggggtg ctccgctacg acttcgcgga actgacggcg    1080
gagcgccgcc aaggttacag ctactacggc acttggccgg cgccattgct ggccacggaa    1140
tatccgcgct ggcgcaggat gaacgagtcc gccctgctcg agtcgtcctt catctcgcat    1200
tga                                                                  1203

<210> SEQ ID NO 106
<211> LENGTH: 400
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(43)
<220> FEATURE:
<221> NAME/KEY: DOMAIN
<222> LOCATION: (44)...(400)
<223> OTHER INFORMATION: Catalytic domain

<400> SEQUENCE: 106

Met Gln Phe Ile Glu Thr Gln Gln Leu Gly Thr Ala Ala Lys Pro Val
1               5                   10                  15
```

```
Ala Gly Arg Gly Gly Asp Arg Arg Phe Pro Arg Val Met Pro Ala Val
            20                  25                  30

Cys Ala Gly Leu Ala Leu Ala Val Ser Ser Ala Glu Pro Val Arg Ala
            35                  40                  45

Gln Gly Ala Asp Ala Asp Ala Asp Gly Pro Leu Pro Arg Trp Asn Arg
 50                  55                  60

Arg Leu Val Asp Arg Pro Glu Asp Trp Phe Ala Ser Asp Glu Gly Gln
 65                  70                  75                  80

Arg Val Ala Ala Asn Val Leu Arg Tyr Gln Ser Ala Glu Gly Ala Trp
                85                  90                  95

Pro Lys Asn Thr Asn Leu Ala Ala Thr Pro Leu Arg Pro Glu Asp Ile
            100                 105                 110

Pro Ser Ser Thr Ser Gly Val Ala Asn Thr Ile Asp Asn Glu Ala Thr
            115                 120                 125

Thr Val Pro Ile Arg Phe Leu Ala Arg Phe Ala Gln Ile Asn Glu Asp
            130                 135                 140

Thr Ala Ser Arg Glu Ala Val Gln Arg Gly Leu Asp Tyr Leu Leu Lys
145                 150                 155                 160

Ala Gln Tyr Pro Asn Gly Gly Trp Pro Gln Tyr Phe Pro Leu Arg Arg
                165                 170                 175

Gly Tyr His Ser His Ile Thr Tyr Asn Asp Asp Ala Met Val Asn Val
            180                 185                 190

Leu Asp Leu Leu Leu Asp Val Ser Leu Gly Glu Glu Pro Phe Asp Phe
            195                 200                 205

Val Asp Glu Asp Arg Arg Gln Arg Ala Ala Thr Ala Val Glu Arg Gly
            210                 215                 220

Ile Glu Cys Ile Leu Arg Thr Gln Ile Arg Gln Glu Asp Gln Pro Thr
225                 230                 235                 240

Gly Trp Cys Ala Gln Tyr Asp Pro Glu Thr Leu Ala Pro Ala Trp Gly
                245                 250                 255

Arg Ala Tyr Glu Pro Pro Ser Ile Ser Gly Ala Glu Thr Val Gly Val
            260                 265                 270

Ala Arg Phe Leu Met Arg Leu Glu Ser Pro Ser Pro Glu Ala Val Glu
            275                 280                 285

Ala Ile Glu Gly Ala Ile Ala Trp Leu Asp Thr Val Gly Ile Glu Glu
            290                 295                 300

Leu Arg Leu Glu Trp Phe Thr Asn Ser Glu Gly Lys Arg Asp Arg Arg
305                 310                 315                 320

Val Val Glu Asp Ala Ser Val Gly Thr Leu Trp Ala Arg Phe Tyr Glu
                325                 330                 335

Leu Glu Thr Asn Arg Pro Leu Phe Val Asp Arg Asp Gly Val Leu Arg
            340                 345                 350

Tyr Asp Phe Ala Glu Leu Thr Ala Glu Arg Arg Gln Gly Tyr Ser Tyr
            355                 360                 365

Tyr Gly Thr Trp Pro Ala Pro Leu Leu Ala Thr Glu Tyr Pro Arg Trp
            370                 375                 380

Arg Arg Met Asn Glu Ser Ala Leu Leu Glu Ser Ser Phe Ile Ser His
385                 390                 395                 400

<210> SEQ ID NO 107
<211> LENGTH: 1074
<212> TYPE: DNA
<213> ORGANISM: Unknown
<220> FEATURE:
```

-continued

<223> OTHER INFORMATION: Obtained from an environmental sample

<400> SEQUENCE: 107

```
atgacgctac ccgttgtttc cctgcgcgta ctgctggcgc tgctggccac gtcgccggtc      60
gcctgcgcgg gcgctgcggc acccgcgact gcgaccgatc cggtcgccga gaacatgctg     120
cttctgcaga ccgcctccgg cggctggtcc aagcactacc gcgagaagaa ggtcgactac     180
gcgcgcgact acgacgccgc cgagcgcgcc gcgctgcgcg cgcccgaccg gcatgacgat     240
gccacgatcg acaacaaggc cacgaccacc gagatcgcat acctggtgca ggcacatgcc     300
aggacgggca atccggccta cctcgacggc gcgcgccgcg gcgtcgagta cctgctgcgc     360
gcgcagtacc cgaacggcgg ctggccgcag ttctaccccg accattcgtc ctaccggcac     420
cagatcacgc tcaacgacga tgcgatggtg cacgccatca ccgtgctgca ggacatcgcc     480
gcgggccgca acggcatgca ggtgctggcg ccggagttcg gcgtccgcgc cgccgcggcc     540
gcgcagcgcg gcatcggaaa cctgctcgag ttgcaggtgc ggatcgacgg ggtgccgacg     600
atctgggccg cgcagtacga cgagaccacc ctgcaaccgg ccaaggcccg tgcgtacgag     660
ttgccctcgc tggccgtggc cgaatcggtg ggcgtgatgc gcctgctgat gcgccagccg     720
gggcctgatg cgcgcacgat cgccgcgatc gaggcggcgg cggactggct ggaggcgcac     780
cgcctgccgg acctcgccct ggaacgcatc gaagcccccg ccgaggaaac cggcaaggac     840
gtccgcgtcg tggccagacc gggcgcgtcg ttgtgggcgc gcttctacga cctcgagcgg     900
caggtgccgc tgttcgtcga tcgcaacagc cgtccggttc cattcgccga gcttcccaac     960
gagcgtcgta ccggctatgg ctggtatggc acctggccgg aaaagctgct ggcacaggaa    1020
ctcccgcgct ggcgcaaggt ccatgcggcc agcgcgggcg ctccggcccg ttga          1074
```

<210> SEQ ID NO 108
<211> LENGTH: 357
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(31)
<220> FEATURE:
<221> NAME/KEY: DOMAIN
<222> LOCATION: (32)...(357)
<223> OTHER INFORMATION: Catalytic domain

<400> SEQUENCE: 108

```
Met Thr Leu Pro Val Val Ser Leu Arg Val Leu Ala Leu Leu Ala
 1               5                  10                  15
Thr Ser Pro Val Ala Cys Ala Gly Ala Ala Pro Ala Thr Ala Thr
                20                  25                  30
Asp Pro Val Ala Glu Asn Met Leu Leu Leu Gln Thr Ala Ser Gly Gly
            35                  40                  45
Trp Ser Lys His Tyr Arg Glu Lys Lys Val Asp Tyr Ala Arg Asp Tyr
    50                  55                  60
Asp Ala Ala Glu Arg Ala Ala Leu Arg Ala Pro Asp Arg His Asp Asp
65                  70                  75                  80
Ala Thr Ile Asp Asn Lys Ala Thr Thr Thr Glu Ile Ala Tyr Leu Val
                85                  90                  95
Gln Ala His Ala Arg Thr Gly Asn Pro Ala Tyr Leu Asp Gly Ala Arg
            100                 105                 110
Arg Gly Val Glu Tyr Leu Leu Arg Ala Gln Tyr Pro Asn Gly Gly Trp
```

```
                115                 120                 125
Pro Gln Phe Tyr Pro Asp His Ser Ser Tyr Arg His Gln Ile Thr Leu
    130                 135                 140
Asn Asp Asp Ala Met Val His Ala Ile Thr Val Leu Gln Asp Ile Ala
145                 150                 155                 160
Ala Gly Arg Asn Gly Met Gln Val Leu Ala Pro Glu Phe Gly Val Arg
                165                 170                 175
Ala Ala Ala Ala Ala Gln Arg Gly Ile Gly Asn Leu Leu Glu Leu Gln
            180                 185                 190
Val Arg Ile Asp Gly Val Pro Thr Ile Trp Ala Ala Gln Tyr Asp Glu
        195                 200                 205
Thr Thr Leu Gln Pro Ala Lys Ala Arg Ala Tyr Glu Leu Pro Ser Leu
    210                 215                 220
Ala Val Ala Glu Ser Val Gly Val Met Arg Leu Leu Met Arg Gln Pro
225                 230                 235                 240
Gly Pro Asp Ala Arg Thr Ile Ala Ala Ile Glu Ala Ala Ala Asp Trp
                245                 250                 255
Leu Glu Ala His Arg Leu Pro Asp Leu Ala Leu Glu Arg Ile Glu Ala
            260                 265                 270
Pro Ala Glu Glu Thr Gly Lys Asp Val Arg Val Val Ala Arg Pro Gly
        275                 280                 285
Ala Ser Leu Trp Ala Arg Phe Tyr Asp Leu Glu Arg Gln Val Pro Leu
    290                 295                 300
Phe Val Asp Arg Asn Ser Arg Pro Val Pro Phe Ala Glu Leu Pro Asn
305                 310                 315                 320
Glu Arg Arg Thr Gly Tyr Gly Trp Tyr Gly Thr Trp Pro Glu Lys Leu
                325                 330                 335
Leu Ala Gln Glu Leu Pro Arg Trp Arg Lys Val His Ala Ala Ser Ala
            340                 345                 350
Gly Ala Pro Ala Arg
        355

<210> SEQ ID NO 109
<211> LENGTH: 1422
<212> TYPE: DNA
<213> ORGANISM: Unknown
<220> FEATURE:
<223> OTHER INFORMATION: Obtained from an environmental sample

<400> SEQUENCE: 109
atgacgacac gacgcgaatt catcaaaggc tttctactta ccggagcagc cgtggccgtc      60
gctccgcgtt tgcttgcgtt cgccgcggag gcaagtccgt gggaaacgat gatgccttcg     120
atcctcgcac gcatcagacc acctcgtttt ccgaaacgca ccttctatct caatcgattc     180
ggcgccaagg gtgatggagt cacagactgc accgcggctt ttcatcgcgc gatcgatgaa     240
tgcaccaaag ccggcggtgg gaaagtcgtc gtgccggcgg gcacttatct caccggcgcg     300
attcatttga gagcaacgt caacctcgaa gtctcggaag cgcgacgat caagttcagt     360 caggacccga aacactacct gcctgttgtc ttctcgcgtt gggaaggtgt cgaagtcttc     420
aactactcgc ctttcattta cgcgttcgaa cagcgaaaca tcgcgatcac cggcaaaggc     480
acgctcgacg acagagtga ttcggaacac tggtggccgt ggaacggccg tccgcagtac     540
ggatggaaag aagggatgaa acagcagcgt cccgatcgca acgcgttgtt cacaatggcg     600
gagaaaggcg tgccggtgcg cgagcgcatc tttggcgaag tcattatttt gaggccgcag     660
```

-continued

```
ttcattcagc cgtaccgctg ccagaacgtg ctgatccagg gcgtgacgat tcggaactcg    720
ccgatgtggg agattcatcc ggtgttgtgc cgtaacgtga ctattcacga cgtgcacatc    780
gatagtcatg gaccaaacaa cgacggctgc aatcccgaat cgtgcagcga cgtgttgatt    840
aaggatagct acttcgatac cggcgacgac tgcatcgcga tcaaatcggg acgcaacgcc    900
gacgggcggc ggcttaaagc gccgactgag aacatcatcg ttcaaggatg tcgcatgaaa    960
gacggccacg gtggaatcac ggtcggcagc gagatctcgg gcggcgtgcg aaacctgttt   1020
gccgagaatt gccggctcga cagtccaaac ctcgatcacg ccctgcgcgt gaagaacaat   1080
gccatgcgcg gcggattact cgagaacttc cacttccgta acatcgaagt cgggcaggtg   1140
gcccatgccg tgattacgat cgacttcaac tacgaagagg gcgcgaaagg gtcgttcacg   1200
ccggtcgttc gcgattacac ggtcgatcgt ttgcgcagca cgaagagcaa gcacgcactc   1260
gacgtccagg gtctgcccgg cgcgccggtc atcaacctgc gattgacgaa ctgcacattc   1320
aacgatgtgc agcaaccgaa cattctcaag aacgtcgaac aatcaacctt tgaaaacgtc   1380
acgattaacg gaaagacgat cacacaaaca ggatccaaag aa                      1422
```

<210> SEQ ID NO 110
<211> LENGTH: 474
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(21)
<220> FEATURE:
<221> NAME/KEY: DOMAIN
<222> LOCATION: (28)...(308)
<223> OTHER INFORMATION: Pectin methyl esterase domain
<220> FEATURE:
<221> NAME/KEY: DOMAIN
<222> LOCATION: (309)...(637)
<223> OTHER INFORMATION: Catalytic domain

<400> SEQUENCE: 110

```
Met Thr Thr Arg Arg Glu Phe Ile Lys Gly Phe Leu Leu Thr Gly Ala
  1               5                  10                  15

Ala Val Ala Val Ala Pro Arg Leu Leu Ala Phe Ala Ala Glu Ala Ser
             20                  25                  30

Pro Trp Glu Thr Met Met Pro Ser Ile Leu Ala Arg Ile Arg Pro Pro
         35                  40                  45

Arg Phe Pro Lys Arg Thr Phe Tyr Leu Asn Arg Phe Gly Ala Lys Gly
     50                  55                  60

Asp Gly Val Thr Asp Cys Thr Ala Ala Phe His Arg Ala Ile Asp Glu
 65                  70                  75                  80

Cys Thr Lys Ala Gly Gly Gly Lys Val Val Val Pro Ala Gly Thr Tyr
                 85                  90                  95

Leu Thr Gly Ala Ile His Leu Lys Ser Asn Val Asn Leu Glu Val Ser
            100                 105                 110

Glu Gly Ala Thr Ile Lys Phe Ser Gln Asp Pro Lys His Tyr Leu Pro
        115                 120                 125

Val Val Phe Ser Arg Trp Glu Gly Val Glu Val Phe Asn Tyr Ser Pro
    130                 135                 140

Phe Ile Tyr Ala Phe Glu Gln Arg Asn Ile Ala Ile Thr Gly Lys Gly
145                 150                 155                 160

Thr Leu Asp Gly Gln Ser Asp Ser Glu His Trp Trp Pro Trp Asn Gly
                165                 170                 175
```

Arg Pro Gln Tyr Gly Trp Lys Glu Gly Met Lys Gln Arg Pro Asp
            180                 185                 190

Arg Asn Ala Leu Phe Thr Met Ala Glu Lys Gly Val Pro Val Arg Glu
        195                 200                 205

Arg Ile Phe Gly Glu Gly His Tyr Leu Arg Pro Gln Phe Ile Gln Pro
    210                 215                 220

Tyr Arg Cys Gln Asn Val Leu Ile Gln Gly Val Thr Ile Arg Asn Ser
225                 230                 235                 240

Pro Met Trp Glu Ile His Pro Val Leu Cys Arg Asn Val Thr Ile His
                245                 250                 255

Asp Val His Ile Asp Ser His Gly Pro Asn Asn Asp Gly Cys Asn Pro
            260                 265                 270

Glu Ser Cys Ser Asp Val Leu Ile Lys Asp Ser Tyr Phe Asp Thr Gly
        275                 280                 285

Asp Asp Cys Ile Ala Ile Lys Ser Gly Arg Asn Ala Asp Gly Arg Arg
    290                 295                 300

Leu Lys Ala Pro Thr Glu Asn Ile Ile Val Gln Gly Cys Arg Met Lys
305                 310                 315                 320

Asp Gly His Gly Gly Ile Thr Val Gly Ser Glu Ile Ser Gly Val
                325                 330                 335

Arg Asn Leu Phe Ala Glu Asn Cys Arg Leu Asp Ser Pro Asn Leu Asp
            340                 345                 350

His Ala Leu Arg Val Lys Asn Asn Ala Met Arg Gly Gly Leu Leu Glu
        355                 360                 365

Asn Phe His Phe Arg Asn Ile Glu Val Gly Gln Val Ala His Ala Val
    370                 375                 380

Ile Thr Ile Asp Phe Asn Tyr Glu Glu Gly Ala Lys Gly Ser Phe Thr
385                 390                 395                 400

Pro Val Val Arg Asp Tyr Thr Val Asp Arg Leu Arg Ser Thr Lys Ser
                405                 410                 415

Lys His Ala Leu Asp Val Gln Gly Leu Pro Gly Ala Pro Val Ile Asn
            420                 425                 430

Leu Arg Leu Thr Asn Cys Thr Phe Asn Asp Val Gln Gln Pro Asn Ile
        435                 440                 445

Leu Lys Asn Val Glu Gln Ser Thr Phe Glu Asn Val Thr Ile Asn Gly
    450                 455                 460

Lys Thr Ile Thr Gln Thr Gly Ser Lys Glu
465                 470

<210> SEQ ID NO 111
<211> LENGTH: 1440
<212> TYPE: DNA
<213> ORGANISM: Unknown
<220> FEATURE:
<223> OTHER INFORMATION: Obtained from an environmental sample

<400> SEQUENCE: 111
atgcaaaatc gtcgagaatt tttacaactt ttatttgccg gtgccggtgc cggacttgtt    60
ttgccgcaga tttctttcgg gcagactaaa caagccgacg cctggacgac cgagtatccg    120
aagattttag ccagaatcaa accgccgaaa tttcgcaaaa agattttcc gatcaccaaa    180 tatggagccg ttgcggacgg gaaaaccctg gcgaccgaaa gcatcaaaaa agccatcgaa    240
gcgtgcgcca atcgggcgg cgggcgcgtc gtcgtgcccc agggagaatt tttgaccggc    300
gcgattcatt tgaaatcaaa cgtcaatctg cacatcacga aaggcgcgac cgtcaaattt    360

-continued

```
tccaccaacc cgaaagatta tctgccgatc gttcacacgc gctgggaagg gatggaattg      420
atgcatattt cgcctttaat ttatgcctac gagcaaacca acatcgccgt caccggcgag      480
ggaacgctcg acgggcaggg caaggctttt ttctggaaat ggcacggaaa cccgcgctac      540
ggcggaaatc cggatgtgat cagccagcgt ccggcgcgcg cccggctgta tgaaatgatg      600
gaaaaaggcg tgcctgtggc ggagcggatt tccggcgaaa ctcagtatct tcgcccgcag      660
tttatccagc cctataaatg caaaaatgtt ttgatcgaag gcgttaaaat catcgattcg      720
ccgatgtggg aagttcaccc cgttttgtgc gaaaacgtga cgatccgaaa acttcatatt      780
tctacccacg gaccgaacaa cgacgggtgc gatccggaaa gctgcaagga cgttttgatc      840
gaagactgct atttcgacac cggcgacgat tgcattgcca tcaaggcggg gcgcaatgaa      900
gacgggcgac gcatcaatgt tccgaccgaa aacgtcgtcg tgcgcgggtg cgtgatgaag      960
gacggtcacg gcggaatcac catcggaagc gagatttccg gcggcgtgcg aaatgttttc     1020
gcggaaaaca accggctcga cagcgcggat ttgtggactg cgctgagagt gaaaaacaac     1080
gcttcgcgcg gcgaaaaact ggagaatttt tacttccgcg atatcaccgt cgggcaggtc     1140
tcgcgcgcgg tcgtcgaaat agattttaat tacgaggaag gcgctaaagg aaaacacacg     1200
ccggtcgttc gcaattacgt ggtcgaaaat ctaacctgca ataaaggcaa tcgagcggtc     1260
gatctgcagg gcttggacaa cgccccgatt tacgacatca cgatgaaaaa ctgtacgttt     1320
aacgtggtcg aaaagccgag cgtcgtgaaa acgtcaaag gcgtcaaact ggaaaacgtg     1380
aagattaacg gcaaagtcgt cgagagtctg gaaaatgctg caacgacggc taaaaaataa     1440
```

<210> SEQ ID NO 112
<211> LENGTH: 479
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(27)
<220> FEATURE:
<221> NAME/KEY: DOMAIN
<222> LOCATION: (82)...(461)
<223> OTHER INFORMATION: Catalytic domain

<400> SEQUENCE: 112

```
Met Gln Asn Arg Arg Glu Phe Leu Gln Leu Leu Phe Ala Gly Ala Gly
  1               5                  10                  15

Ala Gly Leu Val Leu Pro Gln Ile Ser Phe Gly Gln Thr Lys Gln Ala
             20                  25                  30

Asp Ala Trp Thr Thr Glu Tyr Pro Lys Ile Leu Ala Arg Ile Lys Pro
         35                  40                  45

Pro Lys Phe Arg Lys Lys Asp Phe Pro Ile Thr Lys Tyr Gly Ala Val
     50                  55                  60

Ala Asp Gly Lys Thr Leu Ala Thr Glu Ser Ile Lys Lys Ala Ile Glu
 65                  70                  75                  80

Ala Cys Ala Lys Ser Gly Gly Gly Arg Val Val Pro Gln Gly Glu
                 85                  90                  95

Phe Leu Thr Gly Ala Ile His Leu Lys Ser Asn Val Asn Leu His Ile
            100                 105                 110

Thr Lys Gly Ala Thr Val Lys Phe Ser Thr Asn Pro Lys Asp Tyr Leu
        115                 120                 125

Pro Ile Val His Thr Arg Trp Glu Gly Met Glu Leu Met His Ile Ser
```

|  | 130 |  |  |  | 135 |  |  |  |  | 140 |  |
|---|---|---|---|---|---|---|---|---|---|---|---|

Pro Leu Ile Tyr Ala Tyr Glu Gln Thr Asn Ile Ala Val Thr Gly Glu
145                 150                 155                 160

Gly Thr Leu Asp Gly Gln Gly Lys Ala Phe Phe Trp Lys Trp His Gly
                165                 170                 175

Asn Pro Arg Tyr Gly Asn Pro Asp Val Ile Ser Gln Arg Pro Ala
            180                 185                 190

Arg Ala Arg Leu Tyr Glu Met Met Glu Lys Gly Val Pro Val Ala Glu
            195                 200                 205

Arg Ile Phe Gly Glu Thr Gln Tyr Leu Arg Pro Gln Phe Ile Gln Pro
210                 215                 220

Tyr Lys Cys Lys Asn Val Leu Ile Glu Gly Val Lys Ile Ile Asp Ser
225                 230                 235                 240

Pro Met Trp Glu Val His Pro Val Leu Cys Glu Asn Val Thr Ile Arg
                245                 250                 255

Lys Leu His Ile Ser Thr His Gly Pro Asn Asn Asp Gly Cys Asp Pro
            260                 265                 270

Glu Ser Cys Lys Asp Val Leu Ile Glu Asp Cys Tyr Phe Asp Thr Gly
        275                 280                 285

Asp Asp Cys Ile Ala Ile Lys Ala Gly Arg Asn Glu Asp Gly Arg Arg
    290                 295                 300

Ile Asn Val Pro Thr Glu Asn Val Val Arg Gly Cys Val Met Lys
305                 310                 315                 320

Asp Gly His Gly Gly Ile Thr Ile Gly Ser Glu Ile Ser Gly Val
                325                 330                 335

Arg Asn Val Phe Ala Glu Asn Arg Leu Asp Ser Ala Asp Leu Trp
            340                 345                 350

Thr Ala Leu Arg Val Lys Asn Ala Ser Arg Gly Gly Lys Leu Glu
            355                 360                 365

Asn Phe Tyr Phe Arg Asp Ile Thr Val Gly Gln Val Ser Arg Ala Val
    370                 375                 380

Val Glu Ile Asp Phe Asn Tyr Glu Gly Ala Lys Gly Lys His Thr
385                 390                 395                 400

Pro Val Val Arg Asn Tyr Val Val Glu Asn Leu Thr Cys Asn Lys Gly
                405                 410                 415

Asn Arg Ala Val Asp Leu Gln Gly Leu Asp Asn Ala Pro Ile Tyr Asp
            420                 425                 430

Ile Thr Met Lys Asn Cys Thr Phe Asn Val Val Glu Lys Pro Ser Val
            435                 440                 445

Val Lys Asn Val Lys Gly Val Lys Leu Glu Asn Val Lys Ile Asn Gly
450                 455                 460

Lys Val Val Glu Ser Leu Glu Asn Ala Ala Thr Thr Ala Lys Lys
465                 470                 475

<210> SEQ ID NO 113
<211> LENGTH: 1017
<212> TYPE: DNA
<213> ORGANISM: Unknown
<220> FEATURE:
<223> OTHER INFORMATION: Obtained from an environmental sample

<400> SEQUENCE: 113
atgaagatat ttttaacaat attgctctcg gcattattca gcatttcaaa tgcacaggtg    60
ctatcggatc ctgttgcgga tcgtatgacc agctaccaac ttaaaaacgg aggctggccg   120

-continued

```
aagcacttgg ccgataaatc tgttgttaac tattcaaaac ctctctcacc tgctttgcaa    180
aaagtcatcg atcaatcgac cgaaaagtct gcgacaattg ataataatgc aaccacacgt    240
gagataaacc atcttctcct cgcttattcc aaaaccaaca atgacaagta tcttcaagcg    300
gcgacaaaag gtgttgagta tatcctgagt gctcaaaatg acaaggagg atggcctcaa     360 tattatccag acagtagctc atatcgtggt cagatcacct acaatgacgg cgcgatgatt    420
aatgtattgg aaattttact ttccatatca acaaaacaag agccctatgc tgttctaacg    480
aataaattta cgaaagaat agaaagggcc ttaacacgag ggattcactg catcttacaa     540
acccaggtta acaaggaga taaactaacc atctgggccg cacagtacga tcagaaaaca    600
atggaacctg ctcaagccag actgtttgaa ccggtagcgt tagcgacagc ggaatcggcg    660
ggcattctcc gctttttaat gcgtcttgac catcctactc ccgaaataaa aaatgcaatc    720
aaccacgctg tagaatggtt ttcctcccat aaagaggtag ctatgatta cgttaaaacg     780 gaaaaaaacg gaaaacttt tgcgggatttg gtttcttcgc cggcctctac cgtatgggca   840 agatttatg acatcaggac gaatcaaccc atctttggtg atcgcgataa tacgataaag     900
tattcgctga atgaaataag cgaggaacga caaaatggct actcttggta tggtaactgg    960
ccagaaaaga taattacaaa agaatatgaa aaatggctta agaaggtaaa tgaataa     1017
```

```
<210> SEQ ID NO 114
<211> LENGTH: 338
<212> TYPE: PRT
<213> ORGANISM: Unknown
<220> FEATURE:
<223> OTHER INFORMATION: Obtained from an environmental sample
<220> FEATURE:
<221> NAME/KEY: SIGNAL
<222> LOCATION: (1)...(18)
<220> FEATURE:
<221> NAME/KEY: DOMAIN
<222> LOCATION: (19)...(388)
<223> OTHER INFORMATION: Catalytic domain

<400> SEQUENCE: 114

Met Lys Ile Phe Leu Thr Ile Leu Leu Ser Ala Leu Phe Ser Ile Ser
 1               5                  10                  15

Asn Ala Gln Val Leu Ser Asp Pro Val Ala Asp Arg Met Thr Ser Tyr
             20                  25                  30

Gln Leu Lys Asn Gly Gly Trp Pro Lys His Leu Ala Asp Lys Ser Val
         35                  40                  45

Val Asn Tyr Ser Lys Pro Leu Ser Pro Ala Leu Gln Lys Val Ile Asp
     50                  55                  60

Gln Ser Thr Glu Lys Ser Ala Thr Ile Asp Asn Asn Ala Thr Arg
 65                  70                  75                  80

Glu Ile Asn His Leu Leu Ala Tyr Ser Lys Thr Asn Asn Asp Lys
                 85                  90                  95

Tyr Leu Gln Ala Ala Thr Lys Gly Val Glu Tyr Ile Leu Ser Ala Gln
            100                 105                 110

Asn Asp Lys Gly Gly Trp Pro Gln Tyr Tyr Pro Asp Ser Ser Tyr
        115                 120                 125

Arg Gly Gln Ile Thr Tyr Asn Asp Gly Ala Met Ile Asn Val Leu Glu
    130                 135                 140

Ile Leu Leu Ser Ile Ser Thr Lys Gln Glu Pro Tyr Ala Val Leu Thr
145                 150                 155                 160

Asn Lys Phe Asn Glu Arg Ile Glu Arg Ala Leu Thr Arg Gly Ile His
                165                 170                 175
```

-continued

```
Cys Ile Leu Gln Thr Gln Val Lys Gln Gly Asp Lys Leu Thr Ile Trp
            180                 185                 190
Ala Ala Gln Tyr Asp Gln Lys Thr Met Glu Pro Ala Gln Ala Arg Leu
        195                 200                 205
Phe Glu Pro Val Ala Leu Ala Thr Ala Glu Ser Ala Gly Ile Leu Arg
    210                 215                 220
Phe Leu Met Arg Leu Asp His Pro Thr Pro Glu Ile Lys Asn Ala Ile
225                 230                 235                 240
Asn His Ala Val Glu Trp Phe Ser Ser His Lys Glu Val Gly Tyr Asp
                245                 250                 255
Tyr Val Lys Thr Glu Lys Asn Gly Lys Leu Leu Arg Asp Leu Val Ser
            260                 265                 270
Ser Pro Ala Ser Thr Val Trp Ala Arg Phe Tyr Asp Ile Arg Thr Asn
        275                 280                 285
Gln Pro Ile Phe Gly Asp Arg Asp Asn Thr Ile Lys Tyr Ser Leu Asn
    290                 295                 300
Glu Ile Ser Glu Glu Arg Gln Asn Gly Tyr Ser Trp Tyr Gly Asn Trp
305                 310                 315                 320
Pro Glu Lys Ile Ile Thr Lys Glu Tyr Glu Lys Trp Leu Lys Lys Val
                325                 330                 335
Asn Glu
```

<210> SEQ ID NO 115
<211> LENGTH: 996
<212> TYPE: DNA
<213> ORGANISM: Unknown
<220> FEATURE:
<223> OTHER INFORMATION: Obtained from an environmental sample

<400> SEQUENCE: 115

```
gtggccaagg cgatcggcgg tccgttgccg ccggcaccag gcagggatc gccggtaacg      60
tgggcgacga ttctccggca gccatcgccg tggtacgcgt ccgcggacgc gaaggcggtt    120
gccgaaaccg tgcgcgcgag ccagagagcc accggcggct ggccgaagaa cacggattgg    180
acggcgctcc agagcgacgc tgagcggcag gcgctgcgaa atgcccgcgc cgagaccgat    240
tcgacgatcg acaatggcgc cacggtcacc gagcttcgct ttctcacccg cgtgtatgtc    300
gccacgcgcg acgagctttt acgggaggcc gtgcttcgcg gcctcgacta cctgctggcg    360
tcgcagtaca gcaacggcgg ctggccacaa tactttccgt tgcggaccga ttactcgcgg    420
gacatcacgt tcaacgacga cgcgatgacc ggcgtggtgc tgctgctgaa ggatgccgcg    480
gacgggtcag caggtttcga attcgtcgac aaggcgagac gtgaccgcgc tgccgcggcc    540
gtgacgcgcg ccatcgcggt gatcctccgc acgcagattc gggtcaacgg tacgctgacc    600
ggctggtgcc agcagtacga cgccgacgcg ctgacgccgg cgcgcgggcg ctcgtacgag    660
catccgtcga ttgcgagccg cgagacggtc gggatcgcgc ggctgctgat gggcgtgccg    720
aatccgtcgc cagagatcgt ggctgccgtt gacgcggctg ccgcatggtt gggtaaatcg    780
gaactgaagg gtgtgcccga ggcgacggcg ccaggacttt gggcgcgctt ctacgacatc    840
gctacgaatc ggccgatcta ttcgggccgc gacggcgtca tcaagtaccg gctcgacgag    900
atcgagctcg agcggcgcac aggctacagc tgggttggcc cgtacgccgc ggcatttctg    960
acgaccgaat atccgaaatg gcgggcggca cgatga                              996
```

<210> SEQ ID NO 116

```
<211> LENGTH: 331
<212> TYPE: PRT
<213> ORGANISM: Unknown
<220> FEATURE:
<223> OTHER INFORMATION: Obtained from an environmental sample
<220> FEATURE:
<221> NAME/KEY: DOMAIN
<222> LOCATION: (1)...(331)
<223> OTHER INFORMATION: Catalytic domain

<400> SEQUENCE: 116

Met Ala Lys Ala Ile Gly Gly Pro Leu Pro Ala Pro Gly Gln Gly
 1               5                  10                  15

Ser Pro Val Thr Trp Ala Thr Ile Leu Arg Gln Pro Ser Pro Trp Tyr
                20                  25                  30

Ala Ser Ala Asp Ala Lys Ala Val Ala Glu Thr Val Arg Ala Ser Gln
            35                  40                  45

Arg Ala Thr Gly Gly Trp Pro Lys Asn Thr Asp Trp Thr Ala Leu Gln
        50                  55                  60

Ser Asp Ala Glu Arg Gln Ala Leu Arg Asn Ala Arg Ala Glu Thr Asp
65                  70                  75                  80

Ser Thr Ile Asp Asn Gly Ala Thr Val Thr Glu Leu Arg Phe Leu Thr
                85                  90                  95

Arg Val Tyr Val Ala Thr Arg Asp Glu Leu Leu Arg Glu Ala Val Leu
            100                 105                 110

Arg Gly Leu Asp Tyr Leu Leu Ala Ser Gln Tyr Ser Asn Gly Gly Trp
        115                 120                 125

Pro Gln Tyr Phe Pro Leu Arg Thr Asp Tyr Ser Arg Asp Ile Thr Phe
130                 135                 140

Asn Asp Asp Ala Met Thr Gly Val Val Leu Leu Leu Lys Asp Ala Ala
145                 150                 155                 160

Asp Gly Ser Ala Gly Phe Glu Phe Val Asp Lys Ala Arg Arg Asp Arg
                165                 170                 175

Ala Ala Ala Ala Val Thr Arg Ala Ile Ala Val Ile Leu Arg Thr Gln
            180                 185                 190

Ile Arg Val Asn Gly Thr Leu Thr Gly Trp Cys Gln Gln Tyr Asp Ala
        195                 200                 205

Asp Ala Leu Thr Pro Ala Arg Gly Arg Ser Tyr Glu His Pro Ser Ile
210                 215                 220

Ala Ser Arg Glu Thr Val Gly Ile Ala Arg Leu Leu Met Gly Val Pro
225                 230                 235                 240

Asn Pro Ser Pro Glu Ile Val Ala Ala Val Asp Ala Ala Ala Ala Trp
                245                 250                 255

Leu Gly Lys Ser Glu Leu Lys Gly Val Pro Glu Ala Thr Ala Pro Gly
            260                 265                 270

Leu Trp Ala Arg Phe Tyr Asp Ile Ala Thr Asn Arg Pro Ile Tyr Ser
        275                 280                 285

Gly Arg Asp Gly Val Ile Lys Tyr Arg Leu Asp Glu Ile Glu Leu Glu
290                 295                 300

Arg Arg Thr Gly Tyr Ser Trp Val Gly Pro Tyr Ala Ala Ala Phe Leu
305                 310                 315                 320

Thr Thr Glu Tyr Pro Lys Trp Arg Ala Ala Arg
                325                 330

<210> SEQ ID NO 117
<211> LENGTH: 1725
<212> TYPE: DNA
```

<213> ORGANISM: Unknown
<220> FEATURE:
<223> OTHER INFORMATION: Obtained from an environmental sample.

<400> SEQUENCE: 117

```
atgaagaatt ttgggtttgg taactacaag tttttgtag cggcaatgtc tgtcgcgtct      60
ttttcgtatg cggcaagcta tacacccccg tcaacagcag tttcgaaaat caacagctat    120
cgaggctatt cggagctgac ttcagctgca tccggcatgg atatcgacca gtacacctac    180
aacatgacca cttggcaaat cgcaaacggc ggttttttaca agccatggc cgacaagtat    240
aaaagcgcgt atggcggcgg tcaaaaatcc gaatggcaag ctaaaggcgg tggcgacctc    300
ggcactatag acaacaacgc caccatccag gaaatgcgtt tgctcgccgt gcgttacaaa    360
gaaacgacga caacaatta caaatccgca tttaagacaa gtttcaacaa ggcggtcaat    420
tttcttttga ccatgcagcg ctccaaaggc ggactcccac aagtttggcc caaacgcggc    480
aactattctg accaaatcac gctaaatgac aacgccatga tccgcgccat ggtcacgatg    540
atggatatcg ccaacaagac gagtccattt gattcggata tcatcgacga cgccacccgc    600
agcaaaatga atcggctct cgacaaagcg gtcgattact tgctcaaggc gcaaatcgtg    660
aacgacggaa aggtcacggt atggtgcgcc cagcacgaca ccaacagcct cgcccccgta    720
ggcgcacgag cctacgaact cccgagcaaa tccggcaacg aatccatggg cgttgtgtgg    780
tttttgatga actggccaga ccaaaacgaa gcaatccaga aggcggtcaa aggcgcaatc    840
gcttggtaca aaagaataa actaaaagac aaggcgttta gcaagaccgc aggcgttgtg    900
gacaaggcgg gttcatcgct gtggttccgc ttttacgaag tcaacaacga caactacttt    960
ttctgcgacc gcgatggtgc tagcaccaag acgcaggact tcatgaaaat cagcgaagaa   1020
cgtcgcaagg gctaccagtg ggcaggcgat tacggctctg caattctagg caccgaaaat   1080
gcataccttg aagcactcgc caagatggac gacaactatg ttccacctcc gccagcacca   1140
gctatgtgcg gaaacgacac ttgcaaaacg tacatcgatg gcgttgactt tattgacatt   1200
caaggcgtca aggaaacaac caacacggga ttcgttggcg aaggttacgc caacgttgac   1260
aactccaccg gaagctatgt gacctacggc gtcaccgcat tcaaggaagg caaatacact   1320
tgtttcatca gcttttgcaaa cggcggtggt tccgcacgcg gttacagcgt ttctgcagga   1380
gacaagacgt tacttgcaga cggcagcatg gaatctacag ccgcatggac cacttggaaa   1440
atgcaatcca tcgaaatcga attgccaatg ggctatagcg aactcaagtt cacaagcctt   1500
tcgaaagacg gtatggcgaa catcgattac atcggctgga tgaacgatga tttgaaagtt   1560
ggcgaagttg aagtaccacg ctcatccatt gaagcaatac gcgccatccg caaagcccag   1620
caggacaacc gctactttgt ggactttggc ggcaacaata tagcgcagg gcttactttt   1680
aagcgtggca tcaacacgtt ccgcgtgaat gggaagatga ggtaa                    1725
```

<210> SEQ ID NO 118
<211> LENGTH: 574
<212> TYPE: PRT
<213> ORGANISM: Unknown
<220> FEATURE:
<223> OTHER INFORMATION: Obtained from an environmental sample.
<220> FEATURE:
<221> NAME/KEY: SIGNAL
<222> LOCATION: (1)...(24)
<220> FEATURE:
<221> NAME/KEY: DOMAIN
<222> LOCATION: (25)...(574)
<223> OTHER INFORMATION: Catalytic domain

<400> SEQUENCE: 118

```
Met Lys Asn Phe Gly Phe Gly Asn Tyr Lys Phe Val Ala Ala Met
  1               5                  10                  15
Ser Val Ala Ser Phe Ser Tyr Ala Ala Ser Tyr Thr Pro Pro Ser Thr
             20                  25                  30
Ala Val Ser Lys Ile Asn Ser Tyr Arg Gly Tyr Ser Glu Leu Thr Ser
             35                  40                  45
Ala Ala Ser Gly Met Asp Ile Asp Gln Tyr Thr Tyr Asn Met Thr Thr
         50                  55                  60
Trp Gln Ile Ala Asn Gly Gly Phe Tyr Lys Ala Met Ala Asp Lys Tyr
 65                  70                  75                  80
Lys Ser Ala Tyr Gly Gly Gly Gln Lys Ser Glu Trp Gln Ala Lys Gly
                 85                  90                  95
Gly Gly Asp Leu Gly Thr Ile Asp Asn Asn Ala Thr Ile Gln Glu Met
            100                 105                 110
Arg Leu Leu Ala Val Arg Tyr Lys Glu Thr Thr Asn Asn Asn Tyr Lys
            115                 120                 125
Ser Ala Phe Lys Thr Ser Phe Asn Lys Ala Val Asn Phe Leu Leu Thr
130                 135                 140
Met Gln Arg Ser Lys Gly Gly Leu Pro Gln Val Trp Pro Lys Arg Gly
145                 150                 155                 160
Asn Tyr Ser Asp Gln Ile Thr Leu Asn Asp Asn Ala Met Ile Arg Ala
                165                 170                 175
Met Val Thr Met Met Asp Ile Ala Asn Lys Thr Ser Pro Phe Asp Ser
            180                 185                 190
Asp Ile Ile Asp Asp Ala Thr Arg Ser Lys Met Lys Ser Ala Leu Asp
            195                 200                 205
Lys Ala Val Asp Tyr Leu Leu Lys Ala Gln Ile Val Asn Asp Gly Lys
            210                 215                 220
Val Thr Val Trp Cys Ala Gln His Asp Thr Asn Ser Leu Ala Pro Val
225                 230                 235                 240
Gly Ala Arg Ala Tyr Glu Leu Pro Ser Lys Ser Gly Asn Glu Ser Met
                245                 250                 255
Gly Val Val Trp Phe Leu Met Asn Trp Pro Asp Gln Asn Glu Ala Ile
            260                 265                 270
Gln Lys Ala Val Lys Gly Ala Ile Ala Trp Tyr Lys Lys Asn Lys Leu
            275                 280                 285
Lys Asp Lys Ala Phe Ser Lys Thr Ala Gly Val Val Asp Lys Ala Gly
290                 295                 300
Ser Ser Leu Trp Phe Arg Phe Tyr Glu Val Asn Asn Asp Asn Tyr Phe
305                 310                 315                 320
Phe Cys Asp Arg Asp Gly Ala Ser Thr Lys Thr Gln Asp Phe Met Lys
                325                 330                 335
Ile Ser Glu Glu Arg Arg Lys Gly Tyr Gln Trp Ala Gly Asp Tyr Gly
            340                 345                 350
Ser Ala Ile Leu Gly Thr Glu Asn Ala Tyr Leu Glu Ala Leu Ala Lys
            355                 360                 365
Met Asp Asp Asn Tyr Val Pro Pro Pro Ala Pro Ala Met Cys Gly
370                 375                 380
Asn Asp Thr Cys Lys Thr Tyr Ile Asp Gly Val Asp Phe Ile Asp Ile
385                 390                 395                 400
Gln Gly Val Lys Glu Thr Thr Asn Thr Gly Phe Val Gly Glu Gly Tyr
                405                 410                 415
```

```
Ala Asn Val Asp Asn Ser Thr Gly Ser Tyr Val Thr Tyr Gly Val Thr
            420                 425                 430

Ala Phe Lys Glu Gly Lys Tyr Thr Leu Phe Ile Ser Phe Ala Asn Gly
        435                 440                 445

Gly Gly Ser Ala Arg Gly Tyr Ser Val Ser Ala Gly Asp Lys Thr Leu
    450                 455                 460

Leu Ala Asp Gly Ser Met Glu Ser Thr Ala Ala Trp Thr Thr Trp Lys
465                 470                 475                 480

Met Gln Ser Ile Glu Ile Glu Leu Pro Met Gly Tyr Ser Glu Leu Lys
            485                 490                 495

Phe Thr Ser Leu Ser Lys Asp Gly Met Ala Asn Ile Asp Tyr Ile Gly
        500                 505                 510

Trp Met Asn Asp Asp Leu Lys Val Gly Glu Val Glu Val Pro Arg Ser
            515                 520                 525

Ser Ile Glu Ala Ile Arg Ala Ile Arg Lys Ala Gln Gln Asp Asn Arg
    530                 535                 540

Tyr Phe Val Asp Phe Gly Gly Asn Asn Asn Ser Ala Gly Ala Tyr Phe
545                 550                 555                 560

Lys Arg Gly Ile Asn Thr Phe Arg Val Asn Gly Lys Met Arg
            565                 570

<210> SEQ ID NO 119
<211> LENGTH: 1848
<212> TYPE: DNA
<213> ORGANISM: Unknown
<220> FEATURE:
<223> OTHER INFORMATION: Obtained from an environmental sample.

<400> SEQUENCE: 119
gtgtcatggc aggaatccgg tgcggctatc accaacgcct ggaatgcaac gctcagtggc      60
tcaaacccctt acacagccgt atccgctggt tggaatggca cacttgcccc caatgcatcg    120
gccactttg gtttccaggc aaacggttct gccggtgcac ctaaagtgaa tggcagcttg      180
tgcggcacca acacttcatc aacaccggca tccagcagtg ttgccagctc ggttaaatca     240
agcgcgcccg tatcgtccag cagcagatca tccagttcaa tcgctatcac tagcagctct    300
ttagcgagaa gttctattgc ctccagcagc tcactagtta gtagctccag agcgagcagt    360
agtgcgccaa gcgttttctc ttttacgatc caggaagagc aagcgggctt ctgtcgtgtt    420
gatggcattg cgacagaaag caccaacacc ggttttaccg gcaatggcta caccaatgcg    480
aacaacgcgc aaggcgcagc gattgaatgg gcagtcagcg cacctagcag tggccgttat    540
acagtagcct tccgcttcgc caatggcggc acagcagcgc gcaacggctc gttgttaatc    600
aatggcggta gcaatggtaa ttacactgtg gagttacccc tgaccggcgc atgggcaacc    660
tggcaaattg ccagcgtgga aattgattta gtgcaaggca ataatatttt aaaactctcg    720
gcgttaaccg ctgacggttt ggccaatatc gactcattaa aaatagacgg cgcgcaaacc    780
aaagcaggta cttgcagcac tacatcaagc agcagcgttg ccagcagctc gtcgtccgtt    840
aaatccagcg caagttcttc ttcgagttca tccaccgctg caaaaatact gacattagac    900
ggtaaccccgg ccgccagctg gttcaacaaa tccaggacca agtggaatag cagccgcgcc   960
gatattgtgt tgtcttacca gcaatccaac ggcggttggc caaaaaacct ggattacaac  1020
tcagtgagcg caggcaatgg cgggagcgac agcggcacca tcgacaatgg tgcaaccatt  1080
accgaaatgg ttttacctcgc tgaaatttat aaaaacggcg gcaacaccaa atatcgcgat  1140
```

-continued

```
gcagtgcgca gagcagcaaa cttttagtg agctcgcaat acagcacagg cgccttgcca      1200
caattttatc cgttgaaagg cggctatgcg gatcatgcga cctttaacga taacggcatg      1260
gcgtacgcgt tgacggtatt ggatttcgca gtaaacaaac gcgcaccgtt tgataacgac      1320
attttctctg attctgatcg ggcgaaattc aaaaccgctg ttgccaaagg tgtggattac      1380
attttaaaag cgcagtggaa acaaaatgga aaactcactg catggtgtgc acaacacggt      1440
gctacggatt accaaccgaa aaagcgcgc gcttatgaat tggaatcatt gagtggtagc      1500
gagtcggtcg gcattctcgc cttcttgatg acccaaccac aaaccgcgca atcgaagcg      1560 gcggtcaagg cgggtgtcaa ctggttcgcc agtccaaata cttatttggc taactacact      1620
tacgattcat caaaagcgtc taccaacccg attgtgtata atccggaag cagaatgtgg       1680 tatcgcttct atgacctgaa caccaaccgt ggtttcttta gtgatcgcga tggcagcaaa      1740
ttctatgata tcacccaaat gtcagaagag cgtcgcaccg gttatagctg gggtggctct      1800
tacggtgaat ctattatttc cttcgcgcaa aaagtgggtt atctgtaa                   1848
```

<210> SEQ ID NO 120
<211> LENGTH: 615
<212> TYPE: PRT
<213> ORGANISM: Unknown
<220> FEATURE:
<223> OTHER INFORMATION: Obtained from an environmental sample.
<220> FEATURE:
<221> NAME/KEY: BINDING
<222> LOCATION: (1)...(61)
<223> OTHER INFORMATION: Carbohydrate binding module
<220> FEATURE:
<221> NAME/KEY: BINDING
<222> LOCATION: (134)...(257)
<223> OTHER INFORMATION: Carbohydrate binding module
<220> FEATURE:
<221> NAME/KEY: DOMAIN
<222> LOCATION: (258)...(615)
<223> OTHER INFORMATION: Catalytic domain

<400> SEQUENCE: 120

```
Met Ser Trp Gln Glu Ser Gly Ala Ala Ile Thr Asn Ala Trp Asn Ala
  1               5                  10                  15

Thr Leu Ser Gly Ser Asn Pro Tyr Thr Ala Val Ser Ala Gly Trp Asn
                 20                  25                  30

Gly Thr Leu Ala Pro Asn Ala Ser Ala Thr Phe Gly Phe Gln Ala Asn
             35                  40                  45

Gly Ser Ala Gly Ala Pro Lys Val Asn Gly Ser Leu Cys Gly Thr Asn
         50                  55                  60

Thr Ser Thr Pro Ala Ser Ser Val Ala Ser Val Lys Ser
 65                  70                  75                  80

Ser Ala Pro Val Ser Ser Ser Arg Ser Ser Ser Ile Ala Ile
                 85                  90                  95

Thr Ser Ser Leu Ala Arg Ser Ile Ala Ser Ser Ser Leu
                100                 105                 110

Val Ser Ser Arg Ala Ser Ser Ala Pro Ser Val Phe Ser Phe
            115                 120                 125

Thr Ile Gln Glu Glu Gln Ala Gly Phe Cys Arg Val Asp Gly Ile Ala
        130                 135                 140

Thr Glu Ser Thr Asn Thr Gly Phe Thr Gly Asn Gly Tyr Thr Asn Ala
145                 150                 155                 160

Asn Asn Ala Gln Gly Ala Ala Ile Glu Trp Ala Val Ser Ala Pro Ser
                165                 170                 175
```

```
Ser Gly Arg Tyr Thr Val Ala Phe Arg Phe Ala Asn Gly Gly Thr Ala
            180                 185                 190

Ala Arg Asn Gly Ser Leu Leu Ile Asn Gly Gly Ser Asn Gly Asn Tyr
        195                 200                 205

Thr Val Glu Leu Pro Leu Thr Gly Ala Trp Ala Thr Trp Gln Ile Ala
    210                 215                 220

Ser Val Glu Ile Asp Leu Val Gln Gly Asn Asn Ile Leu Lys Leu Ser
225                 230                 235                 240

Ala Leu Thr Ala Asp Gly Leu Ala Asn Ile Asp Ser Leu Lys Ile Asp
                245                 250                 255

Gly Ala Gln Thr Lys Ala Gly Thr Cys Ser Thr Ser Ser Ser Ser
                260                 265                 270

Val Ala Ser Ser Ser Ser Val Lys Ser Ser Ala Ser Ser Ser Ser
                275                 280                 285

Ser Ser Ser Thr Ala Ala Lys Ile Leu Thr Leu Asp Gly Asn Pro Ala
        290                 295                 300

Ala Ser Trp Phe Asn Lys Ser Arg Thr Lys Trp Asn Ser Ser Arg Ala
305                 310                 315                 320

Asp Ile Val Leu Ser Tyr Gln Gln Ser Asn Gly Gly Trp Pro Lys Asn
                325                 330                 335

Leu Asp Tyr Asn Ser Val Ser Ala Gly Asn Gly Gly Ser Asp Ser Gly
                340                 345                 350

Thr Ile Asp Asn Gly Ala Thr Ile Thr Glu Met Val Tyr Leu Ala Glu
        355                 360                 365

Ile Tyr Lys Asn Gly Gly Asn Thr Lys Tyr Arg Asp Ala Val Arg Arg
        370                 375                 380

Ala Ala Asn Phe Leu Val Ser Ser Gln Tyr Ser Thr Gly Ala Leu Pro
385                 390                 395                 400

Gln Phe Tyr Pro Leu Lys Gly Gly Tyr Ala Asp His Ala Thr Phe Asn
                405                 410                 415

Asp Asn Gly Met Ala Tyr Ala Leu Thr Val Leu Asp Phe Ala Val Asn
                420                 425                 430

Lys Arg Ala Pro Phe Asp Asn Asp Ile Phe Ser Asp Ser Asp Arg Ala
                435                 440                 445

Lys Phe Lys Thr Ala Val Ala Lys Gly Val Asp Tyr Ile Leu Lys Ala
450                 455                 460

Gln Trp Lys Gln Asn Gly Lys Leu Thr Ala Trp Cys Ala Gln His Gly
465                 470                 475                 480

Ala Thr Asp Tyr Gln Pro Lys Lys Ala Arg Ala Tyr Glu Leu Glu Ser
                485                 490                 495

Leu Ser Gly Ser Glu Ser Val Gly Ile Leu Ala Phe Leu Met Thr Gln
            500                 505                 510

Pro Gln Thr Ala Gln Ile Glu Ala Ala Val Lys Ala Gly Val Asn Trp
    515                 520                 525

Phe Ala Ser Pro Asn Thr Tyr Leu Ala Asn Tyr Thr Tyr Asp Ser Ser
    530                 535                 540

Lys Ala Ser Thr Asn Pro Ile Val Tyr Lys Ser Gly Ser Arg Met Trp
545                 550                 555                 560

Tyr Arg Phe Tyr Asp Leu Asn Thr Asn Arg Gly Phe Phe Ser Asp Arg
                565                 570                 575

Asp Gly Ser Lys Phe Tyr Asp Ile Thr Gln Met Ser Glu Glu Arg Arg
            580                 585                 590

Thr Gly Tyr Ser Trp Gly Gly Ser Tyr Gly Glu Ser Ile Ile Ser Phe
```

Ala Gln Lys Val Gly Tyr Leu
    610             615

<210> SEQ ID NO 121
<211> LENGTH: 1047
<212> TYPE: DNA
<213> ORGANISM: Bacteria

<400> SEQUENCE: 121

```
atgatgagat caagcatcgt caagctagtt gctttcagtg ttgtggttat gttatggctc      60
ggtgtatcct ttcaaacggc agaagcgaat acgccaaatt tcaacttaca aggctttgcc     120
acgttaaatg ggggaacaac tggtggtgca ggtggagatg tagtgacggt tcgtacaggg     180
aatgaattaa taaacgcttt gaagtccaaa acccctaatc gtccgttaac aatttatgta     240
aacggtacga taacacctag taatacgtct gatagtaaga tcgatattaa ggatgtttcc     300
aatgtatcga ttttaggggt tggtacaaat ggacgattaa atgggatcgg tattaaagta     360
tggcgagcga ataatatcat cattcgcaac ttgacgatcc atgaagtcca tacaggtgat     420
aaagatgcga ttagcattga agggccctct cggaacattt ggattgacca taacgagctt     480
tatgccagct tgaacgttca taaagaccac tatgacggct tgtttgacgt aaagcgcgat     540
gcttacaata ttaccttctc ttggaattat gtccatgatg gctggaaagc gatgctcatg     600
gggaactctg atagtgataa ctacgaccga acataacat tccaccataa ctacttcaaa     660
aacttaaact ctcgcgtacc tgcgtaccgt tttggaaagg cgcacttgtt tagcaattac     720
tttgagaaca ttttagaaac aggcattaat tcacggatgg gagcggaaat gctcgttgaa     780
cataacgttt tgagaatgc caccaacccg ttaggattct ggcatagcag tcgaacaggt     840
tattggaatg ttgccaataa ccgctatatc aatagcacgg gtagcatgcc gaccacttcc     900
acgaccaatt atcgacctcc ttatccctat acgtcacac cagttggtga tgtgaaatcg     960
gttgtcacac gttatgcggg agttggtgtc atccagccgt atgcaagaaa gccatccgag    1020
cgattgctct ggtggctttt tgcataa                                        1047
```

<210> SEQ ID NO 122
<211> LENGTH: 348
<212> TYPE: PRT
<213> ORGANISM: Bacteria
<220> FEATURE:
<221> NAME/KEY: SIGNAL
<222> LOCATION: (1)...(29)
<220> FEATURE:
<221> NAME/KEY: DOMAIN
<222> LOCATION: (30)...(348)
<223> OTHER INFORMATION: Catalytic domain

<400> SEQUENCE: 122

Met Met Arg Ser Ser Ile Val Lys Leu Val Ala Phe Ser Val Val
  1               5                  10                  15

Met Leu Trp Leu Gly Val Ser Phe Gln Thr Ala Glu Ala Asn Thr Pro
           20                  25                  30

Asn Phe Asn Leu Gln Gly Phe Ala Thr Leu Asn Gly Gly Thr Thr Gly
       35                  40                  45

Gly Ala Gly Gly Asp Val Val Thr Val Arg Thr Gly Asn Glu Leu Ile
    50                  55                  60

Asn Ala Leu Lys Ser Lys Asn Pro Asn Arg Pro Leu Thr Ile Tyr Val
65                  70                  75                  80

```
Asn Gly Thr Ile Thr Pro Ser Asn Ser Asp Ser Lys Ile Asp Ile
                85                  90                  95
Lys Asp Val Ser Asn Val Ser Ile Leu Gly Val Gly Thr Asn Gly Arg
            100                 105                 110
Leu Asn Gly Ile Gly Ile Lys Val Trp Arg Ala Asn Asn Ile Ile Ile
            115                 120                 125
Arg Asn Leu Thr Ile His Glu Val His Thr Gly Asp Lys Asp Ala Ile
        130                 135                 140
Ser Ile Glu Gly Pro Ser Arg Asn Ile Trp Ile Asp His Asn Glu Leu
145                 150                 155                 160
Tyr Ala Ser Leu Asn Val His Lys Asp His Tyr Asp Gly Leu Phe Asp
                165                 170                 175
Val Lys Arg Asp Ala Tyr Asn Ile Thr Phe Ser Trp Asn Tyr Val His
            180                 185                 190
Asp Gly Trp Lys Ala Met Leu Met Gly Asn Ser Asp Ser Asp Asn Tyr
        195                 200                 205
Asp Arg Asn Ile Thr Phe His His Asn Tyr Phe Lys Asn Leu Asn Ser
    210                 215                 220
Arg Val Pro Ala Tyr Arg Phe Gly Lys Ala His Leu Phe Ser Asn Tyr
225                 230                 235                 240
Phe Glu Asn Ile Leu Glu Thr Gly Ile Asn Ser Arg Met Gly Ala Glu
                245                 250                 255
Met Leu Val Glu His Asn Val Phe Glu Asn Ala Thr Asn Pro Leu Gly
            260                 265                 270
Phe Trp His Ser Ser Arg Thr Gly Tyr Trp Asn Val Ala Asn Asn Arg
        275                 280                 285
Tyr Ile Asn Ser Thr Gly Ser Met Pro Thr Thr Ser Thr Thr Asn Tyr
    290                 295                 300
Arg Pro Pro Tyr Pro Tyr Thr Val Thr Pro Val Gly Asp Val Lys Ser
305                 310                 315                 320
Val Val Thr Arg Tyr Ala Gly Val Gly Val Ile Gln Pro Tyr Ala Arg
                325                 330                 335
Lys Pro Ser Glu Arg Leu Leu Trp Trp Leu Phe Ala
            340                 345
```

<210> SEQ ID NO 123
<211> LENGTH: 1830
<212> TYPE: DNA
<213> ORGANISM: Unknown
<220> FEATURE:
<223> OTHER INFORMATION: Obtained from an environmental sample.

<400> SEQUENCE: 123

```
ttgagtctac ttagtgtaat gacccttttg cctgtaatgg caagtaacaa cgtagctccc      60
tggggctggg ccacctgctc cgatgagtca gcgacagctt atactctgaa cggaggttgc     120
ttttctgatg catcttccgt tactctgaaa gctcttggca atgaacaaac agatgacaaa     180
caaatcaaac aggctatcgc tcagaaagac atcattatct tagatggttc caatggcgat     240
ttcatcctta atgaatacat caagatttcg accaaaaaca aaccatcat tggtatcaac      300
aacgcccgcc tgtgtacaaa gttctaccta accgctgatg atattacgta ccttaaagca     360
caaggactgg agggactgag tagtacaaat caacatacag gaactctgcc tgatggcaca     420
acagtgacct gtgacgagcg tgccttttc accaagaaag ccatcatgga actccaatat     480
cagaaaacag gatcctatac cctacccaat aaatcaggta tcttttattt agatgccgct     540
```

```
tctgagaata tcatcatccg aaatatttcg ctgataggc caggagccgt agatatagac    600
ggagctgacc tgattaccaa tcagggtaag cacgtctgga ttgaccattg cacgtttgtg    660
gactctcaag atggtgccct ggacagcaag gtatgcgact gggccaccta tacctataac    720
cacttctact atacagaccg cagttactca catgcctaca cttgcggttg cggatgggtc    780
agcaatcatg aaatggtgat tcacatgacc tttgcatgta atatctgggg agcaaaatgt    840
atgcgtcgtc tgccgcaagc agatgactgt ttcatacacc ttgtgaacaa ctatcacaac    900
tgtcctggca atagtgtcgg tatgaccatt aacagttaca gcaaagcatt ggttgagggt    960
aactatgctg ctgcaggtgt caacaagcca ttagatggca gtggggccaa ccgtaatgta   1020
acagctaagg ataatagttt tgcaaactca caagccggtt ctgttgtgtc tgtgccatac   1080
gactatacca agattgcagc cgccgacgtt ccagctacgc tgactggaac agagggtgca   1140
ggcgccacat taggcaacga tgcaacatac attctgtcta ctattccaac tgtcgaccga   1200
caagaaggcg aatcttcact ctactatttc attgatggcc tggtgggaac taatagtgaa   1260
ggctattcca ttatagagtt taatgatggc gcaacattgc tgctgaacaa taaagagaaa   1320
gcatggtcta atggtagtgc aattcaactt ggtgacgata attatacgag tattaaactt   1380
tctaatggag cagaaaacat cttcacagca cctactggca aaaagtaag tggtattacc    1440
ttctattctt atatcaatat aaaagaagaa aaactcgact tcaccaaata tccagaatat   1500
ggtttccgca cctgtttctg cagaaagtt gccaacctca cttattctgc gacttctgat   1560
gacgtacaaa tcttgaaatc tcgtgatcca cagaatactg acgtggcatc attccatttc   1620
actccaacaa atgttgtaag tttcaaaaat tcaggtgaac agctttgttt cttaatgaaa   1680
gtcacctata gtgatgaaag cacaggtatc tctgctatcc agaaaaaaat gcctatcgat   1740
ggcgttacct ataaccttca aggtatccgt atagataatc ccaccaaggg aatctatatt   1800
cagaacggaa agaaaatcat tatcaaataa                                    1830

<210> SEQ ID NO 124
<211> LENGTH: 609
<212> TYPE: PRT
<213> ORGANISM: Unknown
<220> FEATURE:
<223> OTHER INFORMATION: Obtained from an environmental sample.
<220> FEATURE:
<221> NAME/KEY: SIGNAL
<222> LOCATION: (1)...(21)
<220> FEATURE:
<221> NAME/KEY: DOMAIN
<222> LOCATION: (22)...(390)
<223> OTHER INFORMATION: Catalytic domain

<400> SEQUENCE: 124

Leu Ser Leu Leu Ser Val Met Thr Leu Leu Pro Val Met Ala Ser Asn
 1               5                  10                  15

Asn Val Ala Pro Trp Gly Trp Ala Thr Cys Ser Asp Glu Ser Ala Thr
            20                  25                  30

Ala Tyr Thr Leu Asn Gly Gly Cys Phe Ser Asp Ala Ser Ser Val Thr
        35                  40                  45

Leu Lys Ala Leu Gly Asn Glu Gln Thr Asp Asp Lys Gln Ile Lys Gln
    50                  55                  60

Ala Ile Ala Gln Lys Asp Ile Ile Ile Leu Asp Gly Ser Asn Gly Asp
65                  70                  75                  80

Phe Ile Leu Asn Glu Tyr Ile Lys Ile Ser Thr Lys Asn Lys Thr Ile
                85                  90                  95
```

```
Ile Gly Ile Asn Asn Ala Arg Leu Cys Thr Lys Phe Tyr Leu Thr Ala
            100                 105                 110
Asp Asp Ile Thr Tyr Leu Lys Ala Gln Gly Leu Glu Gly Leu Ser Ser
            115                 120                 125
Thr Asn Gln His Thr Gly Thr Leu Pro Asp Gly Thr Thr Val Thr Cys
            130                 135                 140
Asp Glu Arg Ala Phe Phe Thr Lys Lys Ala Ile Met Glu Leu Gln Tyr
145                 150                 155                 160
Gln Lys Thr Gly Ser Tyr Thr Leu Pro Asn Lys Ser Gly Ile Phe Tyr
            165                 170                 175
Leu Asp Ala Ala Ser Glu Asn Ile Ile Ile Arg Asn Ile Ser Leu Ile
            180                 185                 190
Gly Pro Gly Ala Val Asp Ile Asp Gly Ala Asp Leu Ile Thr Asn Gln
            195                 200                 205
Gly Lys His Val Trp Ile Asp His Cys Thr Phe Val Asp Ser Gln Asp
            210                 215                 220
Gly Ala Leu Asp Ser Lys Val Cys Asp Trp Ala Thr Tyr Thr Tyr Asn
225                 230                 235                 240
His Phe Tyr Tyr Thr Asp Arg Ser Tyr Ser His Ala Tyr Thr Cys Gly
            245                 250                 255
Cys Gly Trp Val Ser Asn His Glu Met Val Ile His Met Thr Phe Ala
            260                 265                 270
Cys Asn Ile Trp Gly Ala Lys Cys Met Arg Arg Leu Pro Gln Ala Asp
            275                 280                 285
Asp Cys Phe Ile His Leu Val Asn Asn Tyr His Asn Cys Pro Gly Asn
            290                 295                 300
Ser Val Gly Met Thr Ile Asn Ser Tyr Ser Lys Ala Leu Val Glu Gly
305                 310                 315                 320
Asn Tyr Ala Ala Ala Gly Val Asn Lys Pro Leu Asp Gly Ser Gly Ala
            325                 330                 335
Asn Arg Asn Val Thr Ala Lys Asp Asn Ser Phe Ala Asn Ser Gln Ala
            340                 345                 350
Gly Ser Val Val Ser Val Pro Tyr Asp Tyr Thr Lys Ile Ala Ala Ala
            355                 360                 365
Asp Val Pro Ala Thr Leu Thr Gly Thr Glu Gly Ala Gly Ala Thr Leu
            370                 375                 380
Gly Asn Asp Ala Thr Tyr Ile Leu Ser Thr Ile Pro Thr Val Asp Arg
385                 390                 395                 400
Gln Glu Gly Glu Ser Ser Leu Tyr Tyr Phe Ile Asp Gly Leu Val Gly
            405                 410                 415
Thr Asn Ser Glu Gly Tyr Ser Ile Ile Glu Phe Asn Asp Gly Ala Thr
            420                 425                 430
Leu Leu Leu Asn Asn Lys Glu Lys Ala Trp Ser Asn Gly Ser Ala Ile
            435                 440                 445
Gln Leu Gly Asp Asp Asn Tyr Thr Ser Ile Lys Leu Ser Asn Gly Ala
            450                 455                 460
Glu Asn Ile Phe Thr Ala Pro Thr Gly Lys Lys Val Ser Gly Ile Thr
465                 470                 475                 480
Phe Tyr Ser Tyr Ile Asn Ile Lys Glu Glu Lys Leu Asp Phe Thr Lys
            485                 490                 495
Tyr Pro Glu Tyr Gly Phe Arg Thr Cys Phe Trp Gln Lys Val Ala Asn
            500                 505                 510
Leu Thr Tyr Ser Ala Thr Ser Asp Asp Val Gln Ile Leu Lys Ser Arg
```

```
                515                 520                 525
Asp Pro Gln Asn Thr Asp Val Ala Ser Phe His Phe Thr Pro Thr Asn
        530                 535                 540

Val Val Ser Phe Lys Asn Ser Gly Glu Gln Leu Cys Phe Leu Met Lys
545                 550                 555                 560

Val Thr Tyr Ser Asp Glu Ser Thr Gly Ile Ser Ala Ile Gln Lys Lys
                565                 570                 575

Met Pro Ile Asp Gly Val Thr Tyr Asn Leu Gln Gly Ile Arg Ile Asp
        580                 585                 590

Asn Pro Thr Lys Gly Ile Tyr Ile Gln Asn Gly Lys Lys Ile Ile Ile
        595                 600                 605

Lys
```

<210> SEQ ID NO 125
<211> LENGTH: 1170
<212> TYPE: DNA
<213> ORGANISM: Unknown
<220> FEATURE:
<223> OTHER INFORMATION: Obtained from an environmental sample.

<400> SEQUENCE: 125

```
atgaggtcta aaatcatcag cgccataaat aattatagtg ttattattct cgatggctcg      60
aatggcgatt tcactattag tgctacaatg agtttcagta gcaaatcaaa caaaaccata     120
gttggtgtaa ataatgctcg cctatgcacc aagttctatc taaccgatga aataaagact     180
gcgctcgatg ctgctaatgt aaaatcagca agttcaacca gtggaggtgg tacactctca     240
aatgggaaat cagtgtcaga acaacgtgaa taccttactc gtcaaacaat tatcgatcta     300
actggcgatg cttcggaatc cgtgtcagaaa gcgggcatct ttagcttcag tagttgtacc     360
aatatcatca tgcgaaacct cgttttggtt ggccctggcc catgcgatgt aggtggcaac     420
gatttgcttt cgctcactgg ttctaagcat ttttgggtcg atcactgtga gttaaccgat     480
ggtatagatg caatttcga tattaccaag agtagcgatt tcaatactgt tacttggtgt     540
atattcaatt ataccgatcg tgcatacgac cacatgaact ccaatcttat tggtagctcc     600
gatagcgaag atgctgccta tttgaacact actatggcat gcaatatttg gggctacaag     660
tgcaatcagc gaatgccaat ggctcgtgct ggtaatattc accttgtgaa caacttttac     720
gattgcgctg caatagtgt ggctgttaac cctcgtaaaa attctgagtt cttagtcgag     780
aactgctact tgccacgggg tgtgaagcca ttctcgcaga gtggtgcgtt gggatacaac     840
tttattgatt gctatacaga agattcatac acttttcagc agagtggtac agtgtctgtg     900
ccatacgttt actctaagtt tgatgtgcaa ttagtacccg agcaactcaa taaatatgct     960
ggcgcaacgc ttacttctcc gcttgtcata ggtcgggaag agggtgttgt tactcctatt    1020
agtgctgtct ctgttgatag cgatgttgtg ttggtcgaat actattcgct gactggtaat    1080
cgtgttaaca cgctcaatag aggcatcaat atcgttagaa ctatttacgc caacggcaaa    1140
gtaaccacac aaaaggtttt ggtgaaatag                                     1170
```

<210> SEQ ID NO 126
<211> LENGTH: 389
<212> TYPE: PRT
<213> ORGANISM: Unknown
<220> FEATURE:
<223> OTHER INFORMATION: Obtained from an environmental sample.
<220> FEATURE:
<221> NAME/KEY: DOMAIN
<222> LOCATION: (24)...(325)

<223> OTHER INFORMATION: Catalytic domain

<400> SEQUENCE: 126

```
Met Arg Ser Lys Ile Ile Ser Ala Ile Asn Asn Tyr Ser Val Ile Ile
 1               5                  10                  15

Leu Asp Gly Ser Asn Gly Asp Phe Thr Ile Ser Ala Thr Met Ser Phe
             20                  25                  30

Ser Ser Lys Ser Asn Lys Thr Ile Val Gly Val Asn Asn Ala Arg Leu
         35                  40                  45

Cys Thr Lys Phe Tyr Leu Thr Asp Glu Ile Lys Thr Ala Leu Asp Ala
     50                  55                  60

Ala Asn Val Lys Ser Ala Ser Ser Thr Ser Gly Gly Thr Leu Ser
 65                  70                  75                  80

Asn Gly Lys Ser Val Ser Glu Gln Arg Glu Tyr Leu Thr Arg Gln Thr
                 85                  90                  95

Ile Ile Asp Leu Thr Gly Asp Ala Ser Glu Ser Cys Gln Lys Ala Gly
            100                 105                 110

Ile Phe Ser Phe Ser Ser Cys Thr Asn Ile Ile Met Arg Asn Leu Val
        115                 120                 125

Leu Val Gly Pro Gly Pro Cys Asp Val Gly Gly Asn Asp Leu Leu Ser
130                 135                 140

Leu Thr Gly Ser Lys His Phe Trp Val Asp His Cys Glu Leu Thr Asp
145                 150                 155                 160

Gly Ile Asp Gly Asn Phe Asp Ile Thr Lys Ser Ser Asp Phe Asn Thr
                165                 170                 175

Val Thr Trp Cys Ile Phe Asn Tyr Thr Asp Arg Ala Tyr Asp His Met
            180                 185                 190

Asn Ser Asn Leu Ile Gly Ser Ser Asp Ser Glu Asp Ala Ala Tyr Leu
        195                 200                 205

Asn Thr Thr Met Ala Cys Asn Ile Trp Gly Tyr Lys Cys Asn Gln Arg
210                 215                 220

Met Pro Met Ala Arg Ala Gly Asn Ile His Leu Val Asn Asn Phe Tyr
225                 230                 235                 240

Asp Cys Ala Gly Asn Ser Val Ala Val Asn Pro Arg Lys Asn Ser Glu
                245                 250                 255

Phe Leu Val Glu Asn Cys Tyr Phe Ala Thr Gly Val Lys Pro Phe Ser
            260                 265                 270

Gln Ser Gly Ala Leu Gly Tyr Asn Phe Ile Asp Cys Tyr Thr Glu Asp
        275                 280                 285

Ser Tyr Thr Phe Gln Gln Ser Gly Thr Val Ser Val Pro Tyr Val Tyr
290                 295                 300

Ser Lys Phe Asp Val Gln Leu Val Pro Glu Gln Leu Asn Lys Tyr Ala
305                 310                 315                 320

Gly Ala Thr Leu Thr Ser Pro Leu Val Ile Gly Arg Glu Glu Gly Val
                325                 330                 335

Val Thr Pro Ile Ser Ala Val Ser Val Asp Ser Asp Val Val Leu Val
            340                 345                 350

Glu Tyr Tyr Ser Leu Thr Gly Asn Arg Val Asn Thr Leu Asn Arg Gly
        355                 360                 365

Ile Asn Ile Val Arg Thr Ile Tyr Ala Asn Gly Lys Val Thr Thr Gln
370                 375                 380

Lys Val Leu Val Lys
385
```

<210> SEQ ID NO 127
<211> LENGTH: 1449
<212> TYPE: DNA
<213> ORGANISM: Unknown
<220> FEATURE:
<223> OTHER INFORMATION: Obtained from an environmental sample.

<400> SEQUENCE: 127

```
atgcaatatg gcaaattagt acgcttgtcg gcactgacaa cagcgctggc attcagcgcc      60
ctggcacagg caaataacct ggcaattaca ggccccggag ccggggctga tggttccagc     120
aaagccagtg gcagtagcta cggcgatgta aagacgccg atctgcaaag ctactggcaa      180
ccgcctgcta ataacggcca aagagtgtcg gttaagtgga gcagcgctat cagcgttaat     240
caggtaatac tgcgtgaaca gggcagtaat gtaaccagct ggcggctggt aaataatgac     300
aacggcgcag tattggcaac cggcaccagc attggcagca acagaacggt taacttcagc     360
actgtaagca cgaaaaaact caatctggaa atactaactg ccagcggtgc cccgcgcatt     420
gctgagtttg aagtttattt aaataccaat ggcggcaacc cgccaaatcc tactgacccg     480
gaaccaggcc cggtaacttc ttgcgcagcg tctccacagg gctatgcctc gcttaacggt     540
ggcactaccg gcggcagtgg cagcaacgcg gtcacggtaa cggtaagcac cggcgctcaa     600
atggtatcgg cgctacaaaa ccgcgatcta accggccgc tcactatccg ggttaatggc      660
actatcacac cgggtaattc tggcggtgtc agtaagtttg acattaaaga tatggataat     720
gtcagcatta ttggtgtagg caacaatgcg ttgtttgacg gtatcggtat taaaatctgg     780
cgggccaata acgttattat ccgcaaacctt acaatgcgtt atgttaacac cggcgataaa     840
gacgctatta ccattgaagg cccggcgcgt aatatctgga ttgaccacaa cgaaatctat     900
aacagcctga atgtgggtaa agatttttac gacgagctta taagcggtaa aaaagacgta     960
gataacgtaa ctatctctta caactacctg cacgacagct ggaaaacctc gctgtggggc    1020
agcagtgatt ccgacaacta caaccgccgt attacctttc accataacca ctggcataag    1080
gtaaattcac gcctgccact gttccgtttt ggccagggcc atatttacaa taactattac    1140
aacgacattc aggacaccgg tattaacagc cggatgggtg cggtaattcg tattgaaaac    1200
aatgtgtttg aaaacgcgaa aaacccgata gtgtcgtttt attccagcgg ctacggttac    1260
tgggacaccc gcggtaatag ctttagcaat attacctggc aggaatacc cagcgacggc     1320
attatcgccg ggccaaatgt acaacccaca gcggtgctaa acctgcccta cagctttaac    1380
ctgttaccca ccaaccaggt aaaagcccac gtactggcca acgccggcgt gaataaatgt    1440
agtttctaa                                                             1449
```

<210> SEQ ID NO 128
<211> LENGTH: 482
<212> TYPE: PRT
<213> ORGANISM: Unknown
<220> FEATURE:
<223> OTHER INFORMATION: Obtained from an environmental sample.
<220> FEATURE:
<221> NAME/KEY: SIGNAL
<222> LOCATION: (1)...(24)
<220> FEATURE:
<221> NAME/KEY: DOMAIN
<222> LOCATION: (5)...(482)
<223> OTHER INFORMATION: Catalytic domain

<400> SEQUENCE: 128

```
Met Gln Tyr Gly Lys Leu Val Arg Leu Ser Ala Leu Thr Thr Ala Leu
 1               5                  10                  15
```

-continued

```
Ala Phe Ser Ala Leu Ala Gln Ala Asn Asn Leu Ala Ile Thr Gly Pro
             20                  25                  30

Gly Ala Gly Ala Asp Gly Ser Ser Lys Ala Ser Gly Ser Ser Tyr Gly
             35                  40                  45

Asp Val Lys Asp Ala Asp Leu Gln Ser Tyr Trp Gln Pro Pro Ala Asn
             50                  55                  60

Asn Gly Gln Arg Val Ser Val Lys Trp Ser Ser Ala Ile Ser Val Asn
 65                  70                  75                  80

Gln Val Ile Leu Arg Glu Gln Gly Ser Asn Val Thr Ser Trp Arg Leu
             85                  90                  95

Val Asn Asn Asp Asn Gly Ala Val Leu Ala Thr Gly Thr Ser Ile Gly
            100                 105                 110

Ser Asn Arg Thr Val Asn Phe Ser Thr Val Ser Thr Lys Lys Leu Asn
            115                 120                 125

Leu Glu Ile Leu Thr Ala Ser Gly Ala Pro Arg Ile Ala Glu Phe Glu
            130                 135                 140

Val Tyr Leu Asn Thr Asn Gly Gly Asn Pro Pro Asn Pro Thr Asp Pro
145                 150                 155                 160

Glu Pro Gly Pro Val Thr Ser Cys Ala Ala Ser Pro Gln Gly Tyr Ala
            165                 170                 175

Ser Leu Asn Gly Gly Thr Thr Gly Ser Gly Ser Asn Ala Val Thr
            180                 185                 190

Val Thr Val Ser Thr Gly Ala Gln Met Val Ser Ala Leu Gln Asn Arg
            195                 200                 205

Asp Leu Asn Arg Pro Leu Thr Ile Arg Val Asn Gly Thr Ile Thr Pro
            210                 215                 220

Gly Asn Ser Gly Gly Val Ser Lys Phe Asp Ile Lys Asp Met Asp Asn
225                 230                 235                 240

Val Ser Ile Ile Gly Val Gly Asn Asn Ala Leu Phe Asp Gly Ile Gly
            245                 250                 255

Ile Lys Ile Trp Arg Ala Asn Asn Val Ile Ile Arg Asn Leu Thr Met
            260                 265                 270

Arg Tyr Val Asn Thr Gly Asp Lys Asp Ala Ile Thr Ile Glu Gly Pro
            275                 280                 285

Ala Arg Asn Ile Trp Ile Asp His Asn Glu Ile Tyr Asn Ser Leu Asn
            290                 295                 300

Val Gly Lys Asp Phe Tyr Asp Glu Leu Ile Ser Gly Lys Lys Asp Val
305                 310                 315                 320

Asp Asn Val Thr Ile Ser Tyr Asn Tyr Leu His Asp Ser Trp Lys Thr
            325                 330                 335

Ser Leu Trp Gly Ser Ser Asp Ser Asp Asn Tyr Asn Arg Arg Ile Thr
            340                 345                 350

Phe His His Asn His Trp His Lys Val Asn Ser Arg Leu Pro Leu Phe
            355                 360                 365

Arg Phe Gly Gln Gly His Ile Tyr Asn Asn Tyr Asn Asp Ile Gln
            370                 375                 380

Asp Thr Gly Ile Asn Ser Arg Met Gly Ala Val Ile Arg Ile Glu Asn
385                 390                 395                 400

Asn Val Phe Glu Asn Ala Lys Asn Pro Ile Val Ser Phe Tyr Ser Ser
            405                 410                 415

Gly Tyr Gly Tyr Trp Asp Thr Arg Gly Asn Ser Phe Ser Asn Ile Thr
            420                 425                 430
```

```
Trp Gln Glu Tyr Pro Ser Asp Gly Ile Ile Ala Gly Pro Asn Val Gln
            435                 440                 445

Pro Thr Ala Val Leu Asn Leu Pro Tyr Ser Phe Asn Leu Leu Pro Thr
        450                 455                 460

Asn Gln Val Lys Ala His Val Leu Ala Asn Ala Gly Val Asn Lys Cys
465                 470                 475                 480

Ser Phe

<210> SEQ ID NO 129
<211> LENGTH: 1173
<212> TYPE: DNA
<213> ORGANISM: Bacillus halodurans ATCC 27557
<220> FEATURE:

<400> SEQUENCE: 129
atgagttcga aaatcaaaaa tgctatcaat aactatagtg ttattattct cgatggctcg     60
aatggcgatt ttacagtcaa tgctacaatg agtttcagtg gcaagtccaa taaaactatt    120
gtgggtgtga acaatgctcg cctatgcacc aaattctaca ttacgcccga gataaaagaa    180
gccctcgatg ctgccgatgt gaaatctaag agctcaagta gtggcactgg tggaactctt    240
tctaatggta cgtcggtcag tgaggctcgc gaattggcta ctcgtcaaac gttgattgat    300
tatctcggcg atagctcaga atcgtatcag aaagctggta tctttggctt agcaactgc     360 actaatatta ttatgcgcaa cattgttttc gttggccctg gtccatgcga tgtaggtggc    420
aacgacttgc tttcgctcgt tggttcgaag catttctggg tcgaccactg cgagtttacc    480
gatggcatcg atggcaactt cgacatcacc aagagtagcg acttcaacac cgtttcgtgg    540
tgcactttca gctataccga ccgcgcatac gaccacatga attccaacct tattggtagc    600
tccgattcag agaatgcggc ttaccttaat actactatgg cttccaacgt ctggggcaat    660
aagtgcaatc agcgtatgcc tatggctcgt gccggtaata ttcacctcgt aaataattat    720
tacaactgcc ctggcaatag cgtggctgtg aatcctcgca aaaactcaga attttttggtg   780 gagaattgct atttcgcaag tggcgttaag cctttctcgc agagcggcgc tcttagctat    840
ctatttatcg attgctacac cgaagatact tacaccttcc agaaatctgg ctctactacg    900
gtgccataca catatagcaa attcgatgct cagcttgttc ccgagcaact cacccaattc    960
gctggcgcaa cattgacttc gccgcttgtt attggtaggg aatctgagaa tgttacacca   1020
gtctcagtca ttgctgcaaa tagcgatgtc atatctgtag aatactattc gctcactggc   1080
aagcgcatca gcgaaccaac taaaggcatc aatatcgtta gaactattta tactaacggc   1140
aacgtgacca cacaaaaggt cttggtgaaa taa                                 1173

<210> SEQ ID NO 130
<211> LENGTH: 390
<212> TYPE: PRT
<213> ORGANISM: Bacillus halodurans ATCC 27557
<220> FEATURE:
<221> NAME/KEY: DOMAIN
<222> LOCATION: (38)...(326)
<223> OTHER INFORMATION: Catalytic domain

<400> SEQUENCE: 130

Met Ser Ser Lys Ile Lys Asn Ala Ile Asn Asn Tyr Ser Val Ile Ile
1               5                   10                  15

Leu Asp Gly Ser Asn Gly Asp Phe Thr Val Asn Ala Thr Met Ser Phe
            20                  25                  30

Ser Gly Lys Ser Asn Lys Thr Ile Val Gly Val Asn Asn Ala Arg Leu
```

```
                35                  40                  45
Cys Thr Lys Phe Tyr Ile Thr Pro Glu Ile Lys Glu Ala Leu Asp Ala
 50                  55                  60

Ala Asp Val Lys Ser Lys Ser Ser Ser Gly Thr Gly Thr Leu
 65                  70                  75                  80

Ser Asn Gly Thr Ser Val Ser Glu Ala Arg Glu Leu Ala Thr Arg Gln
                 85                  90                  95

Thr Leu Ile Asp Tyr Leu Gly Asp Ser Ser Glu Ser Tyr Gln Lys Ala
                100                 105                 110

Gly Ile Phe Gly Phe Ser Asn Cys Thr Asn Ile Ile Met Arg Asn Ile
            115                 120                 125

Val Phe Val Gly Pro Gly Pro Cys Asp Val Gly Gly Asn Asp Leu Leu
130                 135                 140

Ser Leu Val Gly Ser Lys His Phe Trp Val Asp His Cys Glu Phe Thr
145                 150                 155                 160

Asp Gly Ile Asp Gly Asn Phe Asp Ile Thr Lys Ser Ser Asp Phe Asn
                165                 170                 175

Thr Val Ser Trp Cys Thr Phe Ser Tyr Thr Asp Arg Ala Tyr Asp His
            180                 185                 190

Met Asn Ser Asn Leu Ile Gly Ser Ser Asp Ser Glu Asn Ala Ala Tyr
        195                 200                 205

Leu Asn Thr Thr Met Ala Ser Asn Val Trp Gly Asn Lys Cys Asn Gln
210                 215                 220

Arg Met Pro Met Ala Arg Ala Gly Asn Ile His Leu Val Asn Asn Tyr
225                 230                 235                 240

Tyr Asn Cys Pro Gly Asn Ser Val Ala Val Asn Pro Arg Lys Asn Ser
                245                 250                 255

Glu Phe Leu Val Glu Asn Cys Tyr Phe Ala Ser Gly Val Lys Pro Phe
            260                 265                 270

Ser Gln Ser Gly Ala Leu Ser Tyr Leu Phe Ile Asp Cys Tyr Thr Glu
        275                 280                 285

Asp Thr Tyr Thr Phe Gln Lys Ser Gly Ser Thr Thr Val Pro Tyr Thr
290                 295                 300

Tyr Ser Lys Phe Asp Ala Gln Leu Val Pro Glu Gln Leu Thr Gln Phe
305                 310                 315                 320

Ala Gly Ala Thr Leu Thr Ser Pro Leu Val Ile Gly Arg Glu Ser Glu
                325                 330                 335

Asn Val Thr Pro Val Ser Val Ile Ala Ala Asn Ser Asp Val Ile Ser
            340                 345                 350

Val Glu Tyr Tyr Ser Leu Thr Gly Lys Arg Ile Ser Glu Pro Thr Lys
        355                 360                 365

Gly Ile Asn Ile Val Arg Thr Ile Tyr Thr Asn Gly Asn Val Thr Thr
370                 375                 380

Gln Lys Val Leu Val Lys
385                 390

<210> SEQ ID NO 131
<211> LENGTH: 972
<212> TYPE: DNA
<213> ORGANISM: Unknown
<220> FEATURE:
<223> OTHER INFORMATION: Obtained from an environmental sample

<400> SEQUENCE: 131
atggcaaaaa tactgacatt agacggtaac ccggccgcca gctggttcaa caaatccagg      60
```

-continued

```
accaagtgga atagcagccg cgccgatatt gtgttgtctt accagcaatc caacggcggt    120
tggccaaaaa acctggatta caactcagtg agcgcaggca atggcgggag cgacagcggc    180
accatcgaca atggtgcaac cattaccgaa atggtttacc tcgctgaaat ttataaaaac    240
ggcggcaaca ccaaatatcg cgatgcagtg cgcagagcag caaactttt agtgagctcg     300 caatacagca caggcgcctt gccacaattt tatccgttga aaggcggcta tgcggatcat    360 gcgacctta acgataacgg catggcgtac gcgttgacgg tattggattt cgcagtaaac     420
aaacgcgcac cgtttgataa cgacattttc tctgattctg atcgggcgaa attcaaaacc    480
gctgttgcca aaggtgtgga ttacattta aaagcgcagt ggaaacaaaa tggaaaactc     540
actgcatggt gtgcacaaca cggtgctacg gattaccaac cgaaaaaagc gcgcgcttat    600
gaattggaat cattgagtgg tagcgagtcg gtcggcattc tcgccttctt gatgacccaa    660
ccacaaaccg cgcaaatcga agcggcggtc aaggcgggtg tcaactggtt cgccagtcca    720
aatacttatt tggctaacta cacttacgat tcatcaaaag cgtctaccaa cccgattgtg    780
tataaatccg gaagcagaat gtggtatcgc ttctatgacc tgaacaccaa ccgtggtttc    840
tttagtgatc gcgatggcag caaattctat gatatcaccc aaatgtcaga gagcgtcgc    900 accggttata gctggggtgg ctcttacggt gaatctatta tttccttcgc gcaaaaagtg    960
ggttatctgt ag                                                         972
```

<210> SEQ ID NO 132
<211> LENGTH: 323
<212> TYPE: PRT
<213> ORGANISM: Unknown
<220> FEATURE:
<223> OTHER INFORMATION: Obtained from an environmental sample

<400> SEQUENCE: 132

```
Met Ala Lys Ile Leu Thr Leu Asp Gly Asn Pro Ala Ala Ser Trp Phe
  1               5                  10                  15

Asn Lys Ser Arg Thr Lys Trp Asn Ser Ser Arg Ala Asp Ile Val Leu
             20                  25                  30

Ser Tyr Gln Gln Ser Asn Gly Gly Trp Pro Lys Asn Leu Asp Tyr Asn
         35                  40                  45

Ser Val Ser Ala Gly Asn Gly Ser Asp Ser Gly Thr Ile Asp Asn
     50                  55                  60

Gly Ala Thr Ile Thr Glu Met Val Tyr Leu Ala Glu Ile Tyr Lys Asn
 65                  70                  75                  80

Gly Gly Asn Thr Lys Tyr Arg Asp Ala Val Arg Arg Ala Ala Asn Phe
                 85                  90                  95

Leu Val Ser Ser Gln Tyr Ser Thr Gly Ala Leu Pro Gln Phe Tyr Pro
            100                 105                 110

Leu Lys Gly Gly Tyr Ala Asp His Ala Thr Phe Asn Asp Asn Gly Met
        115                 120                 125

Ala Tyr Ala Leu Thr Val Leu Asp Phe Ala Val Asn Lys Arg Ala Pro
    130                 135                 140

Phe Asp Asn Asp Ile Phe Ser Asp Ser Asp Arg Ala Lys Phe Lys Thr
145                 150                 155                 160

Ala Val Ala Lys Gly Val Asp Tyr Ile Leu Lys Ala Gln Trp Lys Gln
                165                 170                 175

Asn Gly Lys Leu Thr Ala Trp Cys Ala Gln His Gly Ala Thr Asp Tyr
            180                 185                 190
```

```
Gln Pro Lys Lys Ala Arg Ala Tyr Glu Leu Glu Ser Leu Ser Gly Ser
        195                 200                 205

Glu Ser Val Gly Ile Leu Ala Phe Leu Met Thr Gln Pro Gln Thr Ala
    210                 215                 220

Gln Ile Glu Ala Ala Val Lys Ala Gly Val Asn Trp Phe Ala Ser Pro
225                 230                 235                 240

Asn Thr Tyr Leu Ala Asn Tyr Thr Tyr Asp Ser Ser Lys Ala Ser Thr
                245                 250                 255

Asn Pro Ile Val Tyr Lys Ser Gly Ser Arg Met Trp Tyr Arg Phe Tyr
            260                 265                 270

Asp Leu Asn Thr Asn Arg Gly Phe Phe Ser Asp Arg Asp Gly Ser Lys
        275                 280                 285

Phe Tyr Asp Ile Thr Gln Met Ser Glu Glu Arg Arg Thr Gly Tyr Ser
    290                 295                 300

Trp Gly Gly Ser Tyr Gly Glu Ser Ile Ile Ser Phe Ala Gln Lys Val
305                 310                 315                 320

Gly Tyr Leu

<210> SEQ ID NO 133
<211> LENGTH: 972
<212> TYPE: DNA
<213> ORGANISM: Artificial Sequence
<220> FEATURE:
<223> OTHER INFORMATION: Synthetically generated polynucleotide

<400> SEQUENCE: 133
atggcaaaaa tactgacatt agacggtaac ccggccgcca gctggttcaa caaatccagg      60
accaagtgga atagcagccg cgccgatatt gtgttgtctt accagcaatc caacggcggt     120
tggccaaaaa acctggatta caactcagtg agcgcaggca atggcgggag cgacagcggc     180
accatcgaca atggtgcaac cattaccgaa atggtttacc tcgctgaaat ttataaaaac     240
ggcggcaaca ccaaatatcg cgatgcagtg cgcagagcag caaacttttt agtgagctcg     300
caatacagca caggcgcctt gccacaattt tatccgttga aaggcggcta tcatgatcat     360 gcgacccttta acgataacgg catggcgtac gcgttgacgg tattggattt cgcagtaaac     420
aaacgcgcac cgtttgataa cgacattttc tctgattctg atcgggcgaa attcaaaacc     480
gctgttgcca aaggtgtgga ttcattttta aaagcgcagt ggaaacaaaa tggaaaactc     540
actgcatggt gtgcacaaca cggtgctttg gattaccaac cgaaaaaagg tcgcgcttat     600
gaattggaat cattgagtgg taaggagtcg gtcggcattc tcgccttctt gatgacccaa     660
ccacaaaccg cgcaaatcga agcggcggtc aaggcgggtg tcaactggtt cgccagtcca     720
aatacttatt tggctaacta cacttacgat tcatcaaaag cgtctaccaa cccgattgtg     780
tataaaaagg gaagcagaat gtggtatcgc ttctatgacc tgtataccaa ccgtggttc      840 tttagtgatc gcgatggcag caaattctat gatatcaccc aaatgtcaga gagcgtcgc      900 accggttata gctggggtgg ctcttggggt gaagttatta tttccttcgc gcaaaaagtg     960
ggttatctgt ag                                                         972

<210> SEQ ID NO 134
<211> LENGTH: 323
<212> TYPE: PRT
<213> ORGANISM: Artificial Sequence
<220> FEATURE:
<223> OTHER INFORMATION: Synthetically generated polypeptide

<400> SEQUENCE: 134
```

-continued

```
Met Ala Lys Ile Leu Thr Leu Asp Gly Asn Pro Ala Ala Ser Trp Phe
1               5                   10                  15

Asn Lys Ser Arg Thr Lys Trp Asn Ser Ser Arg Ala Asp Ile Val Leu
            20                  25                  30

Ser Tyr Gln Gln Ser Asn Gly Gly Trp Pro Lys Asn Leu Asp Tyr Asn
            35              40                  45

Ser Val Ser Ala Gly Asn Gly Gly Ser Asp Ser Gly Thr Ile Asp Asn
        50              55                  60

Gly Ala Thr Ile Thr Glu Met Val Tyr Leu Ala Glu Ile Tyr Lys Asn
65                  70                  75                  80

Gly Gly Asn Thr Lys Tyr Arg Asp Ala Val Arg Arg Ala Ala Asn Phe
                85                  90                  95

Leu Val Ser Ser Gln Tyr Ser Thr Gly Ala Leu Pro Gln Phe Tyr Pro
            100                 105                 110

Leu Lys Gly Gly Tyr His Asp His Ala Thr Phe Asn Asp Asn Gly Met
            115                 120                 125

Ala Tyr Ala Leu Thr Val Leu Asp Phe Ala Val Asn Lys Arg Ala Pro
130                 135                 140

Phe Asp Asn Asp Ile Phe Ser Asp Ser Asp Arg Ala Lys Phe Lys Thr
145                 150                 155                 160

Ala Val Ala Lys Gly Val Asp Tyr Ile Leu Lys Ala Gln Trp Lys Gln
                165                 170                 175

Asn Gly Lys Leu Thr Ala Trp Cys Ala Gln His Gly Ala Leu Asp Tyr
            180                 185                 190

Gln Pro Lys Lys Gly Arg Ala Tyr Glu Leu Glu Ser Leu Ser Gly Lys
        195                 200                 205

Glu Ser Val Gly Ile Leu Ala Phe Leu Met Thr Gln Pro Gln Thr Ala
        210                 215                 220

Gln Ile Glu Ala Ala Val Lys Ala Gly Val Asn Trp Phe Ala Ser Pro
225                 230                 235                 240

Asn Thr Tyr Leu Ala Asn Tyr Thr Tyr Asp Ser Ser Lys Ala Ser Thr
            245                 250                 255

Asn Pro Ile Val Tyr Lys Lys Gly Ser Arg Met Trp Tyr Arg Phe Tyr
            260                 265                 270

Asp Leu Tyr Thr Asn Arg Gly Phe Phe Ser Asp Arg Asp Gly Ser Lys
        275                 280                 285

Phe Tyr Asp Ile Thr Gln Met Ser Glu Glu Arg Arg Thr Gly Tyr Ser
        290                 295                 300

Trp Gly Gly Ser Trp Gly Glu Val Ile Ile Ser Phe Ala Gln Lys Val
305                 310                 315                 320

Gly Tyr Leu
```